US012780793B2

(12) United States Patent
Novak et al.

(10) Patent No.: US 12,780,793 B2
(45) Date of Patent: Nov. 3, 2026

(54) SULFONAMIDE INHIBITORS AS CTPS1 INHIBITORS

(71) Applicant: Step Pharma S.A.S., Paris (FR)

(72) Inventors: Andrew Novak, Nottingham (GB); Abdul Quddus, Nottingham (GB); Emma Blackham, Nottingham (GB)

(73) Assignee: Step Pharma S.A.S., Paris (FR)

( * ) Notice: Subject to any disclaimer, the term of this patent is extended or adjusted under 35 U.S.C. 154(b) by 995 days.

(21) Appl. No.: 17/760,886

(22) PCT Filed: Sep. 18, 2020

(86) PCT No.: PCT/IB2020/000800

§ 371 (c)(1),
(2) Date: Mar. 16, 2022

(87) PCT Pub. No.: WO2021/053403

PCT Pub. Date: Mar. 25, 2021

(65) Prior Publication Data

US 2023/0020663 A1 Jan. 19, 2023

(30) Foreign Application Priority Data

Sep. 20, 2019 (EP) .................................... 19306149

(51) Int. Cl.

| | |
|---|---|
| ***C07D 401/12*** | (2006.01) |
| ***C07D 239/42*** | (2006.01) |
| ***C07D 277/54*** | (2006.01) |
| ***C07D 401/14*** | (2006.01) |
| ***C07D 403/12*** | (2006.01) |
| ***C07D 405/14*** | (2006.01) |
| ***C07D 417/12*** | (2006.01) |

(52) U.S. Cl.

CPC ......... *C07D 401/12* (2013.01); *C07D 239/42* (2013.01); *C07D 277/54* (2013.01); *C07D 401/14* (2013.01); *C07D 403/12* (2013.01); *C07D 405/14* (2013.01); *C07D 417/12* (2013.01)

(58) Field of Classification Search

CPC .................................................... C07D 401/12

See application file for complete search history.

(56) References Cited

U.S. PATENT DOCUMENTS

| | | | |
|---|---|---|---|
| 6,048,884 | A | 4/2000 | Maruyama et al. |
| 11,505,547 | B2 | 11/2022 | Novak et al. |
| 11,655,246 | B2 | 5/2023 | Quddus et al. |
| 11,987,573 | B2 | 5/2024 | Quddus et al. |
| 12,319,680 | B2 | 6/2025 | Novak et al. |
| 12,371,419 | B2 | 7/2025 | Quddus |
| 12,466,810 | B2 | 11/2025 | Quddus et al. |
| 12,503,466 | B2 | 12/2025 | Novak et al. |
| 2003/0158218 | A1 | 8/2003 | Nantermet et al. |
| 2003/0176476 | A1 | 9/2003 | Barf et al. |
| 2016/0152583 | A1 | 6/2016 | Arisawa et al. |
| 2021/0002269 | A1 | 1/2021 | Quddus et al. |
| 2021/0024507 | A1 | 1/2021 | Quddus et al. |
| 2021/0380575 | A1 | 12/2021 | Novak et al. |
| 2021/0387965 | A1 | 12/2021 | Quddus et al. |
| 2023/0002352 | A1 | 1/2023 | Novak et al. |
| 2025/0263407 | A1 | 8/2025 | Novak et al. |
| 2025/0282756 | A1 | 9/2025 | Quddus et al. |

FOREIGN PATENT DOCUMENTS

| | | | |
|---|---|---|---|
| CN | 104262071 | | 1/2015 |
| EP | 1659113 | | 5/2006 |
| EP | 2292603 | A1 | 3/2011 |
| GB | 1555007 | | 11/1979 |
| GB | 1575803 | | 10/1980 |
| WO | WO 02/16318 | | 2/2002 |
| WO | 2006050908 | A1 | 5/2006 |
| WO | WO 2006/010751 | A1 | 2/2009 |
| WO | WO 2009/075874 | A1 | 6/2009 |
| WO | WO 2015/094119 | A1 | 6/2015 |
| WO | 2019106156 | A1 | 6/2019 |
| WO | 2019180244 | A1 | 9/2019 |
| WO | WO 2019/179652 | | 9/2019 |

(Continued)

OTHER PUBLICATIONS

Silverman, R. B., & Holladay, M. W. (2014). The Organic Chemistry of drug design and Drug Action. Academic Press. (Year: 2014).*

(Continued)

*Primary Examiner* — Andrew D Kosar
*Assistant Examiner* — Connor K English
(74) *Attorney, Agent, or Firm* — Morgan, Lewis & Bockius LLP

(57) ABSTRACT

The invention provides a compound of formula (I) and processes for the manufacture of such compounds, related intermediates, compositions comprising such compounds and the use of such compounds as cytidine triphosphate synthase 1 inhibitors, particularly in the treatment or prophylaxis of disorders associated with cell proliferation.

(I)

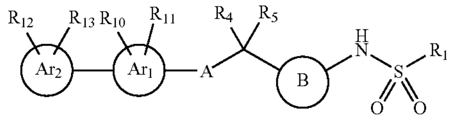

4 Claims, No Drawings

Specification includes a Sequence Listing.

(56) References Cited

FOREIGN PATENT DOCUMENTS

| | | | |
|---|---|---|---|
| WO | 2020245664 | A1 | 12/2020 |
| WO | 2020245665 | A1 | 12/2020 |
| WO | WO 2022/087634 | | 4/2022 |

OTHER PUBLICATIONS

U.S. Appl. No. 17/615,879, Quddus et al.
U.S. Appl. No. 17/615,873, Quddus et al.
U.S. Appl. No. 17/760,861, Novak et al.
Klapars et al., "Copper-Catalyzed Halogen Exchange in Aryl Halides: An Aromatic Finkelstein Reaction," Journal of the American Chemical Society, American Chemical Society, 124: 14844-14845 (2002).
Ananthakrishnanadar et al., "The Effects of Substituents on the Rate of Saponification of Biphenyl-4-carboxylates," Journal of the Chemical Society, Perkin Transactions 2: Physical Organic Chemistry, 11 (1): 35-37 (1984).
Meng et al., "Carboxylation of Aromatic and Aliphatic Bromides and Triflates with CO2 by Dual Visible-Light-Nickel Catalysis," Angewandte Chemie, International Edition, 56: 13426-13430 (2017).
Zhao et al., "Design, synthesis and evaluation of aromatic heterocyclic derivatives as potent antifungal agents," European Journal of Medicinal Chemistry, 137: 96-107 (2017).
Lai et al., "A biocompatible inverse electron demand Diels-Alder reaction of aldehyde and tetrazine promoted by proline," New Journal of Chemistry, 40: 8194-8197 (2016).
Thirumoorthi et al., "A practical metal-free homolytic aromatic alkylation protocol for the synthesis of 3-(pyrazin-2-yl)bicyclo[1.1.1]pentane-1-carboxylic acid," Organic and Biomolecular Chemistry, 14: 9485-9489 (2016).
Wang et al., "Diamondoid-structured polymolybdate-based metal-organic frameworks as high-capactiy anodes for lithium-ion batteries," Chemical Communication, 53: 5204-5207 (2017).
Sandosham et al., "Synthesis of Pyrimidinyl Triflates and Palladium-Catalyzed Coupling with Organotin and Organozinc Reagents Heterocycles," 37 (1) : 501-514 (1994).
Database Registry, Chemical Abstracts Service, XP055772827, Feb. 20, 2014.
Database Registry, Chemical Abstracts Service, XP055772837, Jun. 10, 2009.
Database Registry, Chemical Abstracts Service, XP055772841, Dec. 4, 2017.
Database Registry, Chemical Abstracts Service, XP055772832, Jun. 10, 2009.
Database Registry, Chemical Abstracts Service, XP055772844, Nov. 10, 2011.
Database Registry, Chemical Abstracts Service, XP002801975, Mar. 8, 2019.
Database Registry, Chemical Abstracts Service, XP002801976, Dec. 10, 2013.
Database Registry, Chemical Abstracts Service, XP002801977, Nov. 1, 2013.
Database Registry, Chemical Abstracts Service, XP002801978, Nov. 4, 2013.
Database Registry, Chemical Abstracts Service, XP002801979, Dec. 2, 2013.
Database Registry, Chemical Abstracts Service, XP002801980, Dec. 8, 2013.
Database Registry, Chemical Abstracts Service, XP002801981, Dec. 13, 2013.
Database Registry, Chemical Abstracts Service, XP002801982, Dec. 15, 2013.
Database Registry, Chemical Abstracts Service, XP002801983, Dec. 19, 2013.
Lynch et al., "Structural basis for isoform-specific inhibition of human CTPS1," PNAS, 118 (40): e2107968118 (2021).
Lee et al., "Identification of novel small molecule inhibitors against NS2B/NS3 serine protease from Zika virus," Antiviral Research, 139: 49-58 (2016).
Lubbers et al., "Aminothiazoles as y-secretase modulators," Bioorganic & Medicinal Chemistry Letters, 21: 6554-6558 (2011).
Tang et al., "CTP synthase 1, a smooth muscle-sensitive therapeutic target for effective vascular repair," Atherosclerosis, Thrombosis and Vascular Biology, 33: 2336-2344 (2013).
National Centre for Biotechnology Information, PubChem Substance record for SID69002076, ZINC29974483, May 29, 2009.
Novak, et al., "Delivered and Optimization of Potent and Orally Available CTP Synthetase Inhibitors for Use in Treatment of Disease Driven by Aberrant Immune Cell Proliferation," Journal of Medicinal Chemistry, 2022, pubs.acs.org/jmc, 11 pages.
Schimmel, et al., "Cyclopentenyl Cytosine (CPEC): An Overview of its in vitro and in vivo Activity," Current Cancer Drug Targets, 2007, vol. 7, pp. 504-509.
C.G. Wermuth, in The Practice of Medicinal Chemistry, Academic Press 1996, pp. 203-237 (Year: 1996).

* cited by examiner

SULFONAMIDE INHIBITORS AS CTPS1 INHIBITORS

RELATED APPLICATIONS

This application is a U.S. National Phase Application under 35 U.S.C. § 371 of International Application No. PCT/IB2020/000800, filed Sep. 18, 2020, which claims priority to, and the benefit of, European Application No. 19306149.6, filed Sep. 20, 2019. The contents of each of these applications are incorporated herein by reference in their entirety.

Sequence Listing Submission via EFS-Web

A computer readable text file, entitled "SequenceListing.txt" created on Feb. 22, 2022 with a file size of 867 bytes contains the sequence listing for this application and is hereby incorporated by reference in its entirety.

FIELD OF THE INVENTION

The invention relates to novel compounds, processes for the manufacture of such compounds, related intermediates, compositions comprising such compounds and the use of such compounds as cytidine triphosphate synthase 1 inhibitors, particularly in the treatment or prophylaxis of disorders associated with cell proliferation.

BACKGROUND OF THE INVENTION

Nucleotides are a key building block for cellular metabolic processes such as deoxyribonucleic acid (DNA) and ribonucleic acid (RNA) synthesis. There are two classes of nucleotides, that contain either purine or pyrimidine bases, both of which are important for metabolic processes.

Based on this, many therapies have been developed to target different aspects of nucleotide synthesis, with some inhibiting generation of purine nucleotides and some pyrimidine nucleotides or both.

The pyrimidine nucleotide cytidine 5' triphosphate (CTP) is a precursor required not just for the anabolism of DNA and RNA but also phospholipids and sialyation of proteins. CTP originates from two sources: a salvage pathway and a de novo synthesis pathway that depends on two enzymes, the CTP synthases (or synthetases) 1 and 2 (CTPS1 and CTPS2) (Evans and Guy 2004; Higgins, et al. 2007; Ostrander, et al. 1998).

CTPS1 and CTPS2 catalyse the conversion of uridine triphosphate (UTP) and glutamine into cytidine triphosphate (CTP) and L-glutamate:

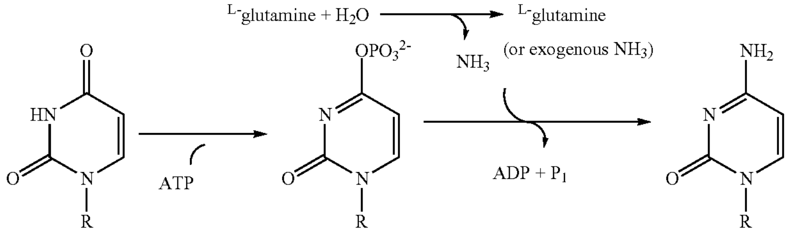

UTP 4-phospho-UTP CTP

Both enzymes have two domains, an N-terminal synthetase domain and a C-terminal glutaminase domain (Kursula, et al. 2006). The synthetase domain transfers a phosphate from adenosine triphosphate (ATP) to the 4-position of UTP to create an activated intermediate, 4-phospho-UTP. The glutaminase domain generates ammonia from glutamine, via a covalent thioester intermediate with a conserved active site cysteine, generating glutamate. This ammonium is transferred from the glutaminase domain to the synthetase domain via a tunnel or can be derived from external ammonium. This ammonium is then used by the synthetase domain to generate CTP from the 4-phospho-UTP (Ueberman, 1956).

Although CTPS exists as two isozymes in humans and other eukaryotic organisms, CTPS1 and CTPS2, functional differences between the two isozymes are not yet fully elucidated (van Kuilenburg, et al. 2000).

The immune system provides protection from infections and has therefore evolved to rapidly respond to the wide variety of pathogens that the individual may be exposed to. This response can take many forms, but the expansion and differentiation of immune populations is a critical element and is hence closely linked to rapid cell proliferation. Within this, CTP synthase activity appears to play an important role in DNA synthesis and the rapid expansion of lymphocytes following activation (Fairbanks, et al. 1995; van den Berg, et al. 1995).

Strong clinical validation that CTPS1 is the critical enzyme in human lymphocyte proliferation came with the identification of a loss-of-function homozygous mutation (rs145092287) in this enzyme that causes a distinct and life-threatening immunodeficiency, characterized by an impaired capacity of activated T- and B-cells to proliferate in response to antigen receptor-mediated activation. Activated CTPS1-deficient cells were shown to have decreased levels of CTP. Normal T-cell proliferation was restored in CTPS1-deficient cells by expressing wild-type CTPS1 or by addition of cytidine. CTPS1 expression was found to be low in resting lymphocytes, but rapidly upregulated following activation of these cells. Expression of CTPS1 in other tissues was generally low. CTPS2 seems to be ubiquitously expressed in a range of cells and tissues but at low levels, and the failure of CTPS2, which is still intact in the patients, to compensate for the mutated CTPS1, supports CTPS1 being the critical enzyme for the immune populations affected in the patients (Martin, et al. 2014).

Overall, these findings suggest that CTPS1 is a critical enzyme necessary to meet the demands for the supply of CTP required by several important immune cell populations.

Normally the immune response is tightly regulated to ensure protection from infection, whilst controlling any response targeting host tissues. In certain situations, the control of this process is not effective, leading to immune-mediated pathology. A wide range of human diseases are thought to be due to such inappropriate responses mediated by different elements of the immune system.

Given the role that cell populations, such as T and B lymphocytes, are thought to play in a wide range of autoimmune and other diseases, CTPS1 represents a target for a new class of immunosuppressive agents. Inhibition of CTPS1 therefore provides a novel approach to the inhibition of activated lymphocytes and selected other immune cell populations such as Natural Killer cells, Mucosal-Associated Invariant T (MAIT) and Invariant Natural Killer T cells, highlighted by the phenotype of the human mutation patients (Martin, et al. 2014).

Cancer can affect multiple cell types and tissues but the underlying cause is a breakdown in the control of cell division. This process is highly complex, requiring careful coordination of multiple pathways, many of which remain to be fully characterised. Cell division requires the effective replication of the cell's DNA and other constituents. Interfering with a cell's ability to replicate by targeting nucleic acid synthesis has been a core approach in cancer therapy for many years. Examples of therapies acting in this way are 6-thioguanine, 6-mecaptopurine, 5-fluorouracil, cytarabine, gemcitabine and pemetrexed.

As indicated above, pathways involved in providing the key building blocks for nucleic acid replication are the purine and pyrimidine synthesis pathways, and pyrimidine biosynthesis has been observed to be up-regulated in tumors and neoplastic cells.

CTPS activity is upregulated in a range of tumour types of both haematological and non-haematological origin, although heterogeneity is observed among patients. Linkages have also been made between high enzyme levels and resistance to chemotherapeutic agents.

Currently, the precise role that CTPS1 and CTPS2 may play in cancer is not completely clear. Several non-selective CTPS inhibitors have been developed for oncology indications up to phase I/II clinical trials, but were stopped due to toxicity and efficacy issues.

Most of the developed inhibitors are nucleoside-analogue prodrugs (3-deazauridine, CPEC, carbodine), which are converted to the active triphosphorylated metabolite by the kinases involved in pyrimidine biosynthesis: uridine/cytidine kinase, nucleoside monophosphate-kinase (NMP-kinase) and nucleoside diphosphatekinase (NDP-kinase). The remaining inhibitors (acivicin, DON) are reactive analogues of glutamine, which irreversibly inhibit the glutaminase domain of CTPS. Gemcitibine is also reported to have some inhibitory activity against CTPS (McClusky et al., 2016).

CTPS therefore appears to be an important target in the cancer field. The nature of all of the above compounds is such that effects on other pathways are likely to contribute to the efficacy they show in inhibiting tumours.

Selective CTPS inhibitors therefore offer an attractive alternative approach for the treatment of tumours. Compounds with different potencies against CTPS1 and CTPS2 may offer important opportunities to target different tumours depending upon their relative dependence on these enzymes.

CTPS1 has also been suggested to play a role in vascular smooth muscle cell proliferation following vascular injury or surgery (Tang, et al. 2013).

As far as is known to date, no selective CTPS1 inhibitors have been developed. Recently, the CTPS1 selective inhibitory peptide CTpep-3 has been identified. The inhibitory effects of CTpep-3 however, were seen in cell free assays but not in the cellular context. This was not unexpected though, since the peptide is unlikely to enter the cell and hence is not easily developable as a therapeutic (Sakamoto, et al. 2017).

In summary, the available information and data strongly suggest that inhibitors of CTPS1 will reduce the proliferation of a number of immune and cancer cell populations, with the potential for an effect on other selected cell types such as vascular smooth muscle cells as well. Inhibitors of CTPS1 may therefore be expected to have utility for treatment or prophylaxis in a wide range of indications where the pathology is driven by these populations.

CTPS1 inhibitors represent a novel approach for inhibiting selected components of the immune system in various tissues, and the related pathologies or pathological conditions such as, in general terms, rejection of transplanted cells and tissues, Graft-related diseases or disorders, allergies and autoimmune diseases. In addition, CTPS1 inhibitors offer therapeutic potential in a range of cancer indications and in enhancing recovery from vascular injury or surgery and reducing morbidity and mortality associated with neointima and restenosis.

International patent applications WO2019/106156, WO2019/106146, VO2019/179652 (PCT/EP2018/086617), WO2019/180244 (PCT/EP2019/057320) and WMO2020/083975 disclose CTPS1 inhibitors. International patent applications PCT/IB2020/000560 and PCT/IB2020/000559 presently unpublished, disclose CTPS1 inhibitors.

SUMMARY OF THE INVENTION

The invention provides a compound of formula (I):

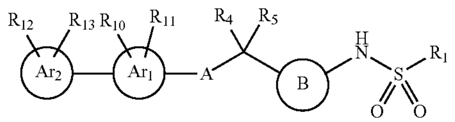

(I)

wherein

A is $A_a$ or $A_b$;

wherein $A_a$ is an amine linker having the following structure: —NH—, —$CH_2$NH— or —NH$CH_2$—; $A_b$ is an amide linker having the following structure: —C(═O)NH— or —NHC(═O)—;

B is

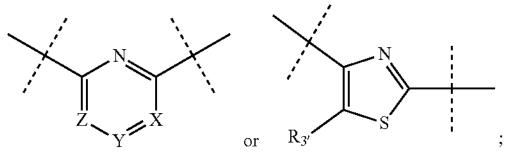

X is N or CH;

Y is N or $CR_2$;

Z is N or $CR_3$;

with the proviso that when at least one of X or Z is N, Y cannot be N;

$R_1$ is $C_{1-5}$fluoroalkyl, with the proviso that $R_1$ is not $CF_3$;

$R_2$ is H, halo, $C_{1-2}$alkyl, $OC_{1-2}$alkyl, $C_{1-2}$haloalkyl or $OC_{1-2}$haloalkyl;

$R_3$ is H, halo, $CH_3$, $OCH_3$, $CF_3$ or $OCF_3$;

wherein at least one of $R_2$ and $R_3$ is H;

$R_{3'}$ is H, halo, $CH_3$, $OC_{1-2}$alkyl or $CF_3$; and when A is —NHC(═O)—, additionally $R_{3'}$ together with $R_5$ forms a 5- or 6-membered cycloalkyl or 5 or 6 membered oxygen-containing heterocycloalkyl;

$R_4$ and $R_5$ are $R_{4a}$ and $R_{5a}$, or $R_{4b}$ and $R_{5b}$;

wherein $R_{4a}$ and $R_{5a}$ together with the carbon atom to which they are attached form a $C_{3-6}$cycloalkyl which is:

substituted by one or two substituents, each substituent being independently selected from the group consisting of $C_{1-3}$alkyl, oxo, OH, $C_{1-3}$ alkylOH, $C_{1-3}$haloalkyl, $C_{0-2}$alkylene$C_{3-6}$cycloalkyl, $C_{0-2}$alkylene$C_{3-6}$heterocycloalkyl, $C_{1-3}$alkyleneO$C_{1-3}$alkyl, halo, O$C_{1-3}$haloalkyl, O$C_{0-2}$alkylene$C_{3-6}$cycloalkyl, O$C_{0-2}$alkylene$C_{3-6}$heterocycloalkyl, O$C_{1-3}$alkyl and $NR_{21}R_{22}$; or one of the carbons of the $C_{3-6}$cycloalkyl is a spiro centre such that a spirocyclic ring system is formed by the $C_{3-6}$cycloalkyl ring and a further $C_{3-6}$cycloalkyl ring or a $C_{3-6}$heterocycloalkyl ring, and wherein the $C_{3-6}$cycloalkyl formed by $R_{4a}$ and $R_{5a}$ together with the carbon atom to which they are attached may be substituted by one or two substituents, each substituent being independently selected from the group consisting of $C_{1-3}$ alkyl or O$C_{1-3}$alkyl; or $R_{4a}$ and $R_{5a}$ together with the carbon atom to which they are attached form a $C_{3-6}$heterocycloalkyl wherein one of the carbons of the $C_{3-6}$heterocycloalkyl is a spiro centre such that a spirocyclic ring system is formed by the $C_{3-6}$heterocycloalkyl ring and a further $C_{3-6}$cycloalkyl ring or a $C_{3-6}$heterocycloalkyl ring, and wherein the $C_{3-6}$heterocycloalkyl formed by $R_{4a}$ and $R_{5a}$ together with the carbon atom to which they are attached may be substituted by one or two substituents, each substituent being independently selected from the group consisting of $C_{1-3}$alkyl or O$C_{1-5}$alkyl; or $R_{4a}$ and $R_{5a}$ together with the carbon atom to which they are attached form a $C_{3-6}$heterocycloalkyl comprising one nitrogen atom, wherein said nitrogen atom is substituted by —$S(O)_2R_{29}$; or $R_{4b}$ and $R_{5b}$ are each independently H, $C_{1-6}$alkyl, $C_{1-6}$alkylOH, $C_{1-6}$haloalkyl, $C_{0-2}$alkylene$C_{3-6}$cycloalkyl, $C_{0-2}$alkylene$C_{3-6}$heterocycloalkyl, $C_{1-3}$alkyleneO$C_{1-3}$alkyl, or $R_{4b}$ and $R_{5b}$ together with the carbon atom to which they are attached form a $C_{3-6}$cycloalkyl or $C_{3-6}$heterocycloalkyl; and when A is —NHC(=O)— or —$NHCH_2$—:

$R_{4b}$ and $R_{5b}$ may additionally be selected from halo, O$C_{1-6}$haloalkyl, O$C_{0-2}$alkylene$C_{3-6}$cycloalkyl, O$C_{0-2}$alkylene$C_{3-6}$heterocycloalkyl, O$C_{1-6}$alkyl and $NR_{21}R_{22}$;

Ar1 is a 6-membered aryl or heteroaryl;

Ar2 is a 6-membered aryl or heteroaryl and is attached to Ar1 in the para position relative to group A;

$R_{10}$ is H, halo, $C_{1-3}$alkyl, $C_{1-2}$haloalkyl, O$C_{1-2}$alkyl, O$C_{1-2}$haloalkyl or CN;

$R_{11}$ is H, F, Cl, $C_{1-2}$alkyl, $CF_3$, $OCH_3$ or CN;

$R_{12}$ is attached to Ar2 in the ortho or mete position relative to Ar1 and $R_{12}$ is H, halo, $C_{1-4}$ alkyl, $C_{2-4}$alkenyl, $C_{0-2}$alkylene$C_{3-5}$cycloalkyl, O$C_{1-4}$alkyl, O$C_{0-2}$alkylene$C_{3-5}$cycloalkyl, $C_{1-4}$ haloalkyl, O$C_{1-4}$haloalkyl, hydroxy, $C_{1-4}$alkylOH, $SO_2C_{1-2}$alkyl, C(O)N($C_{1-2}$alkyl)$_2$, NHC(O)$C_{1-3}$alkyl or $NR_{23}R_{24}$; and when A is —NHC(=O)—, —NH— or —$NHCH_2$—:

$R_{12}$ may additionally be selected from CN, $OCH_2CH_2N(CH_3)_2$ and a $C_{3-6}$heterocycloalkyl comprising one nitrogen located at the point of attachment to Ar2, or $R_{12}$ together with a nitrogen atom to which it is attached forms an N-oxide ($N^+$—$O^-$);

$R_{13}$ is H or halo;

$R_{21}$ is H, $C_{1-5}$alkyl, C(O)$C_{1-5}$alkyl, C(O)O$C_{1-5}$alkyl;

$R_{22}$ is H or $CH_3$;

$R_{23}$ is H or $C_{1-2}$alkyl; and $R_{24}$ is H or $C_{1-2}$alkyl $R_{29}$ is $C_{1-3}$alkyl, $C_{0-2}$alkylene$C_{3-5}$cycloalkyl which cycloalkyl is optionally substituted by $CH_3$, or $CF_3$;

$R_{32}$ is $C_{1-3}$alkyl and $R_{33}$ is $C_{1-3}$alkyl; or $R_{32}$ and $R_{33}$ together with the nitrogen atom to which they are attached form a $C_{3-6}$heterocycloalkyl.

The invention also provides a compound of formula (I):

(I)

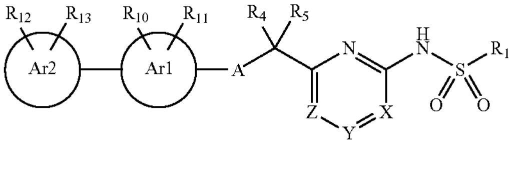

wherein

A is $A_a$ or $A_b$;

wherein $A_a$ is an amine linker having the following structure: —NH—, —$CH_2NH$— or —$NHCH_2$—;

$A_b$ is an amide linker having the following structure: —C(=O)NH— or —NHC(=O)—;

X is N or CH;

Y is N or $CR_2$;

Z is N or $CR_3$;

with the proviso that when at least one of X or Z is N, Y cannot be N;

$R_1$ is $C_{1-5}$fluoroalkyl, with the proviso that $R_1$ is not $CF_3$;

$R_2$ is H, halo, $C_{1-2}$alkyl, O$C_{1-2}$alkyl, $C_{1-2}$haloalkyl or O$C_{1-2}$haloalkyl;

$R_3$ is H, halo, $CH_3$, $OCH_3$, $CF_3$ or $OCF_3$;

wherein at least one of $R_2$ and $R_3$ is H;

$R_4$ and $R_5$ are $R_{4a}$ and $R_{5a}$, or $R_{4b}$ and $R_{5b}$;

wherein $R_{4a}$ and $R_{5a}$ together with the carbon atom to which they are attached form a $C_{3-6}$cycloalkyl which is:

substituted by one or two substituents, each substituent being independently selected from the group consisting of $C_{1-3}$alkyl, oxo, OH, $C_{1-3}$ alkylOH, $C_{1-3}$haloalkyl, $C_{0-2}$alkylene$C_{3-6}$cycloalkyl, $C_{0-2}$alkylene$C_{3-6}$heterocycloalkyl, $C_{1-3}$alkyleneO$C_{1-3}$alkyl, halo, O$C_{1-3}$haloalkyl, O$C_{0-2}$alkylene$C_{3-6}$cycloalkyl, O$C_{0-2}$alkylene$C_{3-6}$heterocycloalkyl, O$C_{1-3}$alkyl and $NR_{21}R_{22}$; or one of the carbons of the $C_{3-6}$cycloalkyl is a spiro centre such that a spirocyclic ring system is formed by the $C_{3-6}$cycloalkyl ring and a further $C_{3-6}$cycloalkyl ring or a $C_{3-6}$heterocycloalkyl ring, and wherein the $C_{3-6}$cycloalkyl formed by $R_{4a}$ and $R_{5a}$ together with the carbon atom to which they are attached may be substituted by one or two substituents, each substituent being independently selected from the group consisting of $C_{1-3}$ alkyl or O$C_{1-3}$alkyl; or $R_{4a}$ and $R_{5a}$ together with the carbon atom to which they are attached form a $C_{3-6}$heterocycloalkyl wherein one of the carbons of the $C_{3-6}$heterocycloalkyl is a spiro centre such that a spirocyclic ring system is formed by the $C_{3-6}$heterocycloalkyl ring and a further $C_{3-6}$cycloalkyl ring or a $C_{3-6}$heterocycloalkyl ring, and wherein the $C_{3-6}$heterocycloalkyl formed by $R_{4a}$ and $R_{5a}$ together with the carbon atom to which they are attached may be substituted by one or two substituents, each substituent being independently selected from the group consisting of $C_{1-3}$alkyl or $OC_{1-3}$alkyl; or $R_{4a}$ and $R_{5a}$ together with the carbon atom to which they are attached form a $C_{3-6}$heterocycloalkyl comprising one nitrogen atom, wherein said nitrogen atom is substituted by —$S(O)_2R_{29}$; or $R_{4b}$ and $R_{5b}$ are each independently H, $C_{1-6}$alkyl, $C_{1-6}$alkylOH, $C_{1-6}$haloalkyl, $C_{0-2}$alkylene$C_{3-6}$cycloalkyl, $C_{0-2}$alkylene$C_{3-6}$heterocycloalkyl, $C_{1-3}$alkylene$OC_{1-3}$alkyl, or $R_{4b}$ and $R_{5b}$ together with the carbon atom to which they are attached form a $C_{3-6}$cycloalkyl or $C_{3-6}$heterocycloalkyl; and when A is —NHC(=O)— or —$NHCH_2$—:

$R_{4b}$ and $R_{5b}$ may additionally be selected from halo, $OC_{1-6}$haloalkyl, $OC_{0-2}$alkylene$C_{3-6}$cycloalkyl, $OC_{0-2}$alkylene$C_{3-6}$heterocycloalkyl, $OC_{1-6}$alkyl and $NR_{21}R_{22}$;

Ar1 is a 6-membered aryl or heteroaryl;

Ar2 is a 6-membered aryl or heteroaryl and is attached to Ar1 in the para position relative to group A;

$R_{10}$ is H, halo, $C_{1-3}$alkyl, $C_{1-2}$haloalkyl, $OC_{1-2}$alkyl, $OC_{1-2}$haloalkyl or CN;

$R_{11}$ is H, F, Cl, $C_{1-2}$alkyl, $CF_3$, $OCH_3$ or CN;

$R_{12}$ is attached to Ar2 in the ortho or meta position relative to Ar1 and $R_{12}$ is H, halo, $C_{1-4}$alkyl, $C_{2-4}$alkenyl, $C_{0-2}$alkylene$C_{3-5}$cycloalkyl, $OC_{1-4}$alkyl, $OC_{0-2}$alkylene$C_{3-5}$cycloalkyl, $C_{1-4}$haloalkyl, $OC_{1-4}$haloalkyl, hydroxy, $C_{1-4}$alkylOH, $SO_2C_{1-2}$alkyl, $C(O)N(C_{1-2}alkyl)_2$, $NHC(O)C_{1-3}$alkyl or $NR_{23}R_{24}$; and when A is —NHC(=O)—, —NH— or —$NHCH_2$—:

$R_{12}$ may additionally be selected from CN, $OCH_2CH_2N(CH_3)_2$ and a $C_{3-6}$heterocycloalkyl comprising one nitrogen located at the point of attachment to Ar2, or $R_{12}$ together with a nitrogen atom to which it is attached forms an N-oxide ($N^+$—$O^-$);

$R_{13}$ is H or halo;

$R_{21}$ is H, $C_{1-5}$alkyl, $C(O)C_{1-5}$alkyl, $C(O)OC_{1-5}$alkyl;

$R_{22}$ is H or $CH_3$;

$R_{23}$ is H or $C_{1-2}$alkyl; and $R_{24}$ is H or $C_{1-2}$alkyl $R_{29}$ is $C_{1-3}$alkyl, $C_{0-2}$alkylene$C_{3-5}$cycloalkyl which cycloalkyl is optionally substituted by $CH_3$, or $CF_3$;

$R_{32}$ is $C_{1-3}$alkyl and $R_{33}$ is $C_{1-3}$alkyl; or $R_{32}$ and $R_{33}$ together with the nitrogen atom to which they are attached form a $C_{3-6}$heterocycloalkyl.

A compound of formula (I) may be provided in the form of a salt and/or solvate thereof and/or derivative thereof. Suitably, the compound of formula (I) may be provided in the form of a pharmaceutically acceptable salt and/or solvate thereof and/or derivative thereof. In particular, the compound of formula (I) may be provided in the form of a pharmaceutically acceptable salt and/or solvate, such as a pharmaceutically acceptable salt.

Also provided is a compound of formula (I), or a pharmaceutically acceptable salt and/or solvate thereof and/or derivative thereof, for use as a medicament, in particular for use in the inhibition of CTPS1 in a subject or the prophylaxis or treatment of associated diseases or disorders, such as those in which a reduction in T-cell and/or B-cell proliferation would be beneficial.

Further, there is provided a method for the inhibition of CTPS1 in a subject or the prophylaxis or treatment of associated diseases or disorders, such as those in which a reduction in T-cell and/or B-cell proliferation would be beneficial, by administering to a subject in need thereof a compound of formula (I) or a pharmaceutically acceptable salt and/or solvate thereof and/or derivative thereof.

Additionally provided is the use of a compound of formula (I), or a pharmaceutically acceptable salt and/or solvate thereof and/or derivative thereof, in the manufacture of a medicament for the inhibition of CTPS1 in a subject or the prophylaxis or treatment of associated diseases or disorders, such as those in which a reduction in T-cell and/or B-cell proliferation would be beneficial.

Suitably the disease or disorder is selected from: inflammatory skin diseases such as psoriasis or lichen planus; acute and/or chronic GVHD such as steroid resistant acute GVHD; acute lymphoproliferative syndrome (ALPS); systemic lupus erythematosus, lupus nephritis or cutaneous lupus; and transplantation. In addition, the disease or disorder may be selected from myasthenia gravis, multiple sclerosis, and scleroderma/systemic sclerosis.

Also provided is a compound of formula (I), or a pharmaceutically acceptable salt and/or solvate thereof and/or derivative thereof, for use in the treatment of cancer.

Further, there is provided a method for treating cancer in a subject, by administering to a subject in need thereof a compound of formula (I) or a pharmaceutically acceptable salt and/or solvate thereof and/or derivative thereof.

Additionally provided is the use of a compound of formula (I), or a pharmaceutically acceptable salt and/or solvate thereof and/or derivative thereof, in the manufacture of a medicament for the treatment of cancer in a subject.

Also provided is a compound of formula (I), or a pharmaceutically acceptable salt and/or solvate thereof and/or derivative thereof, for use in enhancing recovery from vascular injury or surgery and reducing morbidity and mortality associated with neointima and restenosis in a subject.

Further, there is provided a method for enhancing recovery from vascular injury or surgery and reducing morbidity and mortality associated with neointima and restenosis in a subject, by administering to a subject in need thereof a compound of formula (I) or a pharmaceutically acceptable salt and/or solvate thereof and/or derivative thereof.

Additionally provided is the use of a compound of formula (I), or a pharmaceutically acceptable salt and/or solvate thereof and/or derivative thereof, in the manufacture of a medicament for enhancing recovery from vascular injury or surgery and reducing morbidity and mortality associated with neointima and restenosis in a subject.

Also provided are pharmaceutical compositions containing a compound of formula (I), or a pharmaceutically acceptable salt and/or solvate thereof and/or derivative thereof, and a pharmaceutically acceptable carrier or excipient.

Also provided are processes for preparing compounds of formula (I) and novel intermediates of use in the preparation of compounds of formula (I).

DETAILED DESCRIPTION OF THE INVENTION

The invention provides a compound of formula (I):

(I)

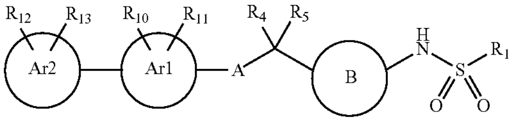

wherein

A is $A_a$ or $A_b$;

wherein $A_a$ is an amine linker having the following structure: —NH—, —$CH_2NH$— or —$NHCH_2$—;

$A_b$ is an amide linker having the following structure: —C(═O)NH— or —NHC(═O)—;

B is

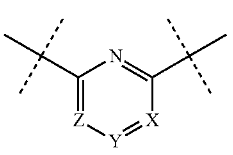

or

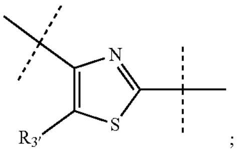

;

X is N or CH;

Y is N or $CR_2$;

Z is N or $CR_3$;

with the proviso that when at least one of X or Z is N, Y cannot be N;

$R_1$ is $C_{1-5}$fluoroalkyl, with the proviso that $R_1$ is not $CF_3$;

$R_2$ is H, halo, $C_{1-2}$alkyl, $OC_{1-2}$alkyl, $C_{1-2}$haloalkyl or $OC_{1-2}$haloalkyl;

$R_3$ is H, halo, $CH_3$, $OCH_3$, $CF_3$ or $OCF_3$;

wherein at least one of $R_2$ and $R_3$ is H;

$R_{3'}$ is H, halo, $CH_3$, $OC_{1-2}$alkyl or $CF_3$; and when A is —NHC(═O)—, additionally $R_{3'}$ together with $R_5$ forms a 5- or 6-membered cycloalkyl or 5 or 6 membered oxygen-containing heterocycloalkyl;

$R_4$ and $R_5$ are $R_{4a}$ and $R_{5a}$, or $R_{4b}$ and $R_{5b}$;

wherein $R_{4a}$ and $R_{5a}$ together with the carbon atom to which they are attached form a $C_{3-6}$cycloalkyl which is:

substituted by one or two substituents, each substituent being independently selected from the group consisting of $C_{1-3}$alkyl, oxo, OH, $C_{1-3}$ alkylOH, $C_{1-3}$haloalkyl, $C_{0-2}$alkylene$C_{3-6}$cycloalkyl, $C_{0-2}$alkylene$C_{3-6}$heterocycloalkyl, $C_{1-3}$alkylene$OC_{1-3}$alkyl, halo, $OC_{1-3}$haloalkyl, $OC_{0-2}$alkylene$C_{3-6}$cycloalkyl, $OC_{0-2}$alkylene$C_{3-6}$heterocycloalkyl, $OC_{1-3}$alkyl and $NR_{21}R_{22}$; or one of the carbons of the $C_{3-6}$cycloalkyl is a spiro centre such that a spirocyclic ring system is formed by the $C_{3-6}$cycloalkyl ring and a further $C_{3-6}$cycloalkyl ring or a $C_{3-6}$heterocycloalkyl ring, and wherein the $C_{3-6}$cycloalkyl formed by $R_{4a}$ and $R_{5a}$ together with the carbon atom to which they are attached may be substituted by one or two substituents, each substituent being independently selected from the group consisting of $C_{1-3}$ alkyl or $OC_{1-3}$alkyl; or $R_{4a}$ and $R_{5a}$ together with the carbon atom to which they are attached form a $C_{3-6}$heterocycloalkyl wherein one of the carbons of the $C_{3-6}$heterocycloalkyl is a spiro centre such that a spirocyclic ring system is formed by the $C_{3-6}$heterocycloalkyl ring and a further $C_{3-6}$cycloalkyl ring or a $C_{3-6}$heterocycloalkyl ring, and wherein the $C_{3-6}$heterocycloalkyl formed by $R_{4a}$ and $R_{5a}$ together with the carbon atom to which they are attached may be substituted by one or two substituents, each substituent being independently selected from the group consisting of $C_{1-3}$alkyl or $OC_{1-3}$alkyl; or $R_{4a}$ and $R_{5a}$ together with the carbon atom to which they are attached form a $C_{3-6}$heterocycloalkyl comprising one nitrogen atom, wherein said nitrogen atom is substituted by —$S(O)_2R_{29}$; or $R_{4b}$ and $R_{5b}$ are each independently H, $C_{1-6}$alkyl, $C_{1-6}$alkylOH, $C_{1-3}$haloalkyl, $C_{0-2}$alkylene$C_{3-6}$cycloalkyl, $C_{0-2}$alkylene$C_{3-6}$heterocycloalkyl, $C_{1-3}$alkylene$OC_{1-3}$alkyl, or $R_{4b}$ and $R_{5b}$ together with the carbon atom to which they are attached form a $C_{3-6}$cycloalkyl or $C_{3-6}$heterocycloalkyl; and when A is —NHC(═O)— or —$NHCH_2$—:

$R_{4b}$ and $R_{5b}$ may additionally be selected from halo, $OC_{1-6}$haloalkyl, $OC_{0-2}$alkylene$C_{3-6}$cycloalkyl, $OC_{0-2}$alkylene$C_{3-6}$heterocycloalkyl, $OC_{1-6}$alkyl and $NR_{21}R_{22}$;

Ar1 is a 6-membered aryl or heteroaryl;

Ar2 is a 6-membered aryl or heteroaryl and is attached to Ar1 in the para position relative to group A;

$R_{10}$ is H, halo, $C_{1-3}$alkyl, $C_{1-2}$haloalkyl, $OC_{1-2}$alkyl, $OC_{1-2}$haloalkyl or CN;

$R_{11}$ is H, F, Cl, $C_{1-2}$alkyl, $CF_3$, $OCH_3$ or CN;

$R_{12}$ is attached to Ar2 in the ortho or meta position relative to Ar1 and $R_{12}$ is H, halo, $C_{1-4}$alkyl, $C_{2-4}$alkenyl, $C_{0-2}$alkylene$C_{3-5}$cycloalkyl, $OC_{1-4}$alkyl, $OC_{0-2}$alkylene$C_{3-5}$cycloalkyl, $C_{1-4}$haloalkyl, $OC_{1-4}$haloalkyl, hydroxy, $C_{1-4}$alkylOH, $SO_2C_{1-2}$alkyl, $C(O)N(C_{1-2}alkyl)_2$, $NHC(O)C_{1-3}$alkyl or $NR_{23}R_{24}$; and when A is —NHC(═O)—, —NH— or —$NHCH_2$—:

$R_{12}$ may additionally be selected from CN, $OCH_2CH_2N(CH_3)_2$ and a $C_{3-6}$heterocycloalkyl comprising one nitrogen located at the point of attachment to Ar2, or $R_{12}$ together with a nitrogen atom to which it is attached forms an N-oxide ($N^+$—$O^-$);

$R_{13}$ is H or halo;

$R_{21}$ is H, $C_{1-5}$alkyl, $C(O)C_{1-5}$alkyl, $C(O)OC_{1-5}$alkyl;

$R_{22}$ is H or $CH_3$;

$R_{23}$ is H or $C_{1-2}$alkyl; and $R_{24}$ is H or $C_{1-2}$alkyl;

$R_{29}$ is $C_{1-3}$alkyl, $C_{0-2}$alkylene$C_{3-5}$cycloalkyl which cycloalkyl is optionally substituted by $CH_3$, or $CF_3$;

$R_{32}$ is $C_{1-3}$alkyl and $R_{33}$ is $C_{1-3}$alkyl; or $R_{32}$ and $R_{33}$ together with the nitrogen atom to which they are attached form a $C_{3-5}$heterocycloalkyl;

or a salt and/or solvate thereof and/or derivative thereof.

The invention also provides a compound of formula (I):

(I)

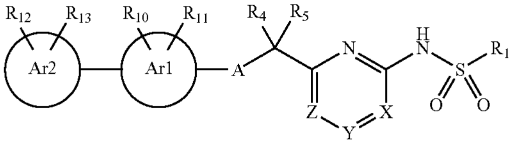

wherein

A is $A_a$ or $A_b$;

wherein $A_a$ is an amine linker having the following structure: —NH—, —$CH_2NH$— or —$NHCH_2$—;

$A_b$ is an amide linker having the following structure: —C(═O)NH— or —NHC(═O)—;

X is N or CH;

Y is N or $CR_2$;

Z is N or $CR_3$.

with the proviso that when at least one of X or Z is N, Y cannot be N;

$R_1$ is $C_{1-5}$fluoroalkyl, with the proviso that $R_1$ is not $CF_3$;

$R_2$ is H, halo, $C_{1-2}$alkyl, $OC_{1-2}$alkyl, $C_{1-2}$haloalkyl or $OC_{1-2}$haloalkyl;

$R_3$ is H, halo, $CH_3$, $OCH_3$, $CF_3$ or $OCF_3$;

wherein at least one of $R_2$ and $R_3$ is H;

$R_4$ and $R_5$ are $R_{4a}$ and $R_{5a}$, or $R_{4b}$ and $R_{5b}$;

wherein $R_{4a}$ and $R_{5a}$ together with the carbon atom to which they are attached form a $C_{3-6}$cycloalkyl which is:

substituted by one or two substituents, each substituent being independently selected from the group consisting of $C_{1-3}$alkyl, oxo, OH, $C_{1-3}$ alkylOH, $C_{1-3}$haloalkyl, $C_{0-2}$alkylene$C_{3-6}$cycloalkyl, $C_{0-2}$alkylene$C_{3-6}$heterocycloalkyl, $C_{1-3}$alkylene$OC_{1-3}$alkyl, halo, $OC_{1-3}$haloalkyl, $OC_{0-2}$alkylene$C_{3-6}$cycloalkyl, $OC_{0-2}$alkylene$C_{3-6}$heterocycloalkyl, $OC_{1-3}$alkyl and $NR_{21}R_{22}$; or one of the carbons of the $C_{3-6}$cycloalkyl is a spiro centre such that a spirocyclic ring system is formed by the $C_{3-6}$cycloalkyl ring and a further $C_{3-6}$cycloalkyl ring or a $C_{3-6}$heterocycloalkyl ring, and wherein the $C_{3-6}$cycloalkyl formed by $R_{4a}$ and $R_{5a}$ together with the carbon atom to which they are attached may be substituted by one or two substituents, each substituent being independently selected from the group consisting of $C_{1-3}$ alkyl or $OC_{1-3}$alkyl; or $R_{4a}$ and $R_{5a}$ together with the carbon atom to which they are attached form a $C_{3-6}$heterocycloalkyl wherein one of the carbons of the $C_{3-6}$heterocycloalkyl is a spiro centre such that a spirocyclic ring system is formed by the $C_{3-6}$heterocycloalkyl ring and a further $C_{3-6}$cycloalkyl ring or a $C_{3-6}$heterocycloalkyl ring, and wherein the $C_{3-6}$heterocycloalkyl formed by $R_{4a}$ and $R_{5a}$ together with the carbon atom to which they are attached may be substituted by one or two substituents, each substituent being independently selected from the group consisting of $C_{1-3}$alkyl or $OC_{1-3}$alkyl; or $R_{4a}$ and $R_{5a}$ together with the carbon atom to which they are attached form a $C_{3-6}$heterocycloalkyl comprising one nitrogen atom, wherein said nitrogen atom is substituted by —$S(O)_2R_{29}$; or $R_{4b}$ and $R_{5b}$ are each independently H, $C_{1-6}$alkyl, $C_{1-6}$alkylOH, $C_{1-6}$haloalkyl, $C_{0-2}$alkylene$C_{3-6}$cycloalkyl, $C_{0-2}$alkylene$C_{3-6}$heterocycloalkyl, $C_{1-3}$alkylene$OC_{1-3}$alkyl, or $R_{4b}$ and $R_{5b}$ together with the carbon atom to which they are attached form a $C_{3-6}$cycloalkyl or $C_{3-6}$heterocycloalkyl; and when A is —NHC(═O)— or —$NHCH_2$—:

$R_{4b}$ and $R_{5b}$ may additionally be selected from halo, $OC_{1-6}$haloalkyl, $OC_{0-2}$alkylene$C_{3-6}$cycloalkyl, $OC_{0-2}$alkylene$C_{3-6}$heterocycloalkyl, $OC_{1-6}$alkyl and $NR_{21}R_{22}$;

Ar1 is a 6-membered aryl or heteroaryl;

Ar2 is a 6-membered aryl or heteroaryl and is attached to Ar1 in the para position relative to group A;

$R_{10}$ is H, halo, $C_{1-3}$alkyl, $C_{1-2}$haloalkyl, $OC_{1-2}$alkyl, $OC_{1-2}$haloalkyl or CN;

$R_{11}$ is H, F, Cl, $C_{1-2}$alkyl, $CF_3$, $OCH_3$ or CN;

$R_{12}$ is attached to Ar2 in the ortho or mete position relative to Ar1 and $R_{12}$ is H, halo, $C_{1-4}$ alkyl, $C_{2-4}$alkenyl, $C_{0-2}$alkylene$C_{3-5}$cycloalkyl, $OC_{1-4}$alkyl, $OC_{0-2}$alkylene$C_{3-5}$cycloalkyl, $C_{1-4}$ haloalkyl, $OC_{1-4}$haloalkyl, hydroxy, $C_{1-4}$alkylOH, $SO_2C_{1-2}$alkyl, $C(O)N(C_{1-2}alkyl)_2$, $NHC(O)C_{1-3}$alkyl or $NR_{23}R_{24}$; and when A is —NHC(═O)—, —NH— or —$NHCH_2$—:

$R_{12}$ may additionally be selected from CN, $OCH_2CH_2N(CH_3)_2$ and a $C_{3-6}$heterocycloalkyl comprising one nitrogen located at the point of attachment to Ar2, or $R_{12}$ together with a nitrogen atom to which it is attached forms an N-oxide ($N^+$—$O^-$);

$R_{13}$ is H or halo;

$R_{21}$ is H, $C_{1-5}$alkyl, $C(O)C_{1-5}$alkyl, $C(O)OC_{1-5}$alkyl;

$R_{22}$ is H or $CH_3$;

$R_{23}$ is H or $C_{1-2}$alkyl; and $R_{24}$ is H or $C_{1-2}$alkyl;

$R_{29}$ is $C_{1-3}$alkyl, $C_{0-2}$alkylene$C_{3-5}$cycloalkyl which cycloalkyl is optionally substituted by $CH_3$, or $CF_3$;

$R_{32}$ is $C_{1-3}$alkyl and $R_{33}$ is $C_{1-3}$alkyl; or $R_{32}$ and $R_{33}$ together with the nitrogen atom to which they are attached form a $C_{3-5}$ heterocycloalkyl;

or a salt and/or solvate thereof and/or derivative thereof.

The term 'alkyl' as used herein, such as in $C_{1-3}$alkyl, $C_{1-4}$alkyl, $C_{1-5}$alkyl or $C_{1-6}$alkyl, whether alone or forming part of a larger group such as an Oalkyl group (e.g. $OC_{1-3}$alkyl, $OC_{1-4}$alkyl and $OC_{1-5}$alkyl), is a straight or a branched fully saturated hydrocarbon chain containing the specified number of carbon atoms. Examples of alkyl groups include the $C_{1-5}$alkyl groups methyl, ethyl, n-propyl, iso-propyl, n-butyl, iso-butyl, sec-butyl, tert-butyl and n-pentyl, sec-pentyl and 3-pentyl, in particular the $C_{1-5}$alkyl groups methyl, ethyl, n-propyl and iso-propyl. Reference to "propyl" includes n-propyl and iso-propyl, and reference to "butyl" includes n-butyl, isobutyl, sec-butyl and tert-butyl. Examples of Oalkyl groups include the $OC_{1-4}$alkyl groups methoxy, ethoxy, propoxy (which includes n-propoxy and iso-propoxy) and butoxy (which includes n-butoxy, iso-butoxy, sec-butoxy and tert-butoxy). $C_6$alkyl groups as used herein, whether alone or forming part of a larger group such as an $OC_6$alkyl group is a straight or a branched fully saturated hydrocarbon chain containing six carbon atoms. Examples of $C_6$alkyl groups include n-hexyl, 2-methylpentyl, 3-methylpentyl, 2,2-dimethylbutyl and 2,3-dimethylbutyl.

The term 'alkylene' as used herein, such as in $C_{0-2}$alkylene$C_{3-5}$cycloalkyl, $C_{1-2}$alkylene$OC_{1-2}$alkyl or $OC_{0-2}$alkylene$C_{3-5}$cycloalkyl is a bifunctional straight or a branched fully saturated hydrocarbon chain containing the specified number of carbon atoms. Examples of $C_{0-2}$alkylene groups are where the group is absent (i.e. $C_0$), methylene ($C_1$) and ethylene ($C_2$).

The term 'alkenyl' as used herein, such as in $C_{2-4}$alkenyl, is a straight or branched hydrocarbon chain containing the specified number of carbon atoms and a carbon-carbon double bond.

The term 'cycloalkyl' as used herein, such as in $C_{3-5}$cycloalkyl or $C_{3-6}$cycloalkyl, whether alone or forming part of a larger group such as $OC_{3-5}$cycloalkyl or $C_{0-2}$alkylene $C_{3-5}$cycloalkyl is a fully saturated hydrocarbon ring containing the specified number of carbon atoms. Examples of cycloalkyl groups include the $C_{3-6}$cycloalkyl groups cyclopropyl, cyclobutyl, cyclopentyl and cyclohexyl, in particular the $C_{3-5}$cycloalkyl groups cyclopropyl, cyclobutyl and cyclopentyl:

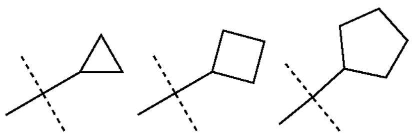

-continued

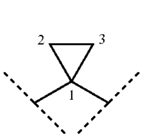
$C_3$cycloalkyl

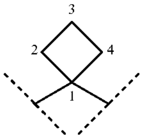
$C_4$cycloalkyl

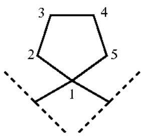
$C_5$cycloalkyl

The term ‘heterocycloalkyl’ as used herein, such as in $C_{3-6}$heterocycloalkyl or $C_{0-2}$alkylene$C_{3-6}$heterocycloalkyl is a fully saturated hydrocarbon ring containing the specified number of carbon atoms, wherein at least one of the carbon atoms in the ring is replaced by a heteroatom such as N, S or O. As required by valency, the nitrogen atom(s) may be connected to a hydrogen atom to form an NH group. Alternatively the nitrogen atom(s) may be substituted (such as one nitrogen atom is substituted), for example by $C_{1-4}$alkyl, C(O)H, C(O)$C_{1-4}$alkyl, C(O)O$C_{1-4}$alkyl, C(O)O$C_{1-4}$ alkylaryl such as C(O)OBz, C(O)NH$C_{1-4}$alkyl, C(O)NH$C_{1-4}$alkylaryl such as C(O)NHBz, an Fmoc group, C(O)$C_{1-4}$haloalkyl, C(O)O$C_{1-4}$haloalkyl or C(O)NH$C_{1-4}$haloalkyl, such as C(O)OtBu. Wherein a ring heteroatom is S, the term ‘heterocycloalkyl’ includes wherein the S atom(s) is substituted (such as one S atom is substituted) by one or two oxygen atoms (i.e. S(O) or $S(O)_2$). Alternatively, any sulphur atom(s) in the $C_{3-6}$heterocycloalkyl ring is not substituted.

Examples of $C_{3-6}$heterocycloalkyl groups include those comprising one heteroatom such as containing one heteroatom (e.g. oxygen) or containing two heteroatoms (e.g. two oxygen atoms or one oxygen atom and one nitrogen atom). Particular examples of $C_{3-6}$heterocycloalkyl comprising one oxygen atom include oxiranyl, oxetanyl, 3-dioxolanyl, morpholinyl, 1,4-oxathianyl, tetrahydropyranyl, 1,4-thioxanyl and 1,3,5-trioxanyl. Examples of $C_{3-6}$heterocycloalkyl include those comprising one oxygen atom such as containing one oxygen atom, or containing two oxygen atoms. Particular examples of $C_{3-6}$heterocycloalkyl comprising one oxygen atom include oxiranyl, oxetanyl, 3-dioxolanyl, morpholinyl, 1,4-oxathianyl, tetrahydropyranyl, 1,4-thioxanyl and 1,3,5-trioxanyl. Particular examples of $C_{3-6}$heterocycloalkyl comprising one nitrogen atom include piperidinyl.

In one embodiment, the term ‘heterocycloalkyl’ as used herein, such as in $C^{3-6}$heterocycloalkyl is a fully saturated hydrocarbon ring containing the specified number of carbon atoms, wherein at least one of the carbon atoms in the ring is replaced by a heteroatom such as N, S or O. Examples of $C_{3-6}$heterocycloalkyl groups include those comprising one heteroatom such as containing one heteroatom (e.g. oxygen) or containing two heteroatoms (e.g. two oxygen atoms or one oxygen atom and one nitrogen atom).

The heterocycloalkyl groups may have the following structures:

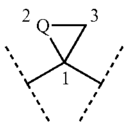
$C_3$heterocycloalkyl

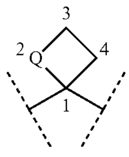
$C_4$heterocycloalkyl

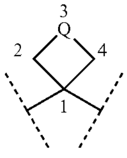
$C_4$heterocycloalkyl

-continued

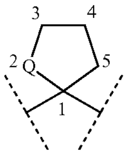
$C_5$heterocycloalkyl

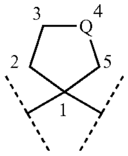
$C_5$heterocycloalkyl

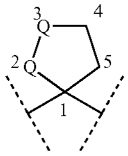
$C_5$heterocycloalkyl

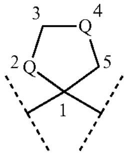
$C_5$heterocycloalkyl

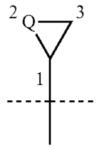
$C_3$heterocycloalkyl

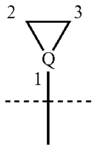
$C_4$heterocycloalkyl

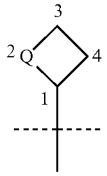
$C_4$heterocycloalkyl

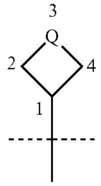
$C_4$heterocycloalkyl

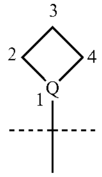
$C_4$heterocycloalkyl

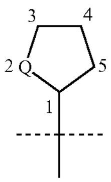
$C_5$heterocycloalkyl

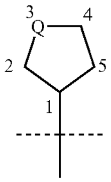
$C_5$heterocycloalkyl

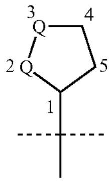
$C_5$heterocycloalkyl

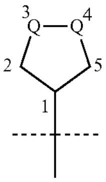
$C_5$heterocycloalkyl

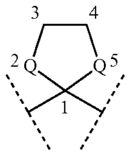
$C_5$heterocycloalkyl

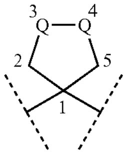
$C_6$heterocycloalkyl

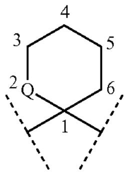
$C_6$heterocycloalkyl

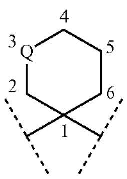
$C_6$heterocycloalkyl

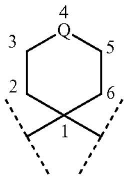
$C_6$heterocycloalkyl

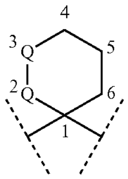
$C_6$heterocycloalkyl

-continued

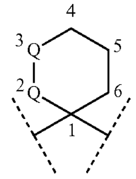

$C_6$ heterocycloalkyl

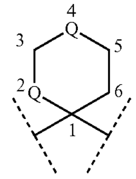

$C_6$ heterocycloalkyl

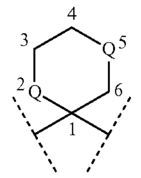

$C_6$ heterocycloalkyl

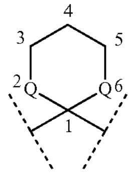

$C_6$ heterocycloalkyl

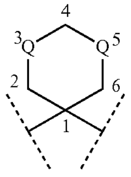

$C_6$ heterocycloalkyl wherein each Q is independently selected from O, N or S, such as O or N. When Q is N, as required by valency, the nitrogen atom(s) may be connected to a hydrogen atom to form an NH group. Alternatively the nitrogen atom(s) may be substituted (such as one nitrogen atom is substituted), for example by $C_{1-4}$alkyl, C(O)H, C(O)$C_{1-4}$alkyl, C(O)O$C_{1-4}$alkyl, C(O)O$C_{1-4}$alkylaryl such as C(O)OBz, C(O)NH$C_{1-4}$alkyl, C(O)NH$C_{1-4}$alkylaryl such as C(O)NHBz, an Fmoc group, C(O)$C_{1-4}$haloalkyl, C(O)O$C_{1-4}$haloalkyl or C(O)NH$C_{1-4}$haloalkyl, such as C(O)OtBu. When any Q is S, the S atoms can be substituted (such as one S atom is substituted) by one or two oxygen atoms (i.e. S(O) or $S(O)_2$). When $R_4$ and $R_5$ are $R_{4a}$ and $R_{5a}$, Q is N substituted by $S(O)_2R_{29}$. Alternatively, any sulphur atom(s) in the $C_{3-6}$heterocycloalkyl ring is not substituted.

When A is —C(=O)NH—, —NH— or —$CH_2$NH— and $R_4$ and/or $R_5$ is $C_0$alkylene$C_{3-6}$heterocycloalkyl, or when $R_4$ and $R_5$ together with the carbon atom to which they are attached form a $C_{3-6}$heterocycloalkyl, any heteroatom in the heterocycloalkyl may not be directly connected to the carbon to which $R_4$ and $R_5$ are connected.

Suitably, heterocycloalkyl is a fully saturated hydrocarbon ring containing the specified number of carbon atoms wherein at least one of the carbon atoms is replaced by a heteroatom such as N, S or O wherein as required by valency, any nitrogen atom is connected to a hydrogen atom, and wherein the S atom is not present as an oxide.

The term 'halo' or 'halogen' as used herein, refers to fluorine, chlorine, bromine or iodine. Particular examples of halo are fluorine and chlorine, especially fluorine.

The term 'haloalkyl' as used herein, such as in $C_{1-5}$haloalkyl, such as in $C_{1-4}$haloalkyl, whether alone or forming part of a larger group such as an Ohaloalkyl group, such as in O$C_{1-6}$haloalkyl, such as in O$C_{1-4}$haloalkyl, is a straight or a branched fully saturated hydrocarbon chain containing the specified number of carbon atoms and at least one halogen atom, such as fluoro or chloro, especially fluoro. An example of haloalkyl is $CF_3$. Further examples of haloalkyl are $CHF_2$ and $CH_2CF_3$. Examples of Ohaloalkyl include $OCF_3$, $OCHF_2$ and $OCH_2CF_3$.

The term 'fluoroalkyl' as used herein, such as in $C_{1-5}$fluoroalkyl, such as in $C_{1-4}$fluoroalkyl, whether alone or forming part of a larger group such as an Ofluoroalkyl group, is a straight or a branched fully saturated hydrocarbon chain containing the specified number of carbon atoms and at least one fluoro atom. Examples of fluoroalkyl are $CF_3$, $CHF_2$, $CH_2CFS$ and $CH_2CHF_2$.

The term '6-membered aryl' as used herein refers to a phenyl ring.

The term '6-membered heteroaryl' as used herein refers to 6-membered aromatic rings containing at least one heteroatom (e.g. nitrogen). Exemplary 6-membered heteroaryls include one nitrogen atom (pyridinyl), two nitrogen atoms (pyridazinyl, pyrimidinyl or pyrazinyl) and three nitrogen atoms (triazinyl).

The phrase '$R_3$' together with $R_5$ forms a 5- or 6-membered cycloalkyl' means that compounds with the following substructure are formed:

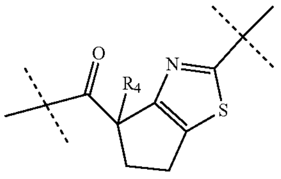

or

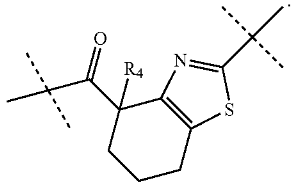

The phrase '$R_3$' together with $R_5$ forms a 5- or 6-membered oxygen containing heterocycloalkyl' means that compounds with the following substructure are formed:

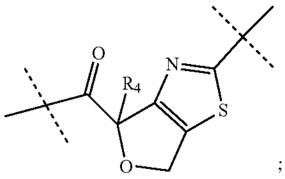

;

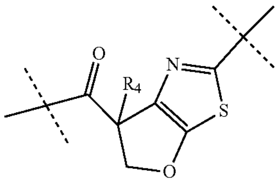

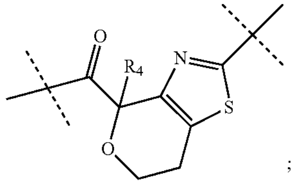

;

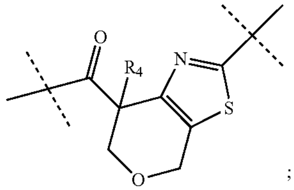

; or

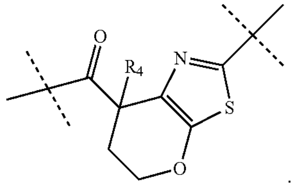

.

The phrase 'in the para position relative to group A' as used herein, such as in relation to the position of Ar2, means that compounds with the following substructure are formed:

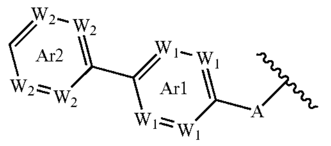

wherein $W_1$ may be N, CH, $CR_{10}$ or $CR_{11}$, and $W_2$ may be N, CH or $CR_{12}$ as allowed by the definitions provided for compounds of formula (I). $W_2$ may also be $CR_{13}$ as allowed by the definitions provided for compounds of formula (I).

The terms 'ortho' and 'meta' as used herein, such as when used in respect of defining the position of $R_{12}$ on Ar2 is with respect to Ar1, means that the following structures may form:

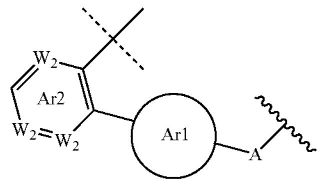

*ortho*

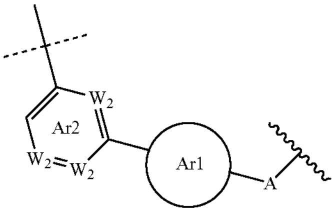

*meta*

The phrase 'A is an amide linker having the following structure: —C(═O)NH— or —NHC(═O)—' means the following structures form:

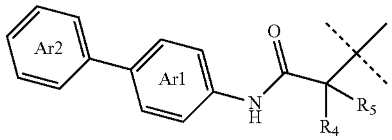

and

——NH(C═O)——

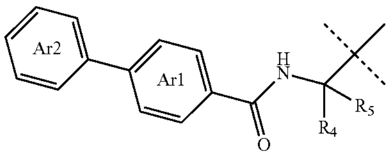

——(C═O)NH——

The phrase 'A is an amine linker having the following structure: —$CH_2$NH— or —NH$CH_2$—' means the following structures form:

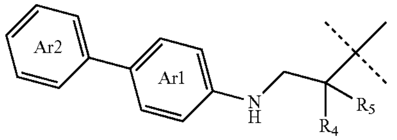

and

——NH$CH_2$-

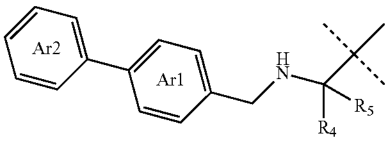

——$CH_2$NH——

In one embodiment, A is —C(═O)NH—. In another embodiment, A is —NHC(═O)—. In an additional embodiment, A is —NH—. In a further embodiment, A is —$CH_2$NH—. In another embodiment, A is —NH$CH_2$—. Suitably, B is

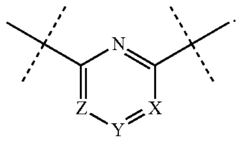

In one embodiment X is N. In another embodiment, X is CH.

In one embodiment, Y is N. In another embodiment, Y is $CR_2$.

In one embodiment, Z is N. In another embodiment, Z is $CR_3$.

Suitably, X is N, Y is $CR_2$ and Z is $CR_3$. Alternatively, X is CH, Y is N and Z is $CR_3$. Alternatively, X is CH, Y is $CR_2$ and Z is $CR_3$. Alternatively, X is CH, Y is $CR_2$ and Z is N. Alternatively, X is N, Y is $CR_2$ and Z is N.

Alternatively, B is

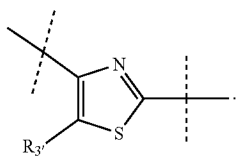

In one embodiment of the invention $R_1$ is $C_1$fluoroalkyl, i.e. $CH_2F$ or $CHF_2$, especially $CHF_2$. In a second embodiment of the invention $R_1$ is $C_2$fluoroalkyl, such as $CH_2CF_3$, $CH_2CHF_2$ or $CF_2CF_3$, especially $CH_2CF_3$ or $CH_2CHF_2$, in particular $CH_2CHF_2$. In a third embodiment of the invention $R_1$ is $C_3$fluoroalkyl, such as a fluorinated n-propyl or isopropyl. In a fourth embodiment of the invention $R_1$ is $C_4$fluoroalkyl, such as a fluorinated n-butyl, isobutyl, sec-butyl or tert-butyl. In a fifth embodiment of the invention $R_1$ is $C_5$fluoroalkyl, such as a fluorinated n-pentyl, sec-pentyl or 3-pentyl.

In certain embodiments of the invention $R_1$ is a $C_{1-5}$monofluoroalkyl. In other embodiments of the invention $R_1$ is a $C_{1-5}$difluoroalkyl. In other embodiments of the invention $R_1$ is a $C_{2-5}$trifluoroalkyl.

In one embodiment, $R_2$ is H. In a second embodiment, $R_2$ is halo such as F, Cl or Br, e.g. Cl or Br. In a third embodiment. $R_2$ is $C_{1-2}$alkyl. When $R_2$ is $C_{1-2}$alkyl. $R_2$ may be methyl or ethyl, such as methyl. In a fourth embodiment, $R_2$ is $OC_{1-2}$alkyl. When $R_2$ is $OC_{1-2}$alkyl, may be $OCH_3$ or OEt, such as $OCH_3$. In a fifth embodiment, $R_2$ is $C_{1-2}$haloalkyl. When $R_2$ is $C_{1-2}$haloalkyl, $R_2$ may be $CF_3$ or $CH_2CF_3$, such as $CF_3$. In a sixth embodiment, $R_2$ is $OC_{1-2}$haloalkyl. When $R_2$ is $OC_{1-2}$haloalkyl, $R_2$ may be $OCF_3$ or $OCH_2CF_3$, such as $OCF_3$.

Suitably, $R_2$ is H, $CH_3$ or $CF_3$, such as H or $CH_3$, in particular H.

In one embodiment $R_3$ is H. In a second embodiment $R_3$ is halo, in particular chloro or fluoro, especially fluoro. In a third embodiment, $R_3$ is $CH_3$. In a fourth embodiment, $R_3$ is $OCH_3$. In a fifth embodiment, $R_3$ is $CF_3$. In a sixth embodiment, $R_3$ is $OCF_3$.

Suitably, $R_3$ is H, halo in particular chloro or fluoro, especially fluoro, $CH_3$ or $CF_3$. More suitably, $R_3$ is H or F, such as H.

Suitably, at least one of $R_2$ and $R_3$ is H.

In one embodiment, $R_{3'}$ is H. In a second embodiment, $R_{3'}$ is halo, in particular chloro or fluoro, especially chloro. In a third embodiment, $R_{3'}$ is $CH_3$. In a fourth embodiment, $R_{3'}$ is $OC_{1-2}$alkyl, in particular $OCH_3$. In a fifth embodiment, $R_{3'}$ is $CF_3$.

When A is —NHC(═O)— $R_{3'}$ may be as defined above. In addition, in a sixth embodiment and when A is —NHC(═O)—, $R_{3'}$ together with $R_5$ forms a 5- or 6-membered cycloalkyl, in particular a 5-membered cycloalkyl. In a seventh embodiment and when A is —NHC(═O)—, $R_{3'}$ together with $R_5$ forms a 5 or 6 membered oxygen-containing heterocycloalkyl, in particular a 5-membered heterocycloalkyl.

In one embodiment, $R_4$ and $R_5$ are $R_{4a}$ and $R_{5a}$.

Suitably, $R_{4a}$ and $R_{5a}$ together with the carbon atom to which they are attached form a $C_{3-6}$cycloalkyl which is substituted by one or two substituents, each substituent being independently selected from the group consisting of $C_{1-3}$alkyl, oxo, OH, $C_{1-3}$alkylOH, $C_{1-3}$haloalkyl, $C_{0-2}$alkyleneC$_{3-6}$cycloalkyl, $C_{0-2}$alkyleneC$_{3-6}$heterocycloalkyl, $C_{1-3}$alkyleneOC$_{1-3}$alkyl, halo, $OC_{1-3}$haloalkyl, $OC_{0-2}$alkylene C$_{3-6}$cycloalkyl, $OC_{0-2}$alkyleneC$_{3-6}$heterocycloalkyl, $OC_{1-3}$alkyl and $NR_{21}R_{22}$.

In one embodiment, the $C_{3-6}$cycloalkyl is cyclopropyl. In another embodiment, the $C_{3-6}$cycloalkyl is cyclobutyl. In another embodiment, the $C_{3-6}$cycloalkyl is cyclopentyl. In another embodiment, the $C_{3-6}$cycloalkyl is cyclohexyl.

In one embodiment the $C_{3-6}$cycloalkyl is substituted by one substituent. In a second embodiment the $C_{3-6}$cycloalkyl is substituted by two substituents.

In one embodiment, the substituent is $C_{1-3}$alkyl. Suitably, the substituent is methyl. Suitably, the substituent is ethyl. Suitably, the substituent is n-propyl. Suitably, the substituent is iso-propyl.

In a second embodiment, the substituent is $C_{1-3}$alkylOH. Suitably, the substituent is $CH_2OH$. Suitably, the substituent is $CH_2CH_2OH$. Suitably, the substituent is $CH_2CH_2CH_2OH$.

In a third embodiment, the substituent is $C_{1-3}$haloalkyl. Suitably the $C_{1-3}$alkyl group is substituted by one, two or three, such as one, halogen atom. Suitably, the halogen atom is fluoro or chloro such as fluoro. Suitably, the substituent is $C_1$haloalkyl such as $CF_3$. Suitably, the substituent is $C_2$haloalkyl such as $CH_2CF_3$.

In a fourth embodiment, the substituent is $C_{0-2}$alkylene C$_{3-6}$cycloalkyl, in particular $C_{0-2}$alkyleneC$_{3-5}$cycloalkyl, such as $C_{3-5}$cycloalkyl, $C_1$alkyleneC$_{3-5}$cycloalkyl or $C_2$alkyleneC$_{3-5}$cycloalkyl.

In a fifth embodiment, the substituent is $C_{0-2}$alkylene C$_{3-6}$heterocycloalkyl such as $C_{0-2}$alkyleneC$_3$heterocycloalkyl, $C_{0-2}$alkyleneC$_4$heterocycloalkyl, $C_{0-2}$alkyleneC$_6$heterocycloalkyl, $C_{0-2}$alkyleneC$_6$heterocycloalkyl, $C_0$alkyleneC$_{3-6}$heterocycloalkyl, $C_1$alkyleneC$_{3-6}$heterocycloalkyl and $C_2$alkyleneC$_{3-6}$heterocycloalkyl. Suitably the heterocycloalkyl is a heterocyclopropyl, heterocyclobutyl, heterocyclopentyl or heterocyclohexyl ring such as a heterocyclohexyl ring. Suitably, the heterocyclopentyl ring is tetrahydrofuranyl or pyrrolidinyl. Suitably, the heterocyclohexyl ring is tetrahydropyranyl or piperidinyl. Any nitrogen atom(s) in the $C_{3-6}$heterocycloalkyl ring may be substituted (such as one nitrogen atom is substituted), for example by $C_{1-4}$alkyl, C(O)H, C(O)C$_{1-4}$alkyl, C(O)OC$_{1-4}$alkyl, C(O)OC$_{1-4}$alkylaryl such as C(O)OBz, C(O)NHC$_{1-4}$alkyl, C(O)NHC$_{1-4}$alkylaryl such as C(O)NHBz, an Fmoc group, C(O)C$_{1-4}$haloalkyl, C(O)OC$_{1-4}$haloalkyl or C(O)NHC$_{1-4}$haloalkyl, such as C(O)OtBu. Suitably, any nitrogen atom in the $C_{3-6}$heterocycloalkyl ring is not substituted.

In a sixth embodiment, the substituent is $C_{1-3}$alkyleneOC$_{1-3}$alkyl, in particular $C_{1-2}$alkyleneOC$_{1-2}$ alkyl such as $C_1$alkyleneOC$_1$alkyl, $C_2$alkyleneOC$_1$alkyl, $C_1$alkyleneOC$_2$alkyl or $C_2$alkyleneOC$_2$alkyl.

In a seventh embodiment, the substituent is halo, in particular fluoro or chloro such as chloro.

In an eighth embodiment, the substituent is $OC_{1-3}$haloalkyl. Suitably the $OC_{1-3}$alkyl group is substituted by one two or three, such as one, halogen atom. Suitably, the halogen atom is fluoro or chloro such as fluoro. Suitably, the substituent is $OC_1$haloalkyl such as $OCF_3$. Suitably, the substituent is $OC_2$haloalkyl such as $OCH_2CF_3$.

In a ninth embodiment, the substituent is $OC_{0-2}$alkyleneC$_{3-6}$cycloalkyl, such as $OC_{3-6}$cycloalkyl, $OC_1$alkylene C$_{3-6}$cycloalkyl or $OC_2$alkyleneC$_{3-6}$cycloalkyl.

In a tenth embodiment, the substituent is $OC_{0-2}$alkyleneC$_{3-6}$heterocycloalkyl such as $OC_{0-2}$alkyleneC$_3$heterocycloalkyl, $OC_{0-2}$alkyleneC$_4$heterocycloalkyl, $OC_{0-2}$alkyleneC$_5$heterocycloalkyl, $OC_{0-2}$alkyleneC$_6$heterocycloalkyl, $OC_0$alkyleneC$_{3-6}$heterocycloalkyl, $OC_1$alkyleneC$_{3-6}$heterocycloalkyl and $OC_2$alkyleneC$_{3-6}$heterocycloalkyl. Suitably the heterocycloalkyl is a heterocyclopropyl, heterocyclobutyl, heterocyclopentyl or heterocyclohexyl ring such as a heterocyclohexyl ring. Suitably, the heterocyclopentyl ring is tetrahydrofuranyl or pyrrolidinyl. Suitably, the heterocyclohexyl ring is tetrahydropyranyl or piperidinyl. Any nitrogen atom(s) (such as one nitrogen atom) in the $C_{3-6}$heterocycloalkyl ring may be substituted, for example by $C_{1-4}$alkyl, C(O)H, C(O)C$_{1-4}$alkyl, C(O)OC$_{1-4}$alkyl, C(O)OC$_{1-4}$alkylaryl such as C(O)OBz, C(O)NHC$_{1-4}$ alkyl, C(O)NHC$_{1-4}$alkylaryl such as C(O)NHBz, an Fmoc group, C(O)C$_{1-4}$haloalkyl, C(O)OC$_{1-4}$ haloalkyl or C(O)NHC$_{1-4}$haloalkyl, such as C(O)OtBu. Suitably, any nitrogen atom in the $C_{3-6}$heterocycloalkyl ring is not substituted.

In an eleventh embodiment, the substituent is $OC_{1-5}$alkyl, such as $OCH_3$ or $OCH_2CH_3$.

In a twelfth embodiment, the substituent is $NR_{21}R_{22}$ wherein $R_{21}$ and $R_{22}$ are defined elsewhere herein.

In an embodiment the substituent is oxo.

In another embodiment the substituent is OH.

Suitably, the one or two substituents, in particular one substituent, are independently selected from the group consisting of $C_{1-3}$alkyl, oxo, OH, $C_{1-3}$alkylOH, $C_{1-3}$haloalkyl, halo, $OC_{1-3}$haloalkyl, $OC_{1-3}$alkyl and $NR_{21}R_{22}$.

More suitably, the substituent is independently selected from the group consisting of oxo, OH, halo, $OC_{1-3}$alkyl and $NR_{21}R_{22}$.

Most suitably, the substituent is independently selected from the group consisting of oxo, OH, fluoro and $NR_{21}R_{22}$.

When the substituent is $NR_{21}R_{22}$, in one embodiment $R_{21}$ is H. In a second embodiment $R_{21}$ is $C_{1-5}$alkyl, such as methyl, ethyl or propyl, especially methyl. In a third embodiment $R_{21}$ is $C(O)C_{1-5}$alkyl, such as $C(O)CH_3$. In a fourth embodiment $R_{21}$ is $C(O)OC_{1-5}$alkyl, such as $C(O)OCH_3$ or C(O)Otert-butyl.

When the substituent is $NR_{21}R_{22}$, in one embodiment $R_{22}$ is H. In a second embodiment $R_2$ is methyl.

Suitably, $R_{21}$ is $C(O)OCH_3$ and $R_{22}$ is H. Suitably, $R_{21}$ is $C(O)CH_3$ and $R_{22}$ is H. Suitably, $R_{21}$ and $R_{22}$ are both $CH_3$. Suitably, $R_{21}$ and $R_{22}$ are both H.

Alternatively, $R_{4a}$ and $R_{5a}$ suitably together with the carbon atom to which they are attached form a $C_{3-6}$cycloalkyl and one of the carbons of the $C_{3-6}$cycloalkyl is a spiro centre such that a spirocyclic ring system is formed by the $C_{3-6}$cycloalkyl ring and a further $C_{3-6}$cycloalkyl ring or a $C_{3-6}$heterocycloalkyl ring, and wherein the $C_{3-5}$cycloalkyl formed by $R_{4a}$ and $R_{5a}$ together with the carbon atom to which they are attached may be substituted by one or two substituents, each substituent being independently selected from the group consisting of $C_{1-5}$alkyl or $OC_{1-3}$alkyl.

In one embodiment the $C_{3-6}$cycloalkyl formed by $R_{4a}$ and $R_{5a}$ together with the carbon atom to which they are attached is unsubstituted. In a second embodiment the $C_{3-6}$cycloalkyl formed by $R_{4a}$ and $R_{5a}$ together with the carbon atom to which they are attached is substituted by one or two substituents, in particular one substituent. Suitably, each substituent being independently selected from the group consisting of $C_{1-2}$alkyl or $OCH_3$.

The following spirocyclic groups are encompassed (which may optionally be substituted as mentioned above):

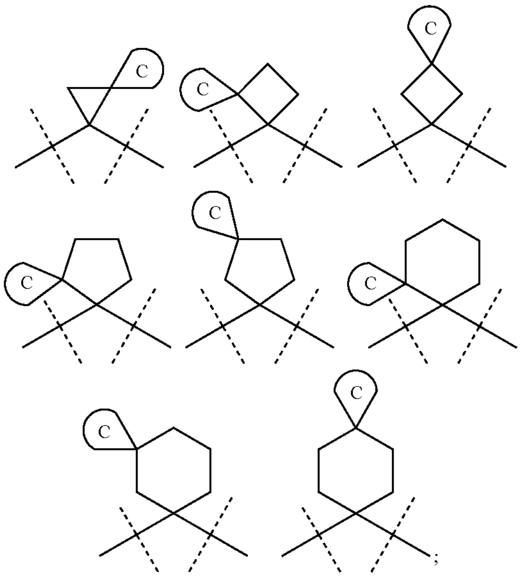

;

wherein C is a $C_{3-6}$cycloalkyl ring or a $C_{3-6}$heterocycloalkyl ring, as defined elsewhere herein. In one embodiment C is a $C_{3-6}$cycloalkyl ring. In a second embodiment C is a $C_{3-6}$heterocycloalkyl ring.

Suitably one of the carbons of the $C_{3-6}$cycloalkyl formed by $R_{4a}$ and $R_{5a}$ together with the carbon atom to which they are attached is a $C_{4-6}$cycloalkyl. Suitably the further $C_{3-6}$heterocycloalkyl is an oxygen containing $C_{3-6}$heterocycloalkyl.

For example, one of the carbons is quaternary and is attached to a 5-membered dioxolane ring to form the following structure:

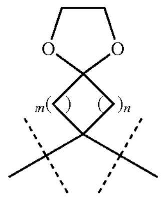

wherein m is 1 or 2 and n is 0, 1 or 2. Suitably m is 2 and n is 2.

Alternatively, $R_{4a}$ and $R_{5a}$ suitably together with the carbon atom to which they are attached form a $C_{3-6}$heterocycloalkyl wherein one of the carbons of the $C_{3-6}$heterocycloalkyl is a spiro centre such that a spirocyclic ring system is formed by the $C_{3-6}$heterocycloalkyl ring and a further $C_{3-6}$cycloalkyl ring or a $C_3$-heterocycloalkyl ring, and wherein the $C_{3-6}$heterocycloalkyl formed by $R_{4a}$ and $R_{5a}$ together with the carbon atom to which they are attached may be substituted by one or two substituents, each substituent being independently selected from the group consisting of $C_{1-3}$alkyl or $OC_{1-3}$alkyl.

In one embodiment the $C_{3-6}$heterocycloalkyl formed by $R_{4a}$ and $R_{5a}$ together with the carbon atom to which they are attached is unsubstituted. In a second embodiment the $C_{3-6}$heterocycloalkyl formed by $R_{4a}$ and $R_{5a}$ together with the carbon atom to which they are attached is substituted by one or two substituents, in particular one substituent. Suitably, each substituent being independently selected from the group consisting of $C_{1-2}$alkyl or $OCH_3$.

The following spirocyclic groups are encompassed (which may optionally be substituted as mentioned above):

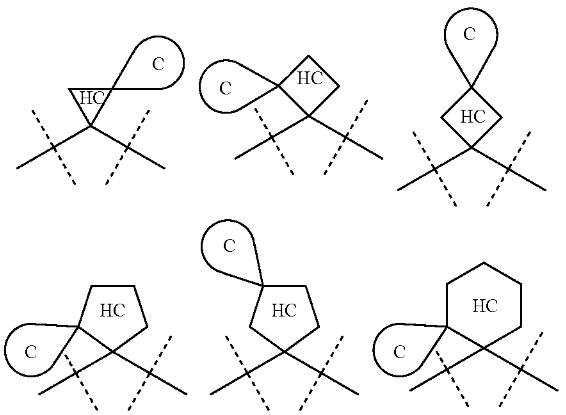

-continued

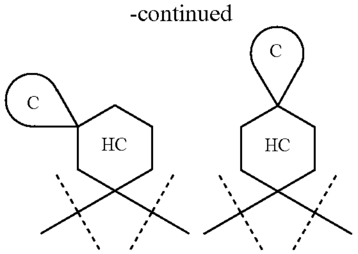

wherein C is a $C_{3-6}$cycloalkyl ring or a $C_{3-6}$heterocycloalkyl ring, as defined elsewhere herein, and HC is a $C_{3-6}$heterocycloalkyl ring as defined elsewhere herein. In one embodiment C is a $C_{3-6}$cycloalkyl ring. In a second embodiment C is a $C_{3-6}$heterocycloalkyl ring.

In an embodiment, $R_{4a}$ and $R_{5a}$ together with the carbon atom to which they are attached form a $C_{3-6}$heterocycloalkyl comprising one nitrogen atom, wherein said nitrogen atom is substituted by —$S(O)_2R_{29}$.

Suitably, the $C_{3-6}$heterocycloalkyl is selected from the group consisting of aziridinyl, azetidinyl, pyrrolidinyl and piperidinyl such as piperidinyl.

Suitably, when the $C_{3-6}$heterocycloalkyl is piperidinyl, the nitrogen atom is in the 4-position relative to the quaternary carbon:

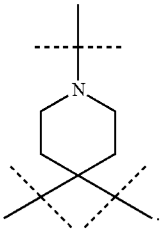

The $C_{3-6}$heterocycloalkyl may be other groups as defined elsewhere herein.

In an embodiment, $R_{29}$ is $C_{1-3}$alkyl, $C_{0-2}$alkylene$C_{3-5}$cycloalkyl which cycloalkyl is optionally substituted by $CH_3$, or $CF_3$. In one embodiment, $R_{29}$ is $C_{1-3}$alkyl such as methyl. In another embodiment, $R_{29}$ is $C_{0-2}$alkylene$C_{3-5}$cycloalkyl which cycloalkyl is optionally substituted by $CH_3$. In some embodiments, $R_{29}$ is $C_{0-2}$alkylene$C_{3-5}$cycloalkyl. In other embodiments, $R_{29}$ is $C_{0-2}$alkylene$C_{3-5}$cycloalkyl which cycloalkyl is substituted by $CH_3$. $R_{29}$ may be $C_{3-5}$cycloalkyl, which cycloalkyl is optionally substituted by $CH_3$. $R_{29}$ may be $C_1$alkylene$C_{3-5}$cycloalkyl, which cycloalkyl is optionally substituted by $CH_3$. $R_{29}$ may be $C_2$alkylene$C_{3-5}$cycloalkyl, which cycloalkyl is optionally substituted by $CH_3$. $R_{29}$ may be $C_{0-2}$alkylene$C_3$cycloalkyl, which cycloalkyl is optionally substituted by $CH_3$. $R_{29}$ may be $C_{0-2}$alkylene$C_4$cycloalkyl, which cycloalkyl is optionally substituted by $CH_3$. $R_{29}$ may be $C_{0-2}$alkylene$C_5$cycloalkyl, which cycloalkyl is optionally substituted by $CH_3$. Suitably, where $C_{0-2}$alkylene$C_{3-5}$cycloalkyl is optionally substituted by $CH_3$, the $CH_3$ is at the point of attachment of the $C_{3-5}$cycloalkyl to the $C_{0-2}$alkylene. In another embodiment, $R_{29}$ is $CF_3$.

In another embodiment, $R_4$ and $R_5$ are $R_{4b}$ and $R_{5b}$.

In one embodiment, $R_{4b}$ and $R_{5b}$ together with the carbon atom to which they are attached form a $C_{3-6}$cycloalkyl, such as cyclopropyl, cyclobutyl or cyclopentyl in particular cyclopropyl or cyclopentyl. In a second embodiment, $R_{4b}$ and $R_{5b}$ together with the carbon atom to which they are attached form a $C_{3-6}$heterocycloalkyl, such as a heterocyclohexyl, in particular a tetrahydropyranyl. Any nitrogen atom such as one nitrogen atom in the $C_{3-6}$heterocycloalkyl ring may be substituted, for example by $C_{1-4}$alkyl, C(O)H, C(O)$C_{1-4}$alkyl, C(O)O$C_{1-4}$alkyl, C(O)O$C_{1-4}$ alkylaryl such as C(O)OBz, C(O)NH$C_{1-4}$alkyl, C(O)NH$C_{1-4}$alkylaryl such as C(O)NHBz, an Fmoc group, C(O)$C_{1-4}$haloalkyl, C(O)O$C_{1-4}$haloalkyl or C(O)NH$C_{1-4}$haloalkyl, such as C(O)OtBu. Suitably, any nitrogen atom in the $C_{3-6}$heterocycloalkyl ring is not substituted. In a third embodiment, $R_{4b}$ is $C_{1-6}$alkyl, in particular $C_{1-4}$alkyl such as methyl, ethyl, propyl (n-propyl or isopropyl) or butyl (n-butyl, isobutyl, sec-butyl or tert-butyl). In a fourth embodiment, $R_{4b}$ is $C_{1-3}$ alkyleneO$C_{1-3}$alkyl, in particular $C_{1-2}$alkyleneO$C_{1-2}$alkyl such as $C_1$alkyleneO$C_1$alkyl, $C_2$alkyleneO$C_1$alkyl, $C_1$alkyleneO$C_2$alkyl or $C_2$alkyleneO$C_2$alkyl. In a fifth embodiment, $R_{4b}$ is H. In a sixth embodiment, $R_{4b}$ is halo, such as chloro or fluoro, especially fluoro. In a seventh embodiment, $R_{4b}$ is $C_{1-6}$haloalkyl, such as $CF_3$ or $CH_2CF_3$. In an eighth embodiment, $R_{4b}$ is $C_{0-2}$alkylene$C_{3-6}$cycloalkyl such as $C_{3-6}$cycloalkyl, $C_1$alkylene$C_{3-6}$cycloalkyl, $C_2$alkylene$C_{3-6}$cycloalkyl, $C_{0-2}$alkylene$C_3$cycloalkyl, $C_{0-2}$alkylene$C_4$cycloalkyl, $C_{0-2}$alkylene$C_5$cycloalkyl or $C_{0-2}$alkylene$C_{3-6}$cycloalkyl. In a ninth embodiment, $R_{4b}$ is $C_{0-2}$alkylene$C_{3-6}$heterocycloalkyl such as $C_{3-6}$heterocycloalkyl, $C_1$alkylene$C_{3-6}$heterocycloalkyl, $C_2$alkylene $C_{3-6}$heterocycloalkyl, $C_{0-2}$alkylene$C_3$heterocycloalkyl, $C_{0-2}$alkylene$C_4$hetero-cycloalkyl, $C_{0-2}$alkylene$C_3$heterocycloalkyl or $C_{0-2}$alkylene$C_6$heterocycloalkyl. Suitably the heterocycloalkyl is a heterocyclopropyl, heterocyclobutyl, heterocyclopentyl or heterocyclohexyl ring such as a heterocyclohexyl ring. Suitably, the heterocyclopentyl ring is tetrahydrofuranyl or pyrrolidinyl. Suitably, the heterocyclohexyl ring is tetrahydropyranyl or piperidinyl. Any nitrogen atom such as one nitrogen atom in the $C_{3-6}$heterocycloalkyl ring may be substituted, for example by $C_{1-4}$alkyl, C(O)H, C(O)$C_{1-4}$ alkyl, C(O)O$C_{1-4}$alkyl, C(O)O$C_{1-4}$alkylaryl such as C(O)OBz, C(O)NH$C_{1-4}$alkyl, C(O)NH$C_{1-4}$alkylaryl such as C(O)NHBz, an Fmoc group, C(O)$C_{1-4}$haloalkyl, C(O)O$C_{1-4}$haloalkyl or C(O)NH$C_{1-4}$haloalkyl, such as C(O)OtBu. Suitably, any nitrogen atom in the $C_{3-6}$heterocycloalkyl ring is not substituted. In a tenth embodiment, $R_{4b}$ is $C_{1-6}$alkylOH, such as $CH_2OH$ or $CH_2CH_2OH$. In an eleventh embodiment, $R_{4b}$ is O$C_{1-6}$haloalkyl, such as O$C_{1-4}$haloalkyl, such as $OCF_3$ or $OCHF_2$. In a twelfth embodiment, $R_{4b}$ is O$C_{0-2}$alkylene$C_{3-6}$cycloalkyl such as O$C_{3-6}$cycloalkyl, O$C_1$alkylene$C_{3-6}$cycloalkyl, O$C_2$alkylene$C_{3-6}$cycloalkyl, O$C_{0-2}$alkylene$C_3$cycloalkyl, O$C_{0-2}$alkylene$C_4$cycloalkyl, O$C_{0-2}$alkylene$C_5$cycloalkyl or O$C_{0-2}$alkylene$C_6$cycloalkyl. In a thirteenth embodiment, $R_{4b}$ is O$C_{1-6}$alkyl, in particular O$C_{1-4}$alkyl such as methoxy, ethoxy, propoxy (n-propoxy or isopropoxy) or butoxy (n-butoxy, isobutoxy, sec-butoxy or tert-butoxy). In a fourteenth embodiment, $R_{4b}$ is O$C_{0-2}$alkylene$C_{3-6}$heterocycloalkyl such as O$C_{3-6}$heterocycloalkyl, O$C_1$alkylene$C_{3-6}$heterocycloalkyl, O$C_2$alkylene$C_{3-6}$heterocycloalkyl, O$C_{0-2}$alkylene$C_3$heterocycloalkyl, O$C_{0-2}$alkylene$C_4$heterocycloalkyl, O$C_{0-2}$alkylene$C_5$heterocycloalkyl or O$C_{0-2}$alkylene$C_6$heterocycloalkyl. Suitably the heterocycloalkyl is a heterocyclopropyl, heterocyclobutyl, heterocyclopentyl or heterocyclohexyl ring such as a heterocyclohexyl ring. Suitably, the heterocyclopentyl ring is tetrahydrofuranyl or pyrrolidinyl. Suitably, the heterocyclohexyl ring is tetrahydropyranyl or piperidinyl. Any nitrogen atom such as one nitrogen atom in the $C_{3-6}$heterocycloalkyl ring may be substituted, for example by $C_{1-4}$alkyl, C(O)H, $C(O)C_{1-4}$ alkyl, $C(O)OC_{1-4}$alkyl, $C(O)OC_{1-4}$alkylaryl such as C(O)OBz, $C(O)NHC_{1-4}$alkyl, $C(O)NHC_{1-4}$ alkylaryl such as C(O)NHBz, an Fmoc group, $C(O)C_{1-4}$haloalkyl, $C(O)OC_{1-4}$haloalkyl or $C(O)NHC_{1-4}$haloalkyl, such as C(O)OtBu. Suitably, any nitrogen atom in the $C_{3-6}$heterocycloalkyl ring is not substituted. In a fifteenth embodiment, $R_{4b}$ is $NR_{21}R_{22}$.

When A is —NHC(═O)— or —C(═O)NH—, suitably, $R_{4b}$ is H, $C_{1-6}$alkyl, $C_{1-6}$haloalkyl, $C_{1-6}$alkylOH, $C_{0-2}$alkyleneC$_{3-6}$cycloalkyl, $C_{0-2}$alkyleneC$_{3-6}$heterocycloalkyl, $C_{1-3}$alkyleneOC$_{1-3}$alkyl, or $R_{4b}$ and $R_{5b}$ together with the carbon atom to which they are attached form a $C_{3-6}$cycloalkyl or $C_{3-6}$heterocycloalkyl. When A is —NHC(═O)—, suitably $R_{4b}$ may additionally be selected from halo, $OC_{1-6}$haloalkyl, $OC_{0-2}$alkyleneC$_3$-cycloalkyl, $OC_{0-2}$alkyleneC$_{3-6}$heterocycloalkyl, $OC_{1-6}$alkyl or $NR_{21}R_{22}$.

When A is —NH—, —$CH_2$NH— or —NH$CH_2$—, suitably, $R_{4b}$ is H, $C_{1-6}$alkyl, $C_{1-6}$haloalkyl, $C_{1-6}$alkylOH, $C_{0-2}$alkyleneC$_{3-6}$cycloalkyl, $C_{0-2}$alkyleneC$_{3-6}$heterocycloalkyl, $C_{1-3}$alkyleneOC$_{1-3}$alkyl, or $R_{4b}$ and $R_{5b}$ together with the carbon atom to which they are attached form a $C_{3-6}$cycloalkyl or $C_{3-6}$heterocycloalkyl. When A is —NH$CH_2$—, suitably $R_{4b}$ may additionally be selected from halo, $OC_{1-6}$haloalkyl, $OC_{0-2}$alkyleneC$_{3-6}$cycloalkyl, $OC_{0-2}$alkyleneC$_{3-6}$heterocycloalkyl, $OC_{1-6}$alkyl or $NR_{21}R_{22}$.

Suitably $R_{4b}$ is H, fluoro. $CH_3$, ethyl, $OCH_3$ or $CH_2CH_2OCH_3$, such as fluoro, ethyl, $OCH_3$ or $CH_2CH_2OCH_3$.

Suitably $R_{4b}$ is H, $CH_3$, ethyl or $CH_2CH_2OCH_3$, in particular $CH_3$ or ethyl.

Suitably $R_{4b}$ and $R_{5b}$ together with the carbon atom to which they are attached form a cyclopropyl or cyclopentyl, in particular a cyclopentyl.

Suitably $R_{4b}$ and $R_{5b}$ together with the carbon atom to which they are attached form a heterocyclohexyl, such as tetrahydropyranyl or piperidinyl, especially tetrahydropyranyl. Any nitrogen atom such as one nitrogen atom in the $C_{3-6}$heterocycloalkyl ring may be substituted, for example by $C_4$alkyl, C(O)H, $C(O)C_{1-4}$alkyl, $C(O)OC_{1-4}$alkyl, $C(O)OC_{1-4}$alkylaryl such as C(O)OBz, $C(O)NHC_{1-4}$alkyl, $C(O)NHC_{1-4}$alkylaryl such as C(O)NHBz, an Fmoc group, $C(O)C_{1-4}$haloalkyl, $C(O)OC_4$haloalkyl or $C(O)NHC_{1-4}$haloalkyl, such as C(O)OtBu. Suitably, any nitrogen atom in the $C_{3-6}$heterocycloalkyl ring is not substituted.

Suitably $R_{4b}$ and $R_{5b}$ together with the carbon atom to which they are attached form a heterocyclobutyl, such as azetidinyl. Any nitrogen atom such as one nitrogen atom in the $C_{3-6}$heterocycloalkyl ring may be substituted, for example by $C_{1-4}$alkyl, C(O)H, $C(O)C_{1-4}$alkyl, $C(O)OC_{1-4}$alkyl, $C(O)OC_{1-4}$alkylaryl such as C(O)OBz, $C(O)NHC_{1-4}$alkyl, $C(O)NHC_{1-4}$alkylaryl such as C(O)NHBz, an Fmoc group, $C(O)C_{1-4}$haloalkyl, $C(O)OC_{1-4}$haloalkyl or $C(O)NHC_{1-4}$ haloalkyl, such as C(O)OtBu. Suitably, any nitrogen atom in the $C_{3-6}$heterocycloalkyl ring is not substituted.

When $R_{4b}$ is $NR_{21}R_{22}$, in one embodiment $R_{21}$ is H. In a second embodiment $R_{21}$ is $C_{1-5}$alkyl, such as methyl, ethyl or propyl, especially methyl. In a third embodiment $R_{21}$ is $C(O)C_{1-5}$alkyl, such as $C(O)CH_3$. In a fourth embodiment $R_{21}$ is $C(O)OC_{1-5}$alkyl, such as $C(O)OCH_3$ or C(O)Otert-butyl.

When $R_{4b}$ is $NR_{21}R_{22}$, in one embodiment $R_{22}$ is H. In a second embodiment $R_{22}$ is methyl.

For example, $R_{4b}$ is $NH_2$, $N(CH_3)_2$, $NHC(O)CH_3$, $NHC(O)OCH_3$, NHC(O)Otert-butyl and $CH_2CH_2OH$, especially, $N(CH_3)_2$, $NHC(O)CH_3$, $NHC(O)OCH_3$.

Suitably, $R_{21}$ is $C(O)OCH_3$ and $R_2$ is H. Suitably, $R_{21}$ is $C(O)CH_3$ and $R_{22}$ is H. Suitably, $R_{21}$ and $R_{22}$ are both $CH_3$. Suitably, $R_{21}$ and $R_{22}$ are both H.

In one embodiment $R_{5b}$ is $C_{1-6}$alkyl, in particular $C_{1-4}$alkyl such as methyl, ethyl, propyl (n-propyl or isopropyl) or butyl (n-butyl, isobutyl, sec-butyl or tert-butyl). In a second embodiment $R_{5b}$ is $C_{1-3}$ alkyleneOC$_{1-3}$alkyl, in particular $C_{1-2}$alkyleneOC$_{1-2}$alkyl such as $C_1$alkyleneOC$_1$alkyl, $C_2$alkyleneOC$_1$alkyl, $C_1$alkyleneOC$_2$alkyl or $C_2$alkyleneOC$_2$alkyl. In a third embodiment $R_{5b}$ is H. In a fourth embodiment, $R_{5b}$ is halo, such as chloro or fluoro, especially fluoro. In a fifth embodiment, $R_{5b}$ is $C_{1-6}$haloalkyl, such as $CF_3$ or $CH_2CF_3$. In a sixth embodiment, $R_{5b}$ is $C_{0-2}$alkyleneC$_{3-6}$cycloalkyl such as $C_{3-6}$cycloalkyl, $C_1$alkyleneC$_{3-6}$cycloalkyl, $C_2$alkyleneC$_{3-6}$cycloalkyl, $C_{0-2}$alkyleneC$_3$cycloalkyl, $C_{0-2}$alkyleneC$_4$cycloalkyl, $C_{0-2}$alkyleneC$_5$cycloalkyl or $C_{0-2}$alkyleneC$_6$cycloalkyl. In a seventh embodiment, $R_{5b}$ is $C_{0-2}$alkyleneC$_{3-6}$heterocycloalkyl such as $C_{3-6}$heterocycloalkyl, $C_1$alkyleneC$_{3-6}$heterocycloalkyl, $C_2$alkyleneC$_{3-6}$heterocycloalkyl, $C_{0-2}$alkyleneC$_3$heterocycloalkyl, $C_{0-2}$alkyleneC$_4$hetero-cycloalkyl, $C_{0-2}$alkyleneC$_5$heterocycloalkyl or $C_{0-2}$alkyleneC$_6$heterocycloalkyl. Suitably the heterocycloalkyl is a heterocyclopropyl, heterocyclobutyl, heterocyclopentyl or heterocyclohexyl ring such as a heterocyclohexyl ring. Suitably, the heterocyclopentyl ring is tetrahydrofuranyl or pyrrolidinyl. Suitably, the heterocyclohexyl ring is tetrahydropyranyl or piperidinyl. Any nitrogen atom such as one nitrogen atom in the $C_{3-6}$heterocycloalkyl ring may be substituted, for example by $C_{1-4}$alkyl, C(O)H, $C(O)C_{1-4}$alkyl, $C(O)OC_{1-4}$alkyl, $C(O)OC_{1-4}$alkylaryl such as C(O)OBz, $C(O)NHC_{1-4}$alkyl, $C(O)NHC_{1-4}$ alkylaryl such as C(O)NHBz, an Fmoc group, $C(O)C_{1-4}$haloalkyl, $C(O)OC_{1-4}$haloalkyl or $C(O)NHC_{1-4}$haloalkyl, such as C(O)OtBu. Suitably, any nitrogen atom in the $C_{0-6}$heterocycloalkyl ring is not substituted. In an eighth embodiment, $R_{5b}$ is $C_{1-6}$alkylOH, such as $CH_2OH$ or $CH_2CH_2OH$. In a ninth embodiment, $R_{5b}$ is $OC_{1-6}$haloalkyl, such as $OC_{1-4}$haloalkyl, such as $OCF_3$ or $OCHF_2$. In a tenth embodiment, $R_{5b}$ is $OC_{0-2}$alkyleneC$_{3-6}$cycloalkyl such as $OC_{3-6}$cycloalkyl, $OC_1$alkyleneC$_{3-6}$cycloalkyl, $OC_2$alkyleneC$_{3-6}$cycloalkyl, $OC_{0-2}$alkyleneC$_3$cycloalkyl, $OC_{0-2}$alkyleneC$_4$cycloalkyl, $OC_{0-2}$alkyleneC$_5$cycloalkyl or $OC_{0-2}$alkyleneC$_6$cycloalkyl. In an eleventh embodiment, $R_{5b}$ is $OC_{1-6}$alkyl, in particular $OC_{1-4}$alkyl such as methoxy, ethoxy, propoxy (n-propoxy or isopropoxy) or butoxy (n-butoxy, isobutoxy, sec-butoxy or tert-butoxy). In a twelfth embodiment, $R_{5b}$ is $OC_{0-2}$alkyleneC$_{3-6}$heterocycloalkyl such as $OC_{3-6}$heterocycloalkyl, $OC_1$alkyleneC$_{3-6}$heterocycloalkyl, $OC_2$alkyleneC$_{3-6}$heterocycloalkyl, $OC_{0-2}$alkyleneC$_3$heterocycloalkyl, $OC_{0-2}$alkyleneC$_4$hetero-cycloalkyl, $OC_{0-2}$alkyleneC$_5$heterocycloalkyl or $OC_{0-2}$alkyleneC$_{3-6}$heterocycloalkyl. Suitably the heterocycloalkyl is a heterocyclopropyl, heterocyclobutyl, heterocyclopentyl or heterocyclohexyl ring such as a heterocyclohexyl ring. Suitably, the heterocyclopentyl ring is tetrahydrofuranyl or pyrrolidinyl. Suitably, the heterocyclohexyl ring is tetrahydropyranyl or piperidinyl. Any nitrogen atom such as one nitrogen atom in the $C_{3-6}$heterocycloalkyl ring may be substituted, for example by $C_{1-4}$alkyl, C(O)H, $C(O)C_{1-4}$ alkyl, $C(O)OC_{1-4}$alkyl, $C(O)OC_{1-4}$alkylaryl such as C(O)OBz, $C(O)NHC_{1-4}$alkyl, $C(O)NHC_{1-4}$alkylaryl such as C(O)NHBz, an Fmoc group, $C(O)C_{1-4}$haloalkyl, $C(O)OC_{1-4}$haloalkyl or $C(O)NHC_{1-4}$haloalkyl, such as C(O)OtBu. Suitably, any nitrogen atom in the $C_{3-6}$heterocycloalkyl ring is not substituted. In a thirteenth embodiment, $R_{5b}$ is $NR_{21}R_{22}$.

When A is —NHC(=O)— or —C(=O)NH—, suitably, $R_{5b}$ is H, $C_{1-6}$alkyl, $C_{1-6}$haloalkyl, $C_{1-6}$alkylOH, $C_{0-2}$alkyleneC$_{3-6}$cycloalkyl, $C_{0-2}$alkyleneC$_{3-6}$heterocycloalkyl, $C_{1-3}$alkyleneOC$_{1-3}$alkyl, or $R_{4b}$ and $R_{5b}$ together with the carbon atom to which they are attached form a $C_{3-6}$cycloalkyl or $C_{3-6}$heterocycloalkyl. When A is —NHC(=O)—, suitably $R_{5a}$ may additionally be selected from halo, OC$_{1-6}$haloalkyl, OC$_{0-2}$alkyleneC$_{3-6}$cycloalkyl, OC$_{0-2}$alkyleneC$_{3-6}$heterocycloalkyl, OC$_{1-6}$alkyl or $NR_{21}R_{22}$.

When A is —NH—, —$CH_2$NH— or —NH$CH_2$—, suitably, $R_{5b}$ is H, $C_{1-6}$alkyl, $C_{1-6}$haloalkyl, $C_{1-6}$alkylOH, $C_{0-2}$alkyleneC$_{3-6}$cycloalkyl, $C_{0-2}$alkyleneC$_{3-6}$heterocycloalkyl, $C_{1-3}$alkyleneOC$_{1-3}$alkyl, or $R_{4b}$ and $R_{5b}$ together with the carbon atom to which they are attached form a $C_{3-6}$cycloalkyl or $C_{3-6}$heterocycloalkyl. When A is —NH$CH_2$—, suitably $R_{5b}$ may additionally be selected from halo, OC$_{1-6}$haloalkyl, OC$_{0-2}$alkyleneC$_{3-6}$cycloalkyl, OC$_{0-2}$alkyleneC$_{3-6}$heterocycloalkyl, OC$_{1-6}$alkyl or $NR_{21}R_{22}$.

When $R_{5b}$ is $NR_{21}R_{22}$, in one embodiment $R_{21}$ is H. In a second embodiment $R_{21}$ is $C_{1-5}$alkyl, such as methyl, ethyl or propyl, especially methyl. In a third embodiment $R_{21}$ is C(O)C$_{1-5}$alkyl, such as C(O)$CH_3$. In a fourth embodiment $R_{21}$ is C(O)OC$_{1-5}$alkyl, such as C(O)O$CH_3$ or C(O)Otert-butyl.

When $R_{5b}$ is $NR_{21}R_{22}$, in one embodiment $R_{22}$ is H. In a second embodiment $R_{22}$ is methyl.

For example, $R_{5b}$ is $NH_2$, $N(CH_3)_2$, NHC(O)$CH_3$, NHC(O)O$CH_3$, NHC(O)Otert-butyl and $CH_2CH_2OH$, especially, $N(CH_3)_2$, NHC(O)$CH_3$, NHC(O)O$CH_3$.

Suitably, $R_{21}$ is C(O)O$CH_3$ and $R_{22}$ is H. Suitably, $R_{21}$ is C(O)$CH_3$ and $R_{22}$ is H. Suitably, $R_{21}$ and $R_{22}$ are both $CH_3$. Suitably, $R_{21}$ and $R_{22}$ are both H.

Suitably $R_{5b}$ is H, F, $CH_3$ or ethyl such as H, $CH_3$ or ethyl.

Suitably $R_{5b}$ is H, $CH_3$, ethyl or $CH_2CH_2OCH_3$ and $R_{5b}$ is H, $CH_3$ or ethyl, in particular $R_{4b}$ is $CH_3$, or ethyl and $R_{5b}$ is H, methyl or ethyl. For example, $R_{4b}$ and $R_{5b}$ are H, $R_{4b}$ and $R_{5b}$ are methyl, $R_{4b}$ and $R_{5b}$ are ethyl or $R_{4b}$ is $CH_2CH_2OCH_3$ and $R_{5b}$ is H.

Suitably, $R_{4b}$ is F and $R_{5b}$ is ethyl.

Suitably, $R_{4b}$ is F and $R_{5b}$ is F.

Suitably, $R_{4b}$ is ethyl and $R_{5b}$ is H.

Suitably $R_{4b}$ and $R_{5b}$ are arranged in the following configuration:

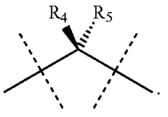

In one embodiment Ar1 is a 6-membered aryl, i.e. phenyl. In a second embodiment Ar1 is a 6-membered heteroaryl, in particular containing one nitrogen atom (pyridyl) or two nitrogen atoms (pyridazinyl, pyrimidinyl or pyrazinyl).

In particular Ar1 is phenyl, 2-pyridyl or 3-pyridyl, such as phenyl or 2-pyridyl. The position numbering for Ar1 is in respect of group A, with the carbon at the point of attachment designated position 1 and other numbers providing the relative location of the nitrogen atoms, for example:

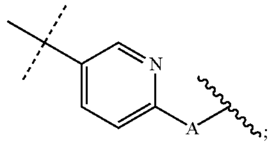
;
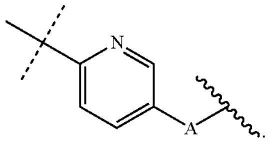
.

2-pyridyl 3-pyridyl

In one embodiment $R_{10}$ is H. In a second embodiment $R_{10}$ is halo, for example fluoro or chloro. In a third embodiment $R_{10}$ is $C_{1-3}$alkyl such as $C_{1-2}$alkyl, such as $CH_3$ or ethyl. In a fourth embodiment $R_{10}$ is OC$_{1-2}$alkyl, such as O$CH_3$ or ethoxy. In a fifth embodiment $R_{10}$ is OC$_{1-2}$haloalkyl, such as $OCF_3$. In a sixth embodiment $R_{10}$ is CN. In a seventh embodiment, $R_{10}$ is $C_{1-2}$ haloalkyl such as $CF_3$.

Suitably $R_{10}$ is H, fluoro, chloro, $CH_3$, $CF_3$, $OCH_3$, $OCF_3$ or CN, such as H, fluoro, chloro, $CH_3$, $OCH_3$, $OCF_3$ or CN, in particular H, fluoro, chloro, $OCH_3$, $OCF_3$ or CN especially H or fluoro.

Suitably, $R_{10}$ is H, F or $CH_3$.

In one embodiment $R_{11}$ is H. In a second embodiment $R_{11}$ is F. In a third embodiment, $R_1$, is $C_{1-2}$ alkyl such as $CH_3$ or Et, such as $CH_3$. In a fourth embodiment $R_{11}$ is $OCH_3$. In a fifth embodiment, $R_1$, is Cl. In a sixth embodiment, $R_{11}$ is Et. In a seventh embodiment, $R_{11}$ is $CF_3$. In an eighth embodiment, $R_{11}$ is CN.

Suitably, $R_{11}$ is H, F, $CH_3$ or $OCH_3$, such as H, F or $CH_3$, such as H or F, such as H.

In one embodiment, $R_{10}$ is in the ortho position with respect to group A. In another embodiment, $R_{10}$ is in the meta position with respect to group A. Suitably $R_{10}$ is in the ortho position with respect to group A.

In one embodiment, $R_{11}$ is in the ortho position with respect to group A. In another embodiment, $R_{11}$ is in the meta position with respect to group A. Suitably $R_{11}$ is in the ortho position with respect to group A.

In one embodiment Ar2 is a 6-membered aryl, i.e. phenyl. In a second embodiment Ar2 is a 6-membered heteroaryl, in particular containing one nitrogen atom (pyridyl) or two nitrogen atoms (pyridazinyl, pyrimidinyl or pyrazinyl).

The position numbering for Ar2 is in respect of the point of attachment to Ar1, for example:

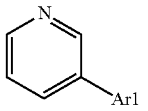
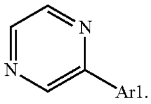
.

3-pyridyl 2,5-pyrazinyl

In particular Ar2 is 3-pyridyl or 2,5-pyrazinyl, especially 2,5-pyrazinyl.

In one embodiment $R_{12}$ is H. In a second embodiment $R_{12}$ is halo, for example fluoro or chloro. In a third embodiment $R_{12}$ is $C_{1-4}$alkyl, such as methyl, ethyl, propyl (n-propyl or isopropyl) or butyl (n-butyl, isobutyl, sec-butyl or tert-butyl). In a fourth embodiment $R_{12}$ is OC$_{1-4}$alkyl, such as $OCH_3$, ethoxy, isopropoxy or n-propoxy. In a fifth embodiment $R_{12}$ is OC$_{0-2}$alkyleneC$_{3-5}$cycloalkyl, such as OC$_{3-5}$cycloalkyl (e.g. cyclopropoxy or cyclobutoxy), OC$_1$alkyleneC$_{3-5}$cycloalkyl or OC$_2$alkyleneC$_{3-5}$cycloalkyl. In a sixth embodiment $R_{12}$ is CN. In a seventh embodiment $R_{12}$ is $C_{1-4}$ haloalkyl, such as $CF_3$. In an eighth embodiment $R_{12}$ is OC$_{1-4}$haloalkyl, such as $OCF_3$, $OCHF_2$ or $OCH_2CF_3$. In a ninth embodiment, $R_{12}$ is $C_{2-4}$alkenyl such as C(=$CH_2$)

$CH_3$. In a tenth embodiment, $R_{12}$ is $C_{0-2}$alkylene$C_{3-5}$cycloalkyl such as $C_{3-5}$cycloalkyl, $C_1$alkylene$C_{3-5}$cycloalkyl, $C_2$alkylene$C_{3-6}$cycloalkyl, $C_{0-2}$alkylene$C_3$cycloalkyl, $C_{0-2}$alkylene$C_4$cycloalkyl or $C_{0-2}$alkylene$C_5$cycloalkyl. In an eleventh embodiment, $R_{12}$ is hydroxy. In a twelfth embodiment, $R_{12}$ is $C_{1-4}$alkylOH such as $CH_2OH$. In a thirteenth embodiment, $R_{12}$ is $SO_2C_{1-2}$alkyl such as $SO_2CH_3$. In a fourteenth embodiment, $R_{12}$ is C(O)N($C_{1-2}$alkyl)$_2$ such as C(O)N($CH_3$)$_2$. In a fifteenth embodiment, $R_{12}$ is NHC(O)$C_{1-5}$alkyl. In a sixteenth embodiment, $R_{12}$ is $NR_{23}R_{24}$. In a seventeenth embodiment, $R_{12}$ is $OCH_2CH_2N(CH_3)_2$. In an eighteenth embodiment, $R_{12}$ is a $C_{3-6}$heterocycloalkyl comprising one nitrogen located at the point of attachment to Ar2. Suitably the heterocycloalkyl is a heterocyclopropyl, heterocyclobutyl, heterocyclopentyl or heterocyclohexyl ring such as a heterocyclohexyl ring. Suitably, the heterocyclopentyl ring is pyrrolidinyl. Suitably, the heterocyclohexyl ring is piperidinyl or piperazinyl. Any nitrogen atom such as one nitrogen atom in the $C_{3-6}$heterocycloalkyl ring may be substituted, for example by $C_{1-4}$alkyl, C(O)H, C(O)$C_{1-4}$alkyl, C(O)O$C_{1-4}$alkyl, C(O)O$C_{1-4}$alkylaryl such as C(O)OBz, C(O)NH$C_{1-4}$alkyl, C(O)NH$C_{1-4}$alkylaryl such as C(O)NHBz, an Fmoc group, C(O)$C_{1-4}$haloalkyl, C(O)O$C_{1-4}$haloalkyl or C(O)NH$C_{1-4}$haloalkyl, such as C(O)OtBu. Suitably, any nitrogen atom in the $C_{3-6}$heterocycloalkyl ring is not substituted. In a nineteenth embodiment, $R_{12}$ together with a nitrogen atom to which it is attached forms an N-oxide ($N^+$—$O^-$).

When A is —NHC(═O)— or —C(═O)NH—, suitably, $R_{12}$ is attached to Ar2 in the ortho or meta position relative to Ar1 and $R_{12}$ is H, halo, $C_{1-4}$alkyl, $C_{2-4}$alkenyl, $C_{0-2}$alkylene$C_{3-6}$cycloalkyl, O$C_{1-4}$alkyl, O$C_{0-2}$alkylene$C_{3-5}$cycloalkyl, $C_{1-4}$haloalkyl, O$C_{1-4}$haloalkyl, hydroxy, $C_{1-4}$alkylOH, $SO_2C_{1-2}$alkyl, C(O)N($C_{1-2}$alkyl)$_2$, NHC(O)$C_{1-5}$alkyl or $NR_{23}R_{24}$.

When A is —NHC(═O)—, suitably $R_{12}$ may additionally be selected from CN, $OCH_2CH_2N(CH_3)_2$ and a $C_{3-6}$heterocycloalkyl comprising one nitrogen located at the point of attachment to Ar2, or $R_{12}$ together with a nitrogen atom to which it is attached forms an N-oxide ($N^+$—$O^-$).

When A is —NH—, —$CH_2$NH— or —NH$CH_2$—, suitably, $R_{12}$ is attached to Ar2 in the ortho or meta position relative to Ar1 and $R_{12}$ is H, halo, $C_{1-4}$alkyl, $C_{2-4}$alkenyl, $C_{0-2}$alkylene$C_{3-5}$cycloalkyl, O$C_{1-4}$alkyl, O$C_{0-2}$alkylene $C_{3-5}$cycloalkyl, $C_{1-4}$haloalkyl, O$C_{1-4}$haloalkyl, hydroxy, $C_{1-4}$alkylOH, $SO_2C_{1-2}$alkyl, C(O)N($C_{1-2}$alkyl)$_2$, NHC(O)$C_{1-3}$alkyl or $NR_{23}R_{24}$.

When A is —NH— or —NH$CH_2$—, suitably $R_{12}$ may additionally be selected from CN, $OCH_2CH_2N(CH_3)_2$ and a $C_{3-6}$heterocycloalkyl comprising one nitrogen located at the point of attachment to Ar2, or $R_{12}$ together with a nitrogen atom to which it is attached forms an N-oxide ($N^+$—$O^-$).

The present invention provides N-oxides of the compound of formula (I). Suitably, when $R_{12}$ together with a nitrogen atom to which it is attached forms an N-oxide ($N^+$—$O^-$), the example following structures are formed:

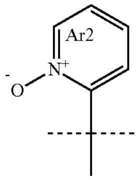
or
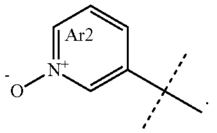

$R_{12}$ is suitably H, F, Cl, $CH_3$, $OCH_3$, OEt, OiPr, OCyclopropyl, CN, $CF_3$, $OCHF_2$ or $OCH_2CF_3$. In particular, $R_{12}$ is Cl, CN, $CF_3$, $OCHF_2$, $OCH_2CF_3$, $OCH_3$, OEt, OiPr, OCyclopropyl, such as $CF_3$, $OCHF_2$, $OCH_2CF_3$, $OCH_3$, OEt, OiPr, OCyclopropyl, e.g. OEt $R_{12}$ is suitably H, F, Cl, $CH_3$, iPr, $OCH_3$, OEt, OiPr, OCyclopropyl, CN, $CF_3$, $OCHF_2$, $OCH_2CF_3$, $C_3$cycloalkyl or C(═$CH_2$)$CH_3$. In particular, $R_{12}$ is Cl, iPr, $OCH_3$, OEt, OiPr, OCyclopropyl, CN, $CF_3$, $OCHF_2$, $OCH_2CF_3$, $C_3$cycloalkyl or C(═$CH_2$)$CH_3$, such as Cl, $OCH_3$, OEt, OiPr, OCyclopropyl, $CF_3$, $OCHF_2$, $OCH_2CF_3$ or $C_3$cycloalkyl, e.g. OEt.

When A is —C(═O)NH—, suitably $R_{12}$ is $CF_3$, OEt or OiPr, such as OEt or OiPr.

Suitably $R_{12}$ is in the meta position of Ar2. Alternatively, $R_{12}$ is in the ortho position of Ar2.

In one embodiment, $R_{13}$ is H. In another embodiment, $R_{13}$ is halo such as F or Cl, suitably F.

In one embodiment, $R_{13}$ is in the ortho position with respect to Ar1. In another embodiment, $R_{13}$ is in the para position with respect to Ar1. In another embodiment, $R_{13}$ is in the meta position with respect to Ar1.

In one embodiment, $R_{23}$ is H. In another embodiment, $R_{23}$ is $C_{1-2}$alkyl such as methyl.

In one embodiment, $R_{24}$ is H. In another embodiment $R_{24}$ is $C_{1-2}$alkyl such as methyl.

Suitably, $R_{23}$ is H and $R_{24}$ is ethyl. Suitably, $R_{23}$ is $CH_3$ and $R_{24}$ is $CH_3$.

In one embodiment, at least one of $R_{10}$, $R_{11}$, $R_{12}$ and $R_{13}$ is other than H.

Suitably, at least one of $R_4$, $R_5$, $R_{10}$, $R_{11}$, $R_{12}$ and $R_{13}$ is other than H.

Throughout the specification Ar1 and Ar2 may be depicted as follows:

Ar1

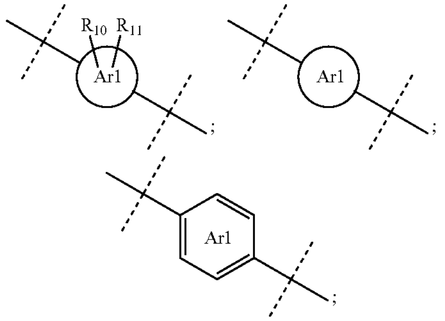

Ar2

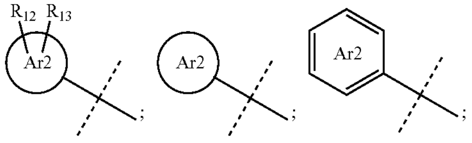

All depictions with respect to Ar1 are equivalent and all depictions with respect to Ar2 are equivalent, unless the context requires otherwise, depictions of Ar1 and Ar2 should not be taken to exclude the presence of heteroatoms or substitutions.

The present invention provides the compounds described in either of Examples P271 and P284.

The present invention provides the following compounds: 4-(2-((2,2-difluoroethyl)sulfonamido)pyrimidin-4-yl)-N-(5-(6-ethoxypyrazin-2-yl)pyridin-2-yl)tetrahydro-2H-pyran-4-carboxamide; and 2-(2-((2,2-difluoroethyl)sulfonamido)pyrimidin-4-yl)-N-(5-(6-ethoxypyrazin-2-yl)pyridin-2-yl)-2-fluorobutanamide.

The compounds of the invention may be provided in the form of a pharmaceutically acceptable salt and/or solvate thereof and/or derivative thereof. In particular, the compound of formula (I) may be provided in the form of a pharmaceutically acceptable salt and/or solvate, such as a pharmaceutically acceptable salt.

Compounds of the invention of particular interest are those demonstrating an $IC_{50}$ of 1 uM or lower, especially 100 nM or lower, in respect of CTPS1 enzyme, using the methods of the examples (or comparable methods).

Compounds of the invention of particular interest are those demonstrating a selectivity for CTPS1 over CTPS2 of 2-30 fold, suitably >30-60 fold or more suitably >60 fold, using the methods of the examples (or comparable methods). Desirably the selectivity is for human CTPS1 over human CTPS2.

It will be appreciated that for use in medicine the salts of the compounds of formula (I) should be pharmaceutically acceptable. Non-pharmaceutically acceptable salts of the compounds of formula (I) may be of use in other contexts such as during preparation of the compounds of formula (I). Suitable pharmaceutically acceptable salts will be apparent to those skilled in the art. Pharmaceutically acceptable salts include those described by Berge et al. (1977). Such pharmaceutically acceptable salts include acid and base addition salts. Pharmaceutically acceptable acid additional salts may be formed with inorganic acids e.g. hydrochloric, hydrobromic, sulphuric, nitric or phosphoric acid and organic acids e.g. succinic, maleic, acetic, fumaric, citric, tartaric, benzoic, p-toluenesulfonic, methanesulfonic or naphthalenesulfonic acid. Other salts e.g. oxalates or formates, may be used, for example in the isolation of compounds of formula (I) and are included within the scope of this invention.

Certain of the compounds of formula (I) may form acid or base addition salts with one or more equivalents of the acid or base. The present invention includes within its scope all possible stoichiometric and non-stoichiometric forms.

The compounds of formula (I) may be prepared in crystalline or non-crystalline form and, if crystalline, may optionally be solvated, e.g. as the hydrate. This invention includes within its scope stoichiometric solvates (e.g. hydrates) as well as compounds containing variable amounts of solvent (e.g. water).

It will be understood that the invention includes pharmaceutically acceptable derivatives of compounds of formula (I) and that these are included within the scope of the invention.

As used herein "pharmaceutically acceptable derivative" includes any pharmaceutically acceptable prodrug such as an ester or salt of such ester of a compound of formula (I) which, upon administration to the recipient is capable of providing (directly or indirectly) a compound of formula (I) or an active metabolite or residue thereof.

It is to be understood that the present invention encompasses all isomers of formula (I) and their pharmaceutically acceptable derivatives, including all geometric, tautomeric and optical forms, and mixtures thereof (e.g. racemic mixtures). Where additional chiral centres are present in compounds of formula (I), the present invention includes within its scope all possible diastereoisomers, including mixtures thereof. The different isomeric forms may be separated or resolved one from the other by conventional methods, or any given isomer may be obtained by conventional synthetic methods or by stereospecific or asymmetric syntheses.

The present disclosure includes all isotopic forms of the compounds of the invention provided herein, whether in a form (i) wherein all atoms of a given atomic number have a mass number (or mixture of mass numbers) which predominates in nature (referred to herein as the "natural isotopic form") or (ii) wherein one or more atoms are replaced by atoms having the same atomic number, but a mass number different from the mass number of atoms which predominates in nature (referred to herein as an "unnatural variant isotopic form"). It is understood that an atom may naturally exist as a mixture of mass numbers. The term "unnatural variant isotopic form" also includes embodiments in which the proportion of an atom of given atomic number having a mass number found less commonly in nature (referred to herein as an "uncommon isotope") has been increased relative to that which is naturally occurring e.g. to the level of >20%, >50%, >75%, >90%, >95% or >99% by number of the atoms of that atomic number (the latter embodiment referred to as an "isotopically enriched variant form"). The term "unnatural variant isotopic form" also includes embodiments in which the proportion of an uncommon isotope has been reduced relative to that which is naturally occurring. Isotopic forms may include radioactive forms (i.e. they incorporate radioisotopes) and non-radioactive forms. Radioactive forms will typically be isotopically enriched variant forms.

An unnatural variant isotopic form of a compound may thus contain one or more artificial or uncommon isotopes such as deuterium ($^{2}H$ or D), carbon-11 ($^{11}C$), carbon-13 ($^{13}C$), carbon-14 ($^{14}C$), nitrogen-13 ($^{13}N$), nitrogen-15 ($^{15}N$), oxygen-15 ($^{15}O$), oxygen-17 ($^{17}O$), oxygen-18 ($^{18}O$), phosphorus-32 ($^{32}P$), sulphur-35 ($^{35}S$), chlorine-36 ($^{36}Cl$), chlorine-37 ($^{37}C$), fluorine-18 ($^{18}F$) iodine-123 ($^{123}I$), iodine-125 ($^{125}I$) in one or more atoms or may contain an increased proportion of said isotopes as compared with the proportion that predominates in nature in one or more atoms.

Unnatural variant isotopic forms comprising radioisotopes may, for example, be used for drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection. Unnatural variant isotopic forms which incorporate deuterium i.e. $^{2}H$ or D may afford certain therapeutic advantages resulting from greater metabolic stability, for example, increased in vivo half-life or reduced dosage requirements, and hence may be preferred in some circumstances. Further, unnatural variant isotopic forms may be prepared which incorporate positron emitting isotopes, such as $^{11}C$, $^{18}F$, $^{15}O$ and $^{13}N$, and would be useful in Positron Emission Topography (PET) studies for examining substrate receptor occupancy.

In one embodiment, the compounds of the invention are provided in a natural isotopic form.

In one embodiment, the compounds of the invention are provided in an unnatural variant isotopic form. In a specific embodiment, the unnatural variant isotopic form is a form in which deuterium (i.e. $^{2}H$ or D) is incorporated where hydrogen is specified in the chemical structure in one or more atoms of a compound of the invention. In one embodiment, the atoms of the compounds of the invention are in an isotopic form which is not radioactive. In one embodiment, one or more atoms of the compounds of the invention are in an isotopic form which is radioactive. Suitably radioactive isotopes are stable isotopes. Suitably the unnatural variant isotopic form is a pharmaceutically acceptable form.

In one embodiment, a compound of the invention is provided whereby a single atom of the compound exists in an unnatural variant isotopic form. In another embodiment, a compound of the invention is provided whereby two or more atoms exist in an unnatural variant isotopic form.

Unnatural isotopic variant forms can generally be prepared by conventional techniques known to those skilled in the art or by processes described herein e.g. processes analogous to those described in the accompanying Examples for preparing natural isotopic forms. Thus, unnatural isotopic variant forms could be prepared by using appropriate isotopically variant (or labelled) reagents in place of the normal reagents employed in the Examples. Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

In general, the compounds of formula (I) may be made according to the organic synthesis techniques known to those skilled in this field, as well as by the representative methods set forth below, those in the Examples, and modifications thereof.

General Routes:

Generic routes by which compounds disclosed herein and compound examples of the invention may be conveniently prepared are summarised below and adaptations thereof.

Compounds of formula (I) when B is

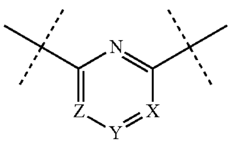

may be synthesised as follows:

Scheme 1a

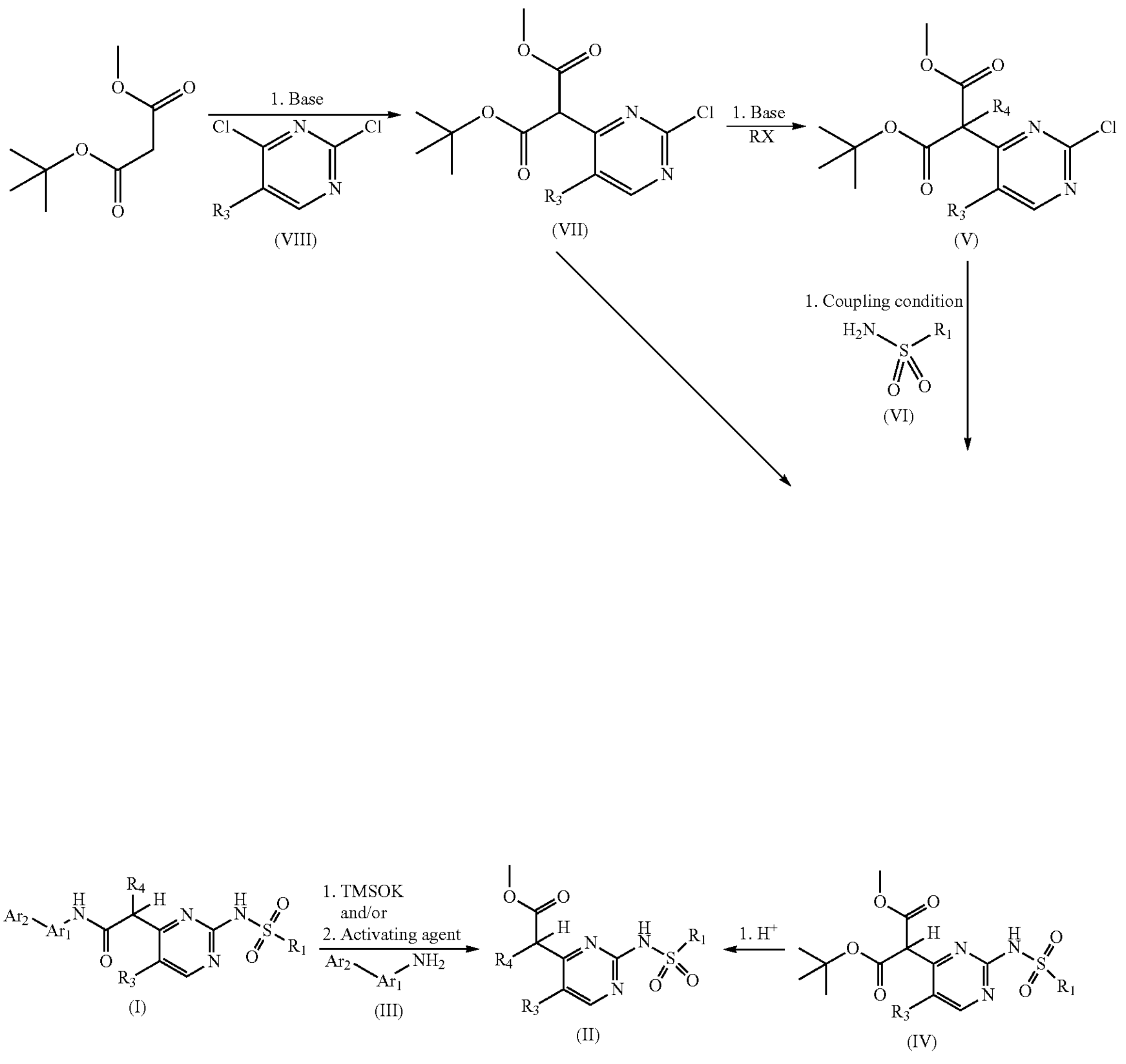

Scheme 1b

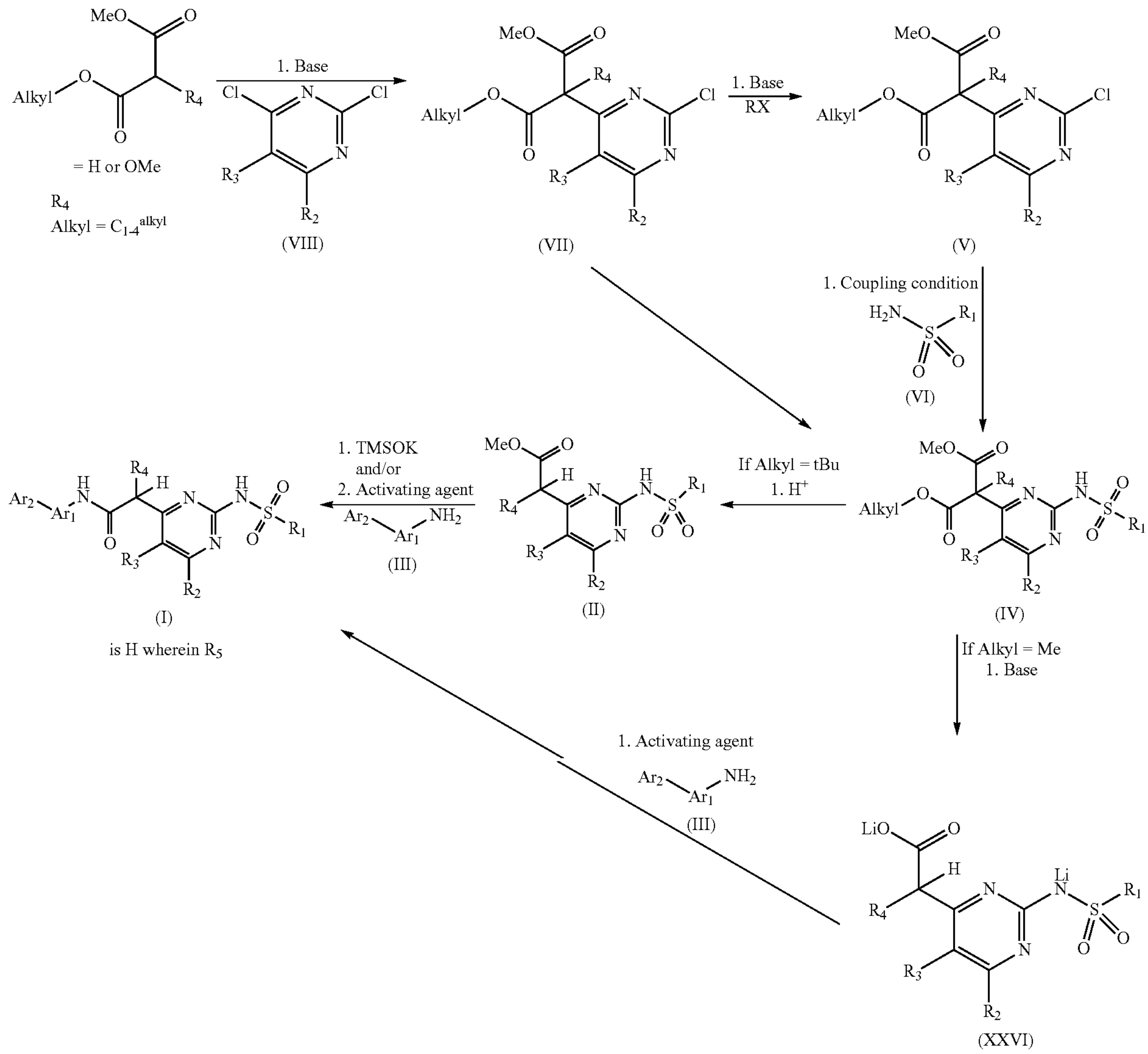

In general and as illustrated in Scheme 1a (wherein $R_4$ is H or Et) where $R_1$, $R_3$, Ar1 and Ar2 are defined above, or Scheme 1b (wherein $R_4$ is H or OMe) where $R_1$, $R_2$, $R_3$, Ar1 and Ar2 are defined above, the compounds of formula (I) may be prepared in four or five steps starting from a 2,4-dichloropyrimidine derivative of general formula (VIII). The derivative (VIII) can be reacted with an unsymmetrical malonate ester derivative to displace the more reactive chloride and form intermediate compounds of formula (VII). Such reactions may be carried out in the presence of a strong base such as sodium hydride and in a polar solvent such as DMF. If mono alkylation is desired then treatment of intermediate (VII) with an inorganic base, such as sodium hydroxide, in the presence of an alkylating agent, such as iodoethane (EtI), yields compounds of the general formula (V). If a desmethyl ($R_4$=H) linker is desired, compounds of general formula (VII) can be taken directly to compounds of general formula (IV) (see below).

Palladium catalysed sulfamination of 2-chloropyrimidine derivative (VII) and (V) can be undertaken using a catalyst such as [t-BuXPhos Pd(allyl)]OTf and substituted sulfonamide nucleophile (VI), in the presence of an inorganic base, for example potassium carbonate to form intermediate derivative (IV). This compound can then be deprotected via a decarboxylation, initiated by the use of a strong acid such as TFA to yield intermediate derivative (II). Such reactions are carried out in DCM at temperatures of 0° C. to room temperature.

Compounds of general formula (I) can be prepared by conversion of intermediate (II) by a one or two step process. Firstly, saponification using an agent such as TMSOK gives the intermediate carboxylic acid derivative followed by reaction with an activating agent, to generate a reactive, electrophilic carboxylic acid derivative, followed by subsequent reaction with an amine of formula (III), or a suitably protected derivative thereof. 2,4,6-Tripropyl-1,3,5,2,4,6-trioxatriphosphorinane-2,4,6-trioxide (T3P) is a reagent suitable for the activation of the carboxylate group. An alternative approach involves activation of the ester moiety directly using trimethylaluminium (usually a 2.0M solution in toluene or heptane) and addition of amine (III). These reactions are typically heated to 80-100° C. for a few hours in a solvent such as toluene.

If an alkoxy ($R_4$=OMe) linker is required, compounds may be prepared in four steps starting from a 2,4-dichloropyrimidine derivative of general formula (VIII) (Scheme 1b). The derivative (VIII) can be reacted with a symmetrical malonate ester to form intermediate compounds of formula (VII) where $R_4$=OMe. Compounds such as (VII) can then be coupled with a primary sulfonamide under conditions previously described. Compounds of formula (IV) where both alkyl groups are methyl can then be deprotected via a decarboxylation, initiated by the use of an alkali metal base to yield intermediate derivative (XXVI). The intermediate carboxylate derivative (XXVI) can undergo amide coupling as previously described to give final compounds of formula (I).

Scheme 2a

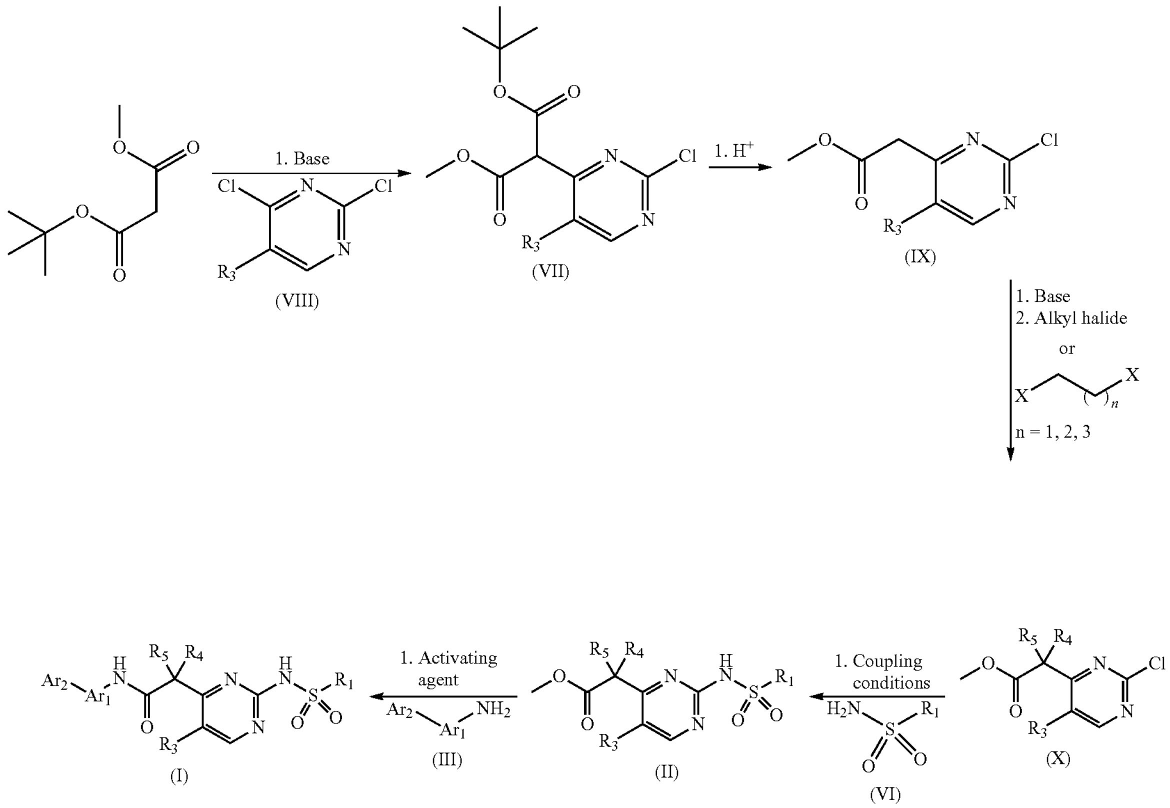

Scheme 2b

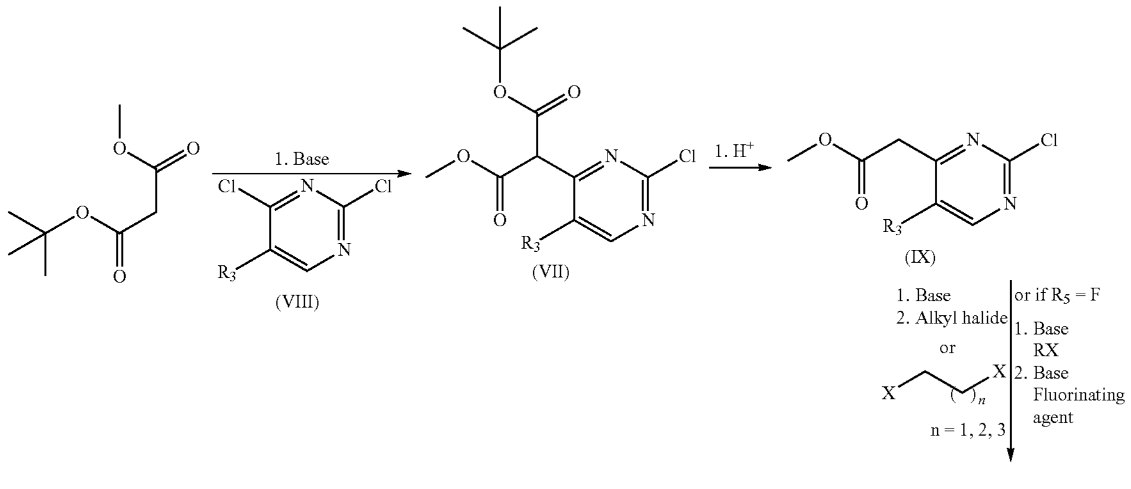

-continued

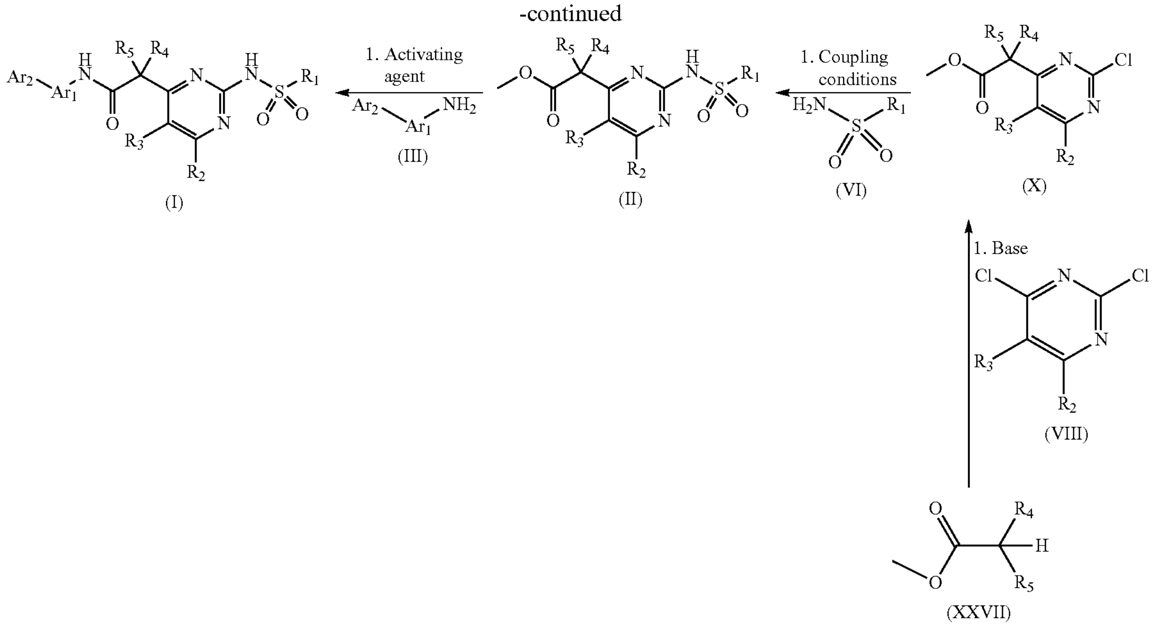

Suitably, $R_2$ is H, (IX) is converted to (X) using a base and alkyl halide or X—$CH_2$—$(CH_2)$n-X wherein n=1,2,3 and the compounds of general formula (I) are obtained by a five step process.

In general and as illustrated in Schemes 2a and 2b, compounds of general formula (I) may be obtained by a five or six step process from a 2,4-dichloropyrimidine derivative of general formula (VIII). Firstly, the derivative (VIII) can be reacted with an unsymmetrical malonate ester as shown in Schemes 1a, 1b, 2a or 2b. For example, the unsymmetrical malonate ester can be treated with a base such as $Cs_2CO_3$ in the presence of di-chloropyrimidine (VIII) in a solvent such as DMF and heated to an elevated temperature such as 80° C., followed by an aqueous work-up to obtain compounds of formula (VII). This intermediate compound can then be deprotected at this stage via a decarboxylation, initiated by the use of a strong acid such as TFA to yield intermediate derivative (IX). Certain intermediates such as (IX) where $R_3$=H, are commercially available. Reaction of a methyl 2-(2-chloropyrimidin-4-yl)acetate derivative of general formula (IX) with an inorganic base such as potassium carbonate, in the presence of an alkylating agent leads to alkylation alpha to the ester. It will be understood by persons skilled in the art that both mono- and dialkylation may be achieved with careful control of the reaction conditions, but for a more reliable synthesis of the monoalkylated product, an alternative procedure should be considered (as in Scheme 1a). $R_4$ and $R_5$ can be connected to form a $C_{3-6}$cycloalkyl ring as defined above ((IX) to (X)). Such compounds may be prepared by double alkylation with a dihaloalkane, such as 1,2-dibromoethane or 1,3-dibromobutane in the presence of an inorganic base such as sodium hydroxide. For compounds of general formula (I) wherein $R_4$ and $R_5$ together with the carbon to which they are attached form a $C_{3-6}$heterocycloalkyl, double alkylation of intermediates (IX) using a dihaloheteroalkane (such as $BrCH_2CH_2OCH_2CH_2Br$) in the presence of a base such as $Cs_2CO_3$ in a solvent such as MeCN at an elevated temperature such as 60° C. followed by direct column chromatography can be used to provide compounds of formula (X).

Palladium catalysed sulfamination of intermediate (X) may be achieved using a catalyst such as [t-BuXPhosPd(allyl)]OTf or t-BuXPhos-Pd-G3 and substituted sulfonamide nucleophile (VI), in the presence of an inorganic base, for example potassium carbonate to form intermediate derivative (II). Alternatively, sulfamination of intermediate (X) may be achieved using a substituted sulfonamide nucleophile (VI), in the presence of an inorganic base, for example $Cs_2CO_3$ and a solvent such as N-methyl pyrrolidinone to form intermediates (II) which may be obtained by precipitation following dilution in aqueous 4M HCl.

Final transformation to compounds of general formula (I) can be prepared by conversion of intermediate (II) by activation of the ester moiety using trimethylaluminium (usually a 2.0 M solution in toluene or heptane) and addition of amine (III) (commercially available or prepared as in Schemes 6a, 6b, 7a or 7b). Alternatively, compounds of formula (I) may be obtained by a strong base-mediated amide formation between compounds (II) and (III) at room temperature using bases such as iPrMgCl, LiHMDS or KOtBu.

Compounds of the general formula (VII) where $R_2$ is O-alkyl may be accessed in two steps from commercial 2,4,6-trichloropyrimidine derivatives such as (VIII) where $R_2$ is Cl. Reaction of an unsymmetrical malonate ester can yield compounds such as (VII) which can then be treated with an alkoxide base such as sodium methoxide to displace the more reactive chloride to give compounds of general formula (VII) where $R_2$=O-alkyl. Such compounds can then be progressed to final compounds of formula (I) following the steps previously described in Schemes 2a or 2b.

Compounds of general formula (I) where $R_1$, Ar1 and Ar2 are defined above and $R_4$ and $R_5$ together with the carbon to which they are attached form a $C_{3-6}$heterocycloalkyl, may be prepared in five steps starting from intermediate of general formula (VIII). Firstly, alkyl esters of general formula (XXVII) can be treated with a strong base such as LHMDS then reacted with 2,4-dichloropyrimidines such as derivative (VIII). Such compounds can then be converted to final compounds using the methods described in Scheme 2b. If any protecting groups remain after amide coupling, treatment with a strong acid such as TFA may yield final compounds of formula (I).

Following deprotection compounds of general formula (I) where $R_1$, Ar1 and Ar2 are defined above and $R_4$ and $R_5$ together with the carbon to which they are attached form a $C_{3-6}$ aminocycloalkyl, may be further elaborated by treatment with a suitable electrophile such as an acid chloride or an isocyanate, to yield the corresponding amide or urea. Such compounds may also undergo reductive amination in the presence of a suitable aldehyde or ketone followed by treatment with sodium triacetoxyborohydride.

For compounds where $R_5$ is halo such as F and $R_4$ is $C_{1-6}$alkyl, a two-step procedure may be carried out to convert intermediates of formula (IX) to (X), see Scheme 2b. Firstly mono alkylation alpha to the ester may be achieved by treatment with an inorganic base such as potassium carbonate, in the presence of an alkylating agent. Reaction of these products with a strong base such as LHMDS followed by exposure to a fluorinating agent such as N-fluoro-N-(phenylsulfonyl)benzenesulfonamide may produce compounds of formula (X).

Scheme 3

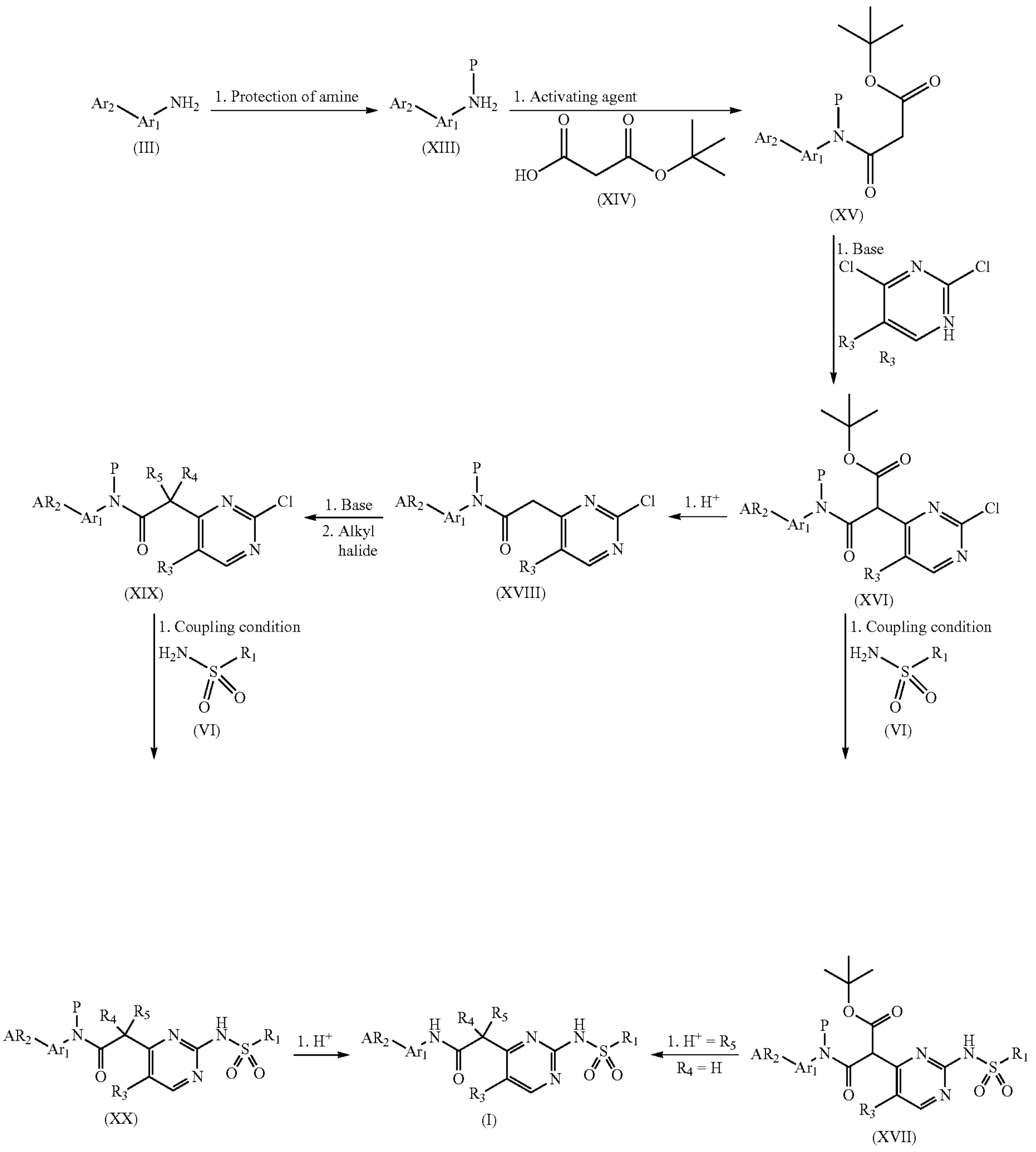

(III) (XIII) (XIV) (XV) (XVI) (XVIII) (XIX) (VI) (VI) (XX) (I) (XVII)

In general and as illustrated in Scheme 3, compounds of general formula (I) wherein $R_3$ is H may be obtained by a seven step process when $R_4$ and/or $R_5$=alkyl (or five step process when $R_4$=$R_5$=H) from anilines of formula (III) defined in Scheme 4 and 5. Firstly, aniline (III) can be protected with a suitable nitrogen protecting group such as a para-methoxybenzyl ether group by reacting aniline (III) with 4-methoxybenzaldehyde followed by reduction in situ with reducing agents such as sodium triacetoxyborohydride. Protected aniline of formula (XIII) can then be reacted with 3-(tert-butoxy)-3-oxopropanoic acid (XIV) in presence of a coupling reagent such as HATU to obtain intermediates (XV). Such intermediates (XV) may undergo $S_NAr$ with 2,4-dichloropyrimidine (VIII) ($R_3$=H) in the presence of a strong base such as NaH to give pyrimidines of formula (XVI). The Intermediate (XVI) may then undergo two transformations.

Firstly, decarboxylation with a strong acid such as TFA to obtain intermediates of formula (XVIII) followed by alkylation in the presence of a base such as $K_2CO_3$ results in the formation compounds of formula (XIX). Palladium catalysed sulfonamidation of intermediate (XIX) may be achieved using a catalytic system such as Pd-174 in the presence of a sulphonamide of the type (VI) to obtain compounds of the formula (XX). Compounds of formula (I) may be obtained by deprotection of the aniline nitrogen using a strong acidic system such as TFA/triflic acid.

Alternatively compounds of formula (XVI) may undergo sulfonamidation using sulphonamide of the type (VI) followed by double deprotection using a strong acidic system such as TFA/triflic acid to yield compounds of formula (I).

Scheme 4a

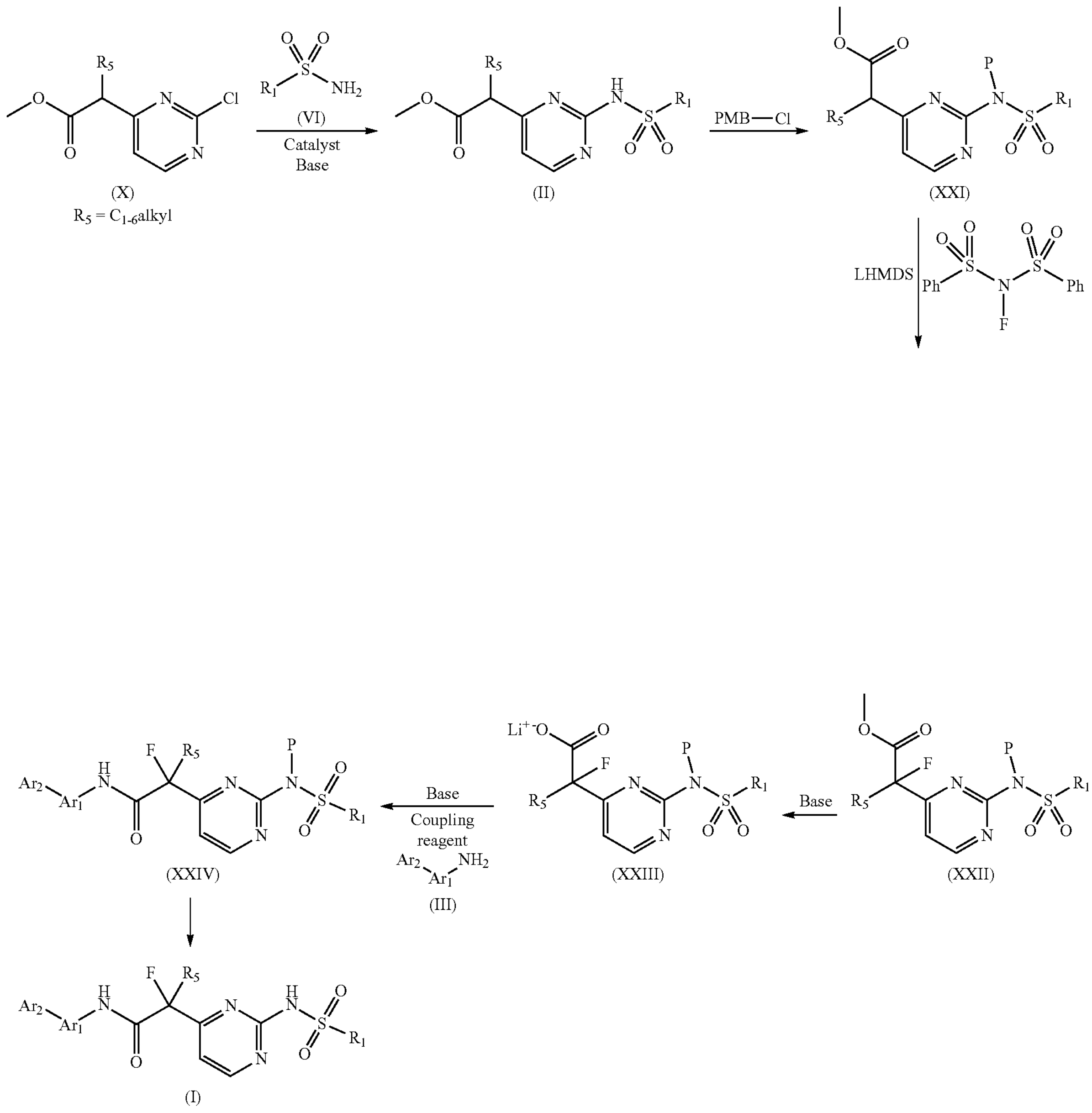

Scheme 4b

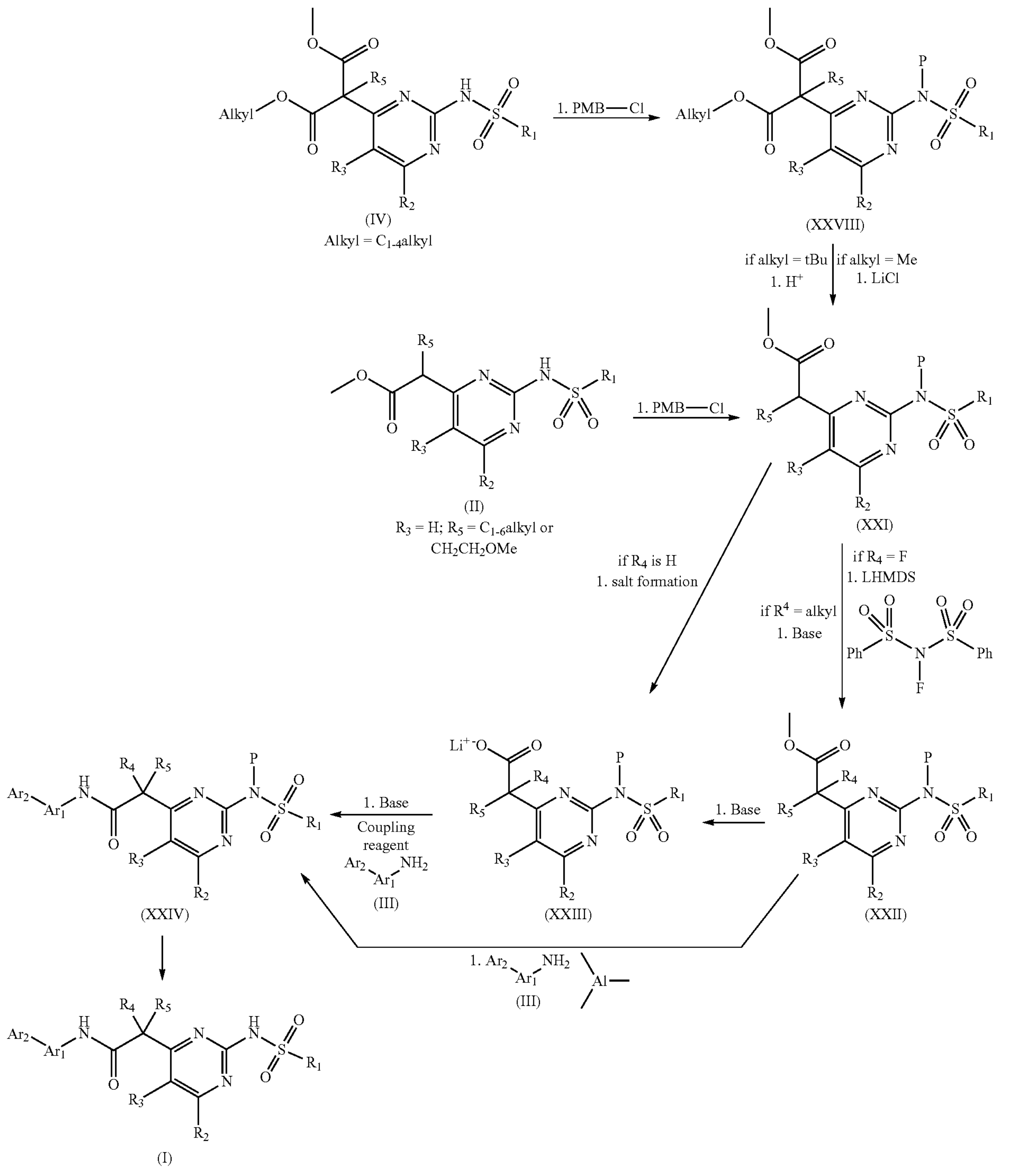

Suitably, $R_2$ is H, $R_3$ is H, $R_4$ is F and $R_5$ is $C_{1-6}$alkyl.

In general and as illustrated in Scheme 4a, compounds of general formula (I) where $R_1$, Ar1 and Ar2 are defined above, P is a nitrogen protecting group such as PMB, $R_4$ is halo such as F and $R_5$=$C_{1-5}$alkyl may be prepared starting from the methyl ester (II) which may undergo protection such as with PMB-Cl to give intermediate (XXI) which can then undergo fluorination using a fluorinating agent such as N-fluoro-N-(phenylsulfonyl)benzenesulfonamide after being treated with an appropriate base such as LHMDS. Intermediate (XXII) can undergo salt formation using an inorganic base such as LiOH to yield intermediate (XXIII) which can then be activated with a coupling reagent such as T3P in presence of base and coupled with an aniline such as (III) to obtain the protected final compound (XXIV). To follow is the final deprotection step under strongly acidic conditions such as TFA in DCM to give the desired final compounds of general formula (I).

As shown in Scheme 4b, intermediates of formula (XXI) may also be prepared starting from pyrimidine (IV) which can undergo protection such as with PMB-Cl to give intermediate (XXVIII).

Decarboxylation when the alkyl ester is tBu can be carried out with a strong acid such as TFA to yield derivatives of formula (XXI). Alternatively if the alkyl group is methyl, decarboxylation can be performed under Krapcho conditions employing a chloride ion source such as LiCl, in a polar aprotic solvent such as DMSO at elevated temperatures such as 140° C. to give derivatives of general formula (XXI).

For compounds where $R_4$ is $C_{1-6}$alkyl but where $R_4 \neq R_5$, derivatives of general formula (XXI) may be reacted with an inorganic base such as potassium carbonate, in the presence of an alkylating agent to give compounds of formula (XXII). Such compounds can be converted to final compounds using methods previously described in Scheme 4a.

For compounds where $R_4$=H is desired, compounds of formula (XXI) may be converted directly to carboxylate salts such as (XXIII) by treatment with a suitable agent such as TMSOK as previously described. Intermediates (XXIII) may be converted to compounds of formula (I) as described above, or in two steps by direct coupling of (XXII) with amines of formula (III) in the presence of an activating agent such as $AlMe_3$ followed by conversion of (XXIV) to compounds of formula (I) as described above.

-continued

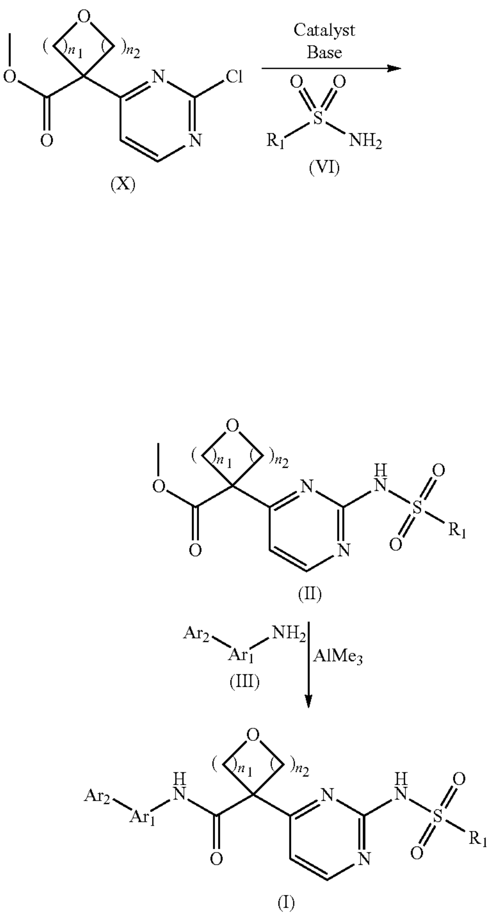

(X) (VI) (II) (III) (I)

Scheme 5a

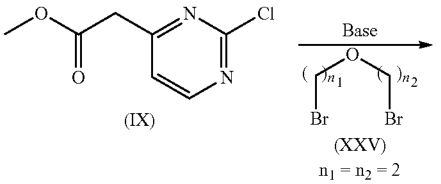

(IX) (XXV)

Scheme 5b

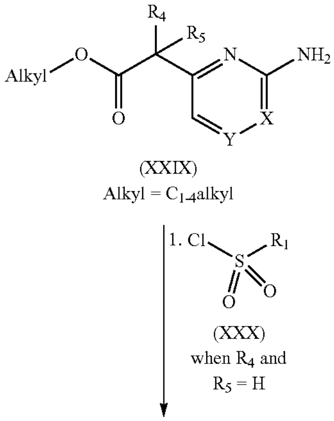

(XXIX) (XXX)

-continued

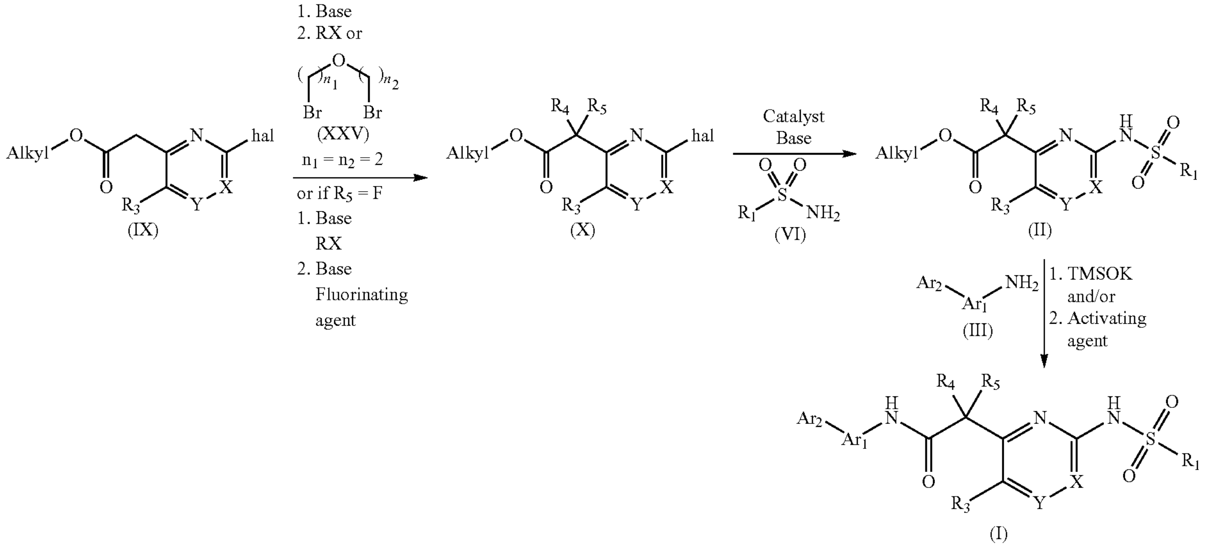

Suitably, X is N, Y is CH, $R_3$ is H, (IX) is converted to (X) using a base and compounds of formula (XXV) wherein $n_1=n_2=2$, hal is Cl, alkyl is methyl, $R_4$ and $R_5$ together with the carbon atom to which they are attached form a tetrahydropyranyl ring, and compounds of formula (II) are converted to compounds of formula (I) using $AlMe_3$ and compounds of formula (III).

Compounds of general formula (I) where $R_1$, Ar1 and Ar2 are defined above and $R_4$ and $R_5$ together with the carbon to which they are attached form a $C_{3-6}$heterocycloalkyl, may be prepared in three steps starting from intermediate of general formula (IX), see Scheme 5a. Firstly, the derivative (IX) can be reacted with a symmetric di-bromoether of general formula (XXV) as shown in Scheme 5a to give an alpha-cyclic compound of formula (X). The intermediate thus obtained may be further reacted with sulfonamides of general formula (VI) to give compounds of formula (II). Finally, subjecting derivatives (II) to $AlMe_3$ in the presence of anilines of type (III) yields compounds of general formula (I). Alternative reaction conditions for converting compounds of formula (IX) to compounds of formula (I) are described above in respect of Schemes 2a and 2b.

Compounds of general formula (I) where $R_1$, $R_3$, Ar1 and Ar2 are defined above, X=Y═CH or X═CH and Y═N, hal=Br or Cl, $R_4$ is $C_{1-6}$alkyl and $R_5$ is H or $C_{1-6}$alkyl may be prepared in three or four steps starting from intermediate of general formula (IX). Reaction of a derivative of general formula (IX) with an inorganic base such as potassium carbonate, in the presence of an alkylating agent leads to alkylation alpha to the ester to give compounds of formula (X). It will be understood by persons skilled in the art that both mono- and dialkylation may be achieved with careful control of the reaction conditions. Compounds of formula (X) may then be progressed to final compounds of formula (I) following the steps described above in Scheme 5b.

Compounds of general formula (I) where $R_1$, $R_3$, Ar1 and Ar2 are defined above, X=Y═CH or X═CH and Y═N and $R_4$ and $R_5$ together with the carbon to which they are attached form a $C_{3-6}$heterocycloalkyl, may be prepared in the same manner as described above for compounds when X═N and Y═CH.

Compounds of general formula (II) when $R_1$ and $R_3$ are as defined above, $R_4$═$R_5$═H and X and Y═CH may also be obtained by sulfonylation of commercial amines of formula (XXIX) with a suitable sulfonyl chloride (XXX) in pyridine. Intermediate (II) may then undergo hydrolysis and amide coupling using methods previously described.

Compounds of general formula (I) where $R_1$, Ra, Ar1 and Ar2 are defined above, X═CH and Y═N, hal=Br or Cl, $R_4$ is $C_{1-6}$alkyl and $R_5$ is F may be prepared starting from intermediate of general formula (IX). Firstly mono alkylation alpha to the ester may be achieved by treatment with an inorganic base such as potassium carbonate, in the presence of an alkylating agent. Reaction of these products with a strong base such as LHMDS followed by exposure to a fluorinating agent such as N-fluoro-N-(phenylsulfonyl)benzenesulfonamide may produce compounds of formula (X). Compounds of formula (X) can then be progressed to compounds of formula (I) following the steps described in Scheme 5b.

Scheme 6a

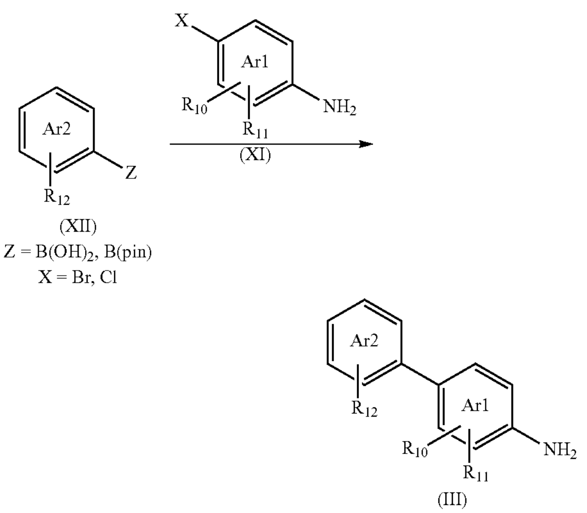

Scheme 6b

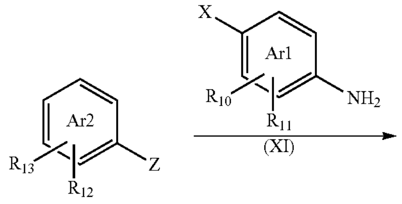

(XII)
Z = B(OH)$_2$, B(pin)
X = Br, Cl

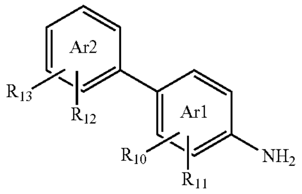

(III)

Intermediates of formula (III) wherein Ar1, $R_{10}$, $R_{11}$, $R_{12}$ and $R_{13}$ are defined above and Ar2 is an unsubstituted or substituted 3-pyridyl ring, may be synthesised by coupling under Suzuki conditions of a boronate of general formula (XII), wherein $R_{12}$ is defined above and Z represents a dihydroxyboryl or dialkyloxyboryl group, usually a 4,4,5,5-tetramethyl-1,3,3,2-dioxaborolan-2-yl group, to a substituted pyridine of formula (XI) where X denotes a halide. The couplings according to the Suzuki method are performed, for example, by heating in the presence of a catalyst such as [1,1'-bis(diphenylphosphino)ferrocene]dichloropalladium (II) complex with dichloromethane and an inorganic base such as potassium carbonate in a solvent mixture of dioxane and water.

Scheme 7a

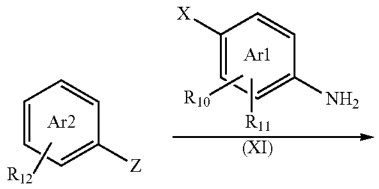

(XII)
Z = Br, Cl
X = B(OH)$_2$, B(pin)

-continued

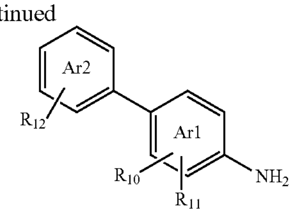

(III)

Scheme 7b

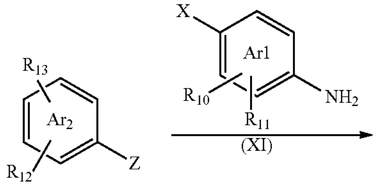

(XII)
Z = Br, Cl
X = B(OH)$_2$, B(pin)

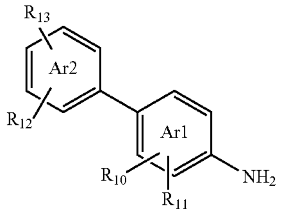

(III)

Intermediates of formula (III) wherein Ar1, $R_{10}$, $R_{11}$, $R_{12}$ and $R_{13}$are defined above and Ar2 is an unsubstituted or substituted 2,5-pyrazinyl ring, may be synthesised by coupling under Suzuki conditions of an aromatic halide of general formula (XII) and Z represents a halide, to a boronate of general formula (XI) where X denotes a dihydroxyboryl or dialkyloxyboryl group, usually a 4,4,5,5-tetramethyl-1,3,3,2-dioxaborolan-2-yl group. The couplings according to the Suzuki method are performed, for example, by heating in the presence of a catalyst such as tetrakis (triphenylphosphine)palladium or [1,1'-bis(diphenylphosphino)ferrocene]dichloro palladium(II) and an inorganic base such as potassium carbonate in a solvent mixture of dioxane and water.

Scheme 8

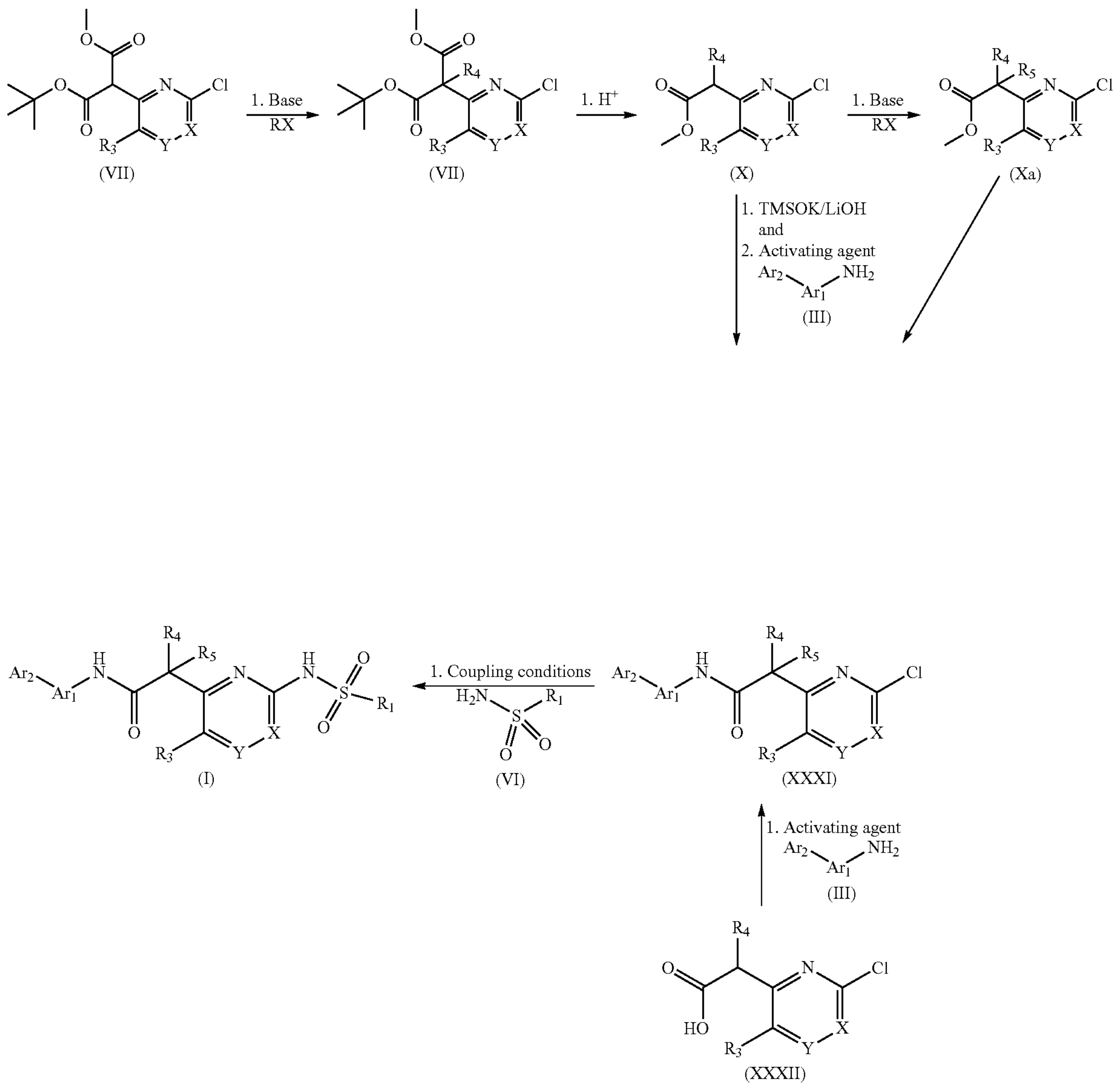

In general and as illustrated in Scheme 8, the compounds of formula (I) where $R_1$, $R_3$, Ar1 and Ar2 are defined above, where X=N and Y=CH, where $R_4$=H, $C_{1-6}$alkyl or $CH_2CH_2OMe$ and where $R_5$=H may be prepared in four or five steps starting from an intermediate of general formula (VII). Alkylation can be achieved by treatment of intermediate (VII) with an inorganic base, such as sodium hydroxide, in the presence of an alkylating agent, such as iodoethane to yield compounds of the general formula (V). Decarboxylation can be initiated with a strong acid such as TFA to obtain intermediates of formula (X). Such intermediates may then undergo saponification and amide coupling according to methods described in Scheme 1 to give compounds of formula (XXXI). Final compounds of formula (I) can be accessed by coupling intermediates of formula (XXXI) with a primary sulfonamide as previously described in Schemes 1a and 1b.

In general and as illustrated in Scheme 8, the compounds of formula (I) where $R_1$, $R_3$, Ar1 and Ar2 are defined above, where X=CH and Y=N, where $R_4$=H or $CH_2CH_2OMe$ and where $R_5$=H or Me, may be prepared in starting from an intermediate of general formula (VIII) following comparable methods to those described for when X=N and Y=CH in Scheme 8. If a linker where $R_5$=Me is required alkylation of intermediates of formula (X) may be treated with an alkylating agent in the presence of a base to generate intermediates such as (Xa). Compounds of formula (Xa) can then be converted to final compounds via a three step procedure as described in Scheme 8.

Compounds of general formula (XXXI) when $R_4$=$R_5$=H and X=CH and Y=N may also be obtained by coupling commercial acids of formula (XXXII) with anilines of formula (III) under amide coupling conditions previously described. Compounds of this type can then be progressed to compounds of formula (I) using the previously described sulfamidation conditions.

Scheme 9a

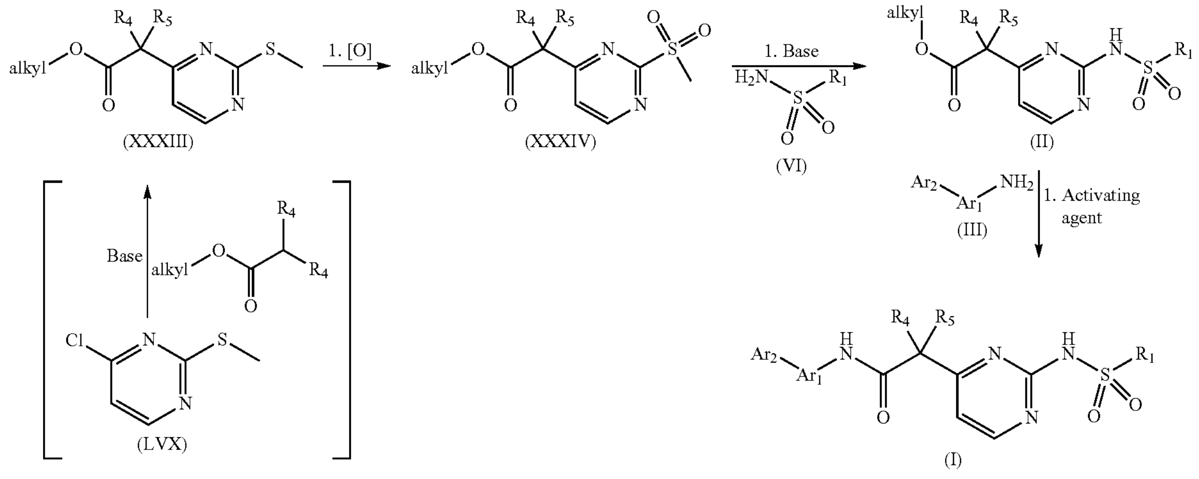

In general and as illustrated in Scheme 9a, compounds of formula (I) wherein $R_1$, Ar1 and Ar2 are as defined above, alkyl is $C_{1-4}$alkyl such as methyl or ethyl, e.g. methyl, and for example, $R_4$ and $R_5$ together with the carbon atom to which they are attached form a $C_{3-6}$heterocycloalkyl ring may be prepared in four steps from chloro-pyrimidine (LVX). Intermediates (XXXVII) are coupled to chloro-pyrimidine (LVX) in the presence of a base such as LHMDS to give intermediates (XXXIII). Thioethers of the general formula (XXXIII) may be transformed to sulfones (XXXIV) in the presence of an oxidising agent such as mCPBA. Displacement of the sulfone group with a primary sulphonamide (VI) in the presence of a base such as $Cs_2CO_3$ and a solvent such as N-methyl pyrrolidone gives compounds of formula (II). Compounds of formula (I) may be obtained by a strong base-mediated amide formation between compounds (II) and (III) at room temperature using bases such as iPrMgCl, LiHMDS or KOtBu.

Scheme 9b

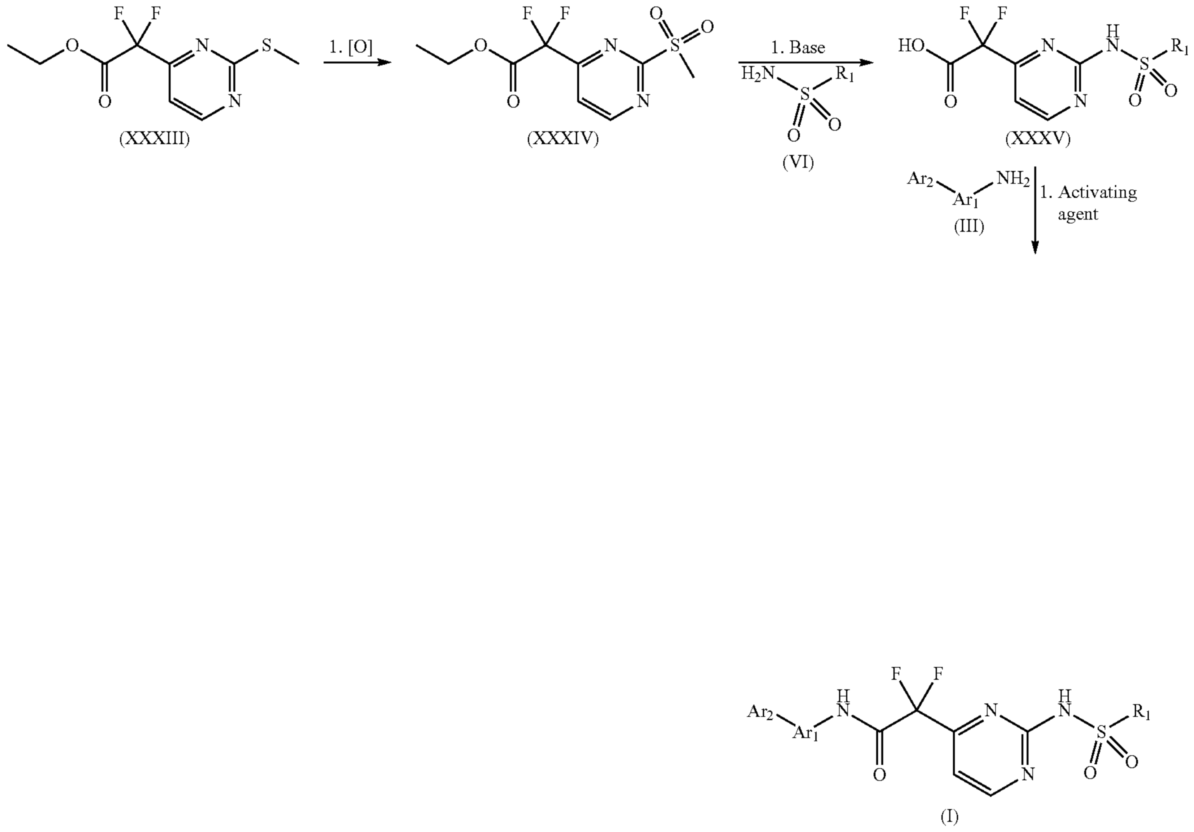

In general and as illustrated in Scheme 9b, compounds of general formula (I) wherein $R_4$ and $R_5$ are both F, $R_1$, Ar1 and Ar2 are defined above may be prepared in 3 steps from literature compound ethyl 2,2-difluoro-2-(2-(methylthio)pyrimidin-4-yl)acetate (XXXIII) i.e. $R_4$=$R_5$=F.

Thioethers of the general formula (XXXIII) may be transformed to sulfones (XXXIV) in the presence of an oxidising agent such as Oxone® at room temperature in a polar protic solvent such as MeOH. Displacement of the sulfone group with a primary sulphonamide (VI) and subsequent ester hydrolysis to give acids of the general formula (XXXV) can be performed in a one pot procedure in the presence of a strong base such as NaH and in a polar aprotic solvent such as DMF. Acid derivative (XXXV) can then be activated with a coupling reagent such as HATU in the presence of a base and coupled with an aniline such as (III) to obtain the final compounds of formula (I).

-continued

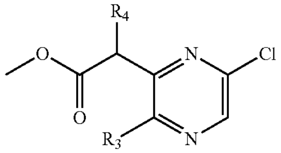

(X)

Scheme 10

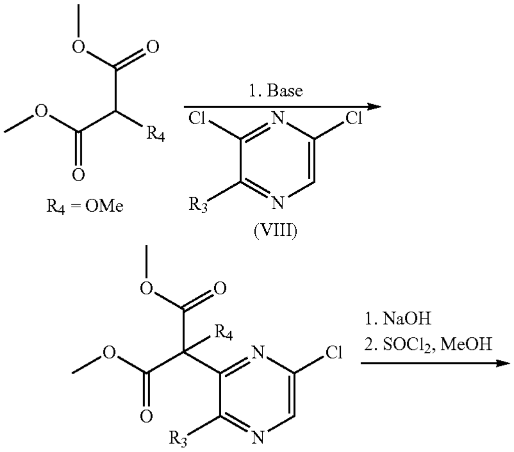

$R_4$ = OMe (VIII)

(V)

In general and as illustrated in Scheme 10, the compounds of general formula (X) where $R_1$, $R_3$, Ar1 and Ar2 are defined above and where $R_4$=OMe may be prepared in four, five or six steps starting from a 2,4-dichloropyrazine derivative of general formula (VIII). Derivative (VIII) can be reacted with a symmetrical malonate ester when $R_4$. =OMe in the presence of a strong base such as sodium hydride and in a polar solvent such as DMF to form intermediate compounds of formula (V). A two-step procedure can then be carried out to access compounds of general structure (X). Firstly saponification using an alkali metal hydroxide such as NaOH can generate the biscarboxylic acid which once acidified may undergo spontaneous decarboxylation. The resulting carboxylic acid can then be converted to esters of general formula (X) by treatment with an activating agent such as thionyl chloride in the presence of an alcoholic solvent such as methanol. Derivatives of formula (X) can be converted to final compounds for formula (I) using methods previously described in Schemes 5a and 5b.

Scheme 11

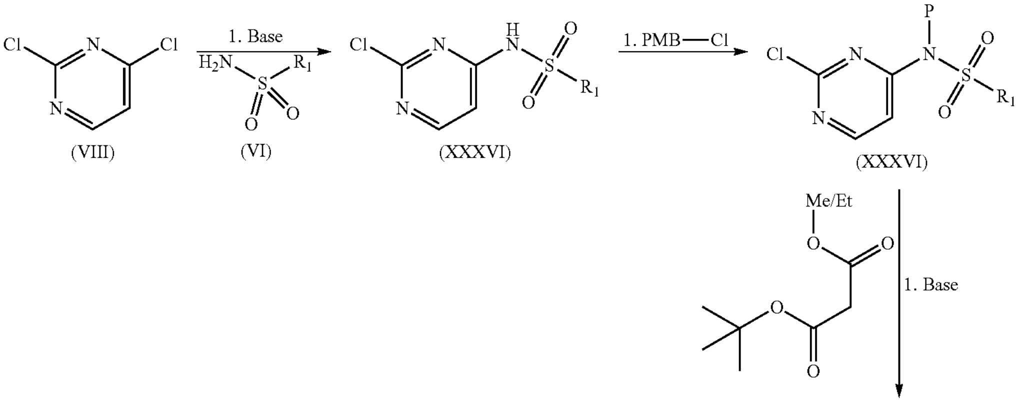

(VIII) (VI) (XXXVI) (XXXVI)

-continued

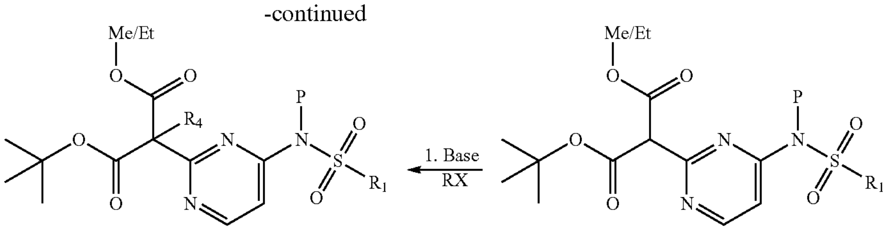

(XXXVIII) (XXXVIII)

In general and as illustrated in Scheme 11, the compounds of formula (XXVIII) where $R_1$ is defined above and where $R_4$=H or Et, may be prepared in seven steps starting from a 2,4-dichloropyrimidine derivative of general formula (VIII). The derivative (VIII) can be reacted with sulfonamide of type (VI) in the presence of an inorganic base such as potassium carbonate to displace the more reactive chloride and form intermediate compounds of formula (XXXVI). Compounds of formula (XXXVI) may be protected e.g. using PMB-Cl to give compounds of formula (XXXVII).

This compound can then be converted to compounds of general formula (XXXVIII) by treatment with an unsymmetrical malonate in the presence of a base such as cesium carbonate in a solvent such as dimethoxyethane.

If mono alkylation is desired then treatment of intermediate (XXXVIII) with an inorganic base, such as potassium carbonate, in the presence of an alkylating agent, such as EtI, yields compounds of the general formula (XXVIII). This compound can then be converted to final compounds of formula (I) using methods previously described in Scheme 4b.

Wherein $R_4$=H, compounds of general formula (XXXVIII) can be taken directly to compounds of general formula (I) (such as described above).

Benzamide Pyrimidines

Scheme 12

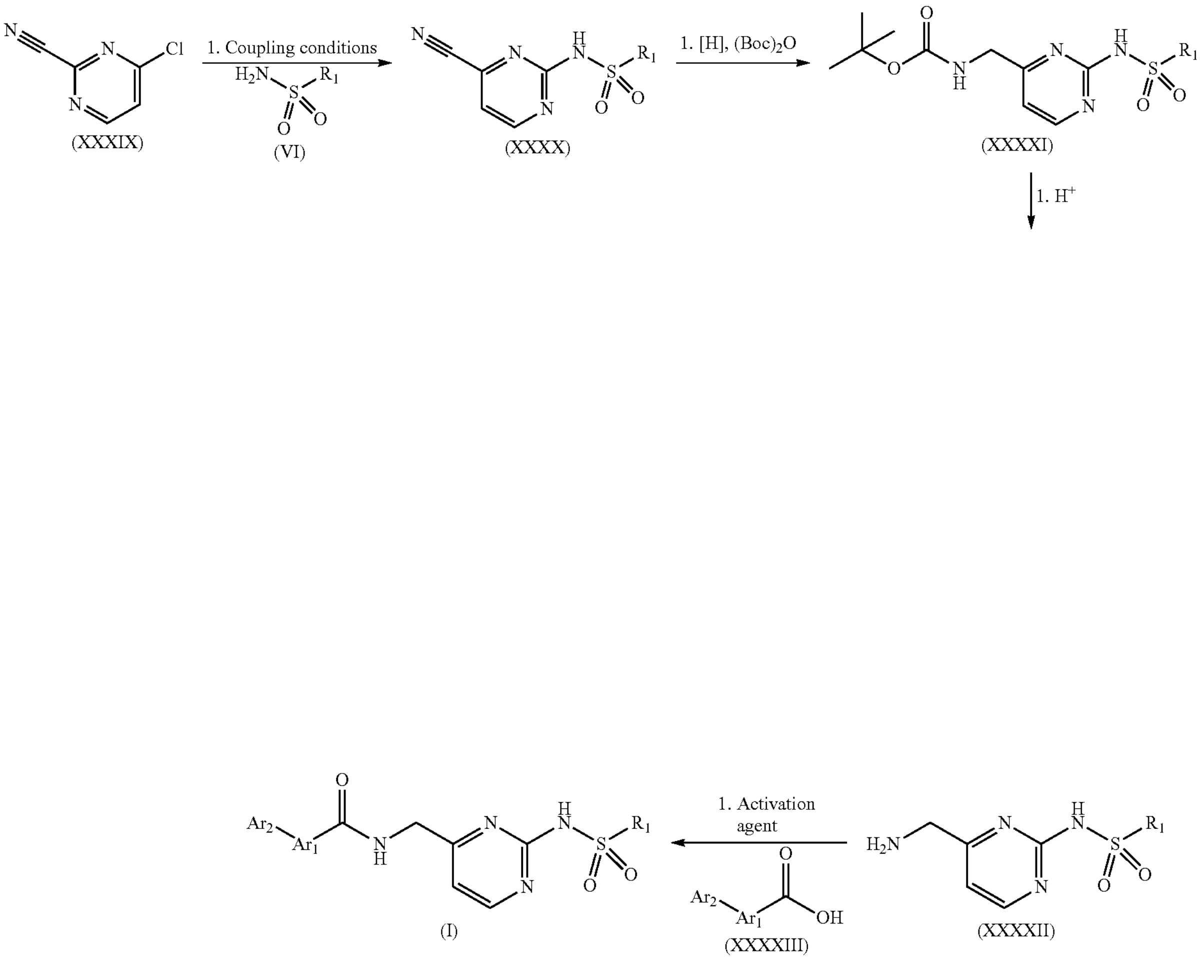

(XXXIX) (VI) (XXXX) (XXXXI) (I) (XXXXIII) (XXXXII)

Compounds of general formula (I) may be obtained by a four step process, as shown in Scheme 12. 2-Chloropyrimidine-4-carbonitrile (XXXIX) can be converted to the corresponding sulfonamide (XXXX) using palladium catalysed sulfamination conditions previously reported in Scheme 1. Reduction of the nitrile group using sodium borohydride in the presence of nickel (II) chloride and di-tert-butyl dicarbonate may yield the protected benzylamine derivative of general formula (XXXXI). Deprotection can be carried out by acid hydrolysis using HCl in dioxane to yield benzylamine derivative of general formula (XXXXII). Amide coupling conditions may then be employed to convert the benzylamine derivative (XXXXII) to amides of general formula (I) by employing a coupling reagent together with a biaryl carboxylic acid (XXXXIII) (commercially available or prepared as in Schemes 19a and 19b).

Compounds of general formula (I) where A is an amine linker such as —$CH_2NH$—, where $R_1$, $Ar_1$ and $Ar_2$ are defined above, $R_4$ is $C_{1-6}$alkyl and $R_5$ is H or $C_{1-6}$alkyl or $R_4$ and $R_5$ together with the carbon to which they are attached form a $C_{3-6}$cycloalkyl or $C_{3-6}$heterocycloalkyl may be accessed in one step from benzyl amines such as (XXXXII). Reaction of (XXXXII) with aromatic aldehydes (LXXII) in the presence of a hydride source such as sodium triacetoxyborohydride may yield amines of formula (I).

Scheme 13a

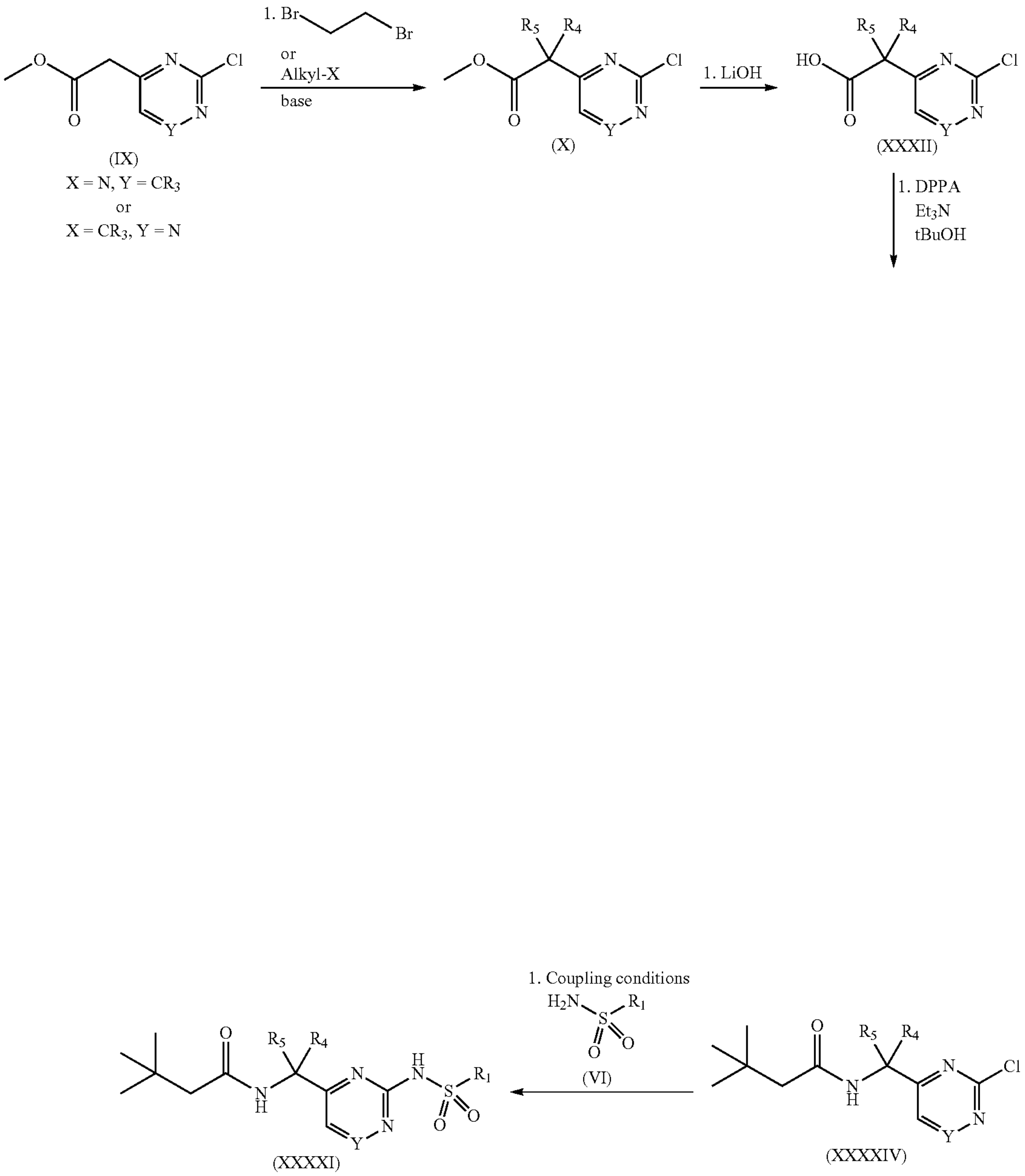

(IX)
X = N, Y = $CR_3$
or
X = $CR_3$, Y = N (X)

(XXXII)

(XXXXI)

(XXXXIV)

Compounds of general formula (I) where $R_1$, $Ar_1$ and $Ar_2$ are defined above, X═N and Y═CH, $R_3$ is H, $R_4$ is $C_{1-6}$alkyl and $R_5$ is H or $C_{1-6}$alkyl or $R_4$ and $R_5$ together with the carbon to which they are attached form a $C_{3-6}$cycloalkyl may be obtained by a six step process, as shown in Scheme 13 (and Scheme 12 for certain steps). Firstly, the derivative (IX) can be reacted with an alkyl halide to give compounds of general formula (X) where $R_4$=alkyl and $R_5$═H. Alternatively derivative (IX) can be reacted with an alkyl bis-halide to give compounds of general formula (X) where $R_4$ and $R_5$ can be connected to form a $C_{3-6}$heterocycloalkyl ring as defined above. Carboxylic acid (XXXII) can be obtained by hydrolysis of methyl ester (X) using an alkali metal base such as lithium hydroxide in a solvent mixture such as THF/MeOH. Curtius rearrangement can be carried out, for example, using diphenylphosphoryl azide in the presence of triethylamine and tert-butanol to yield carbamates such as (XXXXIV). The corresponding sulfonamide (XXXXI) may then be accessed by a palladium catalysed sulfamination employing conditions previously reported in Scheme 1. Carbamates of formula (XXXXI) can then be progressed to final compounds of formula (I) following Scheme 12.

Compounds of general formula (I) where $R_1$, $Ar_1$ and $Ar_2$ are defined above, X═CH and Y═N, $R_4$ is $C_{1-6}$alkyl and $R_5$ is H may be obtained by a four step process starting from a commercially available acid of formula (XXXII) following the subsequent steps described in Scheme 13a.

Scheme 13b

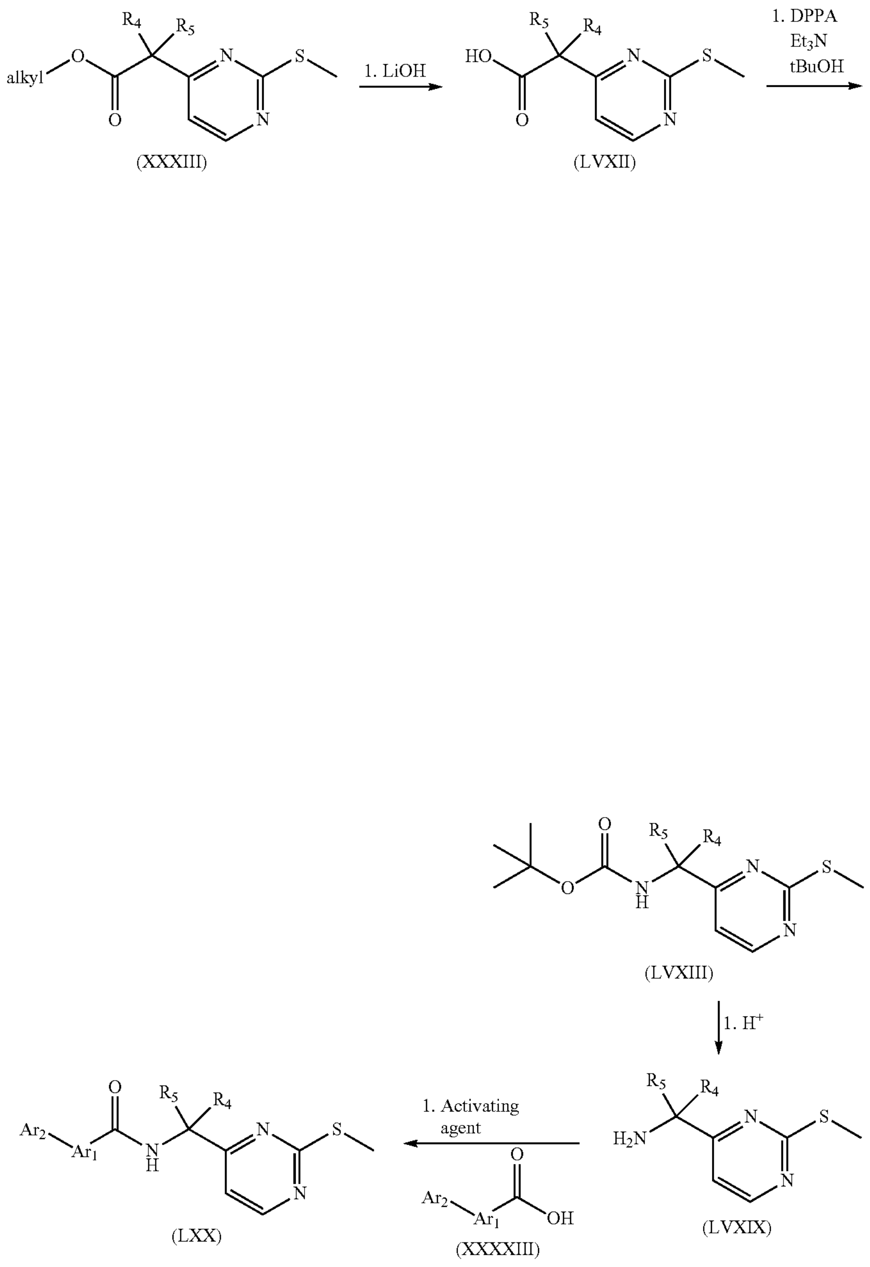

(XXXIII)

(LVXII)

(LVXIII)

(LVXIX)

(XXXXIII)

(LXX)

Compounds of general formula (I) where $R_1$, $Ar_1$ and $Ar_2$ are defined above, $R_4$ is $C_{1-6}$alkyl and $R_5$ is H or $C_{1-5}$alkyl or $R_4$ and $R_5$ together with the carbon to which they are attached form a $C_{3-6}$cycloalkyl or $C_{3-6}$heterocycloalkyl may be obtained by a six step process, as shown in Scheme 13b. Firstly, the carboxylic acid (LVXII) can be obtained by hydrolysis of methyl ester (XXXII) using an alkali metal base such as lithium hydroxide. Curtius rearrangement can be carried out, for example, using diphenylphosphoryl azide in the presence of propylphosphonic anhydride, triethylamine and tert-butanol to yield carbamates such as (LVXIII). Deprotection can be carried out by acid hydrolysis using HCl in dioxane to yield benzylamine derivative of general formula (LVXIX). Amide coupling conditions may then be employed to convert the benzylamine derivative (LVXIX) to amides of general formula (LXX) by employing a coupling reagent together with a biaryl carboxylic acid (XXXXIII) (commercially available or prepared as in Scheme 19). Compound of formula (LXX) can then be progressed to compounds of formula (I) following the oxidation, displacement sequence described in Scheme 22.

Scheme 14

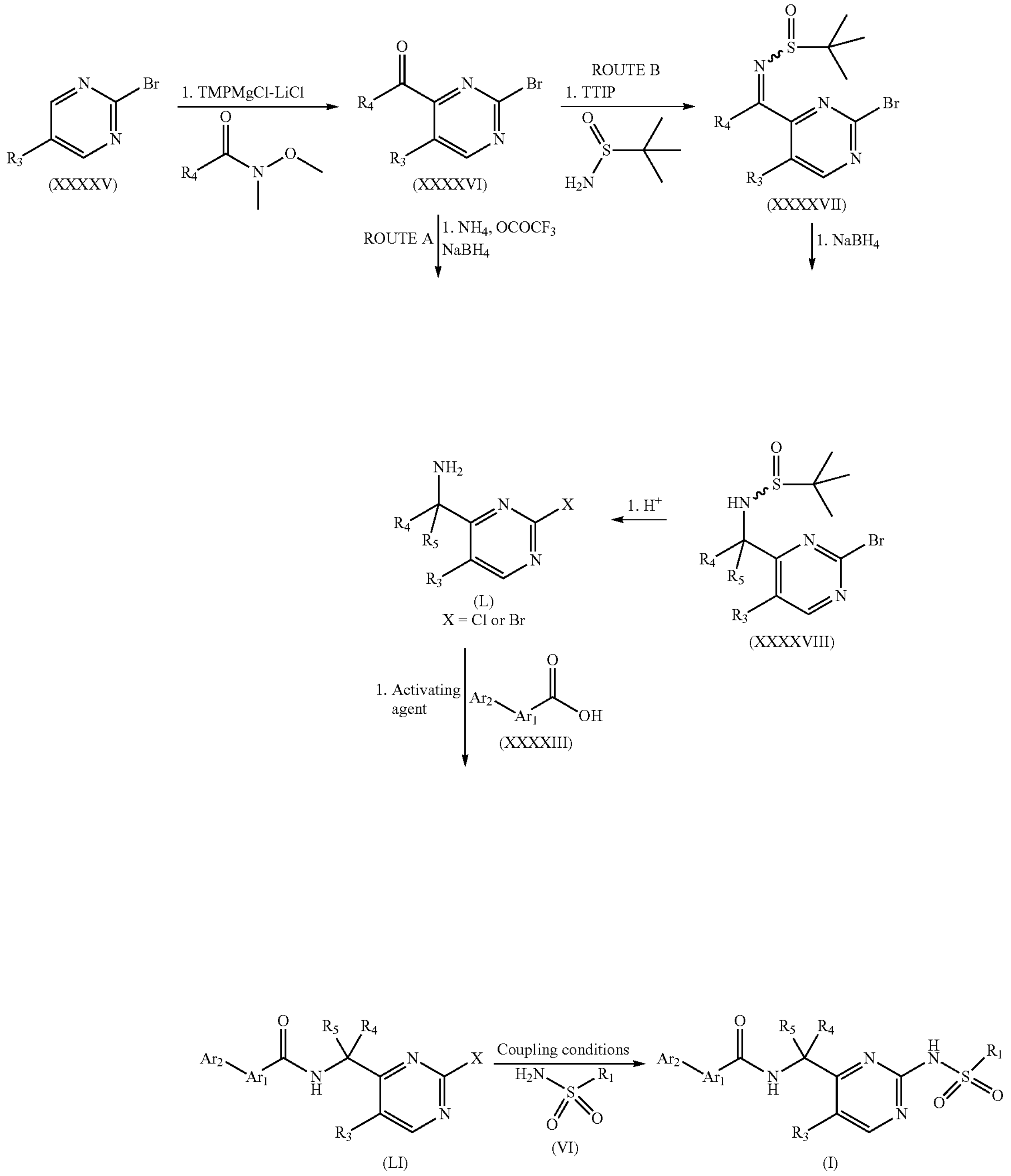

The pyrimidin-4-yl(propan-2-yl)benzamide derivatives of formula (I) in which $R_1$, $R_3$, Ar1 and Ar2 are defined above, $R_4$=alkyl and $R_5$=H may be prepared by two different routes as shown in Scheme 14. The two routes both begin by conversion of 2-bromopyrimidine to the corresponding ketone (XXXXVI) by treatment with a suitable base such as TMPMgCl.LiCl followed by exposure to the Weinreb amide derivative. The two routes then converge at compounds of general formula (L) where they are then taken onto the final analogues by a two-step process.

ROUTE A: Treatment of ketone derivatives (XXXXVI) with ammonium trifluoroacetate followed by reduction using sodium borohydride may yield the benzylamine (L).

ROUTE B: Ketone of the general formula (XXXXVI) is converted to sulfinamide (XXXXVII) by treatment with a Lewis acid such as titanium isopropoxide followed by exposure to a sulfinimine such as 2-methylpropane-2-sulfinamide. Reduction using sodium borohydride may yield the sulfinamide (XXXXVIII). The intermediate of formula (XXXXVIII) may then be deprotected using a strong acid, such as HCl which may also lead to halogen exchange to give amines of general formula (L) where X=Cl.

Amide coupling conditions reported in Scheme 12 may then be employed to convert the benzylamine derivatives (L) to amides of general formula (U). A palladium catalysed sulfamination as described in Scheme 12 may yield compounds of the general formula (I).

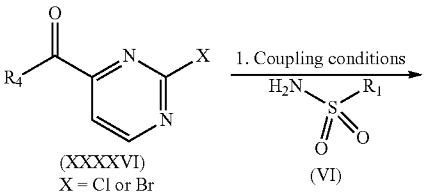

(XXXXVI)
X = Cl or Br (VI)

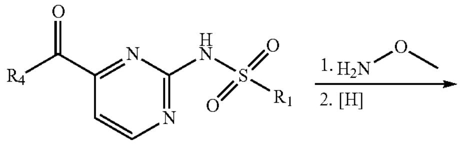

(LII)

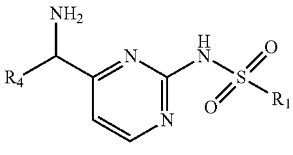

(XXXXII)

In general and as illustrated in Scheme 15, compounds of general formula (XXXXII) may be obtained by a three step process from a ketone derivative of general formula (XXXXVI). Sulfamidation of derivative (XXXXVI) may be carried out using conditions described in Scheme 12 to give compounds of formula (LII). Oxime formation with methoxyamine can be followed by reduction in the presence of a suitable catalyst such as Pd/C under an atmosphere of $H_2$ gas in a polar protic solvent such as MeOH to afford amine derivatives of general formula (XXXXII). Amines of this type can be progressed to final compounds following Scheme 12.

Scheme 16

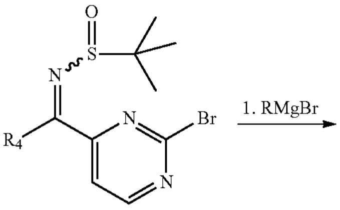

(XXXXVII)

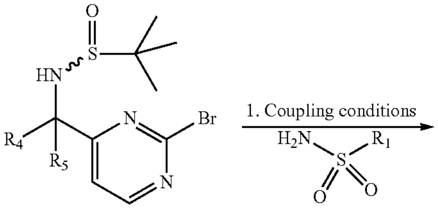

(XXXXVIII)

(VI)

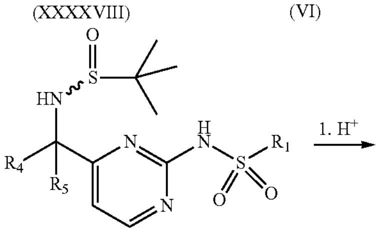

(LIII)

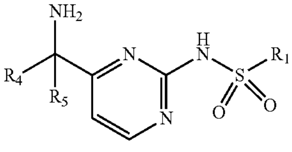

(XXXXII)

Alternatively, compounds of general formula (XXXXII) may be obtained by a three step process, as shown in Scheme 16. N-(2-(2-bromopyrimidin-4-yl)butan-2-yl)-2-methylpropane-2-sulfinamide (XXXXVII) can be synthesized as described above (Scheme 14). The imine can then be exposed to a nucleophile such as MeMgBr to yield intermediates such as (XXXXVIII). The corresponding sulfonamide (LIII) may then be accessed by a palladium catalysed sulfamination as described in Scheme 1. Deprotection can be carried out by acid hydrolysis using HCl to yield the benzylamine derivatives of general formula (XXXXII) which can then be converted to final compounds following Scheme 12.

Scheme 17

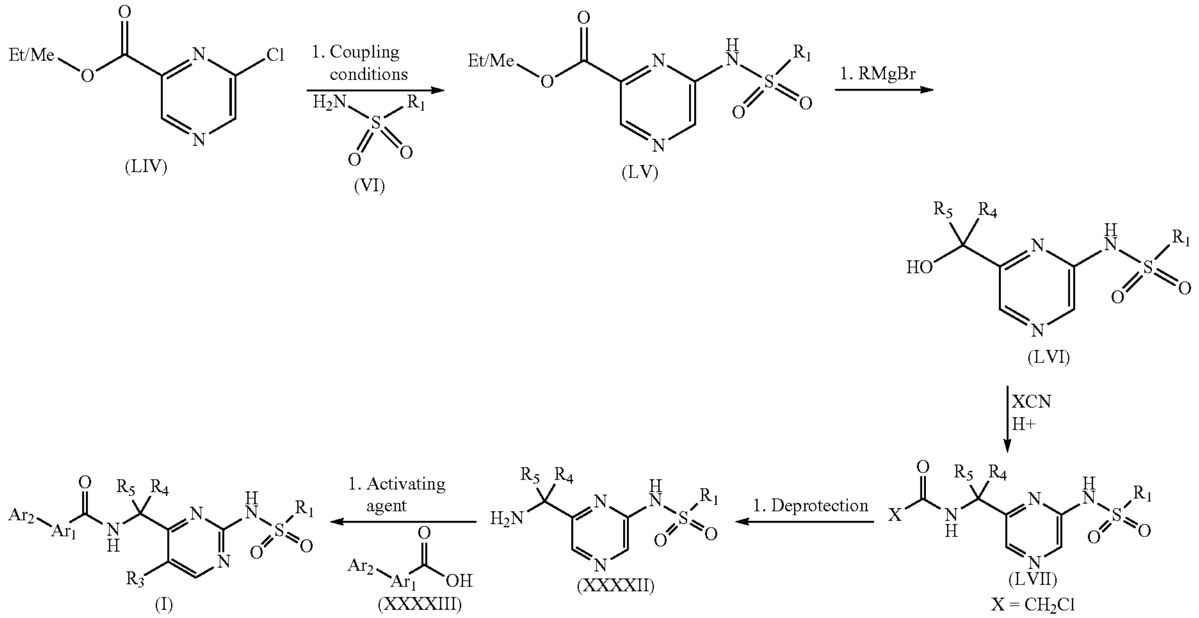

(LIV) (VI) (LV) (LVI) (LVII) (XXXXII) (XXXXIII) (I)

The benzamide derivatives of formula (I) in which $R_1$, $R_3$, Ar1 and Ar2 are defined above and $R_4 = R_5 =$alkyl may be prepared in 5 steps as described in Scheme 17 by coupling a commercial aromatic chloride such as (UV) with a primary sulfonamide using sulfamidation conditions described in Schemes 1a and 1b. A double Grignard addition may then be carried out in an aprotic solvent such as THF to form intermediates of formula (LVI). A Ritter type reaction may then be undertaken using an alkylnitrile, such as 2-chloro-acetonitrile in the presence of an acid such as $H_2SO_4$. The intermediate of formula (LVII) can be deprotected by reaction with thiourea in a protic solvent such as ethanol in the presence of acetic acid and heated under reflux to yield the benzylamine derivatives (XXXXII). Final compounds of formula (I) can be accessed using amide coupling conditions reported in Scheme 12.

-continued

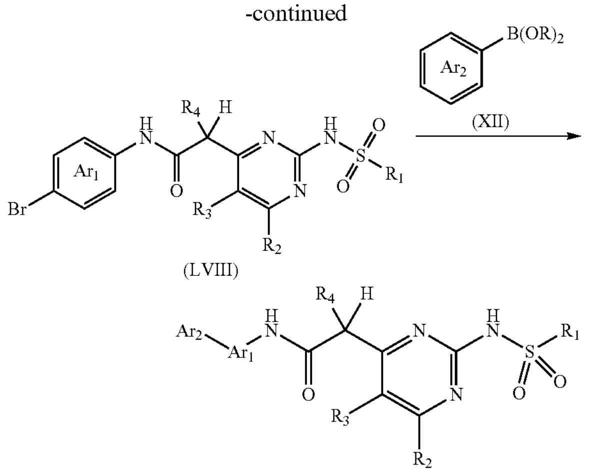
(XII) (LVIII) (I)

Scheme 18

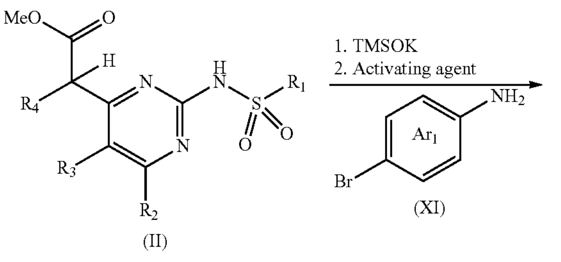

(II) (XI)

In general and as illustrated in Scheme 18 compounds of general formula (I) can be prepared by conversion of intermediate (II) by a three step process. Firstly, saponification of (II) using an agent such as TMSOK gives the intermediate carboxylic acid derivative, which may be followed by reaction with an activating agent such as T3P and a bromo-aniline of formula (XI). Intermediates of formula (LVIII) are then converted to compound of the invention of general formula (I) by coupling under Suzuki conditions with a boronate ester of general formula (XII). The boronate is usually a dihydroxyboryl or dialkyloxyboryl group, usually a 4,4,5,5-tetramethyl-1,3,3,2-dioxaborolan-2-y group. The couplings according to the Suzuki method are performed, for example, by heating in the presence of a catalyst such as [1,1'-bis(diphenylphosphino)ferrocene]dichloropalladium (II) and an inorganic base such as potassium carbonate in a solvent mixture of dioxane and water. It will be understood by persons skilled in the art that many catalysts and conditions can be employed for such couplings.

Scheme 19a

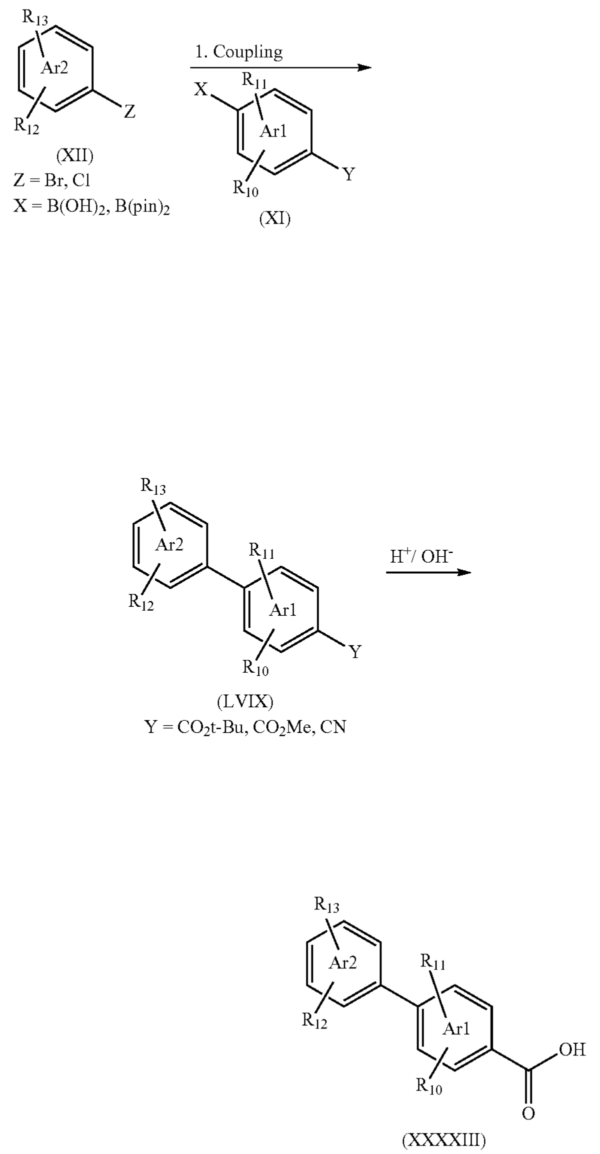

(XII)
Z = Br, Cl
X = B(OH)2, B(pin)2
(XI)
(LVIX)
Y = CO2t-Bu, CO2Me, CN
(XXXXIII)

Intermediates of formula (XXXXIII) where $Ar_2$ is an unsubstituted or substituted 2-pyrazine ring or 3-pyridyl ring, may be synthesised as shown in Scheme 19 by coupling under Suzuki conditions of an aromatic halide of general formula (XII), of which $R_{12}$ and $R_{13}$ are defined above and Z represents Br or Cl, to a boronate of general formula (XI) wherein $R_{10}$ and $R_{11}$ are defined above, X denotes a dihydroxyboryl or dialkyloxyboryl group, such as a 4,4,5,5-tetramethyl-1,3,3,2-dioxaborolan-2-yl group. The couplings according to the Suzuki method are performed, for example, by heating in the presence of a catalyst such as [1,1'-bis(diphenylphosphino)ferrocene]dichloropalladium (II).$CH_2Cl_2$ adduct and an inorganic base such as cesium carbonate in a solvent mixture of dioxane and water under an inert atmosphere such as a nitrogen atmosphere to give compounds of formula (LVIX). The carboxylic acids of general formula (XXXXIII) are obtained by either deprotection of the t-butyl ester using a strong acid, such as TFA in a solvent of $CH_2Cl_2$, hydrolysis of the methyl ester using an alkali metal hydroxide such as NaOH in a solvent mixture such as THF/MeOH or hydrolysis of the nitrile using a strong acid such as concentrated HCl.

Scheme 19b

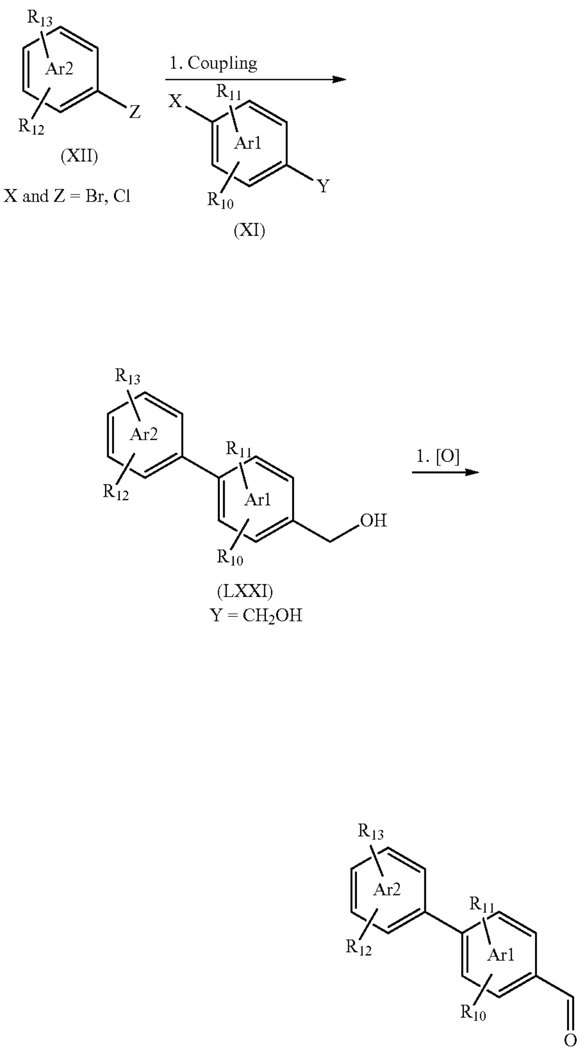

(XII)
X and Z = Br, Cl
(XI)
(LXXI)
Y = CH2OH
(LXXII)

Intermediates of formula (LXXII) where $Ar_2$ is an unsubstituted or substituted 2-pyrazine ring or 3-pyridyl ring, may be synthesised as shown in Scheme 19b, in a one-pot, two step procedure starting with borylation of (XI), where X denotes a halogen such as Br or Cl. followed by coupling under Suzuki conditions with an aromatic halide of general formula (XII), of which $R_{12}$ and $R_{13}$ are defined above and Z represents Br or Cl. Initially compounds such as (XI), can be converted to the corresponding boronate using a catalyst such as [1,1'-bis(diphenylphosphino)ferrocene]dichloropalladium(II).$CH_2Cl_2$ adduct and an inorganic base such as potassium acetate in a solvent such as dioxane. Aromatic halide (XII) may then be added to the reaction mixture along with an aqueous solution of an inorganic base such as caesium carbonate to yield alcohols of formula (LXXI). The aldehydes of general formula (LXXII) are obtained by treatment with an oxidant such as manganese dioxide.

Scheme 20

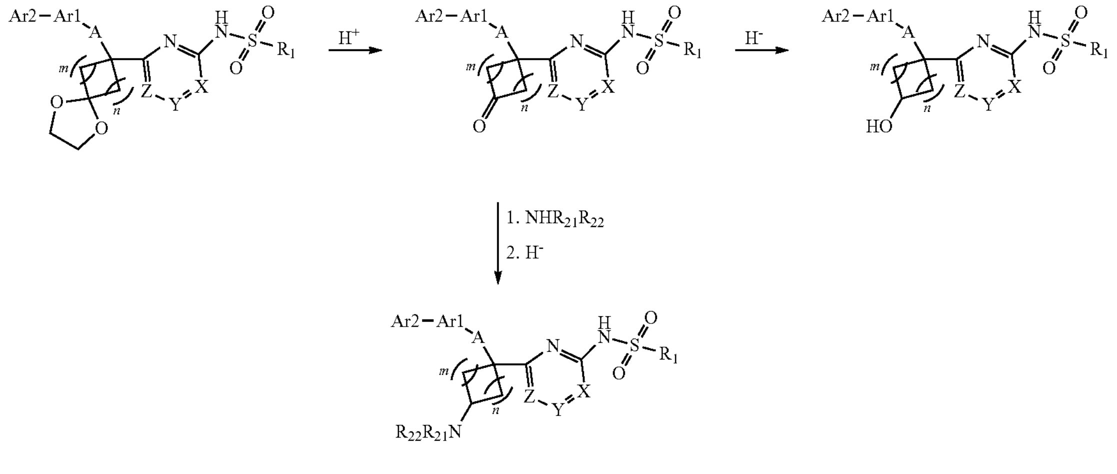

In general compounds of formula (I) where $R_4$ and $R_5$ together with the carbon to which they are attached form a 1,4-dioxaspiro[4.5]decane may be treated with a strong acid, such as HCl, to yield cyclic ketones of formula (I). Such ketones may then be treated with a hydride source, such as sodium borohydride, to yield the corresponding exocyclic alcohol or reacted with an amine, such as dimethylamine, followed by sodium triacetoxyborohydride to yield exocyclic amines of formula (I).

Scheme 21

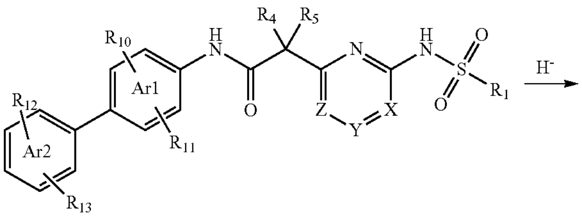

(I) - amide

-continued

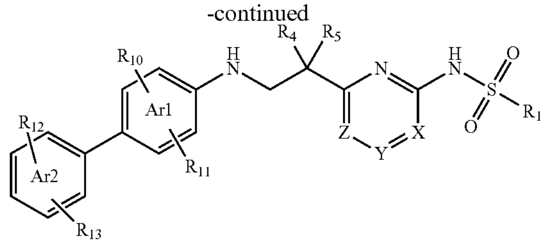

(I) -amine

Compounds of formula (I) wherein A is —$NR_6CH_2$— can be obtained from compounds of formula (I) wherein A is —$NR_6C(=O)$—, by the reduction of the amide to the amine using a reducing agent such as $LiAlH_4$ in a solvent such as THF.

Scheme 22

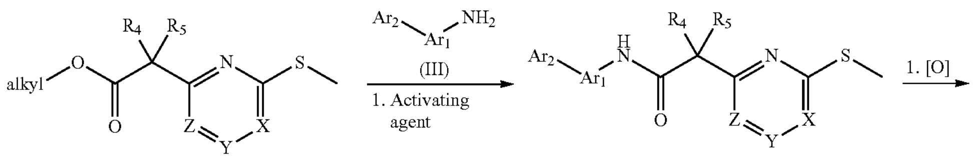

(XXXIII) (LXXIII)

-continued

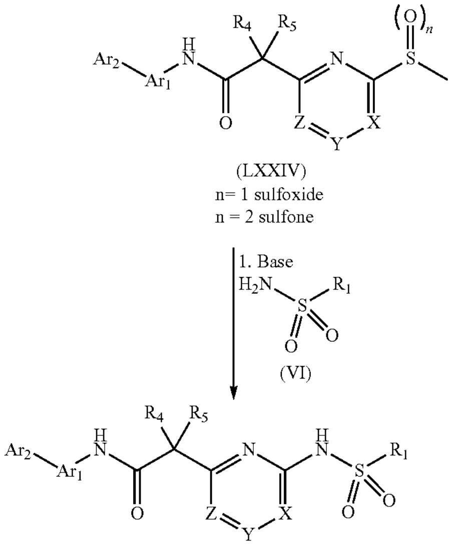

(LXXIV)
n= 1 sulfoxide
n = 2 sulfone (VI)

(I)

In general and as illustrated in Scheme 22, compounds of formula (I) wherein $R_1$, Ar1 and Ar2 are as defined above, alkyl is $C_{1-4}$alkyl such as methyl or ethyl, e.g. methyl, and for example, $R_4$ and $R_5$ together with the carbon atom to which they are attached form a $C_{3-6}$heterocycloalkyl ring may be prepared starting from a general intermediate of formula (XXXIII). Intermediates such as (LXXIV) may be obtained by subjecting compounds such as (XXXIII) to amide coupling conditions such as those described in Scheme 9a using iPrMgCl. Thioethers of the general formula (LXXIII) may be transformed to sulfoxides or sulfones (LXXIV) in the presence of an oxidising agent such as mCPBA. Displacement of the sulfone group with a primary sulphonamide (VI) in the presence of a base such as $Cs_2CO_3$ and a solvent such as N-methyl pyrrolidone gives compounds of formula (I).

Scheme 22b

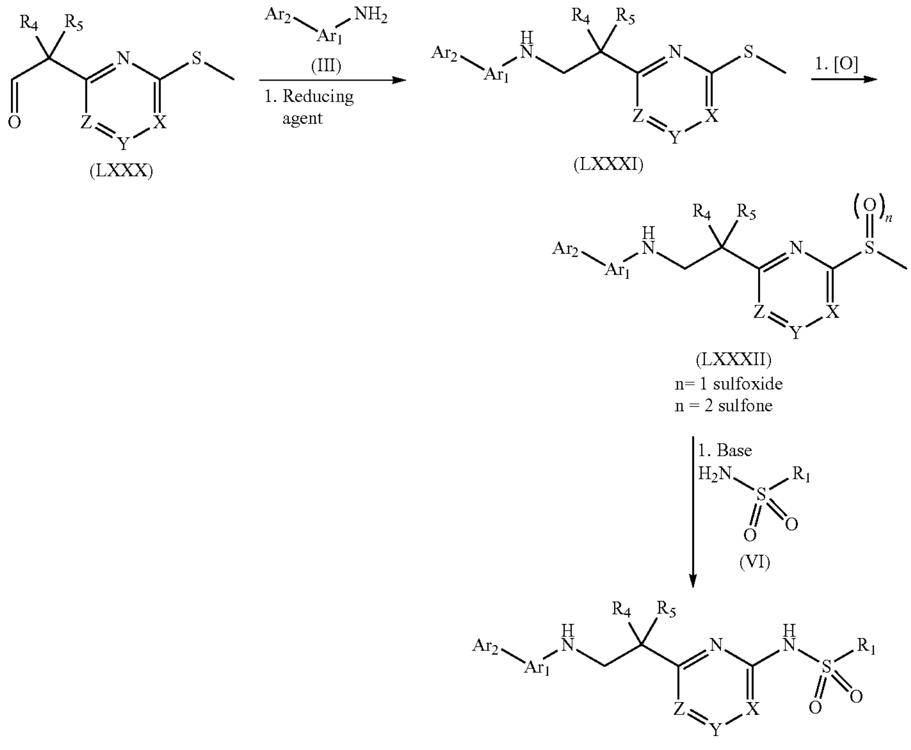

(LXXX)

(III)

(LXXXI)

(LXXXII)
n= 1 sulfoxide
n = 2 sulfone (VI)

(I)

In general and as illustrated in Scheme 22b, compounds of formula (I) wherein $R_1$, Ar1 and Ar2 are as defined above, alkyl is $C_{1-4}$alkyl such as methyl or ethyl, e.g. methyl, and for example, $R_4$ and $R_5$ together with the carbon atom to which they are attached form a $C_{3-6}$heterocycloalkyl ring may be prepared starting from a general intermediate of formula (LXXX). Intermediates such as (LXXXI) may be obtained by subjecting compounds such as (LXXX) and (III) to reductive amination conditions such as those described in Scheme 20. Thioethers of the general formula (LXXXI) may be transformed to sulfoxides or sulfones (LXXXII) in the presence of an oxidising agent such as mCPBA. Displacement of the sulfone group with a primary sulphonamide (VI) in the presence of a base such as $Cs_2CO_3$ and a solvent such as N-methyl pyrrolidone gives compounds of formula (I).

Scheme 23

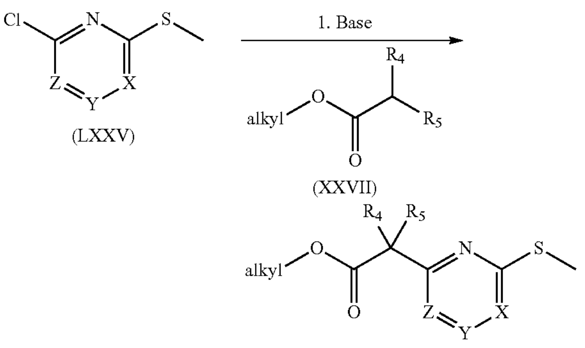

(LXXV)

(XXVII)

(LXXVI)

In general and as illustrated in Scheme 23, compounds of formula (I) wherein $R_1$, Ar1 and Ar2 are as defined above, alkyl is $C_{1-4}$alkyl such as methyl or ethyl, e.g. methyl, and for example, $R_4$ and $R_5$ together with the carbon atom to which they are attached form a $C_{3-6}$heterocycloalkyl ring may be prepared starting from chloro-pyrimidine (LXXV). Intermediates (XXXVII) are coupled to chloro-pyrimidine (LXXV) in the presence of a base such as LHMDS to give intermediates (LXXVI). Thioethers of the general formula (LXXVI) may then be transformed to compounds of formula (I) following the route described in Scheme 9a.

Scheme 24

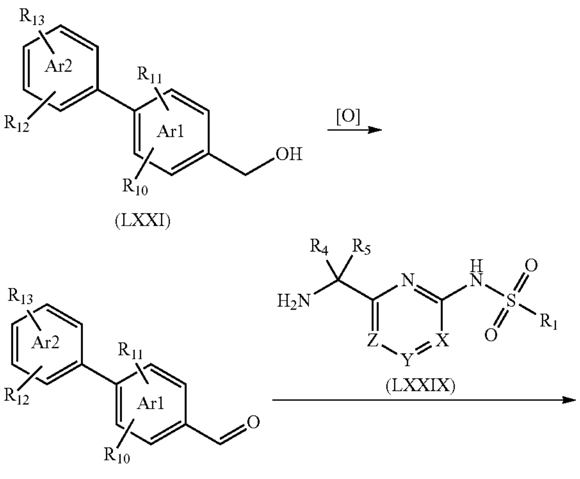

(LXXI)

(LXXIX)

(LXXII)

-continued

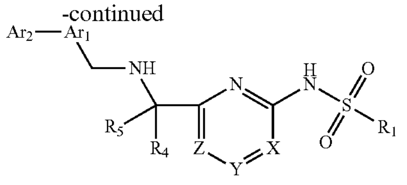

(I)

In general and as illustrated in Scheme 24, compounds of formula (I) wherein $R_1$, Ar1 and Ar2 are as defined above, $R_4$ and $R_5$ together with the carbon atom to which they are attached form a $C_{3-6}$heterocycloalkyl ring may be prepared starting from alcohols (LXXI), which as oxidised to aldehydes (LXXII) in the presence of $MnO_2$ in a non-protic solvent such as DCM. Reductive coupling of amine (LXXIX) and aldehyde (LXXII) in the presence of a hydride source such as sodium triacetoxyborohydride in an aprotic solvent such as DCM in the presence of a proton source such as acetic acid affords compounds of formula (I) following the route described in Scheme 24.

Scheme 25

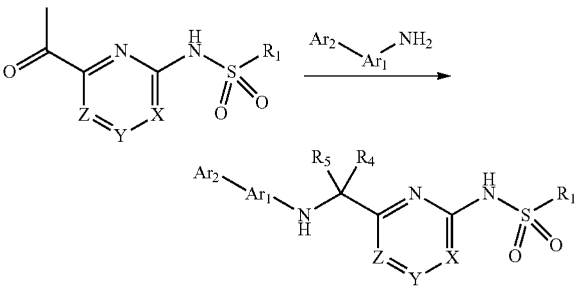

Compounds of formula (I) wherein A is —NH— and $R_4$ or $R_5$ is H may be prepared by reductive coupling of the appropriate amine and aldehyde in the presence of a hydride source such as sodium triacetoxyborohydride.

The skilled person will appreciate that compounds of formula (I) wherein B is

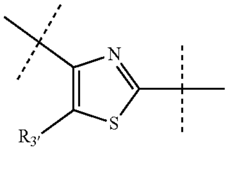

may be synthesised using methods analogous to those shown in the schemes above or those provided in WO2019/106156 and WO2019/106146.

Certain thiazole starting materials are commercially available. Alternatively, the thiazole group may be introduced using the following method:

Scheme 26

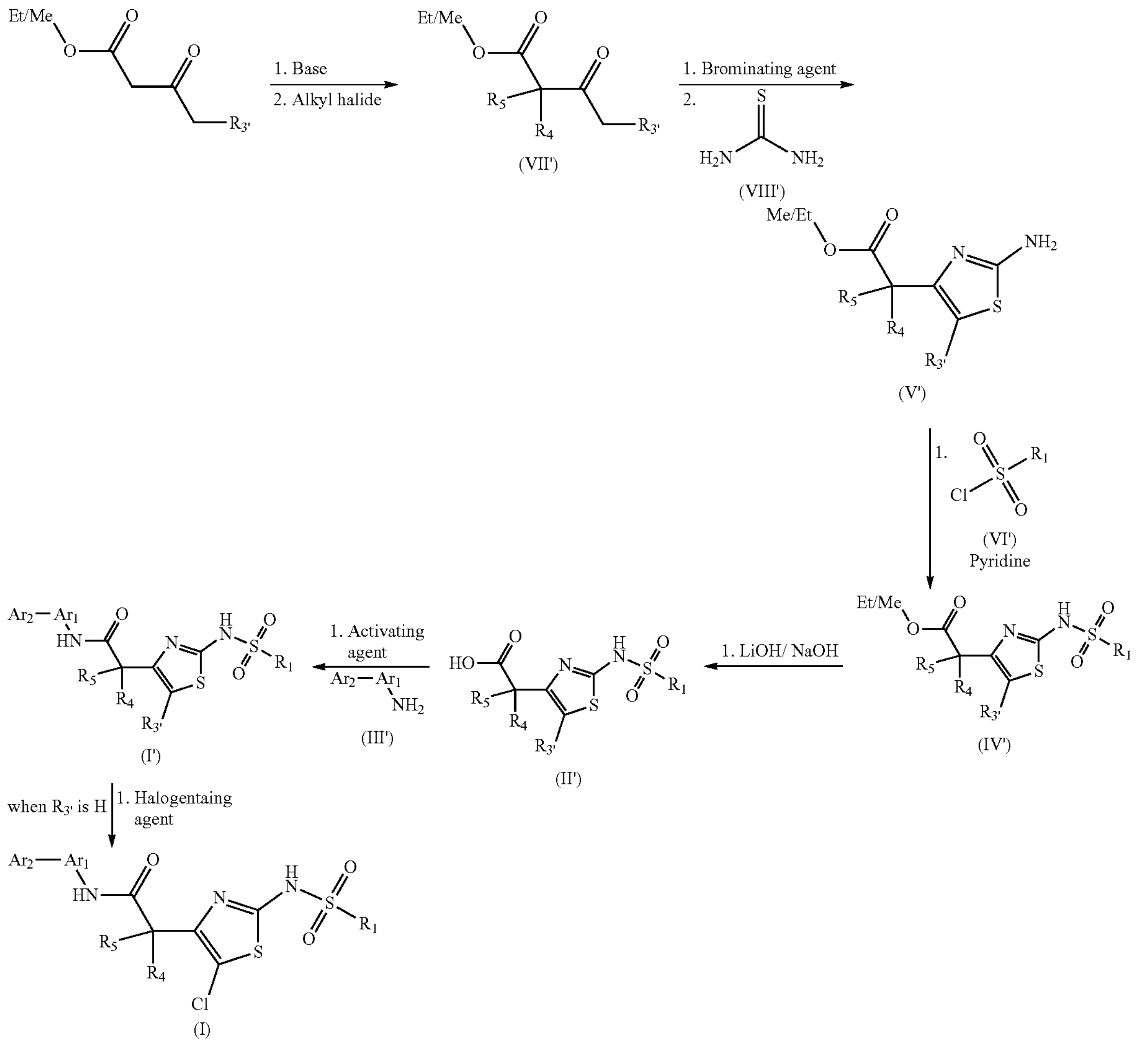

Compounds of general formula (I), where $R_1$, $R_2$, $R_3$, $R_4$, $R_5$, $R_6$, $R_{10}$, $R_{11}$, $R_{12}$, $R_{13}$, Ar1 and Ar2 are defined above, may be synthesised by the general scheme (Scheme 26). Ketoesters of formula (VII') may be prepared by alkylation of an unsubstituted ketoester, which is well established in the literature with many simple derivatives being commercially available.

Intermediates of formula (V') are readily prepared from ketoesters of formula (VII') using a two step procedure. Firstly, bromination using bromine or pyrimidium tribromide can afford the alpha bromoketone ester. This intermediate may be isolated but is routinely used directly without characterisation or purification in the subsequent step. Thiourea (VIII') may be added to form thiazoles of the formula (V') via cyclisation. Such reactions may be subject to gentle heating to, for example, 40° C.

The compound intermediates of formula (M) can be obtained by sulfonylation of amines of formula (V') with a suitable sulfonyl chloride (VI') in pyridine. Such reactions may be subject to gentle heating to, for example, 30-60° C.

The alkyl esters of formula (IV') may be conveniently hydrolysed by exposure to a suitable inorganic base, for example lithium hydroxide, in an aqueous mixture of aprotic and protic solvents, such as THF:methanol:water. Such reactions may be subject to gentle heating to, for example, 30-50° C.

Compounds of formula (I) may be obtained by a general process whereby a carboxylic acid precursor (II'), or a suitably protected derivative thereof, is reacted with an activating agent, to generate a reactive, electrophilic carboxylic acid derivative, followed by subsequent reaction with an amine of formula (III'), or a suitably protected derivative thereof. It will be understood by persons skilled in the art that, in some instances, the activated carboxylic acid derivative, such as an acid chloride, may be isolated or in other cases may be a transient intermediate that is not isolated, but generated in situ and used directly. Reagents suitable for the activation of the carboxylate group include carbonyl diimidazole, 1-chloro-N,N,2-trimethylprop-1-en-1-amine (Ghosez reagent) and a wide selection of peptide coupling agents such as 1-[bis(dimethylamino)methylene]-1H-1,2,3-triazolo[4,5-b]pyridinium 3-oxid hexafluorophosphate (HATU) and the like. Such reactions are conveniently carried out in a non-polar, aprotic solvent, such as DCM at or below ambient temperature.

If $R_{3'}$=H in compounds of the general formula (I), substitution can be undertaken using a halogenating reagent, such as N-chlorosuccinimide, in an organic solvent such as MeCN to generate compounds of the general formula (I) wherein $R_{3'}$=Cl.

Intermediates of the Invention

The present invention also relates to novel intermediates in the synthesis of compounds of formula (I) such as compounds of formula (II) to (LVIX) such as compounds of formula (II) to (XXV), such as compounds of formula (II)-(XX). Particular intermediates of interest are those of the following general formulae, wherein the variable groups and associated preferences are as defined previously for compounds of formula (I):

a compound of formula (II):

(II)

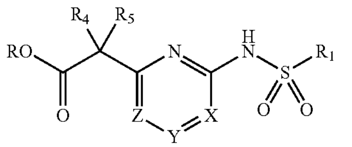

wherein R is H, $C_{1-6}$alkyl (e.g. methyl or ethyl) or benzyl;

a compound of formula (XX):

(XX)

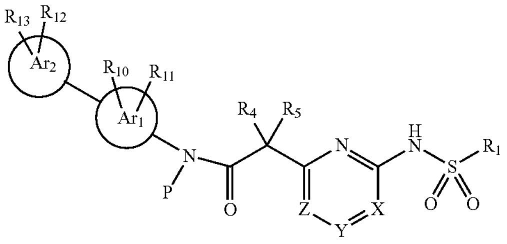

wherein P is a nitrogen protecting group such as para-methoxybenzyl;

a compound of formula (XXIV):

(XXIV)

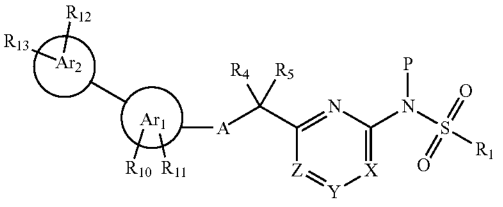

wherein P is a nitrogen protecting group such as para-methoxybenzyl;

a compound of formula (XXXXII):

(XXXXII)

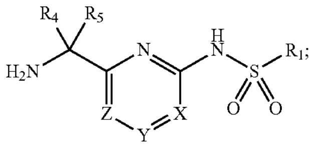

a compound of formula (LVIII):

(LVIII)

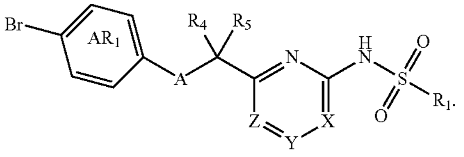

Also provided are intermediates of the following formulae:

a compound of formula (XX-a):

(XX-a)

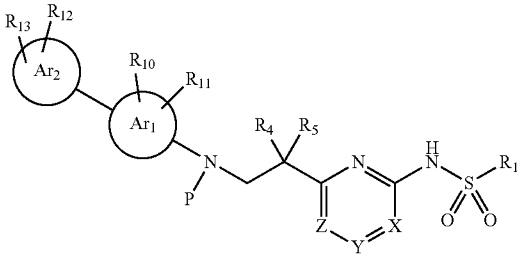

a compound of formula (XX-b):

(XX-b)

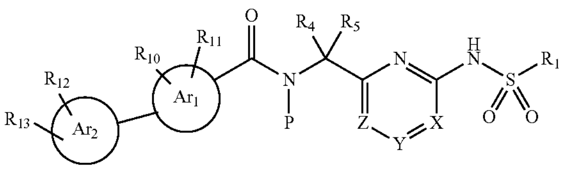

a compound of formula (XX-c):

(XX-c)

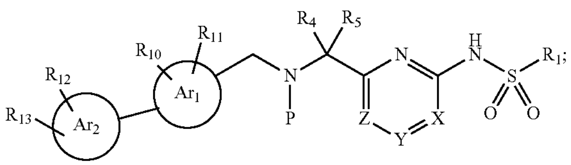

and a compound of formula (XX-d):

(XX-d)

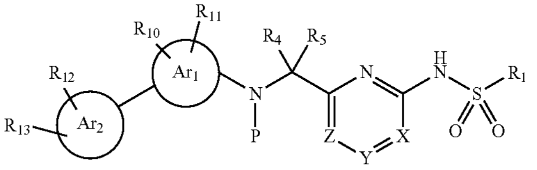

wherein P is a nitrogen protecting group such as para-methoxybenzyl.

Also provided are intermediates of the following formulae:

a compound of formula:

(II)

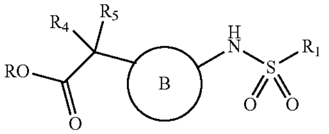

such as (IV')

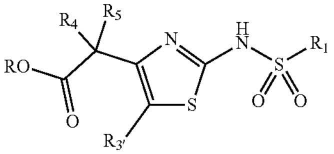

wherein R is H, $C_{1-6}$alkyl (e.g. methyl or ethyl) or benzyl;

a compound of formula (XX):

(XX)

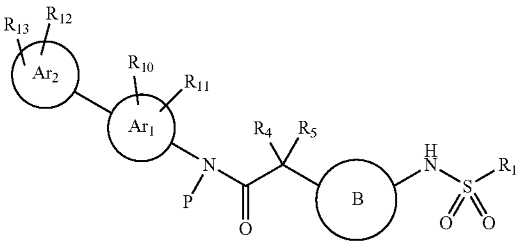

such as

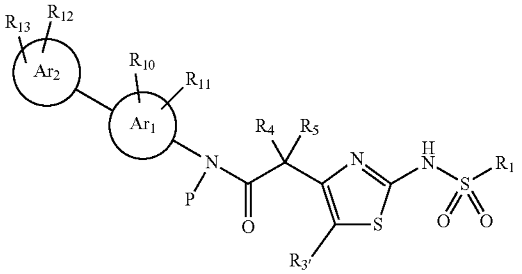

wherein P is a nitrogen protecting group such as para-methoxybenzyl;

a compound of formula (XX-a):

(XX-a)

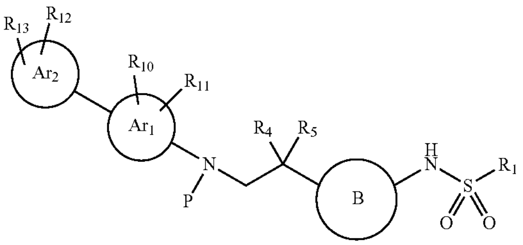

such as

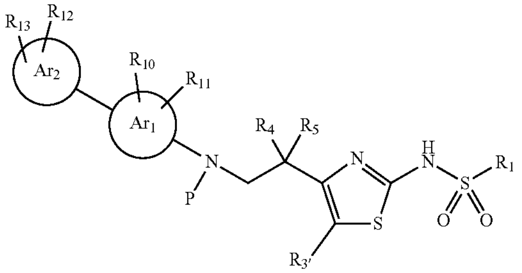

wherein P is a nitrogen protecting group such as para-methoxybenzyl;

a compound of formula (XX-b):

(XX-b)

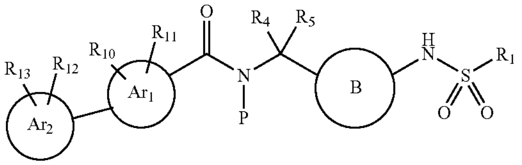

such as

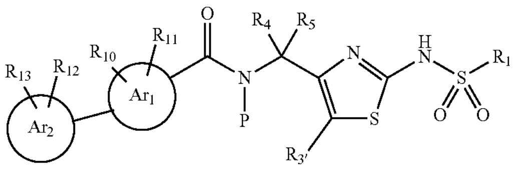

wherein P is a nitrogen protecting group such as para-methoxybenzyl;

a compound of formula (XX-c):

(XX-c)

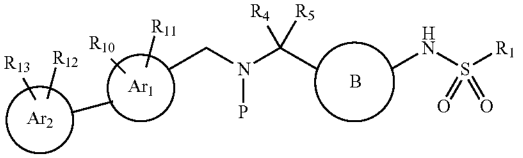

such as

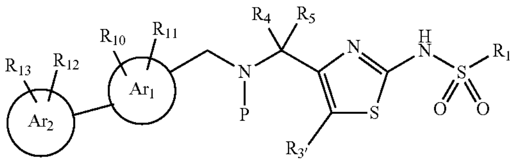

wherein P is a nitrogen protecting group such as para-methoxybenzyl; and a compound of formula (XX-d):

(XX-d)

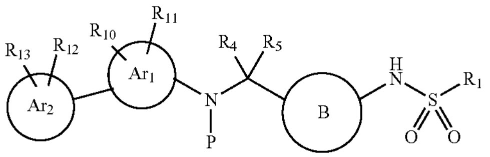

such as

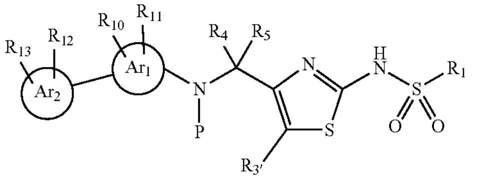

wherein P is a nitrogen protecting group such as para-methoxybenzyl;

a compound of formula (XXIV):

(XXIV)

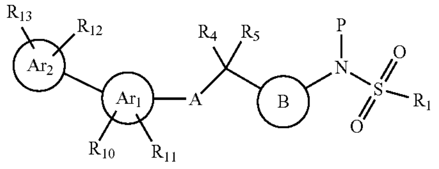

such as

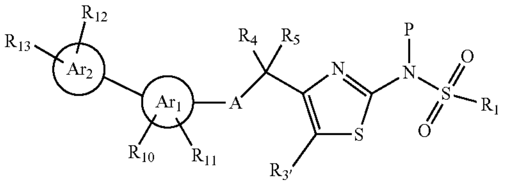

wherein P is a nitrogen protecting group such as para-methoxybenzyl;

a compound of formula (XXXXII):

(XXXXII)

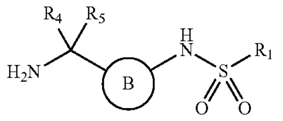

such as

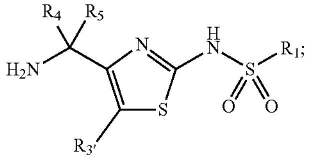

and a compound of formula (LVII):

(LVIII)

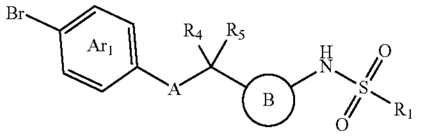

such as

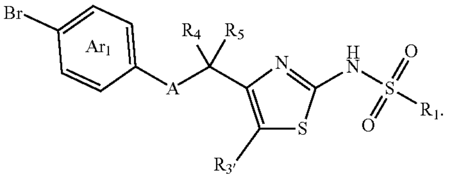

Included as an aspect of the invention are all novel intermediates described in the examples, including:

Intermediates INTC224 to INTC230.

Included as an aspect of the invention are salts such as pharmaceutically acceptable salts of any one of the intermediates disclosed herein, such as any one of compounds of formulae (II), (XX) (including (XX-a) to (XX-d)), (XXIV), (XXXXII) and (LVIII). Also provided are compounds of formula (IV').

Therapeutic Methods

Compounds of formula (I) of the present invention have utility as inhibitors of CTPS1.

Therefore, the invention also provides a compound of formula (I), or a pharmaceutically acceptable salt and/or solvate (e.g. salt) and/or derivative thereof, for use as a medicament, in particular in the treatment or prophylaxis of a disease or disorder wherein an inhibitor of CTPS1 is beneficial, for example those diseases and disorders mentioned herein below.

The invention provides a method for the treatment or prophylaxis of a disease or disorder wherein an inhibitor of CTPS1 is beneficial, for example those diseases and disorders mentioned herein below, which comprises administering to a subject in need thereof an effective amount of a compound of formula (I) or a pharmaceutically acceptable salt and/or solvate (e.g. salt) and/or derivative thereof.

The invention also provides the use of a compound of formula (I), or a pharmaceutically acceptable salt and/or solvate thereof (e.g. salt) and/or derivative, in the manufacture of a medicament for the treatment or prophylaxis of a disease or disorder wherein an inhibitor of CTPS1 is beneficial, for example those diseases and disorders mentioned herein below.

More suitably, the disease or disorder wherein an inhibitor of CTPS1 is beneficial is a disease or disorder wherein a reduction in T-cell and/or B-cell proliferation would be beneficial.

The invention also provides a compound of formula (I), or a pharmaceutically acceptable salt and/or solvate (e.g. salt) and/or derivative thereof, for use in the inhibition of CTPS1 in a subject.

The invention provides a method for the inhibition of CTPS1 in a subject, which comprises administering to the subject an effective amount of a compound of formula (I) or a pharmaceutically acceptable salt and/or solvate (e.g. salt) and/or derivative thereof.

The invention also provides the use of a compound of formula (I), or a pharmaceutically acceptable salt and/or solvate thereof (e.g. salt) and/or derivative, in the manufacture of a medicament for the inhibition of CTPS1 in a subject.

The invention also provides a compound of formula (I), or a pharmaceutically acceptable salt and/or solvate (e.g. salt) and/or derivative thereof, for use in the reduction of T-cell and/or B-cell proliferation in a subject.

The invention provides a method for the reduction of T-cell and/or B-cell proliferation in a subject, which comprises administering to the subject an effective amount of a compound of formula (I) or a pharmaceutically acceptable salt and/or solvate (e.g. salt) and/or derivative thereof.

The invention also provides the use of a compound of formula (I), or a pharmaceutically acceptable salt and/or solvate thereof (e.g. salt) and/or derivative, in the manufacture of a medicament for the reduction of T-cell and/or B-cell proliferation in a subject.

More suitably, the disease or disorder wherein an inhibitor of CTPS1 is beneficial is a disease or disorder wherein a reduction in T-cell and/or B-cell proliferation would be beneficial.

The term 'treatment' or 'treating' as used herein includes the control, mitigation, reduction, or modulation of the disease state or its symptoms.

The term 'prophylaxis' or 'preventing' is used herein to mean preventing symptoms of a disease or disorder in a subject or preventing recurrence of symptoms of a disease or disorder in an afflicted subject and is not limited to complete prevention of an affliction.

Suitably, the disease or disorder is selected from rejection of transplanted cells and tissues, Graft-related diseases or disorders, allergies and autoimmune diseases.

In one embodiment the disease or disorder is the rejection of transplanted cells and tissues. The subject may have been transplanted with a graft selected from the group consisting of heart, kidney, lung, liver, pancreas, pancreatic islets, brain tissue, stomach, large intestine, small intestine, cornea, skin, trachea, bone, bone marrow (or any other source of hematopoietic precursor cells and stem cells including hematopoietic cells mobilized from bone marrow into peripheral blood or umbilical cord blood cells), muscle, or bladder. The compounds of the invention may be of use in preventing or suppressing an immune response associated with rejection of a donor tissue, cell, graft or organ transplant in a subject.

In a further embodiment the disease or disorder is a Graft-related disease or disorder. Graft-related diseases or disorders include graft versus host disease (GVHD), such as GVHD associated with bone marrow transplantation, and immune disorders resulting from or associated with rejection of organ, tissue, or cell graft transplantation (e.g., tissue or cell allografts or xenografts), including, e.g., grafts of skin, muscle, neurons, islets, organs, parenchymal cells of the liver, etc, and Host-Versus-Graft-Disease (HVGD). The compounds of the invention may be of use in preventing or suppressing acute rejection of such transplant in the recipient and/or for long-term maintenance therapy to prevent rejection of such transplant in the recipient (e.g., inhibiting rejection of insulin-producing islet cell transplant from a donor in the subject recipient suffering from diabetes). Thus, the compounds of the invention have utility in preventing Host-Versus-Graft-Disease (HVGD) and Graft-Versus-Host-Disease (GVHD).

A CTPS1 inhibitor may be administered to the subject before, after transplantation and/or during transplantation. In some embodiments, the CTPS1 inhibitor may be administered to the subject on a periodic basis before and/or after transplantation.

In another embodiment, the disease or disorder is an allergy.

In additional embodiments the immune related disease or disorder is an autoimmune disease. As used herein, an "autoimmune disease" is a disease or disorder directed at a subject's own tissues. Examples of autoimmune diseases include, but are not limited to Addison's Disease, Adult-onset Still's disease, Alopecia Areata, Alzheimers disease, Anti-neutrophil Cytoplasmic Antibodies (ANCA)-Associated Vasculitis, Ankylosing Spondylitis, Anti-phospholipid Syndrome (Hughes' Syndrome), Aplastic Anemia, Arthritis, Asthma, Atherosclerosis, Atherosclerotic plaque, Atopic Dermatitis, Autoimmune Hemolytic Anemia, Autoimmune Hepatitis, Autoimmune Hypophysitis (Lymphocytic Hypophysitis), Autoimmune Inner Ear Disease, Autoimmune Lymphoproliferative Syndrome, Autoimmune Myocarditis, Autoimmune Neutropenia, Autoimmune Oophoritis, Autoimmune Orchitis, Auto-Inflammatory Diseases requiring an immunosuppressive treatment, Azoospermia, Bechet's Disease, Berger's Disease, Bullous Pemphigoid, Cardiomyopathy, Cardiovascular disease, Celiac disease including Refractory Celiac Disease (type I and type II), Chronic Fatigue Immune Dysfunction Syndrome (CFIDS), Chronic Idiopathic Polyneuritis, Chronic Inflammatory Demyelinating Polyneuropathy (CIPD), Chronic Relapsing Polyneuropathy (Guillain-Barré syndrome), Churg-Strauss Syndrome (CSS), Cicatricial Pemphigoid, Cold Agglutinin Disease (CAD), chronic obstructive pulmonary disease (COPD), CREST Syndrome, Cryoglobulin Syndromes, Cutaneous Lupus, Dermatitis Herpetiformis, Dermatomyositis, Eczema, Epidermolysis Bullosa Acquisita, Essential Mixed Cryoglobulinemia, Evan's Syndrome, Exophthalmos, Fibromyalgia, Goodpasture's Syndrome, Grave's disease, Hemophagocytic Lymphohistiocytosis (HLH) (including Type 1 Hemophagocytic Lymphohistiocytosis), Histiocytosis/Histiocytic Disorders, Hashimoto's Thyroiditis, Idiopathic Pulmonary Fibrosis, Idiopathic Thrombocytopenia Purpura (ITP), IgA Nephropathy, Immunoproliferative Diseases or Disorders, Inflammatory Bowel Disease (IBD), Interstitial Lung Disease, Juvenile Arthritis, Juvenile Idiopathic Arthritis (JIA), Kawasaki's Disease, Lambert-Eaton Myasthenic Syndrome, Lichen Planus, Localized Scleroderma, Lupus Nephritis, Ménière's Disease, Microangiopathic Hemoytic Anemia, Microscopic Polyangitis, Miller Fischer Syndrome/Acute Disseminated Encephalomyeloradiculopathy, Mixed Connective Tissue Disease, Multiple Sclerosis (MS), Muscular Rheumatism, Myalgic Encephalomyelitis (ME), Myasthenia Gravis, Ocular Inflammation, Pemphigus Foliaceus, Pemphigus Vulgaris, Pemicious Anemia, Polyarteritis Nodosa, Polychondritis, Polyglandular Syndromes (Whitaker's syndrome), Polymyalgia Rheumatica, Polymyositis, Primary Agammaglobulinemia, Primary Biliary Cirrhosis/Autoimmune Cholangiopathy, Primary Glomerulonephritis, Primary Sclerosing Cholangitis, Psoriasis, Psoriatic Arthritis, Pure Red Cell Anemia, Raynaud's Phenomenon, Reiter's Syndrome/Reactive Arthritis, Relapsing Polychondritis, Restenosis, Rheumatic Fever, Rheumatic Disease, Rheumatoid Arthritis, Sarcoidosis, Schmidt's Syndrome, Scleroderma/Systemic Sclerosis, Sjörgen's Syndrome, Stiff-Man Syndrome, The Sweet Syndrome (Febrile Neutrophilic Dermatosis), Systemic Lupus Erythematosus (SLE), Systemic Scleroderma, Takayasu Arteritis, Temporal Arteritis/Giant Cell Arteritis, Thyroiditis, Type 1 diabetes, Type 2 diabetes, Uveitis, Vasculitis, Vitiligo, Wegener's Granulomatosis, and X-linked lymphoproliferative disease.

Of particular interest are diseases and disorders which are mainly driven by T-cell activation and proliferation, including:

- diseases and disorders which are not linked to alloreactivity including:
  - Alopecia areata, atopic dermatitis, eczema, psoriasis, lichen planus, psoriatic arthritis, vitiligo;
  - Uveitis;
  - Ankylosing spondylitis, Reiter's syndrome/reactive arthritis;
  - Aplastic anemia, autoimmune lymphoproliferative syndrome/disorders, hemophagocytic lymphohistiocytosis;
  - Type 1 diabetes; and
  - Refractory celiac disease;
- Acute rejection of grafted tissues and transplanted organs; acute graft versus host disease (GVHD) after transplantation of bone marrow cells or any other source of allogenic cells including hematopoietic precursors cells and/or stem cells.

Also of interest are diseases and disorders which are driven by both T- and B-cell activation and proliferation, with an important involvement of B-cells, including:

- diseases and disorders for which the involvement of pathogenic auto-antibodies is well characterized, including:
  - Allergy;
  - Cicatricial pemphigoid, bullous pemphigoid, epidermolysis bullosa acquisita, pemphigus foliaceus, pemphigus vulgaris, dermatitis herpetiformis;
  - ANCA-associated vasculitis and microscopic polyangitis, vasculitis, Wegener's granulomatosis; Churg-Strauss syndrome (CSS), polyarteritis nodosa, cryoglobulin syndromes and essential mixed cryglobulinemia;
  - Systemic lupus erythematosus (SLE), antiphospholipid syndrome (Hughes' syndrome), cutaneous lupus, lupus nephritis, mixed connective tissue disease;
  - Thyroiditis, Hashimoto thyroiditis, Grave's disease, exophthalmos;
- Autoimmune hemolytic anemia, autoimmune neutropenia, ITP, pernicious anaemia, pure red cell anaemia, micro-angiopathic hemolytic anemia;
  - Primary glomerulonephritis, Berger's disease, Goodpasture's syndrome, IgA nephropathy; and
  - Chronic idiopathic polyneuritis, chronic inflammatory demyelinating polyneuropathy (CIPD), chronic relapsing polyneuropathy (Guillain-Barré syndrome), Miller Fischer syndrome, Stiff man syndrome, Lambert-Eaton myasthenic syndrome, myasthenia gravis.
- diseases and disorders for which the involvement of B-cells is less clearly characterized (although sometimes illustrated by the efficacy of anti-CD20 monoclonal antibodies or intravenous immunoglobulin infusions) and may not correspond or be limited to the production of pathogenic antibodies (nevertheless, non-pathogenic antibodies are sometimes described or even often present and used as a diagnosis biomarker), including:
  - Addison's disease, autoimmune oophoritis and azoospermia, polyglandular syndromes (Whitaker's syndrome), Schmidt's syndrome;
  - Autoimmune myocarditis, cardiomyopathy, Kawasaki's disease;
  - Rheumatoid arthritis, Sjögren's syndrome, mixed connective tissue disease, polymyositis and dermatomyositis; polychondritis;
  - Primary glomerulonephritis;
  - Multiple sclerosis;
  - Autoimmune hepatitis, primary biliary cirrhosis/autoimmune cholangiopathy,
  - Hyper acute rejection of transplanted organs;
  - Chronic rejection of graft or transplants;
  - Chronic Graft versus Host reaction/disease after transplantation of bone marrow cells or hematopoietic precursor cells.

Additionally of interest are diseases and disorders for which the mechanism is shared between activation/proliferation of T-cells and activation/proliferation of innate immune cells and other inflammatory cellular subpopulations (including myeloid cells such as macrophages or granulocytes) and resident cells (such as fibroblasts and endothelial cells), including:

COPD, idiopathic pulmonary fibrosis, interstitial lung disease, sarcoidosis;

Adult onset Still's disease, juvenile idiopathic arthritis, Systemic sclerosis, CREST syndrome where B cells and pathogen antibodies may also play a role; the Sweet syndrome; Takayasu arteritis, temporal arteritis/giant cell arteritis;

Ulcerative cholangitis, inflammatory bowel disease (IBD) including Crohn's disease is and ulcerative colitis, primary sclerosing cholangitis.

Also of interest are diseases and disorders for which the mechanism remains poorly characterized but involves the activation and proliferation of T-cells, including:

Alzheimer's disease, cardiovascular syndrome, type 2 diabetes, restenosis, chronic fatigue immune dysfunction syndrome (CFIDS).

Autoimmune Lymphoproliferative disorders, including:

Autoimmune Lymphoproliferative Syndrome and X-linked lymphoproliferative disease.

Suitably the disease or disorder is selected from: inflammatory skin diseases such as psoriasis or lichen planus; acute and/or chronic GVHD such as steroid resistant acute GVHD; acute lymphoproliferative syndrome; systemic lupus erythematosus, lupus nephritis or cutaneous lupus; or transplantation. In addition, the disease or disorder may be selected from myasthenia gravis, multiple sclerosis, and scleroderma/systemic sclerosis.

The compounds of formula (I) may be used in the treatment of cancer.

Thus, in one embodiment there is provided a compound of formula (I), or a pharmaceutically acceptable salt and/or solvate thereof and/or derivative thereof, for use in the treatment of cancer.

Further, there is provided a method for treating cancer in a subject, by administering to a subject in need thereof a compound of formula (I) or a pharmaceutically acceptable salt and/or solvate thereof and/or derivative thereof.

Additionally provided is the use of a compound of formula (I), or a pharmaceutically acceptable salt and/or solvate thereof and/or derivative thereof, in the manufacture of a medicament for the treatment of cancer in a subject.

Suitably the cancer is a haematological cancer, such as Acute myeloid leukemia, Angioimmunoblastic T-cell lymphoma, B-cell acute lymphoblastic leukemia, Sweet Syndrome, T-cell Non-Hodgkins lymphoma (including natural killer/T-cell lymphoma, adult T-cell leukaemia/lymphoma, enteropathy type T-cell lymphoma, hepatosplenic T-cell lymphoma and cutaneous T-cell lymphoma), T-cell acute lymphoblastic leukemia, B-cell Non-Hodgkins lymphoma (including Burkitt lymphoma, diffuse large B-cell lymphoma, Follicular lymphoma, Mantle cell lymphoma, Marginal Zone lymphoma), Hairy Cell Leukemia, Hodgkin lymphoma, Lymphoblastic lymphoma, Lymphoplasmacytic lymphoma, Mucosa-associated lymphoid tissue lymphoma, Multiple myeloma, Myelodysplastic syndrome, Plasma cell myeloma, Primary mediastinal large B-cell lymphoma, chronic myeloproliferative disorders (such as chronic myeloid leukemia, primary myelofibrosis, essential thrombocytemia, polycytemia vera) or chronic lymphocytic leukemia.

Suitably, the haematological cancer is Peripheral T-cell Lymphoma, such as T-cell prolymphocytic leukaemia, T-cell large granular lymphocytic leukaemia, Aggressive NK cell leukaemia, Systemic Epstein-Barr virus positive T-cell lymphoma disease of childhood, Hydroa vaccineforme-like lymphoma, Adult T-cell leukaemia/lymphoma, Extranodal NK/T-cell lymphoma, nasal type, Enteropathy-associated T-cell lymphoma, Hepatosplenic T-cell lymphoma, Subcutaneous panniculitis-like T-cell lymphoma, Mycosis fungoides, Sézary syndrome, Primary cutaneous anaplastic large cell lymphoma, Primary cutaneous aggressive epidermotropic CD8+ T-cell lymphoma, Primary cutaneous γδ T-cell lymphoma, Primary cutaneous small/medium CD4+ T-cell lymphoma, Anaplastic large cell lymphoma, anaplastic large cell lymphoma kinase-positive, Anaplastic large cell lymphoma, anaplastic large cell lymphoma kinase-negative, and other recognised sub-types.

Alternatively, the cancer is a non-haematological cancer, such as selected from the group consisting of bladder cancer, breast, melanoma, neuroblastoma, malignant pleural mesothelioma, and sarcoma.

In addition, compounds of formula (I) may be used in enhancing recovery from vascular injury or surgery and reducing morbidity and mortality associated with neointima and restenosis in a subject. For example, the compounds of formula (I) may be used in preventing, reducing, or inhibiting neointima formation. A medical device may be treated prior to insertion or implantation with an effective amount of a composition comprising a compound of formula (I) in order to prevent, reduce, or inhibit neointima formation following insertion or implantation of the device or graft into the subject. The device can be a device that is inserted into the subject transiently, or a device that is implanted permanently. In some embodiments, the device is a surgical device. Examples of medical devices include, but are not limited to, needles, cannulas, catheters, shunts, balloons, and implants such as stents and valves.

Suitably the subject is a mammal, in particular the subject is a human.

Pharmaceutical Compositions

For use in therapy the compounds of the invention are usually administered as a pharmaceutical composition. The invention also provides a pharmaceutical composition comprising a compound of formula (I), or a pharmaceutically acceptable salt and/or solvate (e.g. salt) and/or derivative thereof, and a pharmaceutically acceptable carrier or excipient.

In one embodiment, there is provided a pharmaceutical composition comprising a compound of formula (I), or a pharmaceutically acceptable salt and/or solvate (e.g. salt) and/or derivative thereof, for use in the treatment or prophylaxis of a disease or disorder as described herein.

In a further embodiment, there is provided a method for the prophylaxis or treatment of a disease or disorder as described herein, which comprises administering to a subject in need thereof an effective amount of a pharmaceutical composition comprising a compound of formula (I) or a pharmaceutically acceptable salt and/or solvate (e.g. salt) and/or derivative thereof.

The invention also provides the use of a pharmaceutical composition comprising a compound of formula (I), or a pharmaceutically acceptable salt and/or solvate thereof (e.g. salt) and/or derivative thereof, in the manufacture of a medicament for the treatment or prophylaxis of a disease or disorder as described herein.

The compounds of formula (I) or their pharmaceutically acceptable salts and/or solvates and/or derivatives thereof may be administered by any convenient method, e.g. by oral, parenteral, buccal, sublingual, nasal, rectal or transdermal administration, and the pharmaceutical compositions adapted accordingly.

The compounds of formula (I) or their pharmaceutically acceptable salts and/or solvates and/or derivatives thereof may be administered topically, for example to the eye, gut or skin. Thus, in an embodiment there is provided a pharmaceutical composition comprising a compound of the invention optionally in combination with one or more topically acceptable diluents or carriers.

A pharmaceutical composition of the invention may be delivered topically to the skin. Compositions suitable for transdermal administration include ointments, gels and patches. Such a pharmaceutical composition may also suitably be in the form of a cream, lotion, foam, powder, paste or tincture.

The pharmaceutical composition may suitably include vitamin D3 analogues (e.g. calcipotriol and maxacalcitol), steroids (e.g. fluticasone propionate, betamethasone valerate and clobetasol propionate), retinoids (e.g. tazarotene), coal tar and dithranol. Topical medicaments are often used in combination with each other (e.g. a vitamin D3 and a steroid) or with further agents such as salicylic acid.

A pharmaceutical composition of the invention may be delivered topically to the eye. Such a pharmaceutical composition may suitably be in the form of eye drops or an ointment.

A pharmaceutical composition of the invention may be delivered topically to the gut. Such a pharmaceutical composition may suitably be delivered orally, such as in the form of a tablet or a capsule, or rectally, such as in the form of a suppository.

Suitably, delayed release formulations are in the form of a capsule.

The compounds of formula (I) or their pharmaceutically acceptable salts and/or solvates and/or derivatives thereof which are active when given orally can be formulated as liquids or solids, e.g. as syrups, suspensions, emulsions, tablets, capsules or lozenges.

A liquid formulation will generally consist of a suspension or solution of the active ingredient (such as a compound of formula (I) or a pharmaceutically acceptable salt and/or solvate (e.g. salt) and/or derivative thereof) in a suitable liquid carrier(s) e.g. an aqueous solvent such as water, ethanol or glycerine, or a non-aqueous solvent, such as polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient (such as a compound of formula (I) or a pharmaceutically acceptable salt and/or solvate (e.g. salt) and/or derivative thereof) can be prepared using standard carriers and then filled into a hard gelatin capsule; alternatively a dispersion or suspension can be prepared using any suitable pharmaceutical carrier(s), e.g. aqueous gums, celluloses, silicates or oils and the dispersion or suspension then filled into a soft gelatin capsule.

Typical parenteral compositions consist of a solution or suspension of the active ingredient (such as a compound of formula (I) or a pharmaceutically acceptable salt and/or solvate (e.g. salt) and/or derivative thereof) in a sterile aqueous carrier or parenterally acceptable oil, e.g. polyethylene glycol, polyvinyl pyrrolidone, lecithin, *arachis* oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active ingredient in a pharmaceutically acceptable aqueous or non-aqueous solvent and are usually presented in single or multidose quantities in sterile form in a sealed container which can take the form of a cartridge or refill for use with an atomising device. Alternatively the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a fluoro-chloro-hydrocarbon or hydrofluorocarbon. Aerosol dosage forms can also take the form of pump-atomisers.

Compositions suitable for buccal or sublingual administration include tablets, lozenges and pastilles where the active ingredient is formulated with a carrier such as sugar and acacia, tragacanth, or gelatin and glycerin.

Compositions for rectal administration are conveniently in the form of suppositories containing a conventional suppository base such as cocoa butter.

Suitably, the composition is in unit dose form such as a tablet, capsule or ampoule.

The composition may for example contain from 0.1% to 100% by weight, for example from 10 to 60% by weight, of the active material, depending on the method of administration. The composition may contain from 0% to 99% by weight, for example 40% to 90% by weight, of the carrier, depending on the method of administration. The composition may contain from 0.05 mg to 2000 mg, for example from 1.0 mg to 500 mg, of the active material, depending on the method of administration. The composition may contain from 50 mg to 1000 mg, for example from 100 mg to 400 mg of the carrier, depending on the method of administration. The dose of the compound used in the treatment or prophylaxis of the aforementioned disorders will vary in the usual way with the seriousness of the disorders, the weight of the sufferer, and other similar factors. However, as a general guide suitable unit doses may be 0.05 mg to 1000 mg, more suitably 1.0 mg to 500 mg, and such unit doses may be administered more than once a day, for example two or three a day. Such therapy may extend for a number of weeks or months.

The invention provides, in a further aspect, a combination comprising a compound of formula (I) or a pharmaceutically acceptable, salt, solvate and/or derivative thereof (e.g. a combination comprising a compound of formula (I) or a pharmaceutically acceptable derivative thereof) together with a further pharmaceutically acceptable active ingredient or ingredients.

The invention provides a compound of formula (I), for use in combination with a further pharmaceutically acceptable active ingredient or ingredients.

When the compounds are used in combination with other therapeutic agents, the compounds may be administered separately, sequentially or simultaneously by any convenient route.

Optimal combinations may depend on the disease or disorder. Possible combinations include those with one or more active agents selected from the list consisting of: 5-aminosalicylic acid, or a prodrug thereof (such as sulfasalazine, olsalazine or bisalazide); corticosteroids (e.g. prednisolone, methylprednisolone, or budesonide); immunosuppressants (e.g. cyclosporin, tacrolimus, sirolimus, methotrexate, azathioprine mycophenolate mofetil, leflunomide, cyclophosphamide, 6-mercaptopurne or anti-lymphocyte (or thymocyte) globulins); anti-TNF-alpha antibodies (e.g., infliximab, adalimumab, certolizumab pegol or golimumab): anti-IL12/lL23 antibodies (e.g., ustekinumab); anti-IL6 or anti-IL6R antibodies, anti-IL17 antibodies or small molecule IL12/IL23 inhibitors (e.g., apilimod); Anti-alpha-4-beta-7 antibodies (e.g., vedolizumab); MAdCAM-1 blockers (e.g., PF-00547659); antibodies against the cell adhesion molecule alpha-4-integrin (e.g., natalizumab); antibodies against the IL2 receptor alpha subunit (e.g., daclizumab or basiliximab); JAK inhibitors including JAK1 and JAK3 inhibitors (e.g., tofacitinib, baricitinib, R348); Syk inhibitors and prodrugs thereof (e.g., fostamatinib and R-406); Phosphodiesterase-4 inhibitors (e.g., tetomilast); HMPL-004; probiotics; Dersalazine; semapimod/CPSI-2364; and protein kinase C inhibitors (e.g. AEB-071).

For cancer, the further pharmaceutically acceptable active ingredient may be selected from anti-mitotic agents such as vinblastine, paclitaxel and docetaxel; alkylating agents, for example cisplatin, carboplatin, dacarbazine and cyclophosphamide; antimetabolites, for example 5-fluorouracil, cytosine arabinoside and hydroxyurea; intercalating agents for example adriamycin and bleomycin: topoisomerase inhibitors for example etoposide, topotecan and irinotecan; thymidylate synthase inhibitors for example raltitrexed; PI3 kinase inhibitors for example idelalisib; mTor inhibitors for example everolimus and temsirolimus; proteasome inhibitors for example bortezomib; histone deacetylase inhibitors for example panobinostat or vornostat; and hedgehog pathway blockers such as vismodegib.

The further pharmaceutically acceptable active ingredient may be selected from tyrosine kinase inhibitors such as, for example, axitinib, dasatinib, erlotinib, imatinib, nilotinib, pazopanib and sunitinib.

Anticancer antibodies may be included in a combination therapy and may be selected from the group consisting of olaratumab, daratumumab, necitumumab, dinutuximab, traztuzumab emtansine, pertuzumab, obinutuzumab, brentuximab, ofatumumab, panitumumab, catumaxomab, bevacizumab, cetuximab, tositumomab, traztuzumab, gentuzumab ozogamycin and rituximab.

Compounds or pharmaceutical compositions of the invention may also be used in combination with radiotherapy.

Some of the combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations. The individual components of combinations may also be administered separately, through the same or different routes.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

Medical Devices

In an embodiment, compounds of the invention or pharmaceutical compositions comprising said compounds may be formulated to permit incorporation into the medical device, thus providing application of the compound or composition directly to the site to prevent or treat conditions disclosed herein.

In an embodiment, the compounds of the invention or pharmaceutical composition thereof is formulated by including it within a coating onto the medical device. There are various coatings that can be utilized such as, for example, polymer coatings that can release the compound over a prescribed time period. The compound, or a pharmaceutical composition thereof, can be embedded directly within the medical device. In some embodiments, the compound is coated onto or within the device in a delivery vehicle such as a microparticle or liposome that facilitates its release and delivery. In some embodiments, the compound or pharmaceutical composition is miscible in the coating.

In some embodiments, the medical device is a vascular implant such as a stent. Stents are utilized in medicine to prevent or eliminate vascular restrictions. The implants may be inserted into a restricted vessel whereby the restricted vessel is widened. Excessive growth of the adjacent cells following vascular implantation results in a restriction of the vessel particularly at the ends of the implants which results in reduced effectiveness of the implants. If a vascular implant is inserted into a human artery for the elimination of for example an arteriosclerotic stenosis, intima hyperplasia can occur within a year at the ends of the vascular implant and results in renewed stenosis ("restenosis").

Accordingly, in some embodiments, the stents are coated or loaded with a composition including a compound of the invention or pharmaceutical composition thereof and optionally a targeting signal, a delivery vehicle, or a combination thereof. Many stents are commercially available or otherwise know in the art.

In some embodiments, the stent is a drug-eluting stent. Various drug eluting stents that simultaneously deliver a therapeutic substance to the treatment site while providing artificial radial support to the wall tissue are known in the art. Endoluminal devices including stents are sometimes coated on their outer surfaces with a substance such as a drug releasing agent, growth factor, or the like. Stents have also been developed having a hollow tubular structure with holes or ports cut through the sidewall to allow drug elution from a central lumen. Although the hollow nature of the stent allows the central lumen to be loaded with a drug solution that is delivered via the ports or holes in the sidewall of the stent, the hollow tubular structure may not have suitable mechanical strength to provide adequate scaffolding in the vessel.

In some embodiments, the devices are also coated or impregnated with a compound of the invention, or pharmaceutical composition thereof and one or more additional therapeutic agents, including, but not limited to, antiplatelet agents, anticoagulant agents, anti-inflammatory agents, antimicrobial agents, antimetabolic agents, additional anti-neointima agents, additional antiproliferative agents, immunomodulators, antiproliferative agents, agents that affect migration and extracellular matrix production, agents that affect platelet deposition or formation of thrombis, and agents that promote vascular healing and re-endothelialization, such as those and others described in Sousa et al. (2003) and Salu et al. (2004).

Examples of antithrombin agents include, but are not limited to, Heparin (including low molecular heparin), R-Hirudin, Hirulog, Argatroban, Efegatran, Tick anticoagulant peptide, and Ppack.

Examples of antiproliferative agents include, but are not limited to, Paclitaxel (Taxol), QP-2 Vincristin, Methotrexat, Angiopeptin, Mitomycin, BCP 678, Antisense c-myc, ABT 578, Actinomycin-D, RestenASE, 1-Chlor-deoxyadenosin, PCNA Ribozym, and Celecoxib.

Examples of anti-restenosis agents include, but are not limited to, immunomodulators such as Sirolimus (Rapamycin), Tacrolimus, Biorest, Mizoribin, Cyclosporin, Interferon-γ Ib, Leflunomid, Tranilast, Corticosteroide, Mycophenolic acid and Biphosphonate.

Examples of anti-migratory agents and extracellular matrix modulators include, but are not limited to Halofuginone, Propyl-hydroxylase-Inhibitors, C-Proteinase-Inhibitors, MMP-Inhibitors, Batimastat, Probucol.

Examples of antiplatelet agents include, but are not limited to, heparin.

Examples of wound healing agents and endothelialization promoters include vascular epithelial growth factor ("VEGF"), 17-Estradiol, Tkase-Inhibitors, BCP 671, Statins, nitric oxide ("NO")-Donors, and endothelial progenitor cell ("EPC")-antibodies.

Besides coronary applications, drugs and active agents may be incorporated into the stent or stent coating for other indications. For example, in urological applications, antibiotic agents may be incorporated into the stent or stent coating for the prevention of infection. In gastroenterological and urological applications, active agents may be incorporated into the stent or stent coating for the local treatment of carcinoma. It may also be advantageous to incorporate in or on the stent a contrast agent, radiopaque markers, or other additives to allow the stent to be imaged in vivo for tracking, positioning, and other purposes. Such additives could be added to the absorbable composition used to make the stent or stent coating, or absorbed into, melted onto, or sprayed onto the surface of part or all of the stent. Preferred additives for this purpose include silver, iodine and iodine labelled compounds, barium sulfate, gadolinium oxide, bismuth derivatives, zirconium dioxide, cadmium, tungsten, gold tantalum, bismuth, platinum, iridium, and rhodium. These additives may be, but are not limited to, micro- or nano-sized particles or nano particles. Radio-opacity may be determined by fluoroscopy or by x-ray analysis.

A compound of the invention and one or more additional agents, or pharmaceutical composition thereof, can be incorporated into the stent, either by loading the compound and one or more additional agents, or pharmaceutical composition thereof into the absorbable material prior to processing, and/or coating the surface of the stent with the agent(s). The rate of release of agent may be controlled by a number of methods including varying the following: the ratio of the absorbable material to the compound and one or more additional agents, or pharmaceutical composition, the molecular weight of the absorbable material, the composition of the compound and one or more additional agents, or pharmaceutical composition, the composition of the absorbable polymer, the coating thickness, the number of coating layers and their relative thicknesses, and/or the compound and one or more additional agents, or pharmaceutical composition concentration. Top coats of polymers and other materials, including absorbable polymers, may also be applied to active agent coatings to control the rate of release. For example, P4HB can be applied as a top coat on a metallic stent coated with P4HB including an active agent to retard the release of the active agent.

The invention is further exemplified by the following non-limiting examples.

EXAMPLES

Abbreviations used herein are defined below. Any abbreviations not defined are intended to convey their generally accepted meaning.

Abbreviations

Ac acetyl ($C(O)CH_3$)
AcOH glacial acetic acid
$AlMe_3$ trimethylaluminium
aq aqueous
Ar Aromatic ring
BEH ethylene bridged hybrid
Bispin Bis(pinacolato)diboron; 4,4,4',4',5,5,5',5'-Octamethyl-2,2'-bi-1,3,2 dioxaborolane
Bz benzyl ($CH_2$-phenyl)
Boc tert-butyloxycarbonyl protecting group
$Cs_2CO_3$ Cesium carbonate
CSH charged surface hybrid
d doublet
DABAL-$Me_3$ adduct of trimethylaluminum and 1,4-diazabicyclo[2.2.2]octane
DCM dichloromethane
DIPEA N,N-diisopropylethylamine
dioxane 1,4-dioxane
DMAP 4-dimethylaminopyridine
DME dimethoxyethane
DMF N,N-dimethylformamide
DMSO dimethyl sulfoxide
DMP Dess-Martin Periodinane
DPPA diphenylphosphoryl azide
dppf 1,1'-bis(diphenylphosphino)ferrocene
($ES^+$) electrospray ionisation, positive mode
($ES^-$) electrospray ionisation, negative mode
ESI electrospray ionisation
Et ethyl
EtI Ethyl iodide
EtOAc ethyl acetate
EtOH ethanol
g grams
Hal halogen
HATU 1-[bis(dimethylamino)methylene]-1H-1,2,3-triazolo[4,5-b]pyridinium 3-oxid hexafluorophosphate
HPLC high performance liquid chromatography
hr(s) hour(s)
$IC_{50}$ 50% inhibitory concentration
iPr iso-propyl
iPrMgCl iso-propyl magnesium chloride
$K_2CO_3$ potassium carbonate
LCMS liquid chromatography-mass spectrometry
LHMDS lithium hexamethyldisilazide
LiOH lithium hydroxide
$(M+H)^+$ protonated molecular ion
$(M-H)^-$ unprotonated molecular ion
M molar concentration
mCPBA Meta-chloroperoxybenzoic acid
mL millilitre
mm millimiter
mmol millimole
Me methyl
MeCN acetonitrile
Mel iodomethane
MeOH methanol
MesCl methanesulfonyl chloride
MHz megahertz
min(s) minute(s)
MSD mass selective detector
MTBE methyl tert-butyl ether
m/z mass-to-charge ratio
$N_2$ nitrogen gas
$NH_3$ ammonia $NH_4Cl$ ammonium chloride
NaH sodium hydride
$NaHCO_3$ sodium bicarbonate
$NaBH(OAc)_3$ Sodium triacetoxyborohydride
nm nanometre
NMR nuclear magnetic resonance (spectroscopy)
NSFI N-fluorobenzenesulfonimide
P4HB poly-4-hydroxybutyrate
PDA photodiode array
Pd 170 chloro(crotyl)(2-dicyclohexylphosphino-2',4',6'-triisopropybiphenyl)palladium(II) or XPhos Pd(crotyl) Cl
Pd 174 allyl(2-di-tert-butylphosphino-2',4',6'-triisopropyl-1,1'-biphenyl)palladium(II) triflate or [fBuXPhos-Pd(allyl)]OTf
$[Pd(allyl)C_2]_2$ bis(allyl)dichlorodipalladium
$PdCl_2(dppf)$ [1,1'-bis(diphenylphosphino)ferrocene]dichloropalladium(II)
$Pd(PPh_3)_4$ tetrakis(triphenylphosphine)palladium(0)
PMB 4-methoxybenzyl
prep HPLC preparative high performance liquid chromatography
Ph phenyl
pos/neg positive/negative
q quartet
RF/MS RapidFire Mass Spectrometry
RT room temperature
Rt retention time
RP reverse phase
s singlet
$S_NAr$ nucleophilic aromatic substitution
sat saturated
SCX solid supported cation exchange (resin)
Selectfluor N-chloromethyl-N'-fluorotriethylenediammonium bis(tetrafluoroborate)
t triplet
tBu tert-butyl
t-BuOK potassium tert-butoxide
T3P 2,4,6-tripropyl-1,3,5,2,4,6-trioxatriphosphorinane-2,4,6-trioxide
TBME tert-butyl methyl ether
TFA Trifluoroacetic acid
[t-BuXPhos allyl(2-di-tefl-butylphosphino-2',4',6'-triisopropyl-1,1'-Pd(allyl)]OTf biphenyl)palladium(II) triflate
THF tetrahydrofuran
TMP 2,2,6,6-tetramethylpiperidinyl
TMSOK potassium trimethylsilanolate
TTIP titanium tetraisopropoxide
UPLC ultra performance liquid chromatography
UV ultraviolet
v/v volume/volume
VWD variable wave detector
wt weight
um micrometre
uL microlitre
° C. degrees Celsius General Procedures All starting materials and solvents were obtained either from commercial sources or prepared according to the literature. Unless otherwise stated all reactions were stirred. Organic solutions were routinely dried over anhydrous magnesium sulfate. Hydrogenations were performed on a Thales H-cube flow reactor under the conditions stated.

Column chromatography was performed on pre-packed silica (230-400 mesh, 40-63 um) cartridges using the amount indicated. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 0.7 M $NH_3$ in MeOH.

Preparative Reverse Phase High Performance Liquid Chromatography

Prep HPLC

Acidic Prep

Waters X-Select CSH column C18, 5 um (19×50 mm), flow rate 28 mL $min^{-1}$ eluting with a $H_2O$-MeCN gradient containing 0.1% v/v formic acid over 6.5 min using UV detection at 254 nm.

Basic Prep

Waters X-Bridge Prep column C18, 5 um (19×50 mm), flow rate 28 mL $min^{-1}$ eluting with a 10 mM $NH_4HCO_3$-MeCN gradient over 6.5 min using UV detection at 254 nm.

Analytical Methods

Reverse Phase HPLC Conditions for the LCMS Analytical Methods

HPLC acidic: Acidic LCMS 4 minute (5-95%)

Analytical LCMS was carried out using a Waters X-Select CSH C18, 2.5 um, 4.6×30 mm column eluting with a gradient of 0.1% Formic acid in MeCN in 0.1% Formic acid in water. The gradient from 5-95% 0.1% Formic acid in MeCN occurs between 0.00-3.00 minutes at 2.5 mL/min with a flush from 3.01-3.5 minutes at 4.5 mL/min. A column re-equilibration to 5% MeCN is from 3.60-4.00 minutes at 2.5 mL/min. UV spectra of the eluted peaks were measured using an Agilent 1260 Infinity VWD at 254 nm. Mass spectra were measured using an Agilent 6120 MSD running with positive/negative switching.

HPLC basic: Basic LCMS 4 minute (5-95%)

Analytical LCMS was carried out using a Waters X-Select BEH C18, 2.5 um, 4.6×30 mm column eluting with a gradient of MeCN in aqueous 10 mM ammonium bicarbonate. The gradient from 5-95% MeCN occurs between 0.00-3.00 minutes at 2.5 mL/min with a flush from 3.01-3.5 minutes at 4.5 mL/min. A column re-equilibration to 5% MeCN is from 3.60-4.00 minutes at 2.5 mL/min. UV spectra of the eluted peaks were measured using an Agilent 1260 Infinity VWD at 254 nm. Mass spectra were measured using an Agilent 6120 MSD running with positive/negative switching.

Reverse Phase HPLC Conditions for the UPLC Analytical Methods

UPLC acidic: Acidic UPLC 3 minute

Analytical UPLC/MS was carried out using a Waters Acquity CSH C18, 1.7 um, 2.1×30 mm column eluting with a gradient of 0.1% Formic acid in MeCN in 0.1% Formic acid in water. The gradient is structured with a starting point of 5% MeCN held from 0.0-0.11 minutes. The gradient from 5-95% occurs between 0.11-2.15 minutes with a flush from 2.15-2.56 minutes. A column re-equilibration to 5% MeCN is from 2.56-2.83 minutes. UV spectra of the eluted peaks were measured using an Acquity PDA and mass spectra were recorded using an Acquity QDa detector with ESI pos/neg switching.

Acidic UPLC 2 Acidic UPLC 1 minute

Analytical UPLC/MS was carried out using a Waters Acquity CSH C18, 1.7 um, 2.1×30 mm column eluting with a gradient of 0.1% Formic acid in MeCN in 0.1% Formic acid in water. The gradient is structured with a starting point of 5% MeCN held from 0.0-0.08 minutes. The gradient from 5-95% occurs between 0.08-0.70 minutes with a flush from 0.7-0.8 minutes. A column re-equilibration to 5% MeCN is from 0.8-0.9 minutes. UV spectra of the eluted peaks were measured using an Acquity PDA and mass spectra were recorded using an Acquity QDa detector with ESI pos/neg switching.

UPLC basic: Basic UPLC 3 minute

Analytical UPLC/MS was carried out using a Waters Acquity BEH C18, 1.7 um, 2.1×30 mm column eluting with a gradient of MeCN in aqueous 10 mM Ammonium Bicarbonate. The gradient is structured with a starting point of 5% MeCN held from 0.0-0.11 minutes. The gradient from 5-95% occurs between 0.11-2.15 minutes with a flush from 2.15-2.56 minutes. A column re-equilibration to 5% MeCN is from 2.56-2.83 minutes. UV spectra of the eluted peaks were measured using an Acquity PDA and mass spectra were recorded using an Acquity QDa detector with ESI pos/neg switching.

Basic UPLC 2 Basic UPLC 1 minute

Analytical UPLC/MS was carried out using a Waters Acquity BEH C18, 1.7 um, 2.1×30 mm column eluting with a gradient of MeCN in aqueous 10 mM Ammonium Bicarbonate. The gradient is structured with a starting point of 5% MeCN held from 0.0-0.08 minutes. The gradient from 5-95% occurs between 0.08-0.70 minutes with a flush from 0.7-0.8 minutes. A column re-equilibration to 5% MeCN is from 0.8-0.9 minutes. UV spectra of the eluted peaks were measured using an Acquity PDA and mass spectra were recorded using an Acquity QDa detector with ESI pos/neg switching.

Column temperature is 40° C. in all runs. Injection volume is 3 uL and the flow rate is 0.77 mL/min.

PDA scan from 210-400 nm on all runs.

Normal Phase HPLC Conditions for the Chiral Analytical Methods

Chiral IC3 method: Chiral HPLC (Diacel Chiralpak IC, 5 um, 4.6x250 mm, 1.0 mL/min, 25-70% EtOH (0.2% TFA) in iso-hexane (0.2% TFA)

Chiral IC4 method: Chiral HPLC (Diacel Chiralpak IC, 5 um, 4.6x250 mm, 1.0 mL/min, 40% EtOH (0.2% TFA) in 4:1 heptane/chloroform (0.2% TFA).

Chiral IC5 method: Chiral HPLC (Diacel Chiralpak IC, 5 um, 4.6x250 mm, 1.0 mL/min, 20% EtOH (0.2% TFA) in iso-hexane (0.2% TFA).

Reverse Phase HPLC Conditions for the Chiral Analytical Methods

Chiral IC6 method: Chiral HPLC (Diacel Chiralpak IC, 5 um, 4.6x250 mm, 1.0 mL/min, 50% MeCN (0.1% formic acid) in water (0.1% formic acid).

Chiral IC7 method: Chiral HPLC (Diacel Chiralpak IC, 5 um, 4.6x250 mm, 1.0 mL/min, 5-95% MeCN (0.1% formic acid) in water (0.1% formic acid).

$^1$H NMR Spectroscopy $^1$H NMR spectra were acquired on a Bruker Avance III spectrometer at 400 MHz or Bruker Avance III HD spectrometer at 500 MHz using residual undeuterated solvent as reference and unless specified otherwise were run in DMSO-d6.

Preparation of Intermediates

Known synthetic intermediates were procured from commercial sources or were obtained using published literature procedures. Intermediates INTC1 to INTC177 and INTD1 to INTD86 may be prepared using the synthetic routes described in WO2019/179652 and WO2019/180244.

Additional intermediates were prepared by the representative synthetic processes described herein.

Any one of Methods 1-1q (referred to later herein) or A-N and Q-R may be used in the synthesis of the compounds of formula (I). For example, a scheme which is shown using a compound wherein X═N, Y═$CR_2$ and Z═$CR_3$ may also be used in the synthesis of compounds wherein X, Y and Z are as defined in the claims.

Preparation of Bi-Ester Intermediates 1-tert-Butyl 3-methyl 2-(2-(methylthio)pyrimidin-4-yl)malonate INTC224

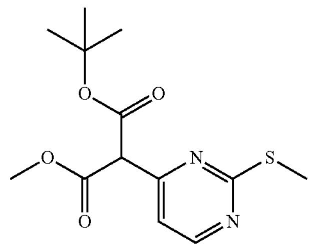

To a solution of tert-butyl methyl malonate (30 mL, 177 mmol) and $Cs_2CO_3$ (127 g, 390 mmol) in DMF (150 mL, 1937 mmol) was heated to 80° C. and 4-chloro-2-(methylthio)pyrimidine (22.7 mL, 195 mmol) was added dropwise as a solution in DMF (30 mL) over 90 mins and then left at this temperature for a further 3 hrs, then allowed to cooled to ambient temperature. The reaction mixture was diluted with MTBE (300 mL) and slowly poured into 4M HCl (aq, 500 mL). The phases were separated and the aqueous was extracted with further MTBE (2×100 mL). The combined organics were washed with 50% brine (aq, 2×100 mL), dried ($MgSO_4$), filtered and concentrated in vacuo to afford 1-tert-butyl 3-methyl 2-(2-(methylthio)pyrimidin-4-yl)malonate (49.38 g, 141 mmol, 79% yield) as an orange oil. Rt 2.20 min (HPLC, acidic); m/z 257 $(M+H)^+$ $(ES^+)$; $^1$H NMR (500 MHz, DMSO-d6) δ 8.66 (d, J=5.2 Hz, 1H), 7.24 (d, J=5.1 Hz, 1H), 5.06 (s, 1H), 3.72 (s, 3H), 2.50 (s, 3H), 1.42 (s, 9H).

Method B: Alkylation

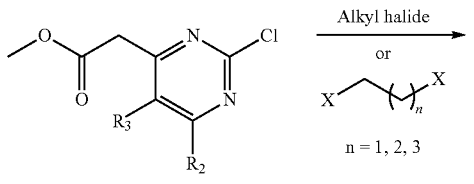

-continued

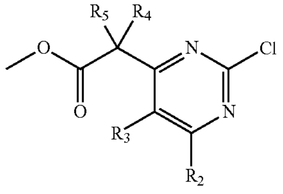

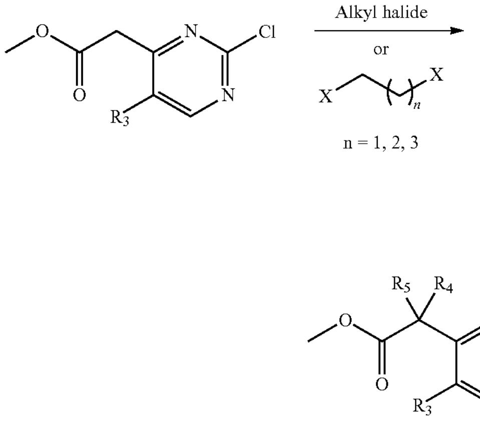

Base (2.5-5 eq) was added to an ice-cooled, stirred mixture of methyl 2-(2-chloropyrimidin-4-yl)acetate (1 eq) in appropriate polar aprotic solvent such as DMF or acetone (10 volumes). After 20 min, alkyl halide (1-5 eq) was added. The reaction vessel was stirred at 0° C. for 30 mins then at RT for 2 hrs. The reaction was quenched with $NH_4Cl$ (aq) or 1M HCl (aq), stirred for 20 mins then extracted with EtOAc. The organic phases were dried (phase separator) and concentrated. The crude product was purified by normal phase chromatography.

Lithium 2-fluoro-2-(2-(methylthio)pyrimidin-4-yl)butanoate INTC228

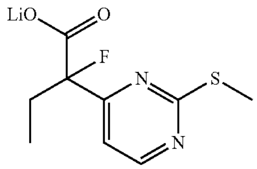

Prepared as for INTC50 using methyl 2-fluoro-2-(2-(methylthio)pyrimidin-4-yl)butanoate (2.88 g, 11.79 mmol) INTC227 to afford lithium 2-fluoro-2-(2-(methylthio)pyrimidin-4-yl)butanoate (100% yield) as a hygroscopic colourless powder used directly in the next step. Rt 0.98 min (HPLC, basic); m/z 231 (M+H as free carboxylate)+(ES+); No $^1$H NMR data collected.

Method H: Benzylic Fluorination of Hetero-Aromatic Esters

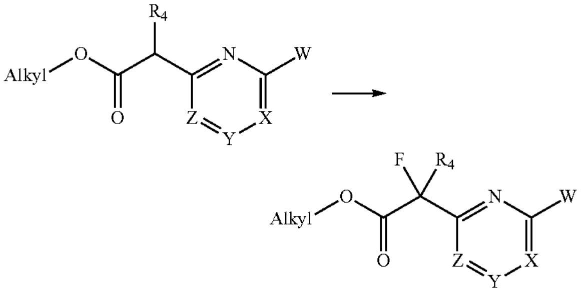

X = CH, N
Y = $CR_2$, N
Z = $CR_3$, N
W = Hal, N(PMB)$SO_2$Alkyl

A solution of hetero-aromatic ester (1 eq) in THF (10 volumes) was cooled to −78° C. to which was added LiHMDS (1.25 eq 1M in THF). The reaction mixture was

TABLE 2

The following intermediates were made according to Method B.

| INTC | Name/Structure (All examples containing chiral centres are racemates unless stated) | Synthesis Method, [LCMS Method], m/z (M + H)$^+$, (Rt/min) | $^1$H NMR Chemical Shift Data (DMSO-d6 unless stated) | Base, RX, solvent |
|---|---|---|---|---|
| INTC225 | 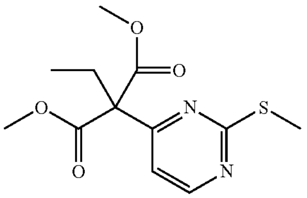 1-tert-butyl 3-methyl 2-ethyl-2-(2-(methylthio)pyrimidin-4-yl)malonate | Method B using INTC224, [HPLC acidic], 327 (2.51). | No NMR data collected | NaOH, EtI, DMF |

then warmed to RT for 1 hr. The solution was cooled to −78° C. and a solution (in THF) of, or solid, NSFI (1.25 eq) was added dropwise then warmed to RT for 2 hrs. The solution was diluted with sat $NaHCO_3$ (aq) and the product was extracted into EtOAc. The crude product was purified by normal phase chromatography.

TABLE 5

The following intermediates were made according to Method H.

| INTC | Name/Structure (All examples containing chiral centres are racemates unless stated) | Synthesis Method, [LCMS Method], m/z $(M + H)^+$, (Rt/min) | $^1H$ NMR Chemical Shift Data (DMSO-d6 unless stated) |
|---|---|---|---|
| INTC227 | 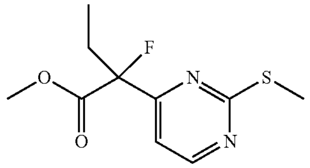<br>methyl 2-fluoro-2-(2-(methylthio)pyrimidin-4-yl)butanoate | Method H using INTC226, [HPLC acidic], 245 (2.04). | 8.76 (d, J = 5.1 Hz, 1H), 7.38 (dd, J = 5.1, 1.2 Hz, 1H), 3.74 (s, 3H), 2.51 (s, 3H), 2.45-2.19 (m, 2H), 0.88 (t, J = 7.4 Hz, 3H).<br>SMe over DMSO peak |

Tetrahydropyran-Derivative Via Thioether

Methyl 4-(2-(methylthio)pyrimidin-4-yl)tetrahydro-2H-pyran-4-carboxylate INTC178

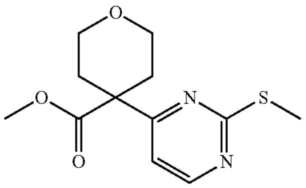

To a solution of 4-chloro-2-(methylthio)pyrimidine (0.55 g, 3.42 mmol) and methyl tetrahydro-2H-pyran-4-carboxylate (494 mg, 3.42 mmol) in THF (5 mL) at 30° C. was added LHMDS (1 M in THF) (4.11 mL, 4.11 mmol) dropwise. The reaction mixture was stirred at 30° C. for 5 min then was poured into water (100 mL) and extracted with EtOAc (2×200 mL). The organic extract was washed with brine (1×100 mL), dried ($MgSO_4$), filtered and solvent removed in vacuo to afford methyl 4-(2-(methylthio)pyrimidin-4-yl)tetrahydro-2H-pyran-4-carboxylate (915 mg, 3.24 mmol, 95% yield) as a pale yellow oil. Rt 1.74 min (HPLC acidic); m/z 269 $(M+H)^+$ (ES+); $^1H$ NMR (500 MHz, DMSO-d6) δ 8.62 (d, J=5.3 Hz, 1H), 7.27 (d, J=5.3 Hz, 1H), 3.76-3.70 (m, 2H), 3.67 (s, 3H), 3.54-3.46 (m, 2H), 2.49 (s, 3H), 2.27-2.20 (m, 2H), 2.14-2.04 (m, 2H).

Methyl 4-(2-(methylsulfonyl)pyrimidin-4-yl)tetrahydro-2H-pyran-4-carboxylate INTC179

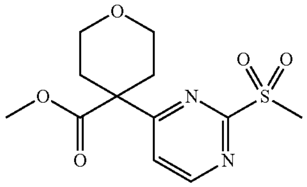

mCPBA (1.60 g, 7.13 mmol) was added portionwise into a stirring solution of methyl 4-(2-(methylthio)pyrimidin-4-yl)tetrahydro-2H-pyran-4-carboxylate INTC178 (915 mg, 3.24 mmol) in DCM (50 mL) and the resulting reaction mixture was stirred at RT for 3 hrs. The reaction mixture was poured into sat. $NaHCO_3$ (aq, 200 mL) and extracted with DCM (3×100 mL). The organic extract was sequentially washed with sat. $NaHCO_3$ (aq, 100 mL) and brine (100 mL), dried ($MgSO_4$), filtered and solvent removed in vacuo to afford methyl 4-(2-(methylsulfonyl)pyrimidin-4-yl)tetrahydro-2H-pyran-4-carboxylate (1.10 g, 3.30 mmol, quant. yield) as thick gum. Rt 1.20 min (HPLC acidic); m/z 301 $(M+H)^+$ $(ES^+)$; $^1H$ NMR (500 MHz, DMSO-d6) δ 9.09 (d, J=5.3 Hz, 1H), 7.95 (d, J=5.3 Hz, 1H), 3.77-3.70 (m, 2H), 3.68 (s, 3H), 3.60-3.49 (m, 2H), 3.42 (s, 3H), 2.34-2.24 (m, 2H), 2.23-2.13 (m, 2H).

Methyl 2-(2-(methylthio)pyrimidin-4-yl)butanoate INTC226

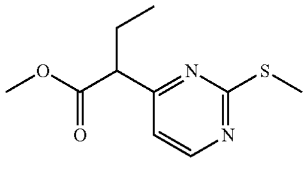

Prepared by Method A using 1-tert-butyl 3-methyl 2-ethyl-2-(2-(methylthio)pyrimidin-4-yl)malonate (14.47 g, 44.3 mmol) INTC225 to methyl 2-(2-(methylthio)pyrimidin-4-yl)butanoate (43% yield) as a clear colourless oil. Rt 2.05 min (HPLC, acidic); m/z 227 $(M+H)^+$ $(ES^+)$; $^1$H NMR (500 MHz, DMSO-d6) δ 8.60 (d, J=5.1 Hz, 1H), 7.19 (d, J=5.1 Hz, 1H), 3.75 (t, J=7.5 Hz, 1H), 3.62 (s, 3H), 2.49 (s, 3H), 2.04-1.95 (m, 1H), 1.92-1.81 (m, 1H), 0.84 (t, J=7.4 Hz, 3H).

N-(5-(6-Ethoxypyrazin-2-yl)pyridin-2-yl)-4-(2-(methylthio)pyrimidin-4-yl)tetrahydro-2H-pyran-4-carboxamide INTC182

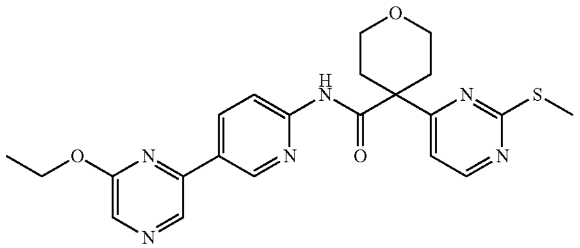 [SMILES: CCOc1cncc(-c2ccc(NC(=O)C3(c4ccnc(SC)n4)CCOCC3)nc2)n1]

Prepared using Method 11 using methyl 4-(2-(methylthio)pyrimidin-4-yl)tetrahydro-2H-pyran-4-carboxylate INTC178 (1.0 eq), 5-(6-ethoxypyrazin-2-yl)pyridin-2-amine INTD33 (1.0 eq) and i-PrMgCl (2.0 eq) to afford N-(5-(6-ethoxypyrazin-2-yl)pyridin-2-yl)-4-(2-(methylthio)pyrimidin-4-yl)tetrahydro-2H-pyran-4-carboxamide (5.5 g, 11.67 mmol, 48% yield) as a pale yellow solid; Rt 2.35 mins (HPLC acidic); m/z 453 $(M+H)^+$ $(ES^+)$. $^1$H NMR (500 MHz, DMSO-d6) δ 10.20 (s, 1H), 9.05 (dd, J=2.5, 0.8 Hz, 1H), 8.85 (s, 1H), 8.64 (d, J=5.3 Hz, 1H), 8.51 (dd, J=8.8, 2.5 Hz, 1H), 8.26 (s, 1H), 8.21 (dd, J=8.7, 0.8 Hz, 1H), 7.33 (d, J=5.3 Hz, 1H), 4.48 (q, J=7.0 Hz, 2H), 3.77-3.70 (m, 2H), 3.65-3.58 (m, 2H), 2.54-2.44 (m, 5H, obscured by DMSO peak), 2.25-2.17 (m, 2H), 1.40 (t, J=7.0 Hz, 3H).

Method P: SNAR using 4-chloro-2-(methylthio)-heterocycles

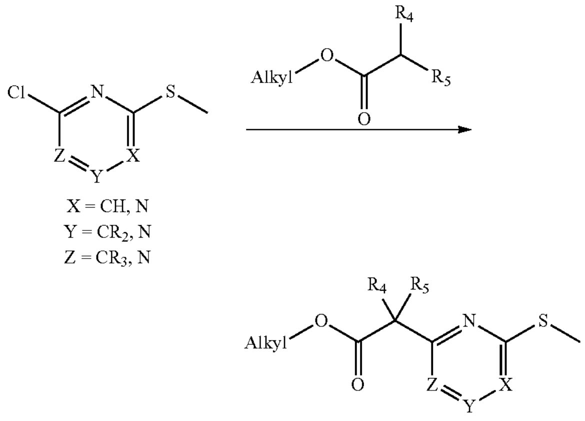

A solution of hetero-aromatic chloride (1 eq) and ester (1 eq) in THF (5-20 volumes) was warmed to 30° C. to which was added LiHMDS (1.25 eq 1-1.5M in THF). The reaction mixture was stirred at this temperature for up to 3 hrs, then was poured into water and extracted with EtOAc. The organic extract was washed with brine, dried ($MgSO_4$), filtered and the solvent removed in vacuo to afford the desired compound. If required, the crude product was purified by normal phase chromatography.

TABLE 17

The following intermediates were made according to Method P.

| INTC | Name/Structure (All examples containing chiral centres are racemates unless stated) | Synthesis Method, [LCMS Method], m/z $(M + H)^+$, (Rt/min) | $^1$H NMR Chemical Shift Data (DMSO-d6 unless stated) |
|---|---|---|---|
| INTC186 | 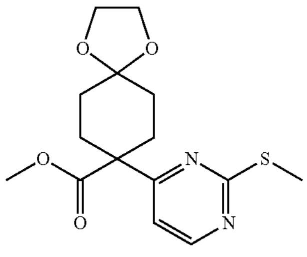 methyl 8-(2-(methylthio)pyrimidin-4-yl)-1,4-dioxaspiro[4.5]decane-8-carboxylate | Method P, [HPLC acidic], 325 (1.99). | 8.60 (d, J = 5.3 Hz, 1H), 7.24 (d, J = 5.3 Hz, 1H), 3.88-3.86 (m, 4H), 3.65 (s, 3H), 2.49 (s, 3H), 2.30-2.24 (m, 2H), 2.16-2.07 (m, 2H), 1.65-1.56 (m, 4H). |

TABLE 17-continued

The following intermediates were made according to Method P.

| INTC | Name/Structure (All examples containing chiral centres are racemates unless stated) | Synthesis Method, [LCMS Method], m/z $(M + H)^+$, (Rt/min) | $^1H$ NMR Chemical Shift Data (DMSO-d6 unless stated) |
|---|---|---|---|
| INTC187 | 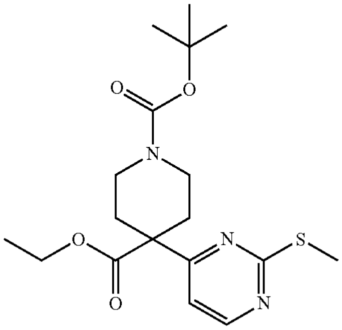 1-(tert-butyl) 4-ethyl 4-(2-(methylthio)pyrimidin-4-yl)piperidine-1,4-dicarboxylate | Method P, [HPLC acidic], 382 (2.54). | 8.61 (d, J = 5.3 Hz, 1H), 7.25 (d, J = 5.3 Hz, 1H), 4.14 (q, J = 7.1 Hz, 2H), 3.73-3.65 (m, 2H), 3.32 (s, 1H), 2.49 (s, 3H), 2.26-2.20 (m, 1H), 2.02-1.93 (m, 2H), 1.40 (s, 9H), 1.14 (t, J = 7.1 Hz, 3H), 1H obscured by DMSO and 1H by obscured by water |
| INTC188 | 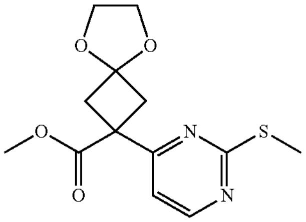 methyl 2-(2-(methylthio)pyrimidin-4-yl)-5,8-dioxaspiro[3.4]octane-2-carboxylate | Method P, [HPLC acidic], 297 (1.76). | No data collected |
| INTC190 | 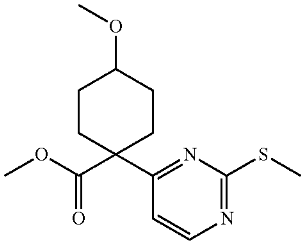 methyl 4-methoxy-1-(2-(methylthio)pyrimidin-4-yl)cyclohexane-1-carboxylate | Method P, [HPLC acidic], 297 (2.00). | 8.63-8.56 (m, 1H), 7.22 (d, J = 5.2 Hz, 1H), 3.65 (s, 3H), 3.24 (s, 3H), 3.23-3.20 (m, 1H), 2.48 (s, 3H), 2.40-2.28 (m, 2H), 1.93-1.80 (m, 4H), 1.36-1.24 (m, 2H). |

Ethyl 4-(2-(methylthio)pyrimidin-4-yl)piperidine-4-carboxylate INTC91

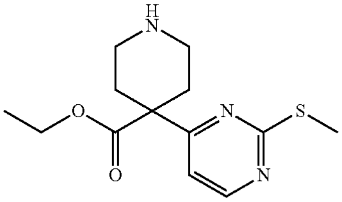 [SMILES: CCOC(=O)C1(c2ccnc(SC)n2)CCNCC1]

To a solution of 1-tert-butyl 4-ethyl 4-(2-(methylthio)pyrimidin-4-yl)piperidine-1,4-dicarboxylate (4 g, 9.44 mmol) INTC187 in DCM (30 mL) at RT was added TFA (5 mL). The reaction mixture was stirred at RT for 1 hr. Additional TFA (5 mL) added and the reaction was stirred at RT for a further 1 hr. The reaction mixture was quenched by addition of $NaHCO_3$ (aq, 100 mL), gas evolved, and was diluted with DCM (50 mL). The organics were isolated and dried ($MgSO_4$), filtered and solvent removed in vacuo to afford ethyl 4-(2-(methylthio)pyrimidin-4-yl)piperidine-4-carboxylate (2.6 g, 9.15 mmol, 97% yield) as a brown oil. Rt 0.97 min (HPLC, acidic): m/z 282 $(M+H)^+$ (ES+); No NMR data collected.

Ethyl 1-(methylsulfonyl)-4-(2-(methylthio)pyrimidin-4-yl)piperidine-4-carboxylate INTC192

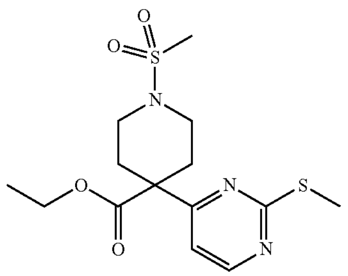 [SMILES: CCOC(=O)C1(c2ccnc(SC)n2)CCN(S(C)(=O)=O)CC1]

To a stirred solution of ethyl 4-(2-(methylthio)pyrimidin-4-yl)piperidine-4-carboxylate (1.3 g, 4.62 mmol) INTC191 in DCM (15 mL) at RT was added TEA (1.42 mL, 10.16 mmol) and then MesCl (0.37 mL, 5.08 mmol). After 1 hr, 1 M HCl (aq, 50 mL) and DCM (30 mL) were added. The organic layer was isolated by passage through a phase separation cartridge and then concentrated in vacuo to afford ethyl 1-(methylsulfonyl)-4-(2-(methylthio)pyrimidin-4-yl)piperidine-4-carboxylate (1.21 g, 3.37 mmol, 73% yield) as a brown oil. Rt 1.93 min (HPLC, acidic); m/z 360 $(M+H)^+$ (ES+); No NMR data collected.

Amide Formation (4-(2-(Methylthio)pyrimidin-4-yl)tetrahydro-2H-pyran-4-yl)methanol INTC197

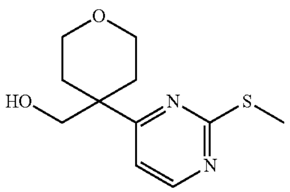 [SMILES: CSc1nccc(C2(CO)CCOCC2)n1]

LiCl (0.95 g, 22.4 mmol) followed by $NaBH_4$ (0.85 g, 22.4 mmol) and EtOH (15 mL) was added into a stirring solution of methyl 4-(2-(methylthio)pyrimidin-4-yl)tetrahydro-2H-pyran-4-carboxylate INTC178 (3 g, 11.2 mmol) in THF (15 mL). The resulting reaction mixture was stirred at RT for 18 hrs. The reaction mixture was acidified with 1M HCl (aq, 20 mL) and the volatiles were removed in vacuo. The residue was extracted with DCM (3×150 mL). The organic extract was dried ($MgSO_4$), filtered and solvent removed in vacuo. The crude product was purified by chromatography on silica gel (40 g column, 0-100% EA/isohexanes) to afford (4-(2-(methylthio)pyrimidin-4-yl)tetrahydro-2H-pyran-4-yl)methanol (2.3 g, 9.09 mmol, 81% yield) as a colourless gum. Rt 0.80 min (UPLC acidic); m/z 241 $(M+H)^+$ $(ES^+)$. $^1H$ NMR (500 MHz, DMSO-d6) δ 8.54 (d, J=5.3 Hz, 1H), 7.23 (d, J=5.3 Hz, 1H), 4.73 (t, J=5.6 Hz, 1H), 3.74-3.67 (m, 2H), 3.49 (d, J=5.7 Hz, 2H), 3.35-3.27 (m, 2H), 2.50 (s, 3H), 2.19-2.10 (m, 2H), 1.77-1.67 (m, 2H).

4-(2-(Methylthio)pyrimidin-4-yl)tetrahydro-2H-pyran-4-carbaldehyde INTC198

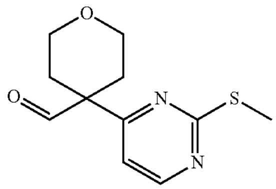 [SMILES: CSc1nccc(C2(C=O)CCOCC2)n1]

DMP (1.77 g, 4.16 mmol) was added portionwise into a stirring solution of (4-(2-(methylthio)pyrimidin-4-yl)tetrahydro-2H-pyran-4-yl)methanol INTC197 (1 g, 4.16 mmol) in DCM (25 ml). The resulting reaction mixture was stirred at RT for 1 hr. The reaction mixture was poured into sat. $NaHCO_3$ (eq, 100 mL) and extracted with DCM (3×100 mL). The organic extract was sequentially washed with saturated sat. $NaHCO_3$ (aq, 100 mL), and brine (100 mL). The organic extract was dried ($MgSO_4$), filtered and solvent in vacuo to afford 4-(2-(methylthio)pyrimidin-4-yl)tetrahydro-2H-pyran-4-carbaldehyde (900 mg, 3.40 mmol, 82% yield) as a colorless oil. Rt 1.61 min (HPLC acidic); m/z 239 $(M+H)^+$ $(ES^+)$. $^1H$ NMR (500 MHz, DMSO-d6) δ 9.63 (s, 1H), 8.65 (d, J=5.2 Hz, 1H), 7.30 (d, J=5.2 Hz, 1H), 3.68-3.59 (m, 2H), 3.56-3.48 (m, 2H), 2.51 (s, 3H), 2.28-2.20 (m, 2H), 2.16-2.09 (m, 2H).

4-(6-Ethoxypyrazin-2-yl)-N-((4-(2-(methylthio)pyrimidin-4-yl)tetrahydro-2H-pyran-4-yl)methyl)aniline INTC199

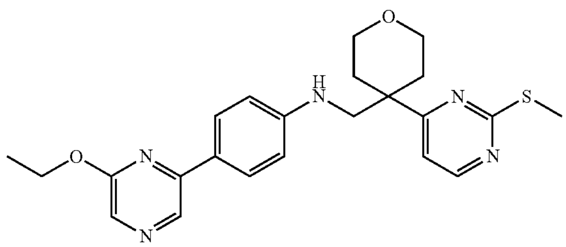 [SMILES: CCOc1cncc(-c2ccc(NCC3(c4ccnc(SC)n4)CCOCC3)cc2)n1]

$NaBH(OAc)_3$ (1.07 g, 5.04 mmol) was added into a suspension of 4-(2-(methylthio)pyrimidin-4-yl)tetrahydro-2H-pyran-4-carbaldehyde INTC198 (400 mg, 1.68 mmol) and 4-(6-ethoxypyrazin-2-yl)aniline INTD18 (542 mg, 2.52 mmol) in DCM (10 ml) and the resulting reaction mixture was stirred at ambient temperature for 18 hrs. The reaction mixture was diluted with DCM (100 mL) and sequentially washed with sat. $NaHCO_3$ (aq, 2×100 mL) and brine (100 mL), dried ($MgSO_4$), filtered and solvent removed in vacuo. The crude product was purified by chromatography on silica gel (25 g cartridge, 0-100% EtOAc/iso-hexanes) to afford 4-(6-ethoxypyrazin-2-yl)-N-((4-(2-(methylthio)pyrimidin-4-yl)tetrahydro-2H-pyran-4-yl)methyl)aniline (312 mg, 0.706 mmol, 42% yield) as a yellow gum. Rt 2.49 min (HPLC acidic); m/z 438 $(M+H)^+$ $(ES^+)$. $^1H$ NMR (500 MHz, DMSO-d6) δ 8.57 (s, 1H), 8.52 (d, J=5.2 Hz, 1H), 7.99 (s, 1H), 7.81-7.74 (m, 2H), 7.29 (d, J=5.3 Hz, 1H), 6.66-6.57 (m, 2H), 6.00 (t, J=6.6 Hz, 1H), 4.42 (q, J=7.0 Hz, 2H), 3.80-3.70 (m, 2H), 3.38 (d, J=6.6 Hz, 2H), 3.32-3.26 (m, 2H), 2.52 (s, 3H), 2.32-2.26 (m, 2H), 1.89-1.80 (m, 2H), 1.38 (t, J=7.0 Hz, 3H).

Method Q: Oxidation of Thioethers to Sulfones or Sulfoxides

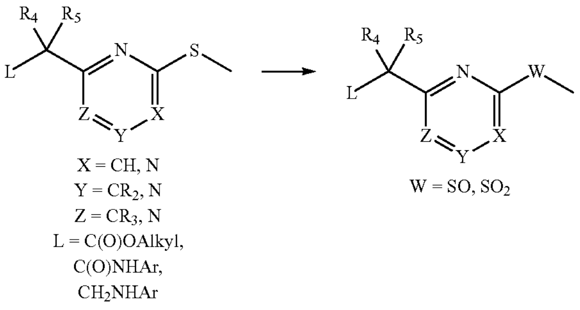

mCPBA (2.2 eq) was portionwise to a stirred solution of thioether (1 eq) in DCM (20-50 volumes) maintaining the internal temperature at RT. The resulting mixture was stirred at RT for a further 3 hrs. The reaction mixture was poured into sat. aq. $Na_2SO_3$ and extracted with DCM. The organic extract was sequentially washed with sat. aq. $NaHCO_3$ and brine, dried ($MgSO_4$), filtered and solvent removed in vacuo to afford the desire compound.

TABLE 18

The following intermediates were made according to Method Q.

| INTC | Name/Structure (All examples containing chiral centres are racemates unless stated) | Synthesis Method, [LCMS Method], m/z $(M + H)^+$, (Rt/min) | $^1H$ NMR Chemical Shift Data (DMSO-d6 unless stated) |
|---|---|---|---|
| INTC203 | 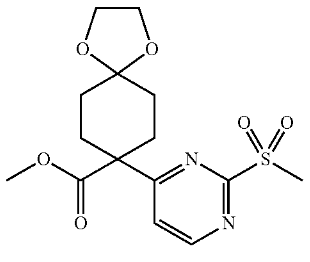 methyl 8-(2-(methylsulfonyl)pyrimidin-4-yl)-1,4-dioxaspiro[4.5]decane-8-carboxylate | Method Q using INTC186, [HPLC acidic], 357 (1.49). | 9.06 (d, J = 5.3 Hz, 1H), 7.93 (d, J = 5.3 Hz, 1H), 3.91-3.83 (m, 4H), 3.66 (s, 3H), 3.41 (s, 3H), 2.37-2.29 (m, 2H), 2.29-2.18 (m, 2H), 1.68-1.56 (m, 4H). |
| INTC204 | 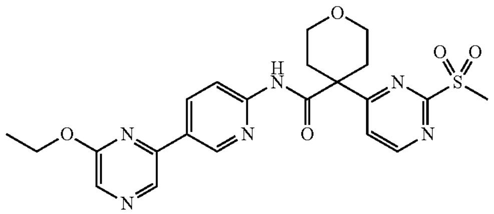 N-(5-(6-ethoxypyrazin-2-yl)pyridin-2-yl)-4-(2-(methylsulfonyl)pyrimidin-4-yl)tetrahydro-2H-pyran-4-carboxamide | Method Q using INTC182, [HPLC acidic], 485 (1.94). | 10.40 (s, 1H), 9.09 (d, J = 5.3 Hz, 1H), 9.04 (dd, J = 2.4, 0.8 Hz, 1H), 8.85 (s, 1H), 8.52 (dd, J = 8.7, 2.5 Hz, 1H), 8.26 (s, 1H), 8.22 (dd, J = 8.8, 0.8 Hz, 1H), 7.94 (d, J = 5.3 Hz, 1H), 4.48 (q, J = 7.0 Hz, 2H), 3.82-3.73 (m, 2H), 3.69-3.60 (m, 2H), 3.42 (s, 3H), 2.55-2.47 (m, 2H, obscured by DMSO peak), 2.33-2.22 (m, 2H), 1.40 (t, J = 7.0 Hz, 3H). |

TABLE 18-continued

The following intermediates were made according to Method Q.

| INTC | Name/Structure (All examples containing chiral centres are racemates unless stated) | Synthesis Method, [LCMS Method], m/z $(M + H)^+$, (Rt/min) | $^1H$ NMR Chemical Shift Data (DMSO-d6 unless stated) |
|---|---|---|---|
| INTC207 | 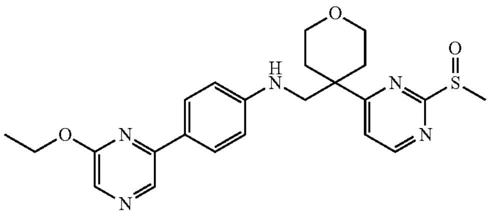 4-(6-ethoxypyrazin-2-yl)-N-((4-(2-(methylsulfinyl)pyrimidin-4-yl)tetrahydro-2H-pyran-4-yl)methyl)aniline | Method Q using INTC199, [HPLC, acidic], 454 (1.89). | 8.87 (d, J = 5.3 Hz, 1H), 8.56 (s, 1H), 7.99 (s, 1H), 7.77-7.71 (m, 3H), 6.57-6.47 (m, 2H), 6.07 (t, J = 6.7 Hz, 1H), 4.41 (q, J = 7.0 Hz, 2H), 3.80-3.74 (m, 2H), 3.47-3.42 (m, 2H), 3.31-3.24 (m, 2H), 2.83 (s, 3H), 2.36 (d, J = 13.4 Hz, 2H), 1.95-1.84 (m, 2H), 1.37 (t, J = 7.0 Hz, 3H). |
| INTC208 | 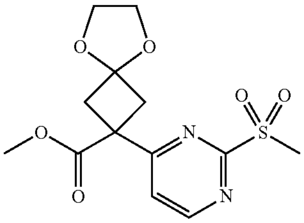 methyl 2-(2-(methylsulfonyl) pyrimidin-4-yl)-5,8-dioxaspiro [3.4]octane-2-carboxylate | Method Q using INTC188, [HPLC, acidic], 329 (1.27). | No data collected |
| INTC210 | 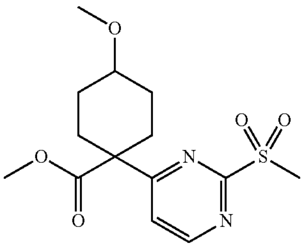 methyl 4-methoxy-1-(2-(methylsulfonyl)pyrimidin-4-yl)cyclohexane-1-carboxylate | Method Q using INTC190, [HPLC acidic], 329 (1.46). | No data collected |
| INTC230 | 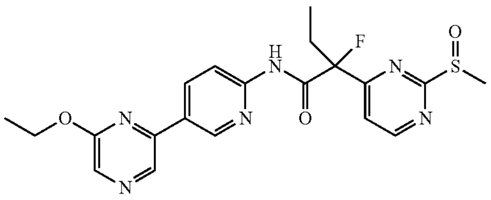 N-(5-(6-ethoxypyrazin-2-yl)pyridin-2-yl)-2-fluoro-2-(2-(methylsulfinyl)pyrimidin-4-yl)butanamide | Method Q using INTC229, sulfoxide 53% [HPLC acidic], 445 (1.92), sulfone 32% [HPLC acidic], 461 (2.12). | No Data collected |

Method R: Formation of Sulfonamides from Aromatic Sulfones

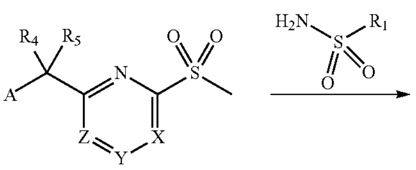

A = $CONHAr_1Ar_2$, $NHCOAr_1Ar_2$ or $CO_2Alkyl$
X = CH, N
Y = $CR_2$, N
Z = $CR_3$, N -continued

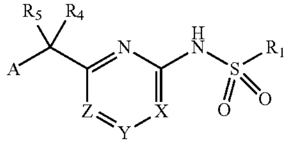

To a solution of sulfone (1.0 eq) and primary sulfonamide (1.1-2.0 eq) in polar aprotic solvent such as NMP (5-100 volumes) was added an inorganic base (3 eq) such as cesium carbonate and heated to 40-90° C. for 1-3 hrs. The reaction mixture was cooled to RT and diluted with water (50-100 volumes) and the mixture was washed with MTBE (100 volumes) and the aqueous was slowly acidified to pH 5 or lower using an appropriate acid such as HCl. The resulting precipitate was filtered to afford desired sulfonamide product.

TABLE 19

The following intermediates were made according to Method R.

| INTC | Name/Structure (All examples containing chiral centres are racemates unless stated) | Synthesis Method, [LCMS Method], m/z $(M + H)^+$, (Rt/min) | $^1H$ NMR Chemical Shift Data (DMSO-d6 unless stated) | Base, Solvent |
|---|---|---|---|---|
| INTC214 | 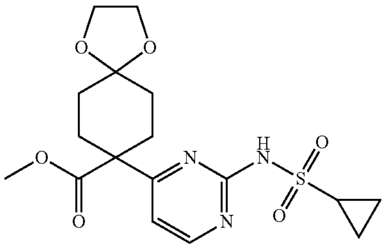 methyl 8-(2-(cyclopropanesulfonamido) pyrimidin-4-yl)-1,4-dioxaspiro[4.5] decane-8-carboxylate | Method R using INTC203, [HPLC acidic], 398 (1.63). | 11.28 (s, 1H), 8.63-8.54 (m, 1H), 7.21-7.11 (m, 1H), 3.87 (s, 3H), 3.65 (s, 4H), 3.24-3.15 (m, 1H), 2.31-2.23 (m, 2H), 2.18-2.02 (m, 2H), 1.70-1.52 (m, 4H), 1.19-0.99 (m, 4H). | $Cs_2CO_3$, NMP |
| INTC215 | 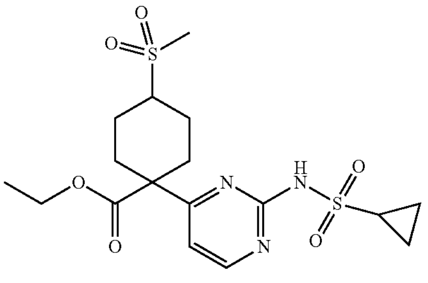 ethyl 4-(2-(cyclopropanesulfonamido)pyrimidin-4-yl)-1-(methylsulfonyl)piperidine-4-carboxylate | Method R using INTC205, [HPLC acidic], 433 (1.63). | No data collected | $Cs_2CO_3$, NMP |
| INTC216 | 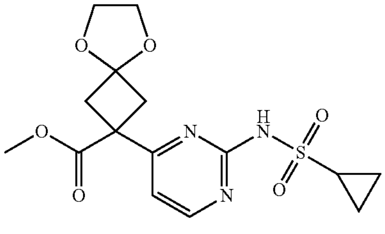 methyl 2-(2-(cyclopropanesulfonamido) pyrimidin-4-yl)-5,8-dioxaspiro[3.4] octane-2-carboxylate | Method R using INTC208, [UPLC acidic], 370 (0.48). | 11.32 (s, 1H), 8.60 (d, J = 5.2 Hz, 1H), 7.20 (d, J = 5.2 Hz, 1H), 3.87-3.82 (m, 2H), 3.82-3.78 (m, 2H), 3.66 (s, 3H), 3.27-3.18 (m, 1H), 3.05-2.97 (m, 2H), 2.98-2.84 (m, 2H), 1.17-1.08 (m, 2H), 1.07-0.99 (m, 2H). | $Cs_2CO_3$, NMP |

TABLE 19-continued

| The following intermediates were made according to Method R. | | | | |
|---|---|---|---|---|
| INTC | Name/Structure (All examples containing chiral centres are racemates unless stated) | Synthesis Method, [LCMS Method], m/z $(M + H)^+$, (Rt/min) | $^1H$ NMR Chemical Shift Data (DMSO-d6 unless stated) | Base, Solvent |
| INTC218 | 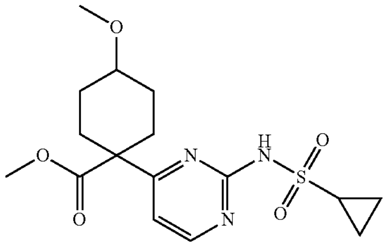 methyl 1-(2-(cyclopropanesulfonamido) pyrimidin-4-yl)-4-methoxycyclohexane-1-carboxylate | Method R using INTC210, [HPLC acidic], 370 (1.62). | 11.25 (s, 1H), 8.57 (d, J = 5.3 Hz, 1H), 7.23-7.11 (m, 1H), 3.65 (s, 3H), 3.24 (s, 3H), 3.23-3.20 (m, 1H), 2.48-2.54 (m 1H, obscured by DMSO peak) 2.37-2.29 (m, 2H), 1.97-1.80 (m, 4H), 1.36-1.24 (m, 2H), 1.16-1.01 (m, 4H). | $Cs_2CO_3$, NMP |

(4-(6-Ethoxypyrazin-2-yl)-2-fluorophenyl)methanol INTD87

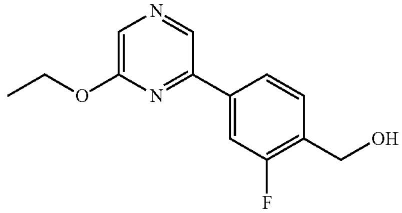 [SMILES: CCOc1cncc(-c2ccc(CO)c(F)c2)n1]

Prepared as for INTD84 using (4-bromo-2-fluorophenyl) methanol (205 mg, 1.00 mmol) and 2-ethoxy-6-(4,4,5,5-tetramethyl-1,3,2-dioxaborolan-2-yl)pyrazine (250 mg, 1.00 mmol) to afford (4-(6-ethoxypyrazin-2-yl)-2-fluorophenyl) methanol (260 mg, 0.995 mmol, quantitative yield) was isolated as a yellow gum. Rt 1.25 min (UPLC, acidic); m/z 249 $(M+H)^+$ $(ES^+)$; $^1H$ NMR (500 MHz, DMSO-d6) δ 8.85 (s, 1H), 8.26 (s, 1H), 7.99 (dd, J=8.0, 1.7 Hz, 1H), 7.91 (dd, J=11.6, 1.7 Hz, 1H), 7.66-7.57 (m, 1H), 5.37 (t, J=5.8 Hz, 1H), 4.62 (d, J=5.8 Hz, 2H), 4.49 (q, J=7.0 Hz, 2H), 1.41 (t, J=7.0 Hz, 3H).

4-(6-Ethoxypyrazin-2-yl)-2-fluorobenzaldehyde INTD88

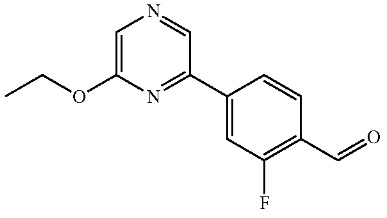 [SMILES: CCOc1cncc(-c2ccc(C=O)c(F)c2)n1]

Prepared as for INTD85 using (4-(6-ethoxypyrazin-2-yl)-2-fluorophenyl)methanol INTD87 (1.00 g, 4.03 mmol) to afford 4-(6-ethoxypyrazin-2-yl)-2-fluorobenzaldehyde (448 mg, 1.78 mmol, 44% yield) as a colourless solid. Rt 0.67 min (UPLC 2, acidic); m/z 247 $(M+H)^+$ $(ES^+)$; $^1H$ NMR (500 MHz, DMSO-d6) δ 10.28 (s, 1H), 8.98 (s, 1H), 8.37 (s, 1H), 8.22-8.13 (m, 2H), 7.99 (dd, J=8.3, 7.3 Hz, 1H), 4.52 (q, J=7.0 Hz, 2H), 1.42 (t, J=7.0 Hz, 3H).

Preparation of Examples

Amide Formation

Method 1: Amide Coupling Using HATU

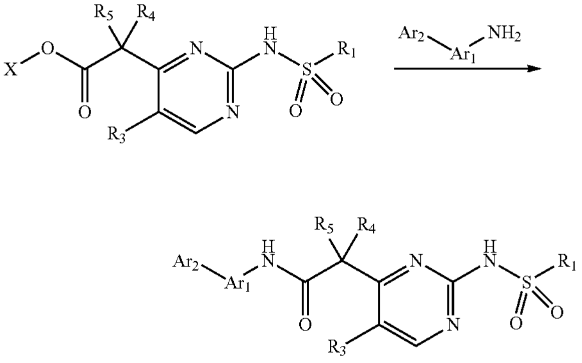

To a stirred suspension of the acid or the potassium salt (1 eq, X═H or K) and DIPEA (6 eq) in DMF (15 vol) the aniline (1 eq) and HATU (1.5 eq) were added. The reaction was stirred at RT for 18 hrs then concentrated in vacuo. MeOH and 2M NaOH (aq) were added. The mixture was stirred for 30 min then concentrated in vacuo. The aqueous phase acidified to pH 6 with 1M HCl (aq) and the product extracted into DCM. The organics were combined, dried (phase separator) and concentrated in vacuo.

The crude product was purified by reverse or normal phase chromatography or a combination of both.

N-(4-(5-Chloropyridin-3-yl)phenyl)-2-(2-(cyclopropanesulfonamido)pyrimidin-4-yl)butanamide P1

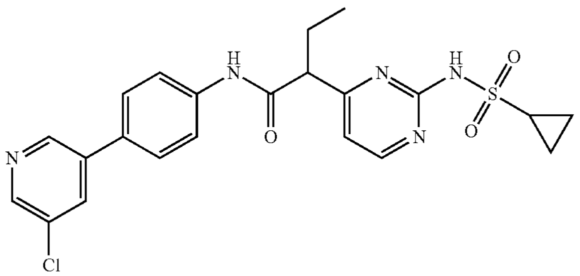 [SMILES: CCC(C(=O)Nc1ccc(-c2cncc(Cl)c2)cc1)c1ccnc(NS(=O)(=O)C2CC2)n1]

4-(5-chloropyridin-3-yl)aniline INTD8 (0.117 g, 0.573 mmol) and HATU (0.327 g, 0.859 mmol) were added to a stirred suspension of potassium 2-(2-(cyclopropanesulfonamido)pyrimidin-4-yl)butanoate INTC37 (0.265 g, 0.573 mmol) and DIPEA (0.60 mL, 3.44 mmol) in DMF (6 mL). The reaction was stirred at RT 18 hrs then concentrated in vacuo. The crude material was dissolved in MeOH (20 mL) and 2M NaOH (aq) (20 mL) was added. The mixture was stirred for 30 min then concentrated in vacuo. The aqueous phase acidified to pH 6 with 1M HCl (aq) (40 mL) and the product extracted into DCM (3×20 mL). The organics were combined, dried (phase separator) and concentrated in vacuo. The crude product was purified by chromatography on silica gel (12 g column, 0-100% EtOAc/iso-hexane) followed by chromatography on RP Flash C18 (5-75% MeCN/Water 0.1% formic acid) to afford N-(4-(5-chloropyridin-3-yl)phenyl)-2-(2 (cyclopropanesulfonamido)pyrimidin-4-yl)butanamide (0.158 g, 0.318 mmol, 56% yield) as a white solid. Rt 1.36 min; m/z 472 $(M+H)^+$ (ES+); $^1H$ NMR (500 MHz, DMSO-d6) δ 11.28 (s, 1H), 10.39 (s, 1H), 8.86 (d, J=2.0 Hz, 1H), 8.63-8.48 (m, 2H), 8.22 (t, J=2.2 Hz, 1H), 7.81-7.71 (m, 4H), 7.19 (d, J=5.2 Hz, 1H), 3.80-3.71 (m, 1H), 3.31-3.24 (m, 1H), 2.14-2.01 (m, 1H), 2.00-1.88 (m, 1H), 1.16-1.04 (m, 2H), 1.03-0.84 (m, 5H).

Method 2: $AlMe_3$ Mediated Amide Coupling from Ester

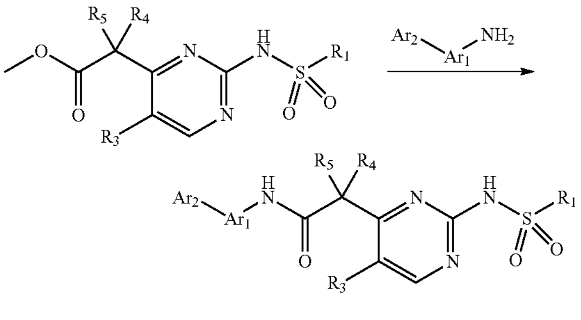

To an ice cooled solution of aniline (2 eq) in toluene (40 volumes) was added $AlMe_3$ (2.0 M in heptane, 2 eq). The mixture was stirred at this temperature for 5 mins then at RT for 10 mins. To this solution was added ester (1 eq) in one portion and the resultant mixture heated and stirred at 80° C. for 2 hrs. The reaction mixture was cooled in an ice bath and carefully quenched with MeOH (10 volumes). After stirring for 20 mins the mixture was diluted in a mixture of DCM/MeOH (10 volumes), filtered through celite and the filtrate concentrated. The crude product was purified by reverse or normal phase chromatography.

1-(2-(Cyclopropanesulfonamido)pyrimidin-4-yl)-N-(4-(6-ethoxypyrazin-2-yl)phenyl)cyclopentanecarboxamide P2

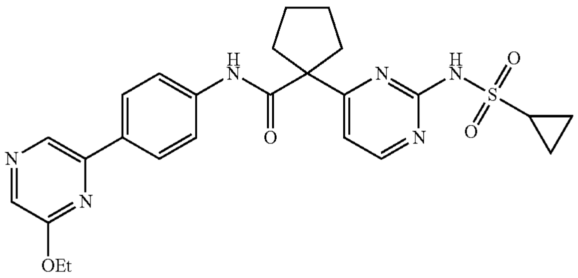 [SMILES: CCOc1cncc(-c2ccc(NC(=O)C3(c4ccnc(NS(=O)(=O)C5CC5)n4)CCCC3)cc2)n1]

To an ice cooled solution of 4-(6-ethoxypyrazin-2-yl)aniline INTD18 (0.099 g, 0.461 mmol) in toluene (4 mL) was added $AlMe_3$ (2.0 M in toluene) (0.307 mL, 0.615 mmol). The mixture was stirred at this temperature for 5 mins then at RT for 20 mins. To this solution was added methyl 1-(2-(cyclopropanesulfonamido)pyrimidin-4-yl)cyclopentanecarboxylate INTC29 (0.1 g, 0.307 mmol) in one portion and the resultant mixture heated and stirred at 100° C. for 3 h under $N_2$. The reaction mixture was carefully quenched with MeOH (2 mL). After stirring for 20 mins the mixture was diluted in MeOH (50 mL), filtered through celite (5 g) and the filtrate was concentrated in vacuo. The crude product was purified by chromatography on RP Flash C18 (25-75% MeCN/Water 0.1% formic acid) to afford 1-(2-(cyclopropanesulfonamido)pyrimidin-4-yl)-N-(4-(6-ethoxypyrazin-2-yl)phenyl)cyclopentanecarboxamide (0.053 g, 0.099 mmol, 32% yield) as a white solid. Rt 1.59 min (UPLC, acidic); m/z 509 $(M+H)^+$ $(ES^+)$; $^1H$ NMR (500 MHz, DMSO-d6) δ 11.33 (s, 1H), 9.58 (s, 1H), 8.76 (s, 1H), 8.62-8.46 (m, 1H), 8.18 (s, 1H), 8.11-8.00 (m, 2H), 7.83-7.70 (m, 2H), 7.17-6.96 (m, 1H), 4.56-4.37 (m, 2H), 3.28-3.16 (m, 1H), 2.51-2.40 (m, 2H), 2.25-2.09 (m, 2H), 1.82-1.60 (m, 4H), 1.46-1.34 (m, 3H), 1.12-0.99 (m, 2H), 0.95-0.80 (m, 2H).

2-(2-(cyclopropanesulfonamido)pyrimidin-4-yl)-N-(4-(6-methoxypyrazin-2-yl)phenyl)-2-methylpropanamide P3

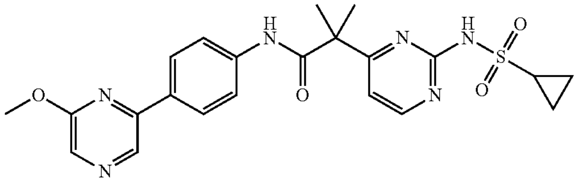 [SMILES: COc1cncc(-c2ccc(NC(=O)C(C)(C)c3ccnc(NS(=O)(=O)C4CC4)n3)cc2)n1]

4-(6-Methoxypyrazin-2-yl)aniline INTD1 (101 mg, 0.501 mmol) was added to an ice cooled solution of $AlMe_3$ (2M in heptane) (0.33 mL, 0.668 mmol) in toluene (4 mL). The mixture was stirred at this temperature for 5 mins then at RT for 10 mins. Methyl 2-(2-(cyclopropanesulfonamido)pyrimidin-4-yl)-2-methylpropanoate INTC21 (100 mg, 0.334 mmol) was added in one portion and the resultant mixture heated at 100° C. for 2 hrs. The reaction mixture was cooled in an ice bath and carefully quenched with MeOH (10 mL). After stirring for 20 mins the mixture was diluted with a mixture of DCM/MeOH (10 mL, 1:1), filtered through celite and the solvent removed to give an orange oil. The crude product was purified by chromatography on silica gel (24 g column, 0-100% EtOAc/iso-hexane) to afford 2-(2-(cyclopropanesulfonamido)pyrimidin-4-yl)-N-(4-(6-methoxypyrazin-2-yl)phenyl)-2-methylpropanamide (37 mg, 0.077 mmol, 23% yield) as a pale beige solid. Rt 2.03 min (HPLC acidic); m/z 469 $(M+H)^+$ $(ES^+)$; $^1H$ NMR (400 MHz, DMSO-d6) δ 11.27 (s, 1H), 9.51 (s, 1H), 8.78 (s, 1H), 8.61 (d, J=5.3 Hz, 1H), 8.21 (s, 1H), 8.14-8.04 (m, 2H), 7.84-7.74 (m, 2H), 7.20 (d, J=5.3 Hz, 1H), 4.02 (s, 3H), 3.25-3.18 (m, 1H), 1.60 (s, 6H), 1.08-0.99 (m, 2H), 0.85-0.74 (m, 2H).

2-(2-(Cyclopropanesulfonamido)pyrimidin-4-yl)-2-methyl-N-(4-(5-(trifluoromethyl)pyridin-3-yl)phenyl)propanamide P4

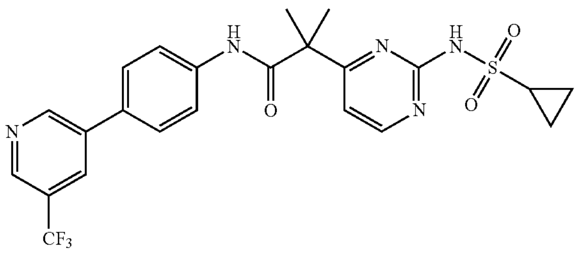 [SMILES: CC(C)(C(=O)Nc1ccc(-c2cncc(C(F)(F)F)c2)cc1)c1ccnc(NS(=O)(=O)C2CC2)n1]

To an ice cooled solution of 4-(5-(trifluoromethyl)pyridin-3-yl)aniline INTD7 (0.119 g, 0.501 mmol) in toluene (4 mL) and THF (2 mL) was added $AlMe_3$ (2.0 M in heptane) (0.334 mL, 0.668 mmol).

The mixture was stirred at this temperature for 5 mins then at RT for 10 min. To this solution was added methyl 2-(2-(cyclopropanesulfonamido)pyrimidin-4-yl)-2-methylpropanoate INTC21 (0.1 g, 0.334 mmol) in one portion and the resultant mixture stirred and heated at 80° C. for 2 hrs in a sealed vessel. The reaction mixture was cooled in an ice bath and carefully quenched with MeOH. After stirring for 20 min the mixture was diluted in a mixture of DCM/MeOH, filtered through celite and the filtrate concentrated in vacuo. The crude product was purified by chromatography on RP Flash C18 (5-75% MeCN/Water 0.1% formic acid) to afford 2-(2-(cyclopropanesulfonamido)pyrimidin-4-yl)-2-methyl-N-(4-(5-(trifluoromethyl)-pyridin-3-yl)phenyl)propanamide (0.109 g, 0.205 mmol, 61% yield) as a white solid. Rt 2.17 (HPLC acidic); m/z 506 $(M+H)^+$ $(ES^+)$; $^1H$ NMR (400 MHz, DMSO-d6) δ 11.28 (s, 1H), 9.49 (s, 1H), 9.28-9.11 (m, 1H), 8.98-8.84 (m, 1H), 8.68-8.54 (m, 1H), 8.50-8.37 (m, 1H), 7.95-7.71 (m, 4H), 7.28-7.12 (m, 1H), 3.27-3.13 (m, 1H), 1.60 (s, 6H), 1.13-0.95 (m, 2H), 0.91-0.69 (m, 2H).

2-Methyl-N-(2-methyl-4-(6-methylpyrazin-2-yl)phenyl)-2-(2-(methylsulfonamido)pyrimidin-4-yl)propanamide P5

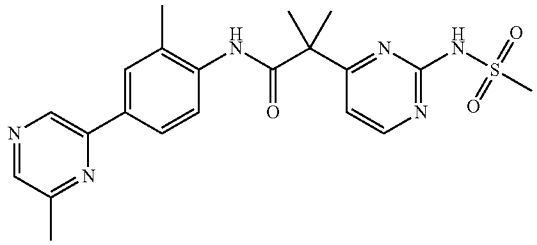 [SMILES: Cc1cncc(-c2ccc(NC(=O)C(C)(C)c3ccnc(NS(C)(=O)=O)n3)c(C)c2)n1]

To an ice cooled solution of 4-(6-chloropyrazin-2-yl)-2-methylaniline INTD26 (0.549 mmol, 121 mg) in toluene (2 mL) was added $AlMe_3$ (0.55 mL, 1.098 mmol, 2.0 M in heptane). The mixture was stirred at this temperature for 5 min then at RT for 10 min. To this solution was added methyl 2-methyl-2-(2-(methylsulfonamido)pyrimidin-4-yl)propanoate INTC19 (100 mg, 0.366 mmol) in one portion and the resultant mixture stirred and heated at 90° C. for 2 hrs. The reactions were cooled to 0° C., 1M HCl (5 mL) was added and the residues were extracted with EtOAc (2×20 mL). The combined organic extract was passed through a phase separator and the solvent was removed under reduced pressure. The crude product was purified by chromatography on RP Flash C18 (0-100% MeCN/Water 0.1% formic acid) to afford 2-methyl-N-(2-methyl-4-(6-methylpyrazin-2-yl)phenyl)-2-(2-(methylsulfonamido)pyrimidin-4-yl)propanamide (78.9 mg, 0.170 mmol, 47% yield) as an off-white solid. Rt 1.74 (HPLC, acidic); m/z 441 $(M+H)^+$ $(ES^+)$; $^1H$ NMR (500 MHz, DMSO-d6) δ 11.35 (s, 1H), 9.07-8.99 (m, 2H), 8.62 (d, J=5.3 Hz, 1H), 8.48 (s, 1H), 7.99 (d, J=2.1 Hz, 1H), 7.93 (dd, J=8.3, 2.2 Hz, 1H), 7.42 (d, J=8.3 Hz, 1H), 7.23 (d, J=5.3 Hz, 1H), 3.39 (s, 3H), 2.56 (s, 3H), 2.19 (s, 3H), 1.62 (s, 6H).

4-(2-(Cyclopropanesulfonamido)pyrimidin-4-yl)-N-(5-(6-ethoxypyrazin-2-yl)pyridin-2-yl)tetrahydro-2H-pyran-4-carboxamide P115

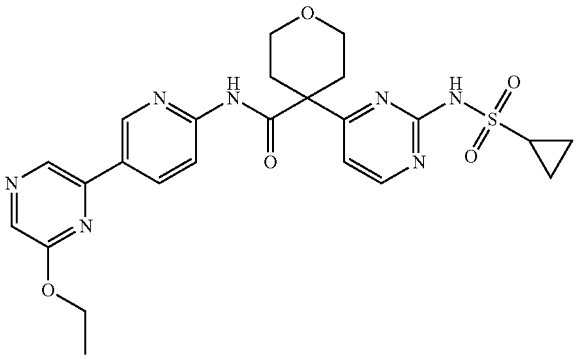 [SMILES: CCOc1cncc(-c2ccc(NC(=O)C3(c4ccnc(NS(=O)(=O)C5CC5)n4)CCOCC3)nc2)n1]

To a solution of 5-(6-ethoxypyrazin-2-yl)pyridin-2-amine INTD33 (0.14 g, 0.66 mmol) in toluene (3.0 mL, 28.2 mmol) at 0° C. was added $AlMe_3$ (0.66 mL, 1.32 mmol, 2.0 M in heptane). The reaction mixture was stirred for 5 mins at 0° C. then 10 mins at RT. Methyl 4-(2-(cyclopropanesulfonamido)pyrimidin-4-yl)tetrahydro-2H-pyran-4-carboxylate INTC53 (0.15 g, 0.44 mmol) was added in one portion and the reaction mixture was heated to 95° C. for 1 h, then cooled to 0° C. The reaction mixture was quenched with 1 M HCl (5 mL) and diluted with EtOAc (10 mL). The phases were separated and the aqueous was extracted using further EtOAc (2×10 mL). The combined organics were dried over $MgSO_4$, filtered and concentrated in vacuo. The crude product was purified by chromatography on silica gel (12 g column, 0-100% EtOAc/iso-hexane) to afford 4-(2-(cyclopropanesulfonamido)pyrimidin-4-yl)-N-(5-(6-ethoxypyrazin-2-yl)pyridin-2-yl)tetrahydro-2H-pyran-4-carboxamide (0.022 g, 0.040 mmol, 9% yield) as a white solid. Rt 1.31 min (UPLC, acidic); m/z 526 $(M+H)^+$ $(ES^+)$; $^1H$ NMR (500 MHz, DMSO-d6) δ 11.31 (s, 1H), 10.13 (s, 1H), 9.03 (d, J=2.5 Hz, 1H), 8.84 (s, 1H), 8.63 (d, J=5.3 Hz, 1H), 8.50 (dd, J=8.8, 2.5 Hz, 1H), 8.26 (s, 1H), 8.20 (d, J=8.8 Hz, 1H), 7.26 (d, J=5.3 Hz, 1H), 4.48 (q, J=7.0 Hz, 2H), 3.81-3.69 (m, 2H), 3.67-3.56 (m, 2H), 3.31-3.20 (m, 1H), 2.49-2.41 (m, 2H), 2.25-2.17 (m, 2H), 1.40 (t, J=7.0 Hz, 3H), 1.09-1.03 (m, 2H), 0.95-0.84 (m, 2H).

Method 2b: $DABALMe_3$ Mediated Amide Coupling from Ester

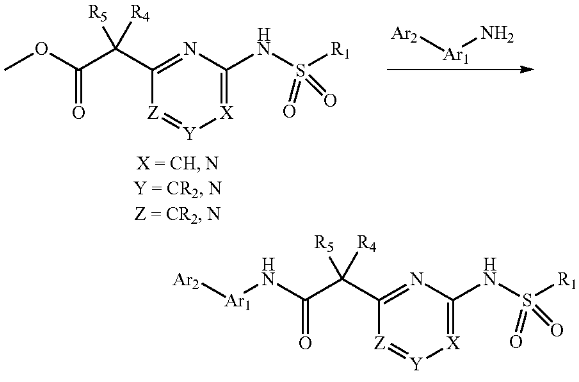

To a solution of ester (1 eq) and aniline (1.5 eq) in toluene (30 volumes) was added $DABAL-Me_3$ (1.5 eq) and the resulting mixture was heated at 100° C. for 4 h. The reaction mixture was cooled to 0° C. and quenched by careful addition of 1 M HCl (aq, 20 volumes). The aqueous phase was extracted with EtOAc (3×20 volumes). The combined organics were washed with 1 M HCl (aq, 2×10 volumes), dried over $Na_2SO_4$, filtered and concentrated in vacuo. The crude product was purified by reverse or normal phase chromatography.

Method 3: Amide Coupling from Potassium Salt Using T3P

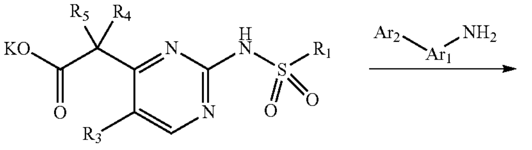

-continued

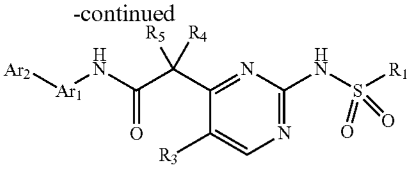

Pyridine (10 eq) followed by T3P (50 wt % in DMF, 2 eq) was added to a stirring solution of amine (1.1 eq) and potassium 2-(2-(cyclopropanesulfonamido)pyrimidin-4-yl) butanoate (1 eq) in DMF (16 volumes). The resulting reaction was stirred at RT for 24 hrs. The crude reaction mixture was concentrated in vacuo then diluted with $NH_4Cl$ (sat. aq) and extracted with DCM. The combined organic extracts were dried (phase separator) and the solvent removed. The crude product was purified by reverse or normal phase chromatography.

2-(2-(Cyclopropanesulfonamido)pyrimidin-4-yl)-N-(2-fluoro-4-(pyrazin-2-yl)phenyl)butanamide P6

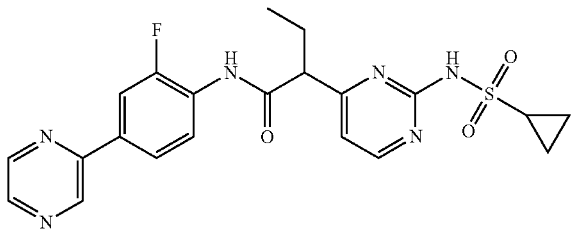 [SMILES: CCC(C(=O)Nc1ccc(-c2cnccn2)cc1F)c1ccnc(NS(=O)(=O)C2CC2)n1]

T3P (50 wt % in DMF) (1.120 mL, 1.546 mmol) was added to a stirred suspension of 2-fluoro-4-(pyrazin-2-yl) aniline INTD23 (154 mg, 0.773 mmol), potassium 2-(2-(cyclopropanesulfonamido)pyrimidin-4-yl)butanoate INTC37 (250 mg, 0.773 mmol) and pyridine (0.313 mL, 3.87 mmol) in DMF (1 mL). The resulting reaction was stirred at RT for 18 hrs. Water (5 mL) was added and the newly formed precipitate filtered. The product was recovered by dissolving in DCM (10 mL) and concentrated in vacuo. The crude product was purified by preparative HPLC (20-50% MeCN/Water 0.1% formic acid) to afford 2-(2-(cyclopropanesulfonamido)pyrimidin-4-yl)-N-(2-fluoro-4-(pyrazin-2-yl)phenyl)butanamide (32 mg, 0.069 mmol, 9% yield) as a colourless powder. Rt 1.15 min (UPLC acidic); m/z 457 $(M+H)^+$ $(ES^+)$; $^1H$ NMR (500 MHz, DMSO-d6) δ 11.26 (s, 1H), 10.25 (s, 1H), 9.29 (d, J=1.6 Hz, 1H), 8.72 (dd, J=2.5, 1.5 Hz, 1H), 8.62 (d, J=2.5 Hz, 1H), 8.57 (d, J=5.2 Hz, 1H), 8.12-8.03 (m, 2H), 8.03-7.97 (m, 1H), 7.20 (d, J=5.2 Hz, 1H), 4.00 (dd, J=7.5 Hz, 1H), 3.31-3.28 (m, 1H), 2.12-2.02 (m, 1H), 2.00-1.92 (m, 1H), 1.16-1.07 (m, 2H), 1.03-0.93 (m, 5H).

2-(2-(Cyclopropanesulfonamido)pyrimidin-4-yl)-N-(4-(5-(trifluoromethyl)pyridin-3-yl)phenyl)butanamide P7

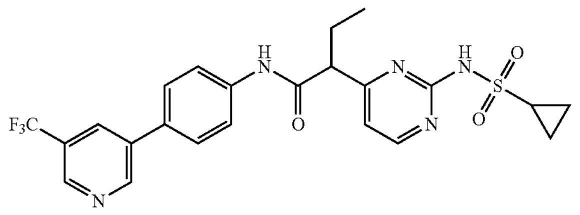 [SMILES: CCC(C(=O)Nc1ccc(-c2cncc(C(F)(F)F)c2)cc1)c1ccnc(NS(=O)(=O)C2CC2)n1]

T3P (50 wt % in DMF) (0.78 mL, 1.082 mmol) was added to a stirred suspension of potassium 2-(2-(cyclopropanesulfonamido)pyrimidin-4-yl)butanoate INTC37 (250 mg, 0.541 mmol) and 4-(5-(trifluoromethyl)pyridin-3-yl)aniline INTD7 (129 mg, 0.541 mmol) in pyridine (0.13 mL, 1.623 mmol) and DMF (3 mL). The resulting reaction was stirred at RT for 18 hrs. The crude reaction mixture was diluted with saturated $NH_4Cl$ (aq) (10 mL) and extracted with DCM (3×10 mL). The combined organic extracts were dried (phase separator) and the solvent removed under reduced pressure. The crude product was purified by chromatography on silica gel (0-10% MeOH in DCM), followed by chromatography on RP Flash C18 (15-75% MeCN/Water 0.1% formic acid) to afford 2-(2-(cyclopropanesulfonamido)pyrimidin-4-yl)-N-(4-(5-(trifluoromethyl)pyridin-3-yl)phenyl)butanamide (19 mg; 0.038 mmol; 7% yield). Rt 1.44 (UPLC, acidic); m/z 506 $(M+H)^+$ $(ES^+)$; $^1H$ NMR (500 MHz, DMSO-d6) δ 11.25 (s, 1H), 10.41 (s, 1H), 9.20 (d, J=2.2 Hz, 1H), 8.94-8.92 (m, 1H), 8.57 (d, J=5.2 Hz, 1H), 8.45-8.42 (m, 1H), 7.87-7.83 (m, 2H), 7.79-7.75 (m, 2H), 7.21 (d, J=5.2 Hz, 1H), 3.77 (dd, J=8.7, 6.3 Hz, 1H), 3.31-3.26 (m, 1H), 2.13-2.03 (m, 1H), 1.98-1.89 (m, 1H), 1.13-1.06 (m, 2H), 1.01-0.89 (m, 5H).

2-(2-(Cyclopropanesulfonamido)pyrimidin-4-yl)-N-(4-(6-(trifluoromethyl)pyrazin-2-yl)phenyl)acetamide P8

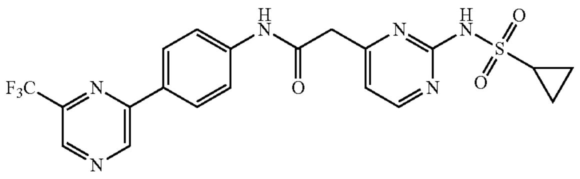 [SMILES: O=C(Cc1ccnc(NS(=O)(=O)C2CC2)n1)Nc1ccc(-c2cncc(C(F)(F)F)n2)cc1]

T3P (50 wt % in DMF) (0.343 mL, 0.474 mmol) was added to a stirred suspension of potassium 2-(2-(cyclopropanesulfonamido)pyrimidin-4-yl)acetate INTC39 (100 mg, 0.237 mmol), 4-(6-(trifluoromethyl)pyrazin-2-yl)aniline INTD19 (56.7 mg, 0.237 mmol) and pyridine (0.096 mL, 1.185 mmol) in DMF (1 mL). The resulting reaction was stirred at RT for 18 hrs. Water (5 mL) was added and the newly formed precipitate was filtered to afford the crude product. The crude product was purified by chromatography on silica gel (0-10% MeOH in DCM) followed by preparative HPLC (5-95% MeCN/Water 0.1% formic acid) to afford 2-(2-(cyclopropanesulfonamido)pyrimidin-4-yl)-N-(4-(6-(trifluoromethyl)pyrazin-2-yl)phenyl)acetamide (10 mg, 0.021 mmol, 9% yield) as a yellow powder. Rt 1.31 min (UPLC, acidic); m/z 479 $(M+H)^+$ $(ES^+)$; $^1H$ NMR (500 MHz, DMSO-d6) observed as mixture of tautomers δ 12.81 (s, 1H, minor), 11.24 (s, 1H, major), 10.95 (s, 1H, minor), 10.58 (s, 1H, major), 10.09 (s, 1H, minor), 9.58 (s, 1H, major), 9.57 (s, 1H, minor), 9.09 (s, 1H, major), 9.06 (s, 1H, minor), 8.57 (d, J=5.1 Hz, 1H, major), 8.24-8.13 (m, 2×2H, major and minor), 7.85-7.79 (m, 2×2H, major and minor), 7.18 (d, J=5.0 Hz, 1H, major), 6.95 (d, J=7.5 Hz, 1H, minor), 5.89 (d, J=7.5 Hz, 1H, minor), 5.06 (s, 1H, minor), 3.89 (s, 2H, major), 3.28-3.22 (m, 1H, major), 2.73-2.65 (m, 1H, minor), 1.13-0.90 (m, 2×4H, major and minor).

Method 4: Amide Coupling from Lithium Salt Using T3P

N-(5-(6-Ethoxypyrazin-2-yl)pyridin-2-yl)-2-fluoro-2-(2-(N-(4-methoxybenzyl)cyclopropanesulfonamido)pyrimidin-4-yl)butanamide INTC51

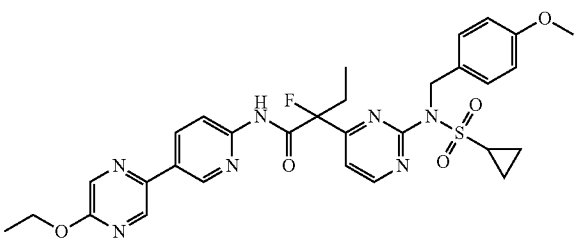 [SMILES: CCOc1cnc(-c2ccc(NC(=O)C(F)(CC)c3ccnc(N(Cc4ccc(OC)cc4)S(=O)(=O)C4CC4)n3)nc2)cn1]

To a solution of lithium 2-fluoro-2-(2-(N-(4-methoxybenzyl)cyclopropane-sulfonamido)pyrimidin-4-yl)butanoate INTC50 (0.50 g, 1.17 mmol) in DMF (5 mL) at 0° C. was added 5-(6-ethoxypyrazin-2-yl)pyridin-2-amine INTD33 (0.30 g, 1.40 mmol) followed by pyridine (0.57 mL, 7.01 mmol) and T3P (50 wt % in DMF) (1.69 mL, 2.34 mmol). The reaction mixture was stirred at 0° C. for 2 hrs then warmed to RT for 20 hrs. The reaction mixture was cooled to 0° C. and further T3P (50 wt % in DMF) (0.5 mL, 0.69 mmol) was added. The reaction mixture was stirred at 0° C. for 1 hr, then RT for 3 hrs. The reaction mixture was diluted with sat. $NH_4Cl$ (aq, 45 mL) and the resultant precipitate was isolated by filtration, washing with water (2×20 mL). The resultant yellow precipitate was dissolved in DCM (30 mL) and MeOH (30 mL) and concentrated onto silica. The crude product was purified by chromatography on silica gel (24 g column, 0-60% EtOAc/iso-hexane) to afford N-(5-(6-ethoxypyrazin-2-yl)pyridin-2-yl)-2-fluoro-2-(2-(N-(4-methoxybenzyl) cyclopropanesulfonamido)pyrimidin-4-yl) butanamide (0.274 g, 0.433 mmol, 37% yield) as a colourless oil. Rt 1.84 min (UPLC, acidic); m/z 622 $(M+H)^+$ $(ES^+)$; $^1H$ NMR (500 MHz, DMSO-d6) δ 10.69 (s, 1H), 9.10 (d, J=2.5 Hz, 1H), 8.88-8.81 (m, 2H), 8.52 (dd, J=8.7, 2.5 Hz, 1H), 8.27 (s, 1H), 8.10 (d, J=8.7 Hz, 1H), 7.52 (dd, J=5.2, 1.3 Hz, 1H), 7.30-7.23 (m, 2H), 6.81-6.74 (m, 2H), 5.20-5.08 (m, 2H), 4.48 (q, J=7.0 Hz, 2H), 3.76-3.70 (m, 1H), 3.65 (s, 3H), 2.50-2.39 (m, 1H), 2.38-2.24 (m, 1H), 1.40 (t, J=7.0 Hz, 3H), 1.14-1.06 (m, 1H), 1.10-0.97 (m, 2H), 0.96-0.92 (m, 1H), 0.89 (t, J=7.3 Hz, 3H).

N-(5-(6-ethoxypyrazin-2-yl)pyridin-2-yl)-2-fluoro-2-(2-(methylthio)pyrimidin-4-yl)butanamide INTC229

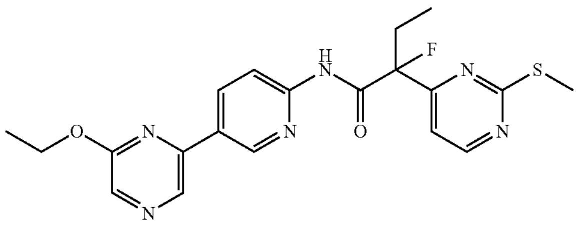 [SMILES: CCOc1cncc(-c2ccc(NC(=O)C(F)(CC)c3ccnc(SC)n3)nc2)n1]

Prepared using Method 4 using 5-(6-ethoxypyrazin-2-yl) pyridin-2-amine (2.72 g, 11.94 mmol) INTD33 and lithium 2-fluoro-2-(2-(methylthio)pyrimidin-4-yl)butanoate (2.82 g, 11.94 mmol) INTC228 to afford N-(5-(6-ethoxypyrazin-2-yl)pyridin-2-yl)-2-fluoro-2-(2-(methylthio)pyrimidin-4-yl) butanamide (45% yield) as a thick colourless oil. Rt 2.59 min (HPLC, acidic); m/z 429 (M+H)+(ES+); 1H NMR (500 MHz, DMSO-d6) δ 10.63 (s, 1H), 9.13-9.09 (m, 1H), 8.87 (s, 1H), 8.78 (d, J=5.2 Hz, 1H), 8.54 (dd, J=8.7, 2.5 Hz, 1H), 8.27 (s, 1H), 8.13 (d, J=8.7 Hz, 1H), 7.54 (dd, J=5.2, 1.2 Hz, 1H), 4.49 (q, J=7.0 Hz, 2H), 2.56 (s, 3H), 2.42-2.27 (m, 2H), 1.40 (t, J=7.0 Hz, 3H), 0.93 (t, J=7.3 Hz, 3H).

Method 5: NH-Amide Formation Via Amide Deprotection and/or Decarboxylation

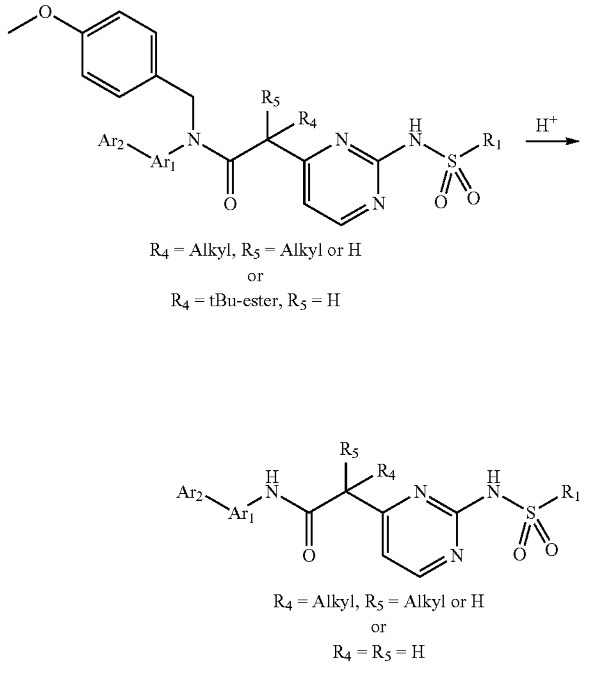

To a solution of the protected amide in DCM a mixture of TFA (88 eq) and triflic acid (1-6 eq) was added and the mixture left stirring at RT for 18-36 hrs and then concentrated in vacuo. The crude product was purified by column chromatography on silica gel or by RP chromatography.

2-(2-(Cyclopropanesulfonamido)pyrimidin-4-yl)-N-(4-(6-ethoxypyrazin-2-yl)phenyl)butanamide P105

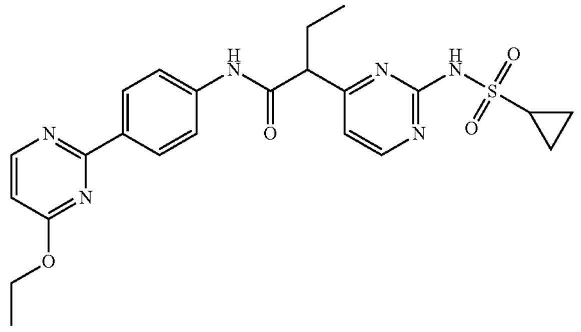 [SMILES: CCOc1ccnc(-c2ccc(NC(=O)C(CC)c3ccnc(NS(=O)(=O)C4CC4)n3)cc2)n1]

A solution of 2-(2-(cyclopropanesulfonamido)pyrimidin-4-yl)-N-(4-(6-ethoxypyrazin-2-yl)phenyl)-N-(4-methoxybenzyl)butanamide INTC46 (0.18 g, 0.299 mmol) in a mixture of TFA (2 mL, 26.0 mmol) and DCM (2 mL) was stirred at 25° C. for 18 hrs. The reaction was heated at 50° C. for 2 hrs. To the reaction was added triflic acid (0.027 mL, 0.299 mmol) and the mixture stirred at 25° C. for 2 hrs. The reaction mixture was concentrated and then diluted in 1 N HCl (aq) (20 mL). The aqueous phase was extracted with DCM (3×20 mL), dried (phase separator) and the solvent was removed under reduced pressure. The crude product was purified by chromatography on RP Flash C18 (24 g column, 5-75% MeCN/Water 0.1% formic acid) to afford 2-(2-(cyclopropanesulfonamido)pyrimidin-4-yl)-N-(4-(6-ethoxypyrazin-2-yl)phenyl)butanamide (0.02 g, 0.041 mmol, 14% yield) as a white solid. Rt 2.23 min (HPLC acidic); 483 $(M+H)^+$ $(ES^+)$.

2-(2-(Cyclopropanesulfonamido)pyrimidin-4-yl)-N-(4-(6-ethoxypyrazin-2-yl)phenyl)acetamide P18

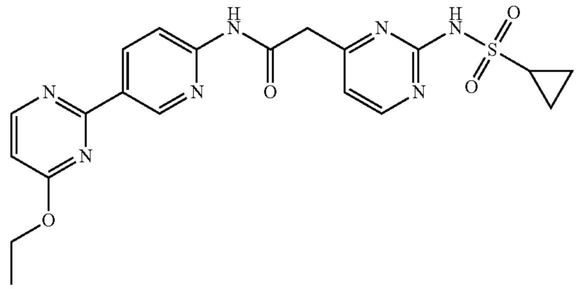 [SMILES: CCOc1ccnc(-c2ccc(NC(=O)Cc3ccnc(NS(=O)(=O)C4CC4)n3)nc2)n1]

To a solution of tert-butyl 2-(2-(cyclopropanesulfonamido)pyrimidin-4-yl)-3-((4-(6-ethoxypyrazin-2-yl)phenyl)(4-methoxybenzyl)amino)-3-oxopropanoate INTC47 (0.1 g, 0.148 mmol) in a mixture of TFA (1 mL, 12.98 mmol) and DCM (20 mL) was added triflic acid (0.039 mL, 0.445 mmol). The mixture was stirred at 25° C. for 18 hrs. Further triflic acid (0.039 mL, 0.445 mmol) was added and the mixture stirred at 25° C. for a further 18 hrs. The reaction mixture was concentrated under reduced pressure. The crude product was purified by chromatography on silica gel (12 g column, 0-10% MeOH/DCM,) to afford 2-(2-(cyclopropanesulfonamido)pyrimidin-4-yl)-N-(4-(6-ethoxypyrazin- 2-yl)phenyl)acetamide (0.03 g, 0.063 mmol, 42% yield) as a pale yellow solid. Rt 1.98 min (HPLC, acidic); m/z 455 $(M+H)^+$ $(ES^+)$.

Method 6: Deprotection of Sulfonamide

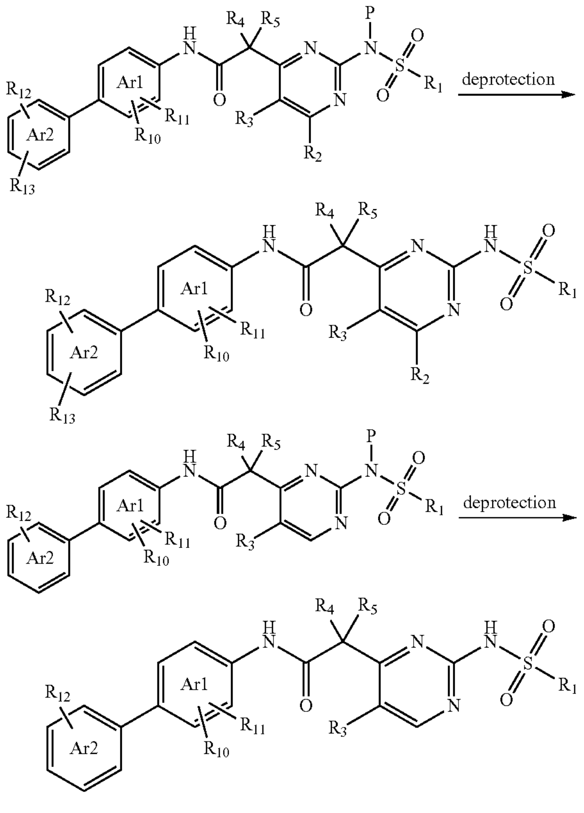

2-(2-(Cyclopropanesulfonamido)pyrimidin-4-yl)-N-(5-(6-ethoxypyrazin-2-yl)pyridin-2-yl)-2-fluorobutanamide P112

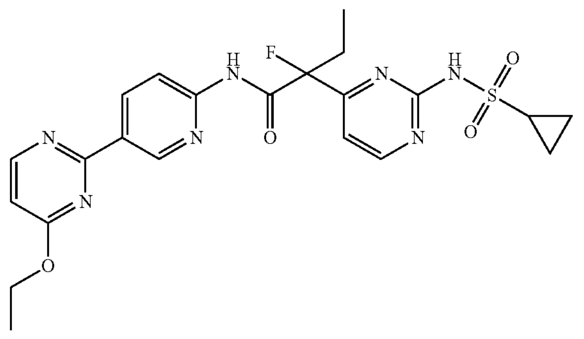 [SMILES: CCOc1ccnc(-c2ccc(NC(=O)C(F)(CC)c3ccnc(NS(=O)(=O)C4CC4)n3)nc2)n1]

TFA (0.28 mL, 3.70 mmol) was added into a stirring solution of N-(5-(6-ethoxypyrazin-2-yl)pyridin-2-yl)-2-fluoro-2-(2-(N-(4-methoxybenzyl)cyclopropanesulfonamido)pyrimidin-4-yl)butanamide INTC51 (115 mg, 0.185 mmol) in DCM (10 mL) and the resulting reaction mixture was stirred at RT for 4 hrs. The reaction mixture was concentrated in vacuo and the crude product was purified by chromatography on silica gel (12 g column, 0-100% EtOAc/iso-hexane) to afford 2-(2-(cyclopropanesulfonamido)pyrimidin-4-yl)-N-(5-(6-ethoxypyrazin-2-yl)pyridin-2-yl)-2-fluorobutanamide (77 mg, 0.15 mmol, 81% yield) as a white solid. Rt 2.28 min (HPLC, acidic); m/z 502 $(M+H)^+$ (ES+); $^1H$ NMR (500 MHz, DMSO-d6) δ 11.50 (s, 1H), 10.60 (d, J=2.3 Hz, 1H), 9.10 (d, J=2.5 Hz, 1H), 8.87 (s, 1H), 8.76 (d, J=5.1 Hz, 1H), 8.53 (dd, J=8.8, 2.5 Hz, 1H), 8.27 (s, 1H), 8.10 (d, J=8.8 Hz, 1H), 7.48 (d, J=5.1 Hz, 1H), 4.49 (q, J=7.0 Hz, 2H), 3.38-3.27 (m, 1H), 2.44-2.29 (m, 2H), 1.40 (t, J=7.0 Hz, 3H), 1.20-0.92 (m, 7H).

The racemate P112 was separated by chiral preparative HPLC using a Diacel Chiralpak IC column (20% EtOH in [4:1 heptane:chloroform (0.2% TFA):]) to afford:

P112 Enantiomer 1 Stereochemistry of Product was not Assigned (P113)

2-(2-(cyclopropanesulfonamido)pyrimidin-4-yl)-N-(5-(6-ethoxypyrazin-2-yl)pyridin-2-yl)-2-fluorobutanamide; Rt 2.28 mins (HPLC acidic); m/z 502 $(M+H)^+$ $(ES^+)$; $^1H$ NMR (500 MHz, DMSO-d6) δ 11.50 (s, 1H), 10.60 (d, J=2.2 Hz, 1H), 9.11 (d, J=2.5 Hz, 1H), 8.87 (s, 1H), 8.76 (d, J=5.1 Hz, 1H), 8.53 (dd, J=8.8, 2.5 Hz, 1H), 8.27 (s, 1H), 8.10 (d, J=8.8 Hz, 1H), 7.48 (d, J=5.1 Hz, 1H), 4.49 (q, J=7.0 Hz, 2H), 3.39-3.26 (m, 1H), 2.54-2.43 (m, 1H), 2.41-2.28 (m, 1H), 1.40 (t, J=7.0 Hz, 3H), 1.22-0.89 (m, 7H).

The product was analysed by Chiral IC3 method HPLC; Rt=10.47 mins, 100% ee at 254 nm.

P112 Enantiomer 2 Stereochemistry of Product was not Assigned (P114)

2-(2-(cyclopropanesulfonamido)pyrimidin-4-yl)-N-(5-(6-ethoxypyrazin-2-yl)pyridin-2-yl)-2-fluorobutanamide; Rt 2.28 min (HPLC acidic); m/z 502 $(M+H)^+$ $(ES^+)$; $^1H$ NMR (500 MHz, DMSO-d6) δ 11.50 (s, 1H), 10.60 (d, J=2.3 Hz, 1H), 9.11 (d, J=2.5 Hz, 1H), 8.87 (s, 1H), 8.76 (d, J=5.1 Hz, 1H), 8.53 (dd, J=8.7, 2.5 Hz, 1H), 8.27 (s, 1H), 8.10 (d, J=8.7 Hz, 1H), 7.48 (d, J=5.1 Hz, 1H), 4.49 (q, J=7.0 Hz, 2H), 3.39-3.25 (m, 1H), 2.55-2.42 (m, 1H), 2.42-2.27 (m, 1H), 1.40 (t, J=7.0 Hz, 3H), 1.25-0.88 (m, 7H).

The product was analysed by Chiral IC3 method HPLC Rt=14.24 mins, 100% ee at 254 nm.

Method 7: Sulfonylation from Aromatic Chloride

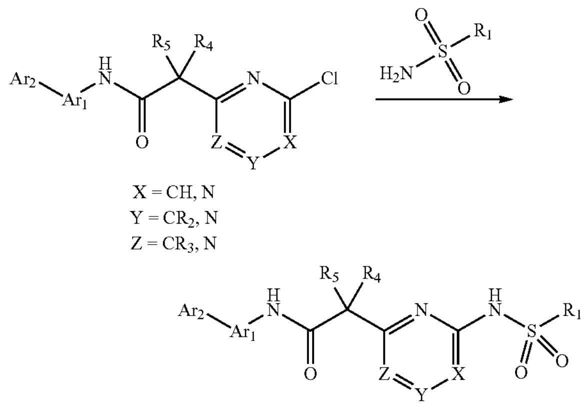

2-Chloro-heteroaromatic intermediate (1 eq), sulfonamide (1.2 eq) and base (2 eq) were dissolved in dioxane (40 volumes). The mixture was degassed (evacuated and back-filled with $N_2$x3) then catalyst (10 mol %) was added. The resulting mixture was heated under nitrogen at 90° C. for 2 hrs. The mixture was cooled to RT, diluted with sat $NH_4Cl$ (aq, 80 volumes) and DCM (80 volumes). The phases were separated and the aqueous was extracted with further DCM (2×80 volumes). The combined organics were dried ($MgSO_4$), filtered and concentrated in vacuo. The crude product was purified by normal phase chromatography or trituration using a suitable solvent.

Method 8: Amide coupling using 1-chloro-N,N,2-trimethylprop-1-en-1-amine

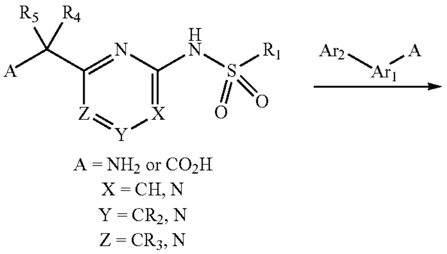

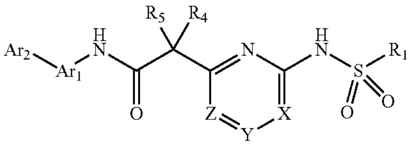

or

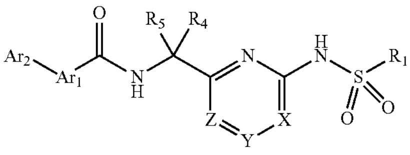

1-Chloro-N,N,2-trimethylprop-1-en-1-amine (2 eq) was added to a solution of carboxylic acid (1 eq) in DCM (20 volumes). The reaction mixture was stirred at RT for 2 hrs. The reaction mixture was concentrated in vacuo and the residue redissolved in DCM (20 volumes) before addition of pyridine (2 mL) followed by addition of the appropriate amine (1.1 eq). The reaction mixture was stirred at RT for 2 hrs. An aqueous work up was performed and the crude product was purified by normal phase chromatography, reverse phase chromatography or trituration from an appropriate solvent.

Method 9: Suzuki ArBr

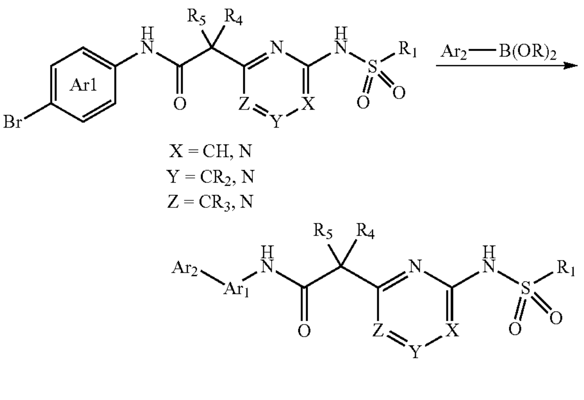

To a suspension of Ar1-Br (1 eq) in dioxane (10 volumes) was added arylboronic acid or ester (1 eq) and a solution of $K_2CO_3$ (2 eq) in water (5 volumes). The resulting suspension was degassed ($N_2$, 5 mins). $PdCl_2(dppf)-CH_2Cl_2$ adduct or other appropriate catalyst (10 mol %) was added and the reaction mixture was stirred at 80° C. for 2 hrs. The reaction mixture was then cooled to RT. An aqueous work up was performed and the crude product was purified by normal phase chromatography, reverse phase chromatography or trituration from an appropriate solvent.

Method 10: T3P with Free Acid

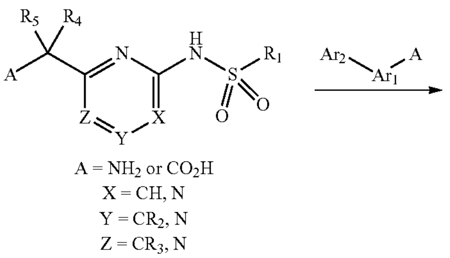

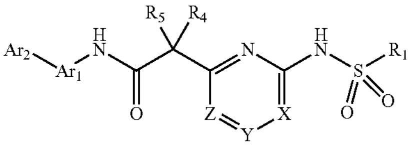

or

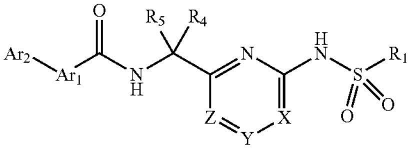

Pyridine (10 eq) followed by T3P (50 wt % in DMF, 2 eq) was added to a stirring solution of amine (1.1 eq) and carboxylic acid (1 eq) in DMF (16 volumes). The resulting reaction was stirred at RT for 24 hrs. The crude reaction mixture was concentrated in vacuo then diluted with $NH_4Cl$ (sat. aq) and extracted with DCM. The combined organic extracts were dried (phase separator) and the solvent removed. The crude product was purified by reverse or normal phase chromatography.

TABLE 20

| P | Name/Structure (All examples containing chiral centres are racemates unless stated) | Synthesis Method, [LCMS Method], m/z $(M + H)^+$, (RT/Min) | $^1$H NMR Chemical Shift Data (DMSO-d6 unless stated) |
|---|---|---|---|
| | Preparation methods and characterisation data of examples P9-P115, P117-P225 | | |
| P9 | 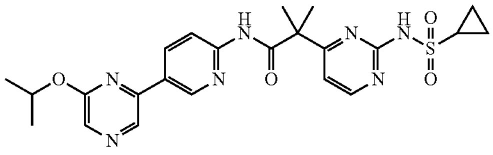<br>2-(2-(cyclopropanesulfonamido)pyrimidin-4-yl)-N-(5-(6-isopropoxypyrazin-2-yl)pyridin-2-yl)-2-methylpropanamide | Method 2: using INTC21 and INTD32 [HPLC acidic], 498, (2.28) | 11.23 (s, 1H), 10.14 (s, 1H), 9.03-8.97 (m, 1H), 8.82 (s, 1H), 8.60 (d, J = 5.3 Hz, 1H), 8.53-8.42 (m, 1H), 8.25-8.16 (m, 2H), 7.21 (d, J = 5.3 Hz, 1H), 5.46-5.34 (m, 1H), 3.23-3.10 (m, 1H), 1.61 (s, 6H), 1.40-1.37 (m, 6H), 1.04-0.98 (m, 2H), 0.81-0.74 (m, 2H). |
| P10 | 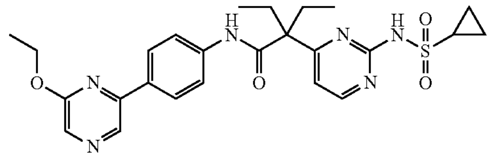<br>2-(2-(cyclopropanesulfonamido)pyrimidin-4-yl)-N-(4-(6-ethoxypyrazin-2-yl)phenyl)-2-ethylbutanamide | Method 2 using INTC27 and INTD18, [UPLC acidic], 511, (1.57) | 11.27 (s, 1H), 9.47 (s, 1H), 8.75 (s, 1H), 8.59 (d, J = 5.3 Hz, 1H), 8.18 (s, 1H), 8.09-8.01 (m, 2H), 7.79-7.73 (m, 2H), 7.14 (d, J = 5.3 Hz, 1H), 4.47 (q, J = 7.1 Hz, 2H), 3.23-3.11 (m, 1H), 2.12 (q, J = 7.6 Hz, 4H), 1.40 (t, J = 7.1 Hz, 3H), 1.05-0.96 (m, 2H), 0.80-0.66 (m, 8H). |
| P11 | 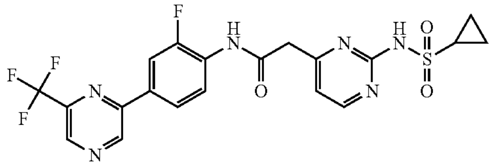<br>2-(2-(cyclopropanesulfonamido)pyrimidin-4-yl)-N-(2-fluoro-4-(6-(trifluoromethyl) pyrazin-2-yl)phenyl)acetamide | Method 2 using INTC33 and INTD25, [HPLC Acidic], 497, (2.09) | 12.77 (s, 1H, minor), 11.24 (s, 1H, major), 10.98 (s, 1H, minor), 10.37 (s, 1H, major), 9.81 (s, 1H, minor), 9.64 (s, 1H, major), 9.63 (s, 1H, minor), 9.14 (s, 1H, major), 9.12 (s, 1H, minor), 8.57 (d, J = 5.1 Hz, 1H, major), 8.34 (t, J = 8.3 Hz, 1H, minor), 8.24 (t, J = 8.3 Hz, 1H, major), 8.17-8.04 (m, 2 × 2H, major and minor), 7.18 (d, J = 5.1 Hz, 1H, major), 6.96 (d, J = 7.6 Hz, 1H, minor), 5.85 (dd, J = 7.7, 1.6 Hz, 1H, minor), 5.34 (s, 1H, minor), 4.00 (s, 2H, major), 3.30-3.23 (m, 1H, major), 2.71-2.61 (m, 1H, minor), 1.15-0.88 (m, 2 × 4H, major and minor). |
| P12 | 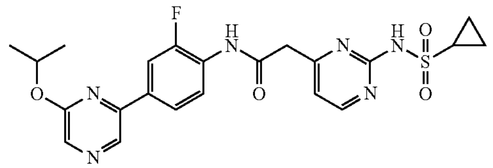<br>2-(2-(cyclopropanesulfonamido)pyrimidin-4-yl)-N-(2-fluoro-4-(6-isopropoxypyrazin-2-yl)phenyl)acetamide | Method 2 using INTC33 and INTD35, [HPLC Acidic], 487, (2.17) | 12.79 (s, 1H, minor), 11.23 (s, 1H, major), 10.95 (s, 1H, minor), 10.29 (s, 1H, major), 9.74 (s, 1H, minor), 8.81 (s, 1H, major), 8.80 (s, 1H, minor), 8.57 (d, J = 5.0 Hz, 1H, major), 8.23 (t, J = 8.5 Hz, 1H, minor), 8.19 (s, 1H, major), 8.17 (s, 1H, minor), 8.13 (t, J = 8.3 Hz, 1H, major), 8.06-7.93 (m, 2 × 2H, major and minor), 7.17 (d, J = 5.2 Hz, 1H, major), 6.94 (d, J = 7.5 Hz, 1H, minor), 5.84 (dd, J = 7.6, 1.7 Hz, 1H, minor), 5.47-5.38 (m, 2 × 1H, major and minor), 5.31 (s, 1H, minor), 3.98 (s, 2H, major), 3.26 (s, 1H, major), 2.69-2.62 (m, 1H, minor), 1.39 (dd, J = 6.2, 1.9 Hz, 2 × 6H, major and minor), 1.13-0.90 (m, 2 × 4H, major and minor). |

TABLE 20-continued

Preparation methods and characterisation data of examples P9-P115, P117-P225

| P | Name/Structure (All examples containing chiral centres are racemates unless stated) | Synthesis Method, [LCMS Method], m/z (M + H)+, (RT/Min) | $^{1}$H NMR Chemical Shift Data (DMSO-d6 unless stated) |
|---|---|---|---|
| P13 | 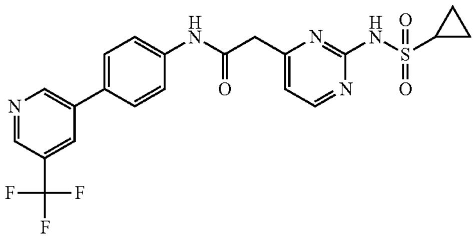 2-(2-(cyclopropanesulfonamido)pyrimidin-4-yl)-N-(4-(5-(trifluoromethyl)pyridin-3-yl)phenyl)acetamide | Method 3 using INTC39 and INTD7, [UPLC Acidic], 478, (1.27) | 12.82 (s, 1H, minor), 11.25 (s, 1H, major), 10.92 (s, 1H, minor), 10.47 (s, 1H, major), 9.98 (s, 1H, minor), 9.23-9.19 (m, 2 × 1H, major and minor), 8.95-8.90 (m, 2 × 1H, major and minor), 8.56 (d, J = 5.0 Hz, 1H, major), 8.46-8.41 (m, 2 × 1H, major and minor), 7.89-7.81 (m, 2 × 2H, major and minor), 7.80-7.74 (m, 2 × 2H, major and minor), 7.17 (d, J = 5.0 Hz, 1H, major), 6.93 (d, J = 7.5 Hz, 1H, minor), 5.88 (d, J = 7.6 Hz, 1H, minor), 5.04 (s, 1H, minor), 3.87 (s, 2H, major), 3.28-3.22 (m, 1H, major), 2.70-2.65 (m, 1H, minor), 1.13-0.90 (m, 2 × 4H, major and minor). |
| P14 | 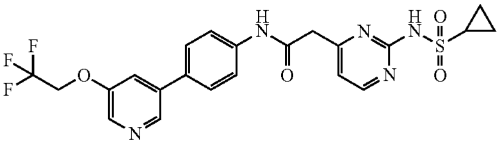 2-(2-(cyclopropanesulfonamido)pyrimidin-4-yl)-N-(4-(5-(2,2,2-trifluoroethoxy)pyridin-3-yl)phenyl)acetamide | Method 2 using INTC33 and INTD15, [HPLC Acidic], 508, (1.87) | 12.83 (s, 1H, minor), 11.26 (s, 1H, major), 10.89 (s, 1H, minor), 10.43 (s, 1H, major), 9.96 (s, 1H, minor), 8.59 (t, J = 2.2 Hz, 2 × 1H, major and minor), 8.57 (d, J = 5.1 Hz, 1H, major), 8.35 (dd, J = 4.6, 2.8 Hz, 2 × 1H, major and minor), 7.83-7.68 (m, 2 × 5H, major and minor), 7.17 (d, J = 5.1 Hz, 1H, major), 6.92 (d, J = 7.6 Hz, 1H, minor), 5.88 (dd, J = 7.6, 1.6 Hz, 1H, minor), 5.05 (s, 1H, minor), 5.01-4.94 (m, 2 × 2H, major and minor), 3.87 (s, 2H, major), 3.30-3.23 (m, 1H, major), 2.71-2.62 (m, 1H, minor), 1.13-0.89 (m, 2 × 4H, major and minor. |
| P15 | 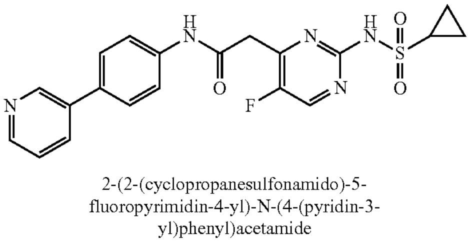 [SMILES: O=C(Cc1nc(NS(=O)(=O)C2CC2)ncc1F)Nc1ccc(-c2cccnc2)cc1] 2-(2-(cyclopropanesulfonamido)-5-fluoropyrimidin-4-yl)-N-(4-(pyridin-3-yl)phenyl)acetamide | Method 1 using INTC40 and a commercial aniline, [UPLC acidic], 428, (0.68) | 11.36 (s, 1H), 10.51 (s, 1H), 8.89 (s, 1H), 8.74-8.61 (m, 1H), 8.60-8.42 (m, 1H), 8.11-7.99 (m, 1H), 7.78-7.59 (m, 4H), 7.55-7.38 (m, 1H), 4.03-3.85 (m, 2H), 3.24-3.11 (m, 1H), 1.15-1.01 (m, 2H), 0.99-0.88 (m, 2H). |
| P16 | 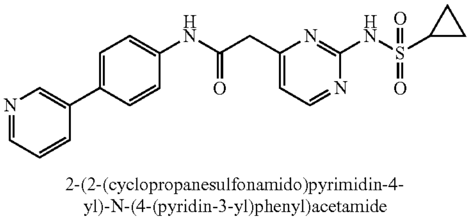 [SMILES: O=C(Cc1ccnc(NS(=O)(=O)C2CC2)n1)Nc1ccc(-c2cccnc2)cc1] 2-(2-(cyclopropanesulfonamido)pyrimidin-4-yl)-N-(4-(pyridin-3-yl)phenyl)acetamide | Method 2 using INTC33 and a commercial aniline, [HPLC basic], 410, (1.20) | 12.82 (s, 1H, minor), 11.22 (s, 2 × 1H, major and minor), 10.42 (s, 2 × 1H, major and minor), 9.92 (s, 1H, minor), 8.89 (d, J = 2.2 Hz, 3H), 8.60-8.50 (m, 4H), 8.11-8.01 (m, 3H), 7.80-7.67 (m, 11H), 7.46 (ddd, J = 7.3, 4.8, 1.7 Hz, 2H), 7.16 (d, J = 5.1 Hz, 1H, major), 6.92 (d, J = 7.5 Hz, 1H, minor), 5.87 (dd, J = 7.6, 1.6 Hz, 1H, minor), 5.03 (s, 1H, minor), 3.86 (s, 2H, major), 3.29-3.22 (m, 1H, major), 3.18 (s, 3H), 2.73-2.61 (m, 1H, minor), 1.13-1.06 (m, 2H, major), 1.05-0.98 (m, 2H, minor), 0.98-0.88 (m, 2 × 2H, major and minor). |

TABLE 20-continued

| P | Name/Structure (All examples containing chiral centres are racemates unless stated) | Synthesis Method, [LCMS Method], m/z $(M + H)^+$, (RT/Min) | $^1H$ NMR Chemical Shift Data (DMSO-d6 unless stated) |
|---|---|---|---|
| Preparation methods and characterisation data of examples P9-P115, P117-P225 | | | |
| P17 | 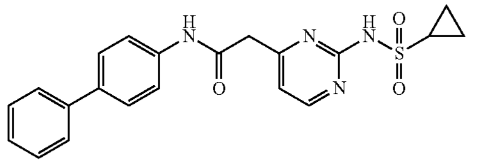 N-([1,1'-biphenyl]-4-yl)-2-(2-(cyclopropanesulfonamido)pyrimidin-4-yl)acetamide | Method 2, using INTC33 and a commercial aniline, [HPLC basic], 409, (1.84) | 12.84 (s, 1H, minor), 11.19 (s, 2H, major), 10.37 (s, 1H, major), 9.89 (s, 1H, minor), 8.59-8.53 (m, 1H, major), 7.71-7.40 (m, 2 × 8H, major and minor) 7.38-7.28 (m, 2 × 1H, major and minor), 7.19-7.13 (m, 1H, major), 6.94-6.87 (m, 1H, minor), 5.90-5.82 (m, 1H, minor), 5.04 (s, 1H, minor), 3.86 (s, 2H, major), 3.30-3.14 (m, 1H, major), 2.69-2.61 (m, 1H, minor), 1.14-0.88 (m, 2 × 4H, major and minor). |
| P18 | 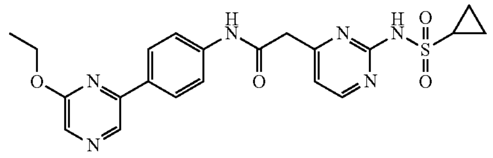 2-(2-(cyclopropanesulfonamido)pyrimidin-4-yl)-N-(4-(6-ethoxypyrazin-2-yl)phenyl)acetamide | Method 3 using INTC39 and INTD18, or Method 5 using INTC47, [UPLC Acidic], 455, (1.26) | 12.83 (s, 1H, minor), 11.23 (s, 1H, major), 10.91 (s, 1H, minor), 10.49 (s, 1H, major), 10.01 (s, 1H, minor), 8.77 (s, 1H, major), 8.76 (s, 1H, minor), 8.57 (d, J = 5.2 Hz, 1H, major), 8.19 (s, 1H, major), 8.17 (s, 1H, minor), 8.13-8.06 (m, 2 × 2H, major and minor), 7.79-7.73 (m, 2 × 2H, major and minor), 7.17 (d, J = 5.0 Hz, 1H, major), 6.93 (d, J = 7.6 Hz, 1H, minor), 5.88 (d, J = 7.6 Hz, 1H, minor), 5.05 (s, 1H, minor), 4.48 (q, J = 7.0 Hz, 2 × 2H, major and minor), 3.87 (s, 2H, major), 3.28-3.22 (m, 1H, major), 2.71-2.65 (m, 1H, minor), 1.40 (t, J = 7.0 Hz, 2 × 3H, major and minor), 1.13-0.90 (m, 2 × 4H, major and minor). |
| P19 | 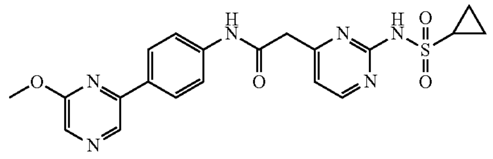 2-(2-(cyclopropanesulfonamido)pyrimidin-4-yl)-N-(4-(6-methoxypyrazin-2-yl)phenyl) acetamide | Method 2, using INTC33 and INTD1, [HPLC Acidic], 441, (1.83) | 12.83 (s, 1H, minor), 11.24 (s, 1H, major), 10.91 (s, 1H, minor), 10.50 (s, 1H, major), 10.02 (s, 1H, minor), 8.79 (s, 1H, major), 8.78 (s, 1H, minor), 8.57 (d, J = 5.1 Hz, 1H, major), 8.22 (s, 1H, major), 8.20 (s, 1H, minor), 8.16-8.09 (m, 2 × 2H, major and minor), 7.79-7.73 (m, 2 × 2H, major and minor), 7.18 (d, J = 5.1 Hz, 1H, major), 6.93 (d, J = 7.6 Hz, 1H, minor), 5.88 (dd, J = 7.7, 1.6 Hz, 1H, minor), 5.06 (s, 1H, minor), 4.02 (s, 2 × 3H, major and minor), 3.88 (s, 2H, major), 3.30-3.21 (m, 1H, major), 2.70-2.62 (m, 1H, minor), 1.14-0.88 (m, 2 × 4H, major and minor). |
| P20 | 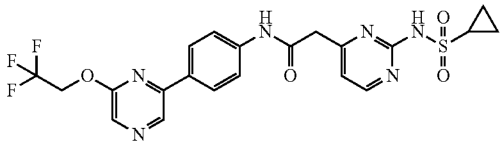 2-(2-(cyclopropanesulfonamido)pyrimidin-4-yl)-N-(4-(6-(2,2,2-trifluoroethoxy)pyrazin-2-yl)phenyl)acetamide | Method 2, using INTC33 and INTD29, [HPLC Acidic], 509, (2.12) | 12.84 (s, 1H, minor), 11.24 (s, 1H, major), 10.92 (s, 1H, minor), 10.51 (s, 1H, major), 10.04 (s, 1H, minor), 8.94 (s, 1H, major), 8.92 (s, 1H, minor), 8.57 (d, J = 5.1 Hz, 1H, major), 8.38 (s, 1H, major), 8.36 (s, 1H, minor), 8.20-8.14 (m, 2 × 2H, major and minor), 7.79-7.75 (m, 2 × 2H, major and minor), 7.18 (d, J = 5.1 Hz, 1H, major), |

TABLE 20-continued

Preparation methods and characterisation data of examples P9-P115, P117-P225

| P | Name/Structure (All examples containing chiral centres are racemates unless stated) | Synthesis Method, [LCMS Method], m/z (M + H)$^+$, (RT/Min) | $^1$H NMR Chemical Shift Data (DMSO-d6 unless stated) |
|---|---|---|---|
| | | | 6.93 (d, J = 7.6 Hz, 1H, minor), 5.89 (dd, J = 7.7, 1.6 Hz, 1H, minor), 5.24-5.15 (m, 2 × 2H, major and minor), 5.06 (s, 1H, minor), 3.88 (s, 2H, major), 3.29-3.22 (m, 1H, major), 2.70-2.63 (m, 1H, minor), 1.12-0.91 (m, 2 × 4H, major and minor). |
| P21 | 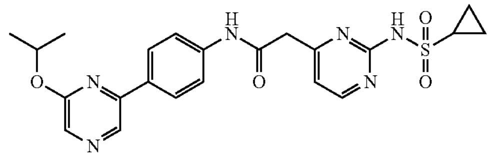 2-(2-(cyclopropanesulfonamido)pyrimidin-4-yl)-N-(4-(6-isopropoxypyrazin-2-yl)phenyl)acetamide | Method 2, using INTC33 and INTD20, [HPLC Acidic], 469, (2.12) | 12.84 (s, 1H, minor), 11.24 (s, 1H, major), 10.91 (s, 1H, minor), 10.49 (s, 1H, major), 10.02 (s, 1H, minor), 8.74 (s, 1H, major), 8.73 (s, 1H, minor), 8.57 (d, J = 5.1 Hz, 1H, major), 8.13 (s, 1H, major), 8.11 (s, 1H, minor), 8.11-8.05 (m, 2 × 2H, major and minor), 7.78-7.72 (m, 2 × 2H, major and minor), 7.18 (d, J = 5.1 Hz, 1H, major), 6.93 (d, J = 7.6 Hz, 1H, minor), 5.88 (dd, J = 7.6, 1.6 Hz, 1H, minor), 5.46-5.36 (m, 2 × 1H, major and minor), 5.06 (s, 1H, minor), 3.88 (s, 2H, major), 3.29-3.21 (m, 1H, major), 2.70-2.61 (m, 1H, minor), 1.42-1.35 (m, 2 × 6H, major and minor), 1.13-0.90 (m, 2 × 4H, major and minor). |
| P22 | 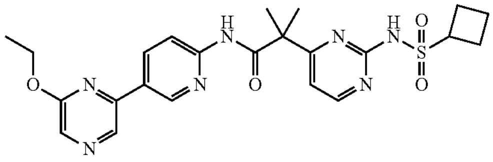 2-(2-(cyclobutanesulfonamido)pyrimidin-4-yl)-N-(5-(6-ethoxypyrazin-2-yl)pyridin-2-yl)-2-methylpropanamide | Method 2, using INTC24 and INTD33, [HPLC Acidic], 498, (2.24) | 11.15 (s, 1H), 10.19 (s, 1H), 9.05 (d, J = 2.4 Hz, 1H), 8.85 (s, 1H), 8.60-8.51 (m, 2H), 8.29 (d, J = 8.8 Hz, 1H), 8.25 (s, 1H), 7.17 (d, J = 5.3 Hz, 1H), 4.55-4.43 (m, 3H), 2.32-2.22 (m, 2H), 2.04-1.92 (m, 2H), 1.80-1.70 (m, 1H), 1.59 (s, 6H), 1.57-1.52 (m, 1H), 1.40 (t, J = 7.0 Hz, 3H) |
| P23 | 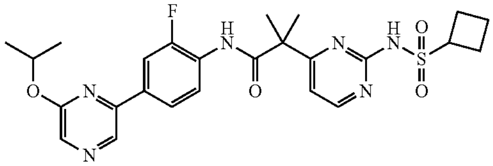 2-(2-(cyclobutanesulfonamido)pyrimidin-4-yl)-N-(2-fluoro-4-(6-isopropoxypyrazin-2-yl)phenyl)-2-methylpropanamide | Method 2, using INTC24 and INTD35, [HPLC Acidic], 529, (2.48) | 11.15 (s, 1H), 9.36 (s, 1H), 8.82 (s, 1H), 8.59 (d, J = 5.2 Hz, 1H), 8.19 (s, 1H), 8.02-7.94 (m, 2H), 7.79-7.73 (m, 1H), 7.20 (d, J = 5.3 Hz, 1H), 5.46-5.38 (m, 1H), 4.64-4.55 (m, 1H), 2.44-2.33 (m, 2H), 2.23-2.12 (m, 2H), 1.90-1.76 (m, 2H), 1.60 (s, 6H), 1.38 (d, J = 6.3 Hz, 6H); |
| P24 | 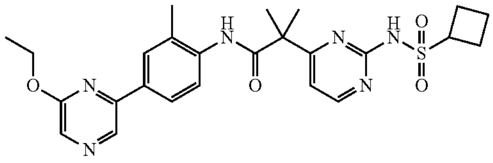 2-(2-(cyclobutanesulfonamido)pyrimidin-4-yl)-N-(4-(6-ethoxypyrazin-2-yl)-2-methylphenyl)-2-methylpropanamide | Method 2, using INTC24 and INTD27, [HPLC Acidic], 511, (2.31) | 11.18 (s, 1H), 9.03 (s, 1H), 8.78 (s, 1H), 8.59 (d, J = 5.2 Hz, 1H), 8.20 (s, 1H), 7.98 (d, J = 2.0 Hz, 1H), 7.93 (dd, J = 8.3, 2.1 Hz, 1H), 7.46 (d, J = 8.3 Hz, 1H), 7.21 (d, J = 5.3 Hz, 1H), 4.66-4.56 (m, 1H), 4.48 (q, J = 7.0 Hz, 2H), 2.45-2.34 (m, 2H), 2.26-2.12 (m, 5H), 1.94-1.83 (m, 2H), 1.61 (s, 6H), 1.40 (t, J = 7.0 Hz, 3H). |

TABLE 20-continued

Preparation methods and characterisation data of examples P9-P115, P117-P225

| P | Name/Structure (All examples containing chiral centres are racemates unless stated) | Synthesis Method, [LCMS Method], m/z (M + H)+, (RT/Min) | 1H NMR Chemical Shift Data (DMSO-d6 unless stated) |
|---|---|---|---|
| P25 | 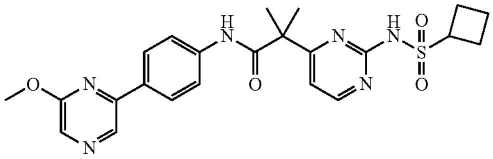 2-(2-(cyclobutanesulfonamido)pyrimidin-4-yl)-N-(4-(6-methoxypyrazin-2-yl)phenyl)-2-methylpropanamide | Method 2, using INTC24 and INTD1, [HPLC Acidic], 483, (2.18) | 11.11 (s, 1H), 9.50 (s, 1H), 8.79 (s, 1H), 8.59 (d, J = 5.3 Hz, 1H), 8.21 (s, 1H), 8.15-8.09 (m, 2H), 7.90-7.81 (m, 2H), 7.21 (d, J = 5.3 Hz, 1H), 4.54 (p, J = 8.4 Hz, 1H), 4.01 (s, 3H), 2.37-2.22 (m, 2H), 2.07-1.97 (m, 2H), 1.64-1.54 (m, 6H), 0.89-0.82 (m, 2H), |
| P26 | 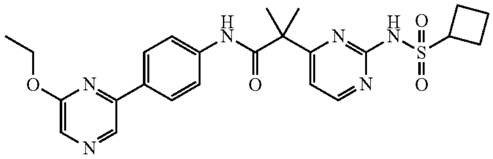 2-(2-(cyclobutanesulfonamido)pyrimidin-4-yl)-N-(4-(6-ethoxypyrazin-2-yl)phenyl)-2-methylpropanamide | Method 2, using INTC24 and INTD18, [HPLC Basic], 497, (2.33) | 11.14 (s, 1H), 9.51 (s, 1H), 8.77 (s, 1H), 8.58 (d, J = 5.3 Hz, 1H), 8.18 (s, 1H), 8.13-8.06 (m, 2H), 7.88-7.77 (m, 2H), 7.19 (d, J = 5.4 Hz, 1H), 4.54 (q, J = 8.3 Hz, 1H), 4.47 (q, J = 7.1 Hz, 2H), 2.36-2.24 (m, 2H), 2.06-1.95 (m, 2H), 1.81-1.69 (m, 1H), 1.66-1.60 (m, 1H), 1.58 (s, 6H), 1.40 (t, J = 7.0 Hz, 3H). |
| P27 | 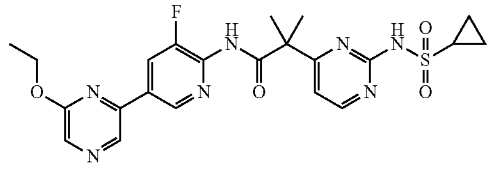 2-(2-(cyclopropanesulfonamido)pyrimidin-4-yl)-N-(5-(6-ethoxypyrazin-2-yl)-3-fluoropyridin-2-yl)-2-methylpropanamide | Method 2, using INTC21 and INTD31, [UPLC Acidic], 502, (1.27) | 11.28 (s, 1H), 10.08 (s, 1H), 8.99-8.97 (m, 1H), 8.93 (s, 1H), 8.62 (d, J = 5.3 Hz, 1H), 8.45-8.40 (m, 1H), 8.32 (s, 1H), 7.19 (d, J = 5.3 Hz, 1H), 4.50 (q, J = 7.0 Hz, 2H), 3.33-3.27 (m, 1H), 1.62 (s, 6H), 1.41 (t, J = 7.0 Hz, 3H), 1.15-1.07 (m, 2H), 1.06-0.98 (m, 2H). |
| P28 | 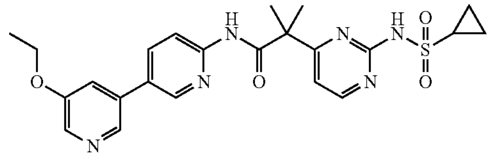 2-(2-(cyclopropanesulfonamido)pyrimidin-4-yl)-N-(5-ethoxy-[3,3'-bipyridin]-6-yl)-2-methylpropanamide | Method 2, using INTC21 and INTD16, [UPLC acidic], 483, (1.09) | 11.25 (s, 1H), 10.06 (s, 1H), 8.72-8.68 (m, 1H), 8.60 (d, J = 5.3 Hz, 1H), 8.52 (d, J = 1.9 Hz, 1H), 8.29 (d, J = 2.7 Hz, 1H), 8.24-8.12 (m, 2H), 7.70-7.65 (m, 1H), 7.20 (d, J = 5.3 Hz, 1H), 4.21 (q, J = 7.0 Hz, 2H), 3.23-3.13 (m, 1H), 1.61 (s, 6H), 1.38 (t, J = 7.0 Hz, 3H), 1.07-0.97 (m, 2H), 0.83-0.73 (m, 2H). |
| P29 | 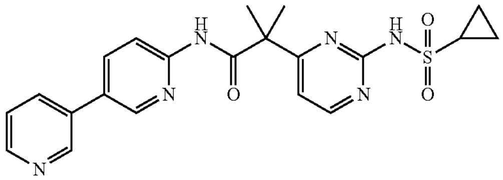 N-([3,3'-bipyridin]-6-yl)-2-(2-(cyclopropanesulfonamido)pyrimidin-4-yl)-2-methylpropanamide | Method 2, using INTC21 and a commercial aniline, [HPLC acidic], 439, (1.29) | 11.25 (s, 1H), 10.06 (s, 1H), 8.94 (d, J = 2.3 Hz, 1H), 8.70-8.67 (m, 1H), 8.61-8.56 (m, 2H), 8.22-8.08 (m, 3H), 7.54-7.46 (m, 1H), 7.18 (d, J = 5.3 Hz, 1H), 3.23-3.13 (m, 1H), 1.61 (s, 6H), 1.07-0.96 (m, 2H), 0.83-0.71 (m, 2H). |

TABLE 20-continued

Preparation methods and characterisation data of examples P9-P115, P117-P225

| P | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
|---|---|---|---|
| P30 | 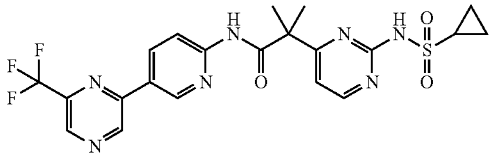 2-(2-(cyclopropanesulfonamido)pyrimidin-4-yl)-2-methyl-N-(5-(6-(trifluoromethyl) pyrazin-2-yl)pyridin-2-yl)propanamide | Method 2 using INTC21 and INTD2, [UPLC Acidic], 508, (1.41) | 11.24 (s, 1H), 10.29 (s, 1H), 9.66 (s, 1H), 9.21-9.02 (m, 2H), 8.69-8.49 (m, 2H), 8.36-8.19 (m, 1H), 7.21 (d, J = 5.3 Hz, 1H), 3.23-3.11 (m, 1H), 1.61 (s, 6H), 1.07-0.91 (m, 2H), 0.83-0.71 (m, 2H). |
| P31 | 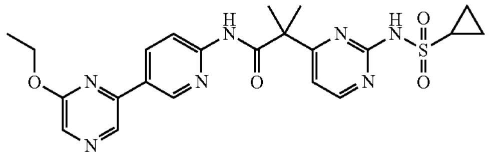 2-(2-(cyclopropanesulfonamido)pyrimidin-4-yl)-N-(5-(6-ethoxypyrazin-2-yl)pyridin-2-yl)-2-methylpropanamide | Method 2, using INTC21 and INTD33, [UPLC Acidic], 484, (1.37) | 11.25 (s, 1H), 10.16 (s, 1H), 9.09-8.98 (m, 1H), 8.84 (s, 1H), 8.59 (d, J = 5.3 Hz, 1H), 8.52-8.46 (m, 1H), 8.25 (s, 1H), 8.23-8.18 (m, 1H), 7.20 (d, J = 5.3 Hz, 1H), 4.48 (q, J = 7.0 Hz, 2H), 3.24-3.11 (m, 1H), 1.61 (s, 6H), 1.40 (t, J = 7.0 Hz, 3H), 1.06-0.95 (m, 2H), 0.83-0.70 (m, 2H). |
| P32 | 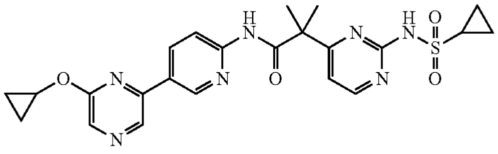 2-(2-(cyclopropanesulfonamido)pyrimidin-4-yl)-N-(5-(6-cyclopropoxypyrazin-2-yl)pyridin-2-yl)-2-methylpropanamide | Method 2, using INTC21 and INTD30, [UPLC acidic], 496, (1.39) | 11.30 (s, 1H), 10.20 (s, 1H), 9.05 (d, J = 2.4 Hz, 1H), 8.92 (s, 1H), 8.58 (d, J = 5.3 Hz, 1H), 8.55-8.49 (m, 1H), 8.31 (s, 1H), 8.21 (d, J = 8.8 Hz, 1H), 7.18 (d, J = 5.3 Hz, 1H), 4.48-4.35 (m, 1H), 3.23-3.10 (m, 1H), 1.61 (s, 6H), 1.06-0.94 (m, 2H), 0.92-0.68 (m, 6H). |
| P33 | 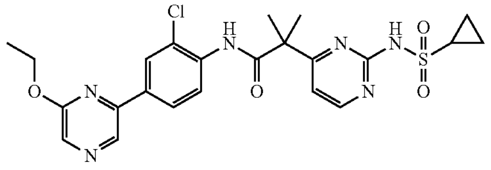 N-(2-chloro-4-(6-ethoxypyrazin-2-yl)phenyl)-2-(2-(cyclopropanesulfonamido)pyrimidin-4-yl)-2-methylpropanamide | Method 2, using INTC21 and INTD49, [UPLC Acidic], 517, (1.53) | 11.30 (s, 1H), 9.24 (s, 1H), 8.85 (s, 1H), 8.63 (d, J = 5.3 Hz, 1H), 8.27-8.20 (m, 2H), 8.10 (dd, J = 8.5, 2.1 Hz, 1H), 7.78 (d, J = 8.4 Hz, 1H), 7.25 (d, J = 5.3 Hz, 1H), 4.48 (q, J = 7.0 Hz, 2H), 3.31-3.20 (m, 1H), 1.63 (s, 6H), 1.40 (t, J = 7.0 Hz, 3H), 1.17-1.07 (m, 2H), 1.03-0.95 (m, 2H). |
| P34 | 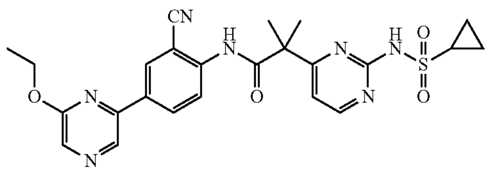 N-(2-cyano-4-(6-ethoxypyrazin-2-yl)phenyl)-2-(2-(cyclopropanesulfonamido) pyrimidin-4-yl)-2-methylpropanamide | Method 2, using INTC21 and INTD51, [UPLC Acidic], 508, (1.45) | 11.28 (s, 1H), 9.85 (s, 1H), 8.90 (s, 1H), 8.62 (d, J = 5.3 Hz, 1H), 8.55 (d, J = 2.1 Hz, 1H), 8.43 (dd, J = 8.6, 2.1 Hz, 1H), 8.29 (s, 1H), 7.69-7.62 (m, 1H), 7.25 (d, J = 5.3 Hz, 1H), 4.50 (q, J = 7.0 Hz, 2H), 3.28-3.19 (m, 1H), 1.63 (s, 6H), 1.40 (t, J = 7.0 Hz, 3H), 1.17-1.08 (m, 2H), 1.04-0.96 (m, 2H). |

TABLE 20-continued

| P | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
|---|---|---|---|
| P35 | 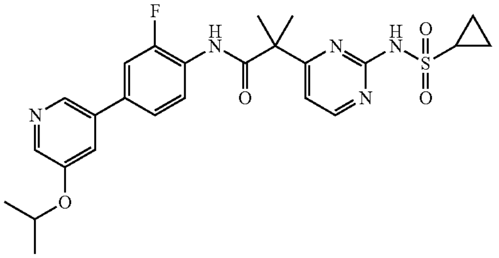 2-(2-(cyclopropanesulfonamido)pyrimidin-4-yl)-N-(2-fluoro-4-(5-isopropoxypyridin-3-yl)phenyl)-2-methylpropanamide | Method 2, using INTC21 and INTD12, [UPLC acidic], 514, (1.25) | 11.52 (s, 1H), 9.48 (s, 1H), 8.57 (d, J = 5.3 Hz, 1H), 8.53-8.46 (m, 1H), 8.25 (d, J = 2.7 Hz, 1H), 7.75-7.53 (m, 4H), 7.12 (d, J = 5.3 Hz, 1H), 4.99-4.78 (m, 1H), 3.26-3.16 (m, 1H), 1.60 (s, 6H), 1.32 (d, J = 6.0 Hz, 6H), 1.12-1.03 (m, 2H), 1.00-0.89 (m, 2H). |
| P36 | 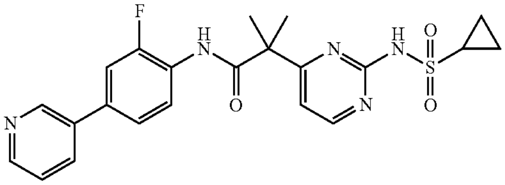 2-(2-(cyclopropanesulfonamido)pyrimidin-4-yl)-N-(2-fluoro-4-(pyridin-3-yl)phenyl)-2-methylpropanamide | Method 2, using INTC21 and INTD50, [HPLC Acidic], 456, (1.37) | 11.41 (s, 1H), 9.41 (s, 1H), 8.97-8.90 (m, 1H), 8.62-8.55 (m, 2H), 8.15-8.09 (m, 1H), 7.72-7.54 (m, 3H), 7.52-7.46 (m, 1H), 7.16 (d, J = 5.3 Hz, 1H), 3.27-3.19 (m, 1H), 1.61 (s, 6H), 1.15-1.05 (m, 2H), 1.02-0.90 (m, 2H). |
| P37 | 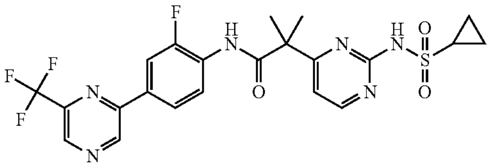 2-(2-(cyclopropanesulfonamido)pyrimidin-4-yl)-N-(2-fluoro-4-(6-(trifluoromethyl) pyrazin-2-yl)phenyl)-2-methylpropanamide | Method 2, using INTC21 and INTD25, [UPLC Acidic], 525, (1.47) | 11.30 (s, 1H), 9.65 (s, 1H), 9.47 (s, 1H), 9.15 (s, 1H), 8.61 (d, J = 5.3 Hz, 1H), 8.13-8.02 (m, 2H), 7.85-7.77 (m, 1H), 7.21 (d, J = 5.3 Hz, 1H), 3.28-3.21 (m, 1H), 1.62 (s, 6H), 1.16-1.05 (m, 2H), 1.03-0.92 (m, 2H). |
| P38 | 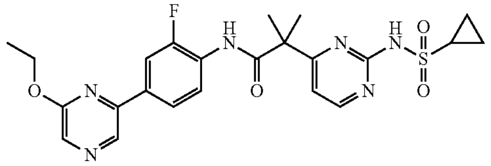 2-(2-(cyclopropanesulfonamido)pyrimidin-4-yl)-N-(4-(6-ethoxypyrazin-2-yl)-2-fluorophenyl)-2-methylpropanamide | Method 2, using INTC21 and INTD24; [UPLC acidic], 501, (1.46) | 11.32 (s, 1H), 9.41 (s, 1H), 8.84 (s, 1H), 8.70-8.51 (m, 1H), 8.25 (s, 1H), 8.06-7.90 (m, 2H), 7.77-7.63 (m, 1H), 7.28-7.13 (m, 1H), 4.56-4.42 (m, 2H), 3.28-3.19 (m, 1H), 1.61 (s, 6H), 1.47-1.32 (m, 3H), 1.18-1.05 (m, 2H), 1.03-0.91 (m, 2H). |
| P39 | 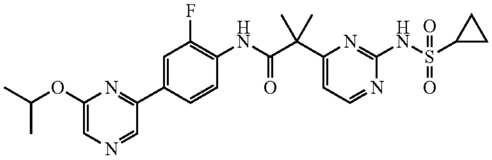 2-(2-(cyclopropanesulfonamido)pyrimidin-4-yl)-N-(2-fluoro-4-(6-isopropoxypyrazin-2-yl)phenyl)-2-methylpropanamide | Method 2, using INTC21 and INTD35, [UPLC acidic], 515, (1.54) | 11.33 (s, 1H), 9.41 (s, 1H), 8.82 (s, 1H), 8.61 (d, J = 5.3 Hz, 1H), 8.19 (s, 1H), 8.04-7.90 (m, 2H), 7.79-7.63 (m, 1H), 7.19 (d, J = 5.3 Hz, 1H), 5.51-5.33 (m, 1H), 3.29-3.17 (m, 1H), 1.61 (s, 6H), 1.39 (d, J = 6.1 Hz, 6H), 1.15-1.06 (m, 2H), 1.02-0.92 (m, 2H). |

Preparation methods and characterisation data of examples P9-P115, P117-P225

TABLE 20-continued

Preparation methods and characterisation data of examples P9-P115, P117-P225

| P | Name/Structure (All examples containing chiral centres are racemates unless stated) | Synthesis Method, [LCMS Method], m/z $(M + H)^+$, (RT/Min) | $^1$H NMR Chemical Shift Data (DMSO-d6 unless stated) |
|---|---|---|---|
| P40 | 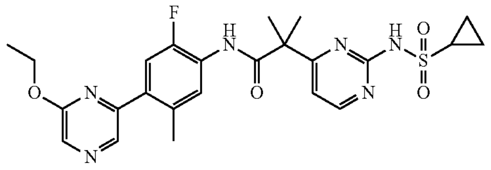 2-(2-(cyclopropanesulfonamido)pyrimidin-4-yl)-N-(4-(6-ethoxypyrazin-2-yl)-2-fluoro-5-methylphenyl)-2-methylpropanamide | Method 2, using INTC21 and INTD39, [UPLC Acidic], 515, (1.46) | 11.29 (s, 1H), 9.34 (s, 1H), 8.61 (d, J = 5.3 Hz, 1H), 8.41 (s, 1H), 8.27 (s, 1H), 7.48 (d, J = 7.7 Hz, 1H), 7.42 (d, J = 11.2 Hz, 1H), 7.19 (d, J = 5.3 Hz, 1H), 4.39 (q, J = 7.1 Hz, 2H), 3.30-3.21 (m, 1H), 2.37 (s, 3H), 1.61 (s, 6H), 1.37 (t, J = 7.0 Hz, 3H), 1.14-1.08 (m, 2H), 1.03-0.96 (m, 2H). |
| P41 | 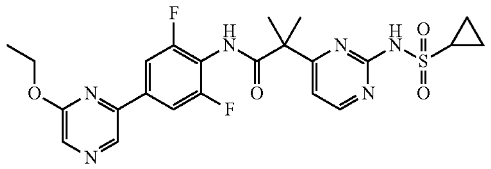 2-(2-(cyclopropanesulfonamido)pyrimidin-4-yl)-N-(4-(6-ethoxypyrazin-2-yl)-2,6-difluorophenyl)-2-methylpropanamide | Method 2, using INTC21 and INTD41, [UPLC Acidic], 519, (1.42) | 11.29 (s, 1H), 9.47 (s, 1H), 8.90 (s, 1H), 8.62 (d, J = 5.3 Hz, 1H), 8.30 (s, 1H), 7.92 (d, J = 8.9 Hz, 2H), 7.16 (d, J = 5.3 Hz, 1H), 4.49 (q, J = 7.0 Hz, 2H), 3.31-3.22 (m, 1H), 1.61 (s, 6H), 1.39 (t, J = 7.0 Hz, 3H), 1.15-1.08 (m, 2H), 1.10-0.99 (m, 2H). |
| P42 | 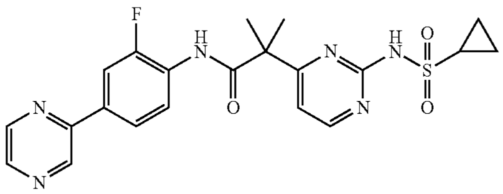 2-(2-(cyclopropanesulfonamido)pyrimidin-4-yl)-N-(2-fluoro-4-(pyrazin-2-yl)phenyl)-2-methylpropanamide | Method 2, using INTC21 and INTD23, [UPLC Acidic], 457, (1.14) | 11.30 (s, 1H), 9.40 (s, 1H), 9.30 (d, J = 1.5 Hz, 1H), 8.74-8.69 (m, 1H), 8.67-8.56 (m, 2H), 8.07-7.95 (m, 2H), 7.73 (t, J = 8.1 Hz, 1H), 7.20 (d, J = 5.3 Hz, 1H), 3.28-3.19 (m, 1H), 1.61 (s, 6H), 1.16-1.03 (m, 2H), 1.02-0.92 (m, 2H). |
| P43 | 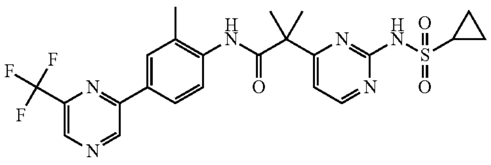 2-(2-(cyclopropanesulfonamido)pyrimidin-4-yl)-2-methyl-N-(2-methyl-4-(6-(trifluoromethyl)pyrazin-2-yl)phenyl)propanamide | Method 2, using INTC21 and INTD34; [UPLC Acidic], 521, (1.45) | 11.28 (s, 1H), 9.60 (s, 1H), 9.12-9.05 (m, 2H), 8.62 (d, J = 5.3 Hz, 1H), 8.09-7.99 (m, 2H), 7.52 (d, J = 8.3 Hz, 1H), 7.23 (d, J = 5.3 Hz, 1H), 3.31-3.21 (m, 1H), 2.21 (s, 3H), 1.62 (s, 6H), 1.17-1.06 (m, 2H), 1.04-0.96 (m, 2H). |
| P44 | 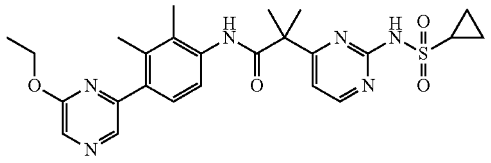 2-(2-(cyclopropanesulfonamido)pyrimidin-4-yl)-N-(4-(6-ethoxypyrazin-2-yl)-2,3-dimethylphenyl)-2-methylpropanamide | Method 2, using INTC21 and INTD36, [UPLC Acidic], 512, (1.39) | 11.28 (s, 1H), 9.16 (s, 1H), 8.62 (d, J = 5.3 Hz, 1H), 8.26 (d, J = 11.0 Hz, 2H), 7.26-7.19 (m, 2H), 7.15 (d, J = 8.2 Hz, 1H), 4.37 (q, J = 7.1 Hz, 2H), 3.31-3.23 (m, 1H), 2.23 (s, 3H), 2.05 (s, 3H), 1.63 (s, 6H), 1.36 (t, J = 7.0 Hz, 3H), 1.16-1.09 (m, 2H), 1.08-0.99 (m, 2H). |

TABLE 20-continued

Preparation methods and characterisation data of examples P9-P115, P117-P225

| P | Name/Structure (All examples containing chiral centres are racemates unless stated) | Synthesis Method, [LCMS Method], m/z $(M + H)^+$, (RT/Min) | $^1$H NMR Chemical Shift Data (DMSO-d6 unless stated) |
|---|---|---|---|
| P45 | 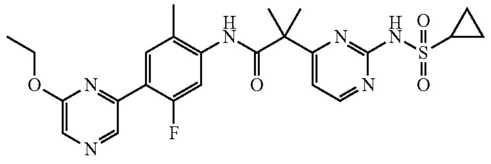 2-(2-(cyclopropanesulfonamido)pyrimidin-4-yl)-N-(4-(6-ethoxypyrazin-2-yl)-5-fluoro-2-methylphenyl)-2-methylpropanamide | Method 2, using INTC21 and INTD36; [UPLC Acidic], 515, (1.50) | 11.29 (s, 1H), 9.08 (s, 1H), 8.65-8.55 (m, 2H), 8.25 (d, J = 2.9 Hz, 1H), 7.82 (dd, J = 8.6, 2.5 Hz, 1H), 7.42 (dd, J = 12.9, 2.6 Hz, 1H), 7.27-7.21 (m, 1H), 4.50-4.41 (m, 2H), 3.26-3.20 (m, 1H), 2.16 (s, 3H), 1.61 (s, 6H), 1.42-1.35 (m, 3H), 1.14-1.05 (m, 2H), 1.03-0.97 (m, 2H). |
| P46 | 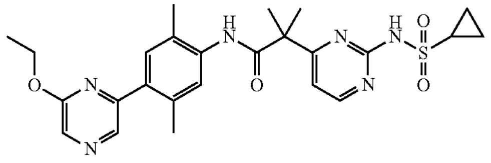 2-(2-(cyclopropanesulfonamido)pyrimidin-4-yl)-N-(4-(6-ethoxypyrazin-2-yl)-2,5-dimethylphenyl)-2-methylpropanamide | Method 2, using INTC21 and INTD40, [UPLC Acidic], 511, (1.44) | 11.28 (s, 1H), 9.01 (s, 1H), 8.62 (d, J = 5.3 Hz, 1H), 8.35 (s, 1H), 8.23 (s, 1H), 7.34 (s, 1H), 7.25-7.20 (m, 2H), 4.38 (q, J = 7.0 Hz, 2H), 3.31-3.22 (m, 1H), 2.34 (s, 3H), 2.10 (s, 3H), 1.62 (s, 6H), 1.36 (t, J = 7.0 Hz, 3H), 1.16-1.09 (m, 2H), 1.05-0.98 (m, 2H). |
| P47 | 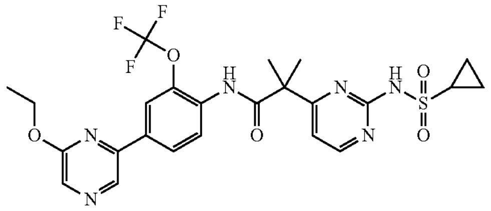 2-(2-(cyclopropanesulfonamido)pyrimidin-4-yl)-N-(4-(6-ethoxypyrazin-2-yl)-2-(trifluoromethoxy)phenyl)-2-methylpropanamide | Method 2, using INTC21 and INTD47, [UPLC Acidic], 567, (1.59) | 11.28 (s, 1H), 9.36 (s, 1H), 8.87 (s, 1H), 8.61 (d, J = 5.3 Hz, 1H), 8.27 (s, 1H), 8.16 (dd, J = 8.5, 2.0 Hz, 1H), 8.12-8.07 (m, 1H), 7.78 (d, J = 8.4 Hz, 1H), 7.21 (d, J = 5.2 Hz, 1H), 4.48 (q, J = 7.0 Hz, 2H), 3.27-3.21 (m, 1H), 1.61 (s, 6H), 1.40 (t, J = 7.0 Hz, 3H), 1.15-1.08 (m, 2H), 1.03-0.96 (m, 2H). |
| P48 | 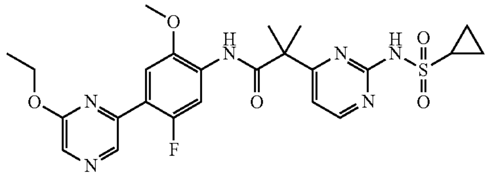 2-(2-(cyclopropanesulfonamido)pyrimidin-4-yl)-N-(4-(6-ethoxypyrazin-2-yl)-5-fluoro-2-methoxyphenyl)-2-methylpropanamide | Method 2, using INTC21 and INTD37, [UPLC Acidic], 531, (1.59) | 11.36 (s, 1H), 9.01 (s, 1H), 8.66-8.58 (m, 2H), 8.25 (s, 1H), 8.00 (d, J = 13.1 Hz, 1H), 7.59 (d, J = 6.9 Hz, 1H), 7.26 (d, J = 5.3 Hz, 1H), 4.51-4.42 (m, 2H), 3.89 (s, 3H), 3.23-3.14 (m, 1H), 1.63 (s, 6H), 1.43-1.36 (m, 3H), 1.13-1.08 (m, 2H), 1.00-0.94 (m, 2H). |
| P49 | 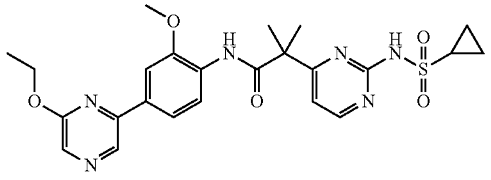 2-(2-(cyclopropanesulfonamido)pyrimidin-4-yl)-N-(4-(6-ethoxypyrazin-2-yl)-2-methoxyphenyl)-2-methylpropanamide | Method 2, using INTC21 and INTD48; [UPLC Acidic], 513, (1.48) | 11.34 (s, 1H), 8.86-8.81 (m, 2H), 8.63 (d, J = 5.3 Hz, 1H), 8.21-8.17 (m, 1H), 8.05 (d, J = 8.7 Hz, 1H), 7.74-7.69 (m, 2H), 7.26 (d, J = 5.3 Hz, 1H), 4.47 (q, 2H), 3.91 (s, 3H), 3.26-3.17 (m, 1H), 1.63 (s, 6H), 1.39 (t, J = 7.0 Hz, 3H), 1.13-1.06 (m, 2H), 0.99-0.91 (m, 2H). |

TABLE 20-continued

Preparation methods and characterisation data of examples P9-P115, P117-P225

| P | Name/Structure (All examples containing chiral centres are racemates unless stated) | Synthesis Method, [LCMS Method], m/z $(M + H)^+$, (RT/Min) | $^1$H NMR Chemical Shift Data (DMSO-d6 unless stated) |
|---|---|---|---|
| P50 | 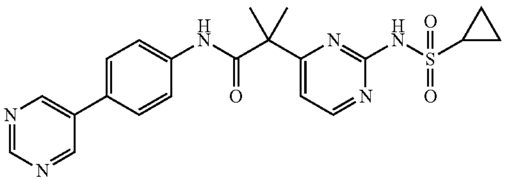 2-(2-(cyclopropanesulfonamido)pyrimidin-4-yl)-2-methyl-N-(4-(pyrimidin-5-yl)phenyl)propanamide | Method 2, using INTC21 and a commer-cial aniline, [UPLC Acidic], 439, (1.04) | 11.25 (s, 1H), 9.46 (s, 1H), 9.17-9.09 (m, 3H), 8.59 (d, J = 5.3 Hz, 1H), 7.81-7.73 (m, 4H), 3.24-3.14 (m, 1H), 1.59 (s, 6H), 1.07-0.99 (m, 2H), 0.85-0.77 (m, 2H). 1 exchangeable proton not observed. |
| P51 | 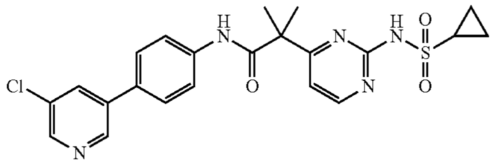 N-(4-(5-chloropyridin-3-yl)phenyl)-2-(2-(cyclopropanesulfonamido)pyrimidin-4-yl)-2-methylpropanamide | Method 2, using INTC21 and INTD8; [UPLC acidic], 472, (1.36) | 11.30 (s, 1H), 9.48 (s, 1H), 8.86 (d, J = 2.0 Hz, 1H), 8.63-8.55 (m, 2H), 8.23 (t, J = 2.2 Hz, 1H), 7.76 (s, 4H), 7.18 (d, J = 5.3 Hz, 1H), 3.25-3.13 (m, 1H), 1.59 (s, 6H), 1.09-0.98 (m, 2H), 0.85-0.75 (m, 2H). |
| P52 | 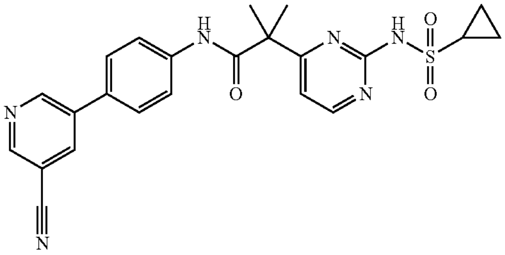 N-(4-(5-cyanopyridin-3-yl)phenyl)-2-(2-(cyclopropanesulfonamido)pyrimidin-4-yl)-2-methylpropanamide | Method 2, using INTC21 and INTD5, [HPLC acidic], 463, (2.46) | 11.34 (s, 1H), 9.52 (s, 1H), 9.19 (d, J = 2.3 Hz, 1H), 8.96 (d, J = 1.9 Hz, 1H), 8.64 (t, J = 2.1 Hz, 1H), 8.59 (d, J = 5.3 Hz, 1H), 7.83-7.73 (m, 4H), 7.17 (d, J = 5.3 Hz, 1H), 3.26-3.13 (m, 1H), 1.59 (s, 6H), 1.08-0.98 (m, 2H), 0.86-0.74 (m, 2H). |
| P53 | 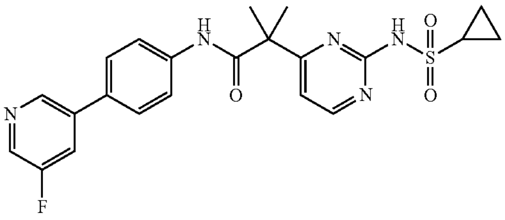 2-(2-(cyclopropanesulfonamido)pyrimidin-4-yl)-N-(4-(5-fluoropyridin-3-yl)phenyl)-2-methylpropanamide | Method 2, using INTC21 and INTD6, [UPLC acidic], 456, (1.25) | 11.30 (s, 1H), 9.48 (s, 1H), 8.88-8.76 (m, 1H), 8.60 (d, J = 5.3 Hz, 1H), 8.53 (d, J = 2.7 Hz, 1H), 8.09-8.00 (m, 1H), 7.76 (s, 4H), 7.19 (d, J = 5.3 Hz, 1H), 3.25-3.15 (m, 1H), 1.60 (s, 6H), 1.08-0.99 (m, 2H), 0.87-0.74 (m, 2H). |
| P54 | 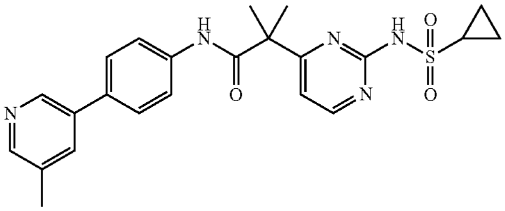 2-(2-(cyclopropanesulfonamido)pyrimidin-4-yl)-2-methyl-N-(4-(5-rnethylpyridin-3-yl)phenyl)propanamide | Method 2, using INTC21 and INTD10, [HPLC acidic], 452, (1.26) | 11.29 (s, 1H), 9.43 (s, 1H), 8.67 (d, J = 2.2 Hz, 1H), 8.60 (d, J = 5.3 Hz, 1H), 8.39-8.35 (m, 1H), 7.90-7.86 (m, 1H), 7.77-7.62 (m, 4H), 7.18 (d, J = 5.3 Hz, 1H), 3.28-3.11 (m, 1H), 2.36 (s, 3H), 1.60 (s, 6H), 1.09-0.97 (m, 2H), 0.86-0.74 (m, 2H). |

TABLE 20-continued

Preparation methods and characterisation data of examples P9-P115, P117-P225

| P | Name/Structure (All examples containing chiral centres are racemates unless stated) | Synthesis Method, [LCMS Method], m/z $(M + H)^+$, (RT/Min) | $^1$H NMR Chemical Shift Data (DMSO-d6 unless stated) |
|---|---|---|---|
| P55 | 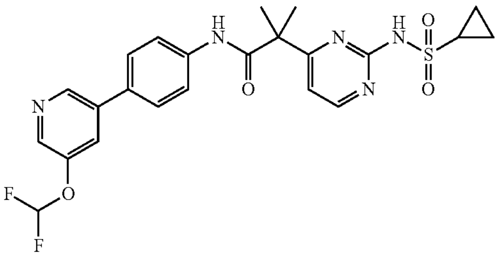 2-(2-(cyclopropanesulfonamido)pyrimidin-4-yl)-N-(4-(5-(difluoromethoxy)pyridin-3-yl)phenyl)-2-methylpropanamide | Method 2, using INTC21 and INTD3, [UPLC acidic], 504, (1.32) | 11.29 (s, 1H), 9.51 (s, 1H), 8.80 (d, J = 1.9 Hz, 1H), 8.59 (d, J = 5.3 Hz, 1H), 8.44 (d, J = 2.6 Hz, 1H), 7.95-7.89 (m, 1H), 7.81-7.71 (m, 4H), 7.34 (t, J = 73.5 Hz, 1H), 7.16 (d, J = 5.3 Hz, 1H), 3.25-3.13 (m, 1H), 1.60 (s, 6H), 1.08-0.98 (m, 2H), 0.87-0.74 (m, 2H). |
| P56 | 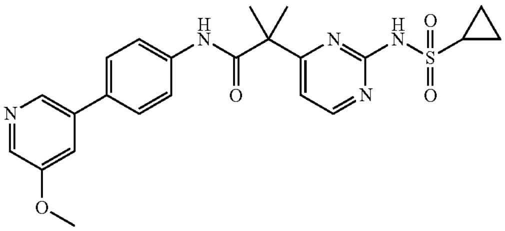 2-(2-(cyclopropanesulfonamido)pyrimidin-4-yl)-N-(4-(5-methoxypyridin-3-yl)phenyl)-2-methylpropanamide | Method 2, using INTC21 and INTD45, [HPLC acidic], 468, (1.89) | 11.34 (s, 1H), 9.46 (s, 1H), 8.60 (d, J = 5.3 Hz, 1H), 8.47 (d, J = 1.9 Hz, 1H), 8.25 (d, J = 2.8 Hz, 1H), 7.79-7.67 (m, 4H), 7.63-7.56 (m, 1H), 7.17 (d, J = 5.3 Hz, 1H), 3.91 (s, 3H), 3.26-3.14 (m, 1H), 1.60 (s, 6H), 1.09-0.96 (m, 2H), 0.88-0.75 (m, 2H). |
| P57 | 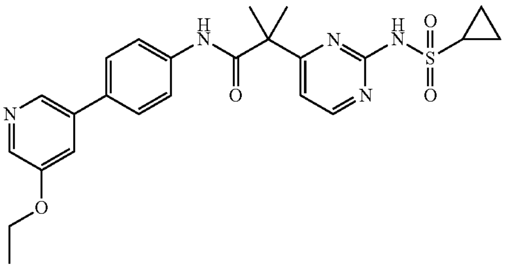 2-(2-(cyclopropanesulfonamido)pyrimidin-4-yl)-N-(4-(5-ethoxypyridin-3-yl)phenyl)-2-methylpropanamide | Method 2, using INTC21 and INTD4, [UPLC acidic], 482, (1.06) | 11.29 (s, 1H), 9.43 (s, 1H), 8.60 (d, J = 5.3 Hz, 1H), 8.46 (d, J = 1.9 Hz, 1H), 8.23 (d, J = 2.7 Hz, 1H), 7.80-7.64 (m, 4H), 7.60-7.54 (m, 1H), 7.18 (d, J = 5.3 Hz, 1H), 4.20 (q, J = 7.0 Hz, 2H), 3.26-3.13 (m, 1H), 1.60 (s, 6H), 1.38 (t, J = 7.0 Hz, 3H), 1.10-0.96 (m, 2H), 0.88-0.75 (m, 2H). |
| P58 | 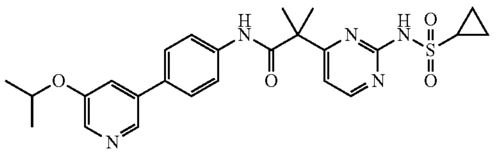 2-(2-(cyclopropanesulfonamido)pyrimidin-4-yl)-N-(4-(5-isopropoxypyridin-3-yl)phenyl)-2-methylpropanamide | Method 2, using INTC21 and INTD11, [UPLC acidic], 496, (1.16) | 11.34 (s, 1H), 9.45 (s, 1H), 8.59 (d, J = 5.2 Hz, 1H), 8.44 (d, J = 1.9 Hz, 1H), 8.21 (d, J = 2.7 Hz, 1H), 7.78-7.65 (m, 4H), 7.59-7.53 (m, 1H), 7.16 (d, J = 5.3 Hz, 1H), 4.92-4.76 (m, 1H), 3.27-3.13 (m, 1H), 1.60 (s, 6H), 1.32 (d, J = 6.0 Hz, 6H), 1.08-0.98 (m, 2H), 0.87-0.73 (m, 2H). |

TABLE 20-continued

Preparation methods and characterisation data of examples P9-P115, P117-P225

| P | Name/Structure (All examples containing chiral centres are racemates unless stated) | Synthesis Method, [LCMS Method], m/z (M + H)$^+$, (RT/Min) | $^1$H NMR Chemical Shift Data (DMSO-d6 unless stated) |
|---|---|---|---|
| P59 | 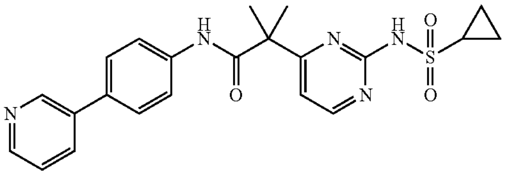 2-(2-(cyclopropanesulfonamido)pyrimidin-4-yl)-2-methyl-N-(4-(pyridin-3-yl)phenyl)propanamide | Method 2, using INTC21 and a commercial aniline, [HPLC acidic], 438, (1.28) | 9.44 (s, 1H), 8.89-8.85 (m, 1H), 8.60 (d, J = 5.3 Hz, 1H), 8.53 (dd, J = 4.7, 1.6 Hz, 1H), 8.15 (s, 1H), 8.07-8.03 (m, 1H), 7.80-7.61 (m, 4H), 7.49-7.41 (m, 1H), 7.18 (d, J = 5.3 Hz, 1H), 3.26-3.15 (m, 1H), 1.60 (s, 6H), 1.08-0.99 (m, 2H), 0.89-0.73 (m, 2H). |
| P60 | 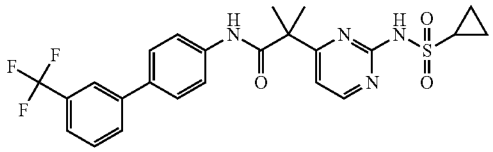 2-(2-(cyclopropanesulfonamido)pyrimidin-4-yl)-2-methyl-N-(3′-(trifluoromethyl)-1,1′-biphenyl]-4-yl)propanamide | Method 2, using INTC21 and a commercial aniline; [UPLC Acidic], 505, (1.65) | 11.25 (s, 1H), 9.42 (s, 1H), 8.59 (d, J = 5.3 Hz, 1H), 7.99-7.91 (m, 2H), 7.77-7.63 (m, 6H), 7.18 (d, J = 5.3 Hz, 1H), 3.24-3.15 (m, 1H), 1.58 (s, 6H), 1.06-0.98 (m, 2H), 0.82-0.75 (m, 2H). |
| P61 | 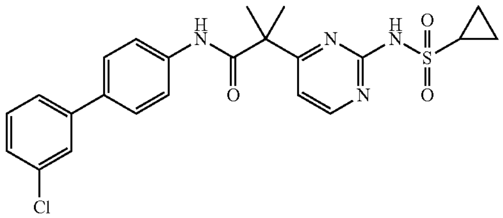 N-(3′-chloro-[1,1′-biphenyl]-4-yl)-2-(2-(cyclopropanesulfonamido)pyrimidin-4-yl)-2-methylpropanamide | Method 2, using INTC21 and a commercial aniline, [UPLC Acidic], 471, (1.63) | 11.26 (s, 1H), 9.41 (s, 1H), 8.59 (d, J = 5.3 Hz, 1H), 7.75-7.69 (m, 3H), 7.67-7.60 (m, 3H), 7.46 (td, J = 7.8, 1.6 Hz, 1H), 7.38 (d, J = 8.0 Hz, 1H), 7.18 (d, J = 5.3 Hz, 1H), 3.24-3.15 (m, 1H), 1.59 (s, 6H), 1.06-0.99 (m, 2H), 0.83-0.75 (m, 2H). |
| P62 | 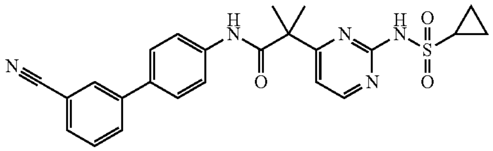 N-(3′-cyano-[1,1′-biphenyl]-4-yl)-2-(2-(cyclopropanesulfonamido)pyrimidin-4-yl)-2-methylpropanamide | Method 2, using INTC21 and a commercial aniline, [UPLC Acidic], 463, (1.42) | 11.27 (s, 1H), 9.42 (s, 1H), 8.59 (d, J = 5.3 Hz, 1H), 8.13 (d, J = 1.7 Hz, 1H), 8.03-7.97 (m, 1H), 7.80-7.69 (m, 5H), 7.63 (t, J = 7.8 Hz, 1H), 7.18 (d, J = 5.3 Hz, 1H), 3.24-3.15 (m, 1H), 1.59 (s, 6H), 1.06-0.99 (m, 2H), 0.83-0.75 (m, 2H). |
| P63 | 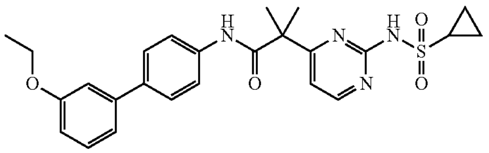 2-(2-(cyclopropanesulfonamido)pyrimidin-4-yl)-N-(3′-ethoxy-[1,1′-biphenyl]-4-yl)-2-methylpropanamide | Method 2, using INTC21 and INTD42, [UPLC Acidic], 481, (1.58) | 11.26 (s, 1H), 9.38 (s, 1H), 8.60 (d, J = 5.3 Hz, 1H), 7.72-7.66 (m, 2H), 7.63-7.57 (m, 2H), 7.37-7.30 (m, 1H), 7.22-7.12 (m, 3H), 6.88 (dd, J = 8.2, 2.5 Hz, 1H), 4.09 (q, J = 6.9 Hz, 2H), 3.25-3.16 (m, 1H), 1.59 (s, 6H), 1.35 (t, J = 6.9 Hz, 3H), 1.07-1.00 (m, 2H), 0.84-0.76 (m, 2H). |

TABLE 20-continued

Preparation methods and characterisation data of examples P9-P115, P117-P225

| P | Name/Structure (All examples containing chiral centres are racemates unless stated) | Synthesis Method, [LCMS Method], m/z $(M + H)^+$, (RT/Min) | $^1H$ NMR Chemical Shift Data (DMSO-d6 unless stated) |
|---|---|---|---|
| P64 | 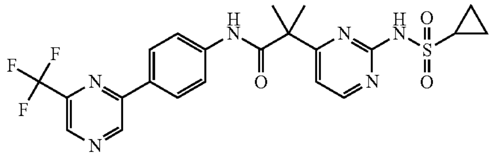 2-(2-(cyclopropanesulfonamido)pyrimidin-4-yl)-2-methyl-N-(4-(6-(trifluoromethyl)pyrazin-2-yl)phenyl)propanamide | Method 2, using INTC21 and INTD19, [HPLC acidic], 507, (2.25) | 11.27 (s, 1H), 9.59 (d, J = 5.0 Hz, 2H), 9.07 (s, 1H), 8.61 (d, J = 5.3 Hz, 1H), 8.22-8.13 (m, 2H), 7.90-7.78 (m, 2H), 7.20 (d, J = 5.3 Hz, 1H), 3.25-3.15 (m, 1H), 1.60 (s, 6H), 1.06-0.98 (m, 2H), 0.85-0.75 (m, 2H). |
| P65 | 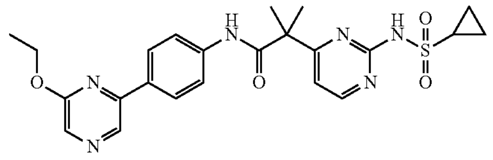 2-(2-(cyclopropanesulfonamido)pyrimidin-4-yl)-N-(4-(6-ethoxypyrazin-2-yl)phenyi)-2-methylpropanamide | Method 2, using INTC21 and INTD18, [HPLC acidic], 483, (2.19) | 11.27 (s, 1H), 9.50 (s, 1H), 8.76 (d, J = 0.5 Hz, 1H), 8.61 (d, J = 5.3 Hz, 1H), 8.18 (d, J = 0.5 Hz, 1H), 8.12-8.02 (m, 2H), 7.83-7.73 (m, 2H), 7.19 (d, J = 5.3 Hz, 1H), 4.48 (q, J = 7.0 Hz, 2H), 3.26-3.15 (m, 1H), 1.60 (s, 6H), 1.40 (t, J = 7.0 Hz, 3H), 1.08-1.00 (m, 2H), 0.87-0.75 (m, 2H). |
| P66 | 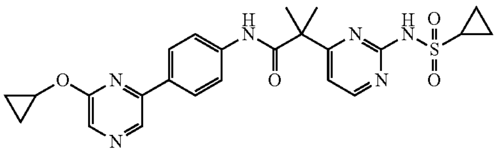 2-(2-(cyclopropanesulfonamido)pyrimidin-4-yl)-N-(4-(6-cyclopropoxypyrazin-2-yl)phenyl)-2-methylpropanamide | Method 2, using INTC21 and INTD21, [UPLC acidic], 495, (1.44) | 11.32 (s, 1H), 9.53 (s, 1H), 8.84 (s, 1H), 8.60 (d, J = 5.3 Hz, 1H), 8.23 (s, 1H), 8.14-8.05 (m, 2H), 7.83-7.74 (m, 2H), 7.19 (d, J = 5.3 Hz, 1H), 4.47-4.33 (m, 1H), 3.27-3.12 (m, 1H), 1.60 (s, 6H), 1.09-0.96 (m, 2H), 0.93-0.69 (m, 6H). |
| P67 | 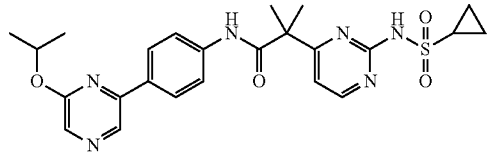 2-(2-(cyclopropanesulfonamido)pyrimidin-4-yl)-N-(4-(6-isopropoxypyrazin-2-yl)phenyl)-2-methylpropanamide | Method 2, using INTC21 and INTD20, [UPLC acidic], 497, (1.53) | 11.34 (s, 1H), 9.52 (s, 1H), 8.73 (s, 1H), 8.60 (d, J = 5.2 Hz, 1H), 8.12 (s, 1H), 8.08-8.03 (m, 2H), 7.80-7.75 (m, 2H), 7.18 (d, J = 5.3 Hz, 1H), 5.47-5.35 (m, 1H), 3.25-3.12 (m, 1H), 1.60 (s, 6H), 1.38 (d, J = 6.2 Hz, 6H), 1.08-0.97 (m, 2H), 0.87-0.74 (m, 2H). |
| P68 | 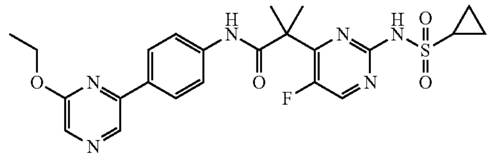 2-(2-(cyclopropanesulfonamido)-5-fluoropyrimidin-4-yl)-N-(4-(6-ethoxypyrazin-2-yl)phenyl)-2-methylpropanamide | Method 2, using INTC22 and INTD18, [UPLC Acidic], 501, (1.48) | 11.36 (s, 1H), 9.70 (s, 1H), 8.76 (s, 1H), 8.61 (s, 1H), 8.19 (s, 1H), 8.12-8.05 (m, 2H), 7.80-7.72 (m, 2H), 4.48 (q, J = 7.0 Hz, 2H), 3.27-3.16 (m, 1H), 1.61 (s, 6H), 1.40 (t, J = 7.0 Hz, 3H), 1.14-1.07 (m, 2H), 1.02-0.97 (m, 2H). |

TABLE 20-continued

| P | Name/Structure (All examples containing chiral centres are racemates unless stated) | Synthesis Method, [LCMS Method], m/z $(M + H)^+$, (RT/Min) | $^1H$ NMR Chemical Shift Data (DMSO-d6 unless stated) |
|---|---|---|---|
| | Preparation methods and characterisation data of examples P9-P115, P117-P225 | | |
| P69 | 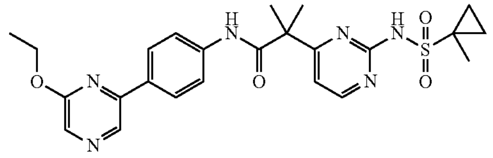 N-(4-(6-ethoxypyrazin-2-yl)phenyl)-2-methyl-2-(2-((1-methylcyclopropane)-1-sulfonamido)pyrimidin-4-yl)propanamide | Method 2, using INTC26 and INTD18, [UPLC Acidic], 497, (1.49) | 11.12-11.08 (m, 1H), 9.48 (s, 1H), 8.77 (s, 1H), 8.59 (d, J = 5.2 Hz, 1H), 8.18 (s, 1H), 8.10-8.04 (m, 2H), 7.79-7.74 (m, 2H), 7.16 (d, J = 5.2 Hz, 1H), 4.47 (q, J = 7.0 Hz, 2H), 1.58 (s, 6H), 1.50-1.46 (m, 2H), 1.43-1.36 (m, 6H), 0.84-0.80 (m, 2H). |
| P70 | 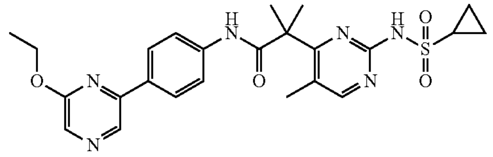 2-(2-(cyclopropanesulfonamido)-5-methylpyrimidin-4-yl)-N-(4-(6-ethoxypyrazin-2-yl)phenyl)-2-methylpropanamide | Method 2, using INTC23 and INTD18; [UPLC Basic], 497, (1.27) | 11.07 (s, 1H), 9.69 (s, 1H), 8.76 (s, 1H), 8.34 (s, 1H), 8.18 (s, 1H), 8.10-8.05 (m, 2H), 7.79-7.74 (m, 2H), 4.47 (q, J = 7.1 Hz, 2H), 3.30-3.25 (m, 1H), 2.09 (s, 3H), 1.56 (s, 6H), 1.40 (t, J = 7.0 Hz, 3H), 1.14-1.09 (m, 2H), 1.06-1.01 (m, 2H). |
| P71 | 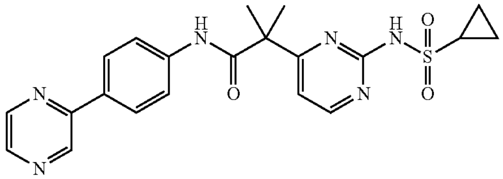 2-(2-(cyclopropanesulfonamido)pyrimidin-4-yl)-2-methyl-N-(4-(pyrazin-2-yl)phenyl)propanamide | Method 2, using INTC21 and INTD43, [HPLC acidic], 439, (1.72) | 11.26 (s, 1H), 9.50 (s, 1H), 9.22 (d, J = 1.5 Hz, 1H), 8.68 (dd, J = 2.5, 1.5 Hz, 1H), 8.61 (d, J = 5.3 Hz, 1H), 8.56 (d, J = 2.5 Hz, 1H), 8.15-8.04 (m, 2H), 7.85-7.74 (m, 2H), 7.20 (d, J = 5.3 Hz, 1H), 3.26-3.15 (m, 1H), 1.60 (s, 6H), 1.06-0.99 (m, 2H), 0.85-0.75 (m, 2H). |
| P72 | 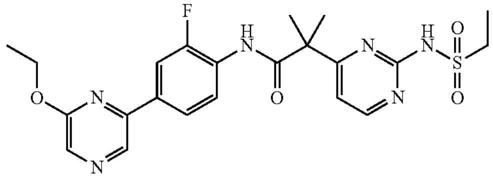 N-(4-(6-ethoxypyrazin-2-yl)-2-fluorophenyl)-2-(2-(ethylsulfonamido)pyrimidin-4-yl)-2-methylpropanamide | Method 2 using INTC20 and INTD24, [UPLC Acidic], 489, (1.41) | 11.23 (s, 1H), 9.35 (s, 1H), 8.85 (s, 1H), 8.61 (d, J = 5.3 Hz, 1H), 8.25 (s, 1H), 8.03-7.93 (m, 2H), 7.70 (t, J = 8.1 Hz, 1H), 7.21 (d, J = 5.3 Hz, 1H), 4.49 (q, J = 7.0 Hz, 2H), 3.55 (q, J = 7.3 Hz, 2H), 1.60 (s, 6H), 1.40 (t, J = 7.0 Hz, 3H), 1.19 (t, J = 7.3 Hz, 3H). |
| P73 | 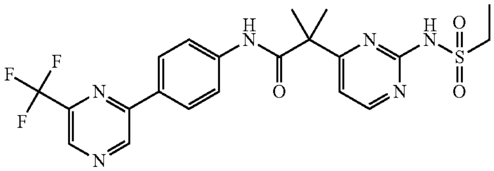 2-(2-(ethylsulfonamido)pyrimidin-4-yl)-2-methyl-N-(4-(6-(trifluoromethyl)pyrazin-2-yl)phenyl)propanamide | Method 2, using INTC20 and INTD19, [UPLC Acidic], 495, (1.44) | 11.21 (s, 1H), 9.57 (d, J = 9.3 Hz, 2H), 9.07 (s, 1H), 8.61 (d, J = 5.3 Hz, 1H), 8.22-8.13 (m, 2H), 7.91-7.79 (m, 2H), 7.20 (d, J = 5.3 Hz, 1H), 3.49 (q, J = 7.3 Hz, 2H), 1.59 (s, 6H), 1.09 (t, J = 7.3 Hz, 3H). |

TABLE 20-continued

Preparation methods and characterisation data of examples P9-P115, P117-P225

| P | Name/Structure (All examples containing chiral centres are racemates unless stated) | Synthesis Method, [LCMS Method], m/z (M + H)+, (RT/Min) | 1H NMR Chemical Shift Data (DMSO-d6 unless stated) |
| --- | --- | --- | --- |
| P74 | 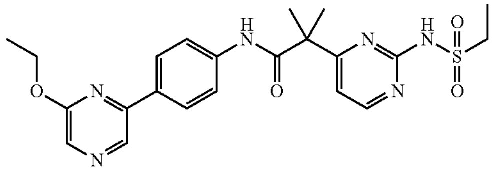 N-(4-(6-ethoxypyrazin-2-yl)phenyl)-2-(2-(ethylsulfonamido)pyrimidin-4-yl)-2-methylpropanamide | Method 2, using INTC20 and INTD18, [UPLC Acidic], 471, (1.4) | 11.21 (s, 1H), 9.47 (s, 1H), 8.77 (s, 1H), 8.60 (d, J = 5.3 Hz, 1H), 8.18 (s, 1H), 8.11-8.04 (m, 2H), 7.82-7.73 (m, 2H), 7.19 (d, J = 5.3 Hz, 1H), 4.48 (q, J = 7.0 Hz, 2H), 3.50 (q, J = 7.3 Hz, 2H), 1.59 (s, 6H), 1.40 (t, J = 7.0 Hz, 3H), 1.10 (t, J = 7.3 Hz, 3H). |
| P75 | 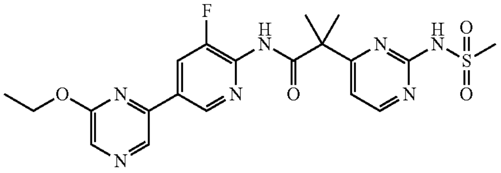 N-(5-(6-ethoxypyrazin-2-yl)-3-fluoropyridin-2-yl)-2-methyl-2-(2-(methylsulfonamido)pyrimidin-4-yl)propanamide | Method 2, using INTC19 and INTD31, [HPLC Acidic], 476, (1.88) | 11.37 (s, 1H), 10.13-10.05 (m, 1H), 9.00 (s, 1H), 8.93 (d, J = 2.6 Hz, 1H), 8.62 (dd, J = 5.3, 2.3 Hz, 1H), 8.43 (dq, J = 10.9, 1.8 Hz, 1H), 8.35-8.30 (m, 1H), 7.17 (d, J = 5.1 Hz, 1H), 4.55-4.46 (m, 2H), 3.32 (s, 3H), 1.61 (d, J = 2.6 Hz, 6H), 1.45-1.37 (m, 3H) |
| P76 | 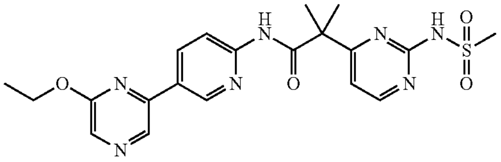 N-(5-(6-ethoxypyrazin-2-yl)pyridin-2-yl)-2-methyl-2-(2-(methylsulfonamido)pyrimidin-4-yl)propanamide | Method 2, using INTC19 and INTD33, [HPLC Acidic], 458, (2.03) | 11.34 (s, 1H), 10.14 (s, 1H), 9.08-8.99 (m, 1H), 8.84 (s, 1H), 8.59 (d, J = 5.3 Hz, 1H), 8.49 (dd, J = 8.8, 2.5 Hz, 1H), 8.25 (s, 1H), 8.23-8.18 (m, 1H), 7.17 (d, J = 5.3 Hz, 1H), 4.48 (q, J = 7.0 Hz, 2H), 3.32 (s, 3H), 1.61 (s, 6H), 1.40 (t, J = 7.0 Hz, 3H) |
| P77 | 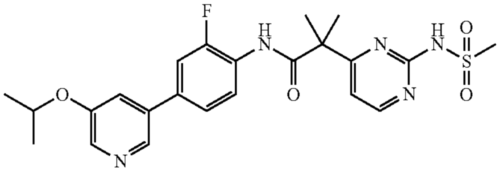 N-(2-fluoro-4-(5-isopropoxypyridin-3-yl)phenyl)-2-methyl-2-(2-(methylsulfonamido)pyrimidin-4-yl)propanamide | Method 2, using INTC19 and INTD12, [HPLC Acidic], 488, (1.79) | 11.39 (s, 1H), 9.35 (s, 1H), 8.61 (d, J = 5.3 Hz, 1H), 8.49 (d, J = 1.9 Hz, 1H), 8.25 (d, J = 2.7 Hz, 1H), 7.72-7.68 (m, 1H), 7.66 (dd, J = 2.7, 1.9 Hz, 1H), 7.62-7.55 (m, 2H), 7.18 (d, J = 5.3 Hz, 1H), 4.91-4.82 (m, 1H), 3.37 (s, 3H), 1.60 (s, 6H), 1.32 (d, J = 6.0 Hz, 6H). |
| P78 | 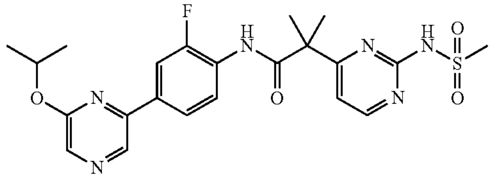 N-(2-fluoro-4-(8-isopropoxypyrazin-2-yl)phenyl)-2-methyl-2-(2-(methylsulfonamido)pyrimidin-4-yl)propanamide | Method 2, using INTC19 and INTD35, [HPLC Acidic], 489, (2.26) | 11.39 (s, 1H), 9.42 (s, 1H), 8.84-8.81 (m, 1H), 8.61 (d, J = 5.3 Hz, 1H), 8.19 (s, 1H), 8.01-7.94 (m, 2H), 7.67 (t, J = 8.1 Hz, 1H), 7.18 (d, J = 5.3 Hz, 1H), 5.45-5.39 (m, 1H), 3.36 (s, 3H), 1.61 (s, 6H), 1.39 (d, J = 6.2 Hz, 6H) |

TABLE 20-continued

| P | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
|---|---|---|---|
| Preparation methods and characterisation data of examples P9-P115, P117-P225 | | | |
| P79 | 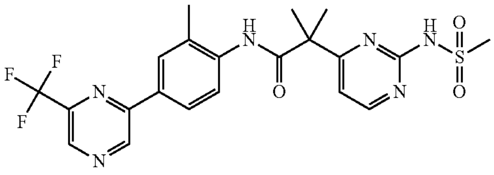 2-methyl-N-(2-methyl-4-(6-(trifluoromethyl)pyrazin-2-yl)phenyl)-2-(2-(methylsulfonamido)pyrimidin-4-yl)propanamide | Method 2 using INTC19 and INTD34; [HPLC Acidic], 495, (2.16) | 11.37 (s, 1H), 9.60 (s, 1H), 9.11 (d, J = 4.4 Hz, 2H), 8.63 (d, J = 5.3 Hz, 1H), 8.07 (d, J = 2.1 Hz, 1H), 8.02 (dd, J = 8.3, 2.2 Hz, 1H), 7.51 (d, J = 8.3 Hz, 1H), 7.23 (d, J = 5.3 Hz, 1H), 3.38 (s, 3H), 2.22 (s, 3H), 1.63 (s, 6H). |
| P80 | 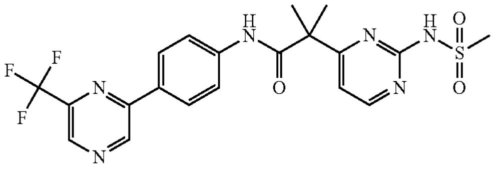 2-methyl-2-(2-(methylsulfonamido)pyrimidin-4-yl)-N-(4-(6-(trifluoromethyl)pyrazin-2-yl)phenyl)propanamide | Method 2, using INTC19 and INTD19, [HPLC Acidic], 481, (2.18) | 11.35 (s, 1H), 9.58 (s, 2H), 9.08 (s, 1H), 8.61 (d, J = 5.3 Hz, 1H), 8.24-8.12 (m, 2H), 7.93-7.77 (m, 2H), 7.18 (d, J = 5.3 Hz, 1H), 3.33 (s, 3H), 1.61 (s, 6H). |
| P81 | 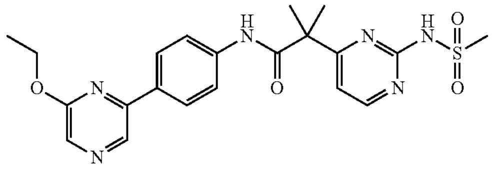 N-(4-(6-ethoxypyrazin-2-yl)phenyl)-2-methyl-2-(2-(methylsulfonamido)pyrimidin-4-yl)propanamide | Method 2, using INTC19 and INTD18, [HPLC Acidic], 457, (2.11) | 11.39 (s, 1H), 9.51 (s, 1H), 8.76 (s, 1H), 8.60 (d, J = 5.3 Hz, 1H), 8.18 (s, 1H), 8.11-8.04 (m, 2H), 7.82-7.70 (m, 2H), 7.16 (d, J = 5.3 Hz, 1H), 4.48 (q, J = 7.0 Hz, 2H), 3.32 (s, 3H), 1.60 (s, 6H), 1.40 (t, J = 7.1 Hz, 3H). |
| P82 | 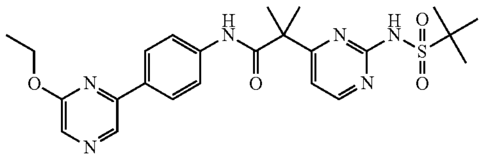 2-(2-((1,1-dimethylethyl)sulfonamido)pyrimidin-4-yl)-N-(4-(6-ethoxypyrazin-2-yl)phenyl)-2-methylpropanamide | Method 2, using INTC25 and INTD18, [UPLC Acidic], 499, (1.56) | 10.85 (s, 1H), 9.52 (s, 1H), 8.77 (s, 1H), 8.61-8.56 (m, 1H), 8.18 (s, 1H), 8.11-8.05 (m, 2H), 7.81-7.74 (m, 2H), 7.17 (s, 1H), 4.48 (q, J = 7.0 Hz, 2H), 1.58 (s, 6H), 1.43-1.36 (m, 12H). |
| P83 | 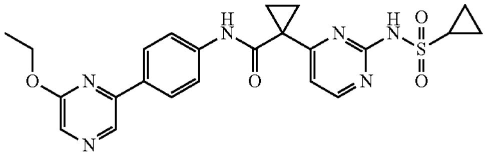 1-(2-(cyclopropanesulfonamido)pyrimidin-4-yl)-N-(4-(6-ethoxypyrazin-2-yl)phenyl)cyclopropanecarboxamide | Method 2, using INTC28 and INTD18, [UPLC acidic], 481, (1.39) | 11.45 (s, 1H), 10.70 (s, 1H), 8.78 (s, 1H), 8.44 (d, J = 5.3 Hz, 1H), 8.19 (s, 1H), 8.13-8.07 (m, 2H), 7.87-7.80 (m, 2H), 6.92 (s, 1H), 4.48 (q, J = 7.1 Hz, 2H), 3.11 (s, 1H), 1.66-1.59 (m, 2H), 1.53-1.46 (m, 2H), 1.40 (t, J = 7.1 Hz, 3H), 1.07-0.99 (m, 2H), 0.95-0.85 (m, 2H). |

TABLE 20-continued

Preparation methods and characterisation data of examples P9-P115, P117-P225

| P | Name/Structure (All examples containing chiral centres are racemates unless stated) | Synthesis Method, [LCMS Method], m/z $(M + H)^+$, (RT/Min) | $^1H$ NMR Chemical Shift Data (DMSO-d6 unless stated) |
|---|---|---|---|
| P84 | 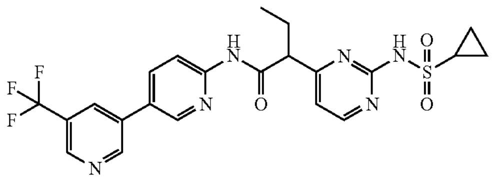<br>2-(2-(cyclopropanesulfonamido)pyrimidin-4-yl)-N-(5′-(trifluoromethyl)-[3,3′-bipyridin]-6-yl)butanamide | Method 3 using INTC37 and INTD44, [UPLC Acidic], 507, (1.36) | 11.24 (s, 1H), 11.04 (s, 1H), 9.27 (d, J = 2.2 Hz, 1H), 8.98 (dd, J = 2.2, 1.0 Hz, 1H), 8.86 (dd, J = 2.6, 0.8 Hz, 1H), 8.59-8.54 (m, 2H), 8.33 (dd, J = 8.7, 2.6 Hz, 1H), 8.21 (d, J = 8.7 Hz, 1H), 7.21 (d, J = 5.2 Hz, 1H), 4.00 (dd, J = 8.6, 6.3 Hz, 1H), 3.32-3.28 (m, 1H), 2.11-2.04 (m, 1H), 2.00-1.90 (m, 1H), 1.16-1.06 (m, 2H), 1.00-0.88 (m, 5H). |
| P85 | 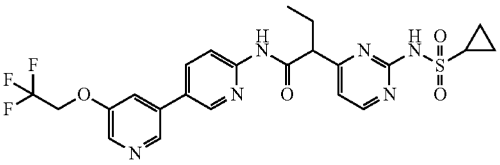<br>2-(2-(cyclopropanesulfonamido)pyrimidin-4-yl)-N-(5′-(2,2,2-trifluoroethoxy)-[3,3′-bipyridin]-6-yl)butanamide | Method 3 using INTC37 and INTD17, [UPLC Acidic], 537, (1.3) | 11.23 (s, 1H), 11.00 (s, 1H), 8.79 (d, J = 2.5 Hz, 1H), 8.66 (d, J = 1.8 Hz, 1H), 8.56 (d, J = 5.2 Hz, 1H), 8.41 (d, J = 2.8 Hz, 1H), 8.24 (dd, J = 8.7, 2.5 Hz, 1H), 8.19 (d, J = 8.7 Hz, 1H), 7.92-7.89 (m, 1H), 7.21 (d, J = 5.2 Hz, 1H), 4.99 (q, J = 8.8 Hz, 2H), 4.00 (dd, J = 7.5 Hz, 1H), 2.12-2.04 (m, 1H), 1.98-1.90 (m, 1H), 1.12-1.08 (m, 2H), 0.98-0.90 (m, 5H), 1H obscured by $H_2O$. |
| P86 | 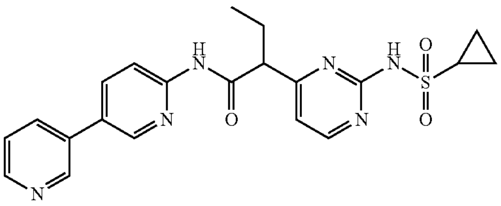<br>N-([3,3′-bipyridin]-6-yl)-2-(2-(cyclopropanesulfonamido)pyrimidin-4-yl)butanamide | Method 3 using INTC37 and a commercial aniline; [UPLC Acidic], 439, (0.81) | 11.25 (s, 1H), 10.96 (s, 1H), 8.94 (d, J = 2.4 Hz, 1H), 8.73 (dd, J = 1.7 Hz, 1H), 8.59 (dd, J = 4.7, 1.6 Hz, 1H), 8.56 (d, J = 5.1 Hz, 1H), 8.19 (d, J = 1.7 Hz, 2H), 8.14 (ddd, J = 8.0, 1.8 Hz, 1H), 7.51 (dd, J = 7.9, 4.8 Hz, 1H), 7.21 (d, J = 5.2 Hz, 1H), 4.04-3.96 (m, 1H), 3.31-3.28 (m, 1H), 2.13-2.02 (m, 1H), 1.99-1.89 (m, 1H), 1.17-1.02 (m, 2H), 0.99-0.86 (m, 5H). |
| P87 | 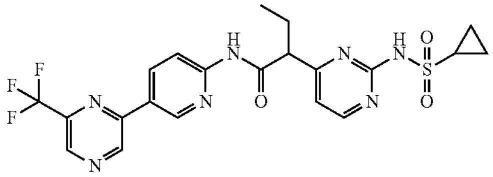<br>2-(2-(cyclopropanesulfonamido)pyrimidin-4-yl)-N-(5-(6-(trifluoromethyl)pyrazin-2-yl)pyridin-2-yl)butanamide | Method 3 using INTC37 and INTD2, [UPLC Acidic], 508, (1.41) | 11.24 (s, 1H), 11.16 (s, 1H), 9.66 (s, 1H), 9.16 (dd, J = 2.5, 0.8 Hz, 2H), 8.61-8.53 (m, 2H), 8.31-8.24 (m, 1H), 7.22 (d, J = 5.2 Hz, 1H), 4.06-3.97 (m, 1H), 3.32-3.26 (m, 1H), 2.15-2.02 (m, 1H), 2.01-1.88 (m, 1H), 1.17-1.03 (m, 2H), 1.03-0.85 (m, 5H). |
| P88 | 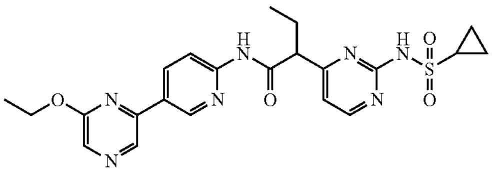<br>2-(2-(cyclopropanesulfonamido)pyrimidin-4-y)-N-(5-(6-ethoxypyrazin-2-yl)pyridin-2-yl)butanamide | Method 3 using INTC37 and INTD33, [UPLC Acidic], 484, (1.38) | 11.24 (s, 1H), 11.04 (s, 1H), 9.11-9.02 (m, 1H), 8.84 (s, 1H), 8.56 (d, J = 5.2 Hz, 1H), 8.53-8.46 (m, 1H), 8.25 (s, 1H), 8.21 (d, J = 8.8 Hz, 1H), 7.21 (d, J = 5.2 Hz, 1H), 4.48 (q, J = 7.0 Hz, 2H), 4.06-3.96 (m, 1H), 3.32-3.26 (m, 1H), 2.15-2.01 (m, 1H), 2.00-1.88 (m, 1H), 1.40 (t, J = 7.0 Hz, 3H), 1.17-1.03 (m, 2H), 1.03-0.87 (m, 5H). |

TABLE 20-continued

Preparation methods and characterisation data of examples P9-P115, P117-P225

| P | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
|---|---|---|---|
| P89 | 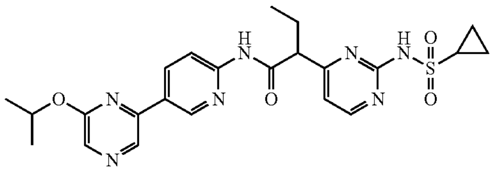 2-(2-(cyclopropanesulfonamido)pyrimidin-4-yl)-N-(5-(6-isopropoxypyrazin-2-yl)pyridin-2-yl)butanamide | Method 3 using INTC37 and INTD32, [UPLC Acidic], 498, (1.48) | 11.23 (s, 1H), 11.03 (s, 1H), 9.05 (dd, J = 2.5, 0.8 Hz, 1H), 8.82 (s, 1H), 8.56 (d, J = 5.2 Hz, 1H), 8.48 (dd, J = 8.8, 2.5 Hz, 1H), 8.25-8.17 (m, 2H), 7.21 (d, J = 5.2 Hz, 1H), 5.41 (hept, J = 6.1 Hz, 1H), 4.01 (dd, J = 8.6, 6.4 Hz, 1H), 3.32-3.28 (m, 1H), 2.13-2.03 (m, 1H), 2.01-1.89 (m, 1H), 1.38 (d, J = 6.2 Hz, 6H), 1.15-1.05 (m, 2H), 1.01-0.88 (m, 5H). |
| P90 | 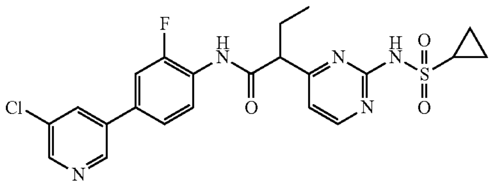 N-(4-(5-chloropyridin-3-yl)-2-fluorophenyl)-2-(2-(cyclopropanesulfonamido)pyrimidin-4-yl)butanamide | Method 3 using INTC37 and INTD13, [UPLC Acidic], 490, (1.37) | 11.27 (s, 1H), 10.21 (s, 1H), 8.91 (d, J = 2.0 Hz, 1H), 8.63 (d, J = 2.3 Hz, 1H), 8.56 (d, J = 5.2 Hz, 1H), 8.31 (dd, J = 2.3 Hz, 1H), 8.00 (dd, J = 8.3 Hz, 1H), 7.81 (dd, J = 12.2, 2.1 Hz, 1H), 7.65 (dd, J = 8.4, 2.1 Hz, 1H), 7.19 (d, J = 5.2 Hz, 1H), 3.97 (dd, J = 8.7, 6.3 Hz, 1H), 3.31-3.27 (m, 1H), 2.11-2.01 (m, 1H), 1.99-1.91 (m, 1H), 1.16-1.08 (m, 2H), 1.05-0.91 (m, 5H). |
| P91 | 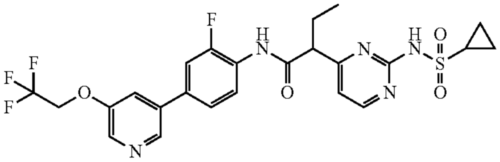 2-(2-(cyclopropanesulfonamido)pyrimidin-4-yl)-N-(2-fluoro-4-(5-(2,2,2-trifluoroethoxy)pyridin-3-yl)phenyl)butanamide | Method 3 using INTC37 and INTD14; [UPLC Acidic], 554, (1.38) | 11.27 (s, 1H), 10.20 (s, 1H), 8.65 (d, J = 1.8 Hz, 1H), 8.57 (d, J = 5.2 Hz, 1H), 8.39 (d, J = 2.8 Hz, 1H), 7.99 (dd, J = 8.3 Hz, 1H), 7.87 (dd, J = 2.3 Hz, 1H), 7.80 (dd, J = 12.2, 2.1 Hz, 1H), 7.64 (dd, J = 8.5, 2.0 Hz, 1H), 7.20 (d, J = 5.2 Hz, 1H), 4.99 (q, J = 8.9 Hz, 2H), 3.97 (dd, J = 8.8, 6.2 Hz, 1H), 2.10-2.01 (m, 1H), 1.99-1.89 (m, 1H), 1.15-1.08 (m, 2H), 1.03-0.92 (m, 5H), 1H obscured by $H_2O$. |
| P92 | 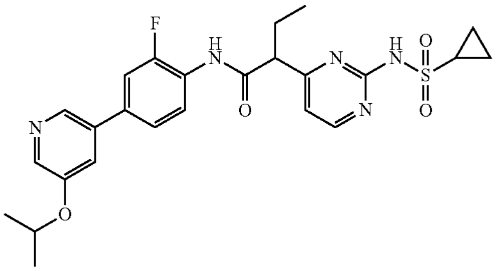 2-(2-(cyclopropanesulfonamido)pyrimidin-4-yl)-N-(2-fluoro-4-(5-isopropoxypyridin-3-yl)phenyl)butanamide | Method 3 using INTC37 and INTD12, [UPLC Acidic], 514, (1.22) | 11.25 (s, 1H), 10.17 (s, 1H), 8.57 (d, J = 5.1 Hz, 1H), 8.49 (d, J = 1.9 Hz, 1H), 8.25 (d, J = 2.7 Hz, 1H), 7.96 (dd, J = 8.3 Hz, 1H), 7.74 (dd, J = 12.2, 2.1 Hz, 1H), 7.69-7.62 (m, 1H), 7.59 (dd, J = 8.4, 2.0 Hz, 1H), 7.20 (s, 1H), 4.92-4.82 (m, 1H), 4.01-3.93 (m, 1H), 3.31-3.27 (m, 1H), 2.13-2.01 (m, 1H), 1.99-1.90 (m, 1H), 1.32 (d, J = 6.0 Hz, 6H), 1.17-1.09 (m, 2H), 1.05-0.92 (m, 5H). |

TABLE 20-continued

| Preparation methods and characterisation data of examples P9-P115, P117-P225 | | | |
|---|---|---|---|
| P | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
| P93 | 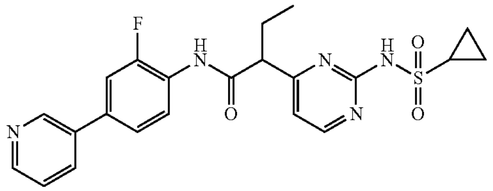 2-(2-(cyclopropanesulfonamido)pyrimidin-4-yl)-N-(2-fluoro-4-(pyridin-3-yl)phenyl)butanamide | Method 3 using INTC37 and INTD50; [UPLC Acidic], 456, (0.85) | 11.27 (s, 1H), 10.17 (s, 1H), 8.93 (d, J = 2.4 Hz, 1H), 8.62-8.54 (m, 2H), 8.11 (dt, J = 8.1, 1.9 Hz, 1H), 7.98 (dd, J = 8.3 Hz, 1H), 7.72 (dd, J = 12.2, 2.1 Hz, 1H), 7.58 (dd, J = 8.4, 2.1 Hz, 1H), 7.52-7.45 (m, 1H), 7.20 (d, J = 5.2 Hz, 1H), 4.00-3.93 (m, 1H), 2.12-2.01 (m, 1H), 2.00-1.91 (m, 1H), 1.16-1.08 (m, 2H), 1.03-0.91 (m, 5H), 1H obscured by $H_2O$. |
| P94 | 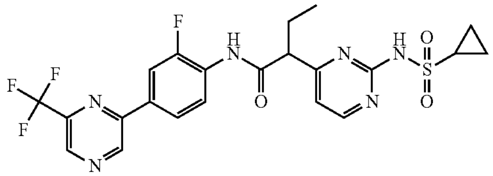 2-(2-(cyclopropanesulfonamido)pyrimidin-4-yl)-N-(2-fluoro-4-(6-(trifluoromethyl) pyrazin-2-yl)phenyl)butanamide | Method 3 using INTC37 and INTD25, [UPLC Acidic], 525, (1.49) | 11.25 (s, 1H), 10.32 (s, 1H), 9.64 (s, 1H), 9.15 (s, 1H), 8.57 (d, J = 5.2 Hz, 1H), 8.21-8.09 (m, 2H), 8.06 (dd, J = 8.6, 2.0 Hz, 1H), 7.21 (d, J = 5.3 Hz, 1H), 4.02 (t, J = 7.5 Hz, 1H), 3.32-3.26 (m, 1H), 2.12-2.02 (m, 1H), 2.01-1.88 (m, 1H), 1.17-1.05 (m, 2H), 1.05-0.92 (m, 5H). |
| P95 | 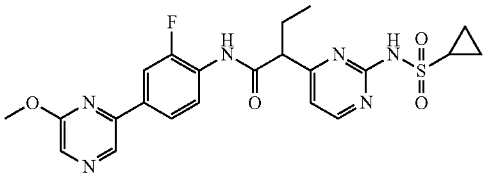 2-(2-(cyclopropanesulfonamido)pyrimidin-4-yl)-N-(2-fluoro-4-(6-methoxypyrazin-2-yl)phenyl)butanamide | Method 3 using INTC37 and INTD46, [UPLC Acidic], 487, (1.35) | 11.25 (s, 1H), 10.24 (s, 1H), 8.85 (s, 1H), 8.57 (d, J = 5.2 Hz, 1H), 8.28 (s, 1H), 8.09-8.03 (m, 2H), 8.00-7.97 (m, 1H), 7.20 (d, J = 4.7 Hz, 1H), 4.03 (s, 3H), 3.99 (dd, J = 10.2, 5.0 Hz, 1H), 3.31-3.27 (m, 1H), 2.12-2.02 (m, 1H), 2.00-1.91 (m, 1H), 1.16-1.08 (m, 2H), 1.02-0.93 (m, 5H). |
| P96 | 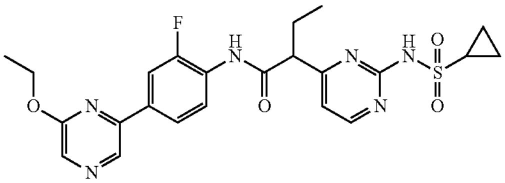 2-(2-(cyclopropanesulfonamido)pyrimidin-4-yl)-N-(4-(6-ethoxypyrazin-2-yl)-2-fluorophenyl)butanamide | Method 3 using INTC37 and INTD24, [UPLC acidic], 501, (1.45) | 11.27 (s, 1H), 10.24 (s, 1H), 8.83 (s, 1H), 8.56 (d, J = 5.2 Hz, 1H), 8.24 (s, 1H), 8.09-8.00 (m, 2H), 7.99-7.94 (m, 1H), 7.19 (d, J = 5.2 Hz, 1H), 4.49 (q, J = 7.1 Hz, 2H), 4.05-3.92 (m, 1H), 3.33-3.28 (m, 1H), 2.12-2.01 (m, 1H), 2.00-1.89 (m, 1H), 1.40 (t, J = 7.0 Hz, 3H), 1.17-1.06 (m, 2H), 1.05-0.89 (m, 5H). |
| P97 | 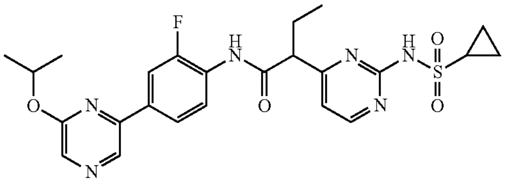 2-(2-(cyclopropanesulfonamido)pyrimidin-4-yl)-N-(2-fluoro-4-(6-isopropoxypyrazin-2-yl)phenyl)butanamide | Method 3 using INTC37 and INTD35, [UPLC Acidic], 515, (1.55) | 11.25 (s, 1H), 10.24 (s, 1H), 8.81 (s, 1H), 8.57 (d, J = 5.2 Hz, 1H), 8.19 (s, 1H), 8.06 (d, J = 8.3 Hz, 1H), 8.00 (dd, J = 12.2, 1.9 Hz, 1H), 7.95 (dd, J = 8.5, 2.0 Hz, 1H), 7.20 (d, J = 5.1 Hz, 1H), 5.45-5.39 (m, 1H), 4.00 (t, J = 7.7 Hz, 1H), 3.31-3.27 (m, 1H), 2.13-2.02 (m, 1H), 1.99-1.90 (m, 1H), 1.39 (d, J = 6.2 Hz, 6H), 1.16-1.08 (m, 2H), 1.03-0.93 (m, 5H). |

TABLE 20-continued

Preparation methods and characterisation data of examples P9-P115, P117-P225

| P | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
|---|---|---|---|
| P98 | 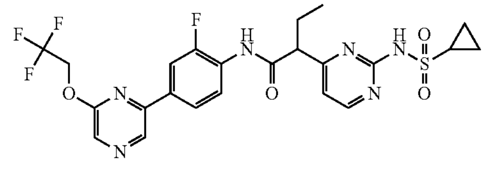<br>2-(2-(cyclopropanesulfonamido)pyrimidin-4-yl)-N-(2-fluoro-4-(6-(2,2,2-trifluoroethoxy)pyrazin-2-yl)phenyl)butanamide | Method 3 using INTC37 and INTD28, [UPLC Acidic], 555, (1.49) | 11.27 (s, 1H), 10.28 (s, 1H), 9.00 (s, 1H), 8.57 (d, J = 5.2 Hz, 1H), 8.44 (s, 1H), 8.15 (dd, J = 12.3, 1.9 Hz, 1H), 8.10 (dd, J = 8.1 Hz, 1H), 8.04 (dd, J = 8.5, 1.9 Hz, 1H), 7.21 (d, J = 5.2 Hz, 1H), 5.22 (q, J = 9.0 Hz, 2H), 4.01 (dd, J = 8.6, 6.2 Hz, 1H), 2.12-2.02 (m, 1H), 1.99-1.90 (m, 1H), 1.17-1.06 (m, 2H), 1.03-0.90 (m, 5H), 1H obscured by $H_2O$. |
| P99 | 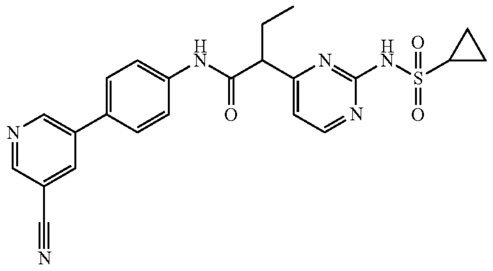<br>N-(4-(5-cyanopyridin-3-yl)phenyl)-2-(2-(cyclopropanesulfonamido)pyrimidin-4-yl)butanamide | Method 3 using INTC37 and INTD5, [UPLC Acidic], 463, (1.23) | 11.24 (s, 1H), 10.41 (s, 1H), 9.18 (d, J = 2.3 Hz, 1H), 8.97 (d, J = 1.9 Hz, 1H), 8.63 (dd, J = 2.1 Hz, 1H), 8.57 (d, J = 5.2 Hz, 1H), 7.83-7.80 (m, 2H), 7.78-7.75 (m, 2H), 7.21 (d, J = 5.2 Hz, 1H), 3.77 (dd, J = 8.7, 6.3 Hz, 1H), 3.31-3.26 (m, 1H), 2.13-2.02 (m, 1H), 1.98-1.89 (m, 1H), 1.13-1.07 (m, 2H), 1.00-0.90 (m, 5H). |
| P100 | 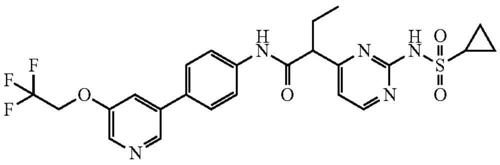<br>2-(2-(cyclopropanesulfonamido)pyrimidin-4-yl)-N-(4-(5-(2,2,2-trifluoroethoxy)pyridin-3-yl)phenyl)butanamide | Method 3 using INTC37 and INTD15, [UPLC Acidic], 536, (1.32) | 11.27 (s, 1H), 10.39 (s, 1H), 8.61-8.53 (m, 2H), 8.36 (d, J = 2.8 Hz, 1H), 7.82-7.70 (m, 5H), 7.21 (d, J = 5.2 Hz, 1H), 4.98 (q, J = 8.8 Hz, 2H), 3.76 (dd, J = 8.7, 6.3 Hz, 1H), 3.31-3.26 (m, 1H), 2.11-2.02 (m, 1H), 1.98-1.90 (m, 1H), 1.13-1.05 (m, 2H), 1.00-0.88 (m, 5H). |
| P101 | 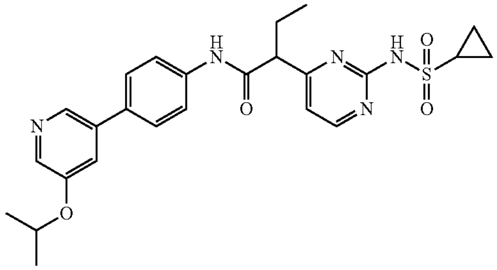<br>2-(2-(cyclopropanesulfonamido)pyrimidin-4-yl)-N-(4-(5-isopropoxypyridin-3-yl)phenyl)butanamide | Method 3 using INTC37 and INTD11, [UPLC Acidic], 496, (1.13) | 11.26 (s, 1H), 10.36 (s, 1H), 8.57 (d, J = 5.2 Hz, 1H), 8.44 (d, J = 1.9 Hz, 1H), 8.21 (d, J = 2.7 Hz, 1H), 7.75-7.69 (m, 4H), 7.58-7.55 (m, 1H), 7.20 (d, J = 5.2 Hz, 1H), 4.84 (hept, J = 6.0 Hz, 1H), 3.76 (dd, J = 8.8, 6.3 Hz, 1H), 3.33-3.27 (m, 1H), 2.13-2.02 (m, 1H), 1.99-1.90 (m, 1H), 1.32 (d, J = 6.0 Hz, 6H), 1.14-1.05 (m, 2H), 1.01-0.88 (m, 5H). |
| P102 | 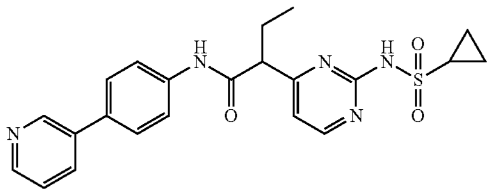<br>2-(2-(cyclopropanesulfonamido)pyrimidin-4-yl)-N-(4-(pyridin-3-yl)phenyl)butanamide | Method 2, using INTC35 and a commercial aniline, [HPLC acidic], 438, (1.31) | 11.27 (s, 1H), 10.36 (s, 1H), 8.94-8.80 (m, 1H), 8.61-8.47 (m, 2H), 8.09-8.01 (m, 1H), 7.78-7.61 (m, 4H), 7.50-7.42 (m, 1H), 7.20 (d, J = 5.2 Hz, 1H), 3.79-3.72 (m, 1H), 3.31-3.25 (m, 1H), 2.14-2.01 (m, 1H), 2.00-1.87 (m, 1H), 1.15-1.04 (m, 2H), 1.02-0.86 (m, 5H). |

TABLE 20-continued

| P | Name/Structure (All examples containing chiral centres are racemates unless stated) | Synthesis Method, [LCMS Method], m/z (M + H)+, (RT/Min) | $^{1}$H NMR Chemical Shift Data (DMSO-d6 unless stated) |
|---|---|---|---|
| Preparation methods and characterisation data of examples P9-P115, P117-P225 | | | |
| P103 | 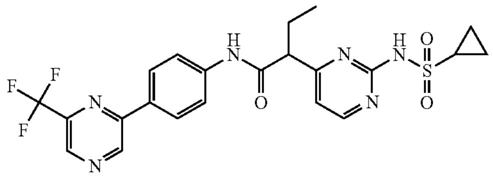 2-(2-(cyclopropanesulfonamido)pyrimidin-4-yl)-N-(4-(6-(trifluoromethyl)pyrazin-2-yl)phenyl)butanamide | Method 1 using INTC37 and INTD19, [UPLC Acidic], 507, (1.47) | 11.27 (s, 1H), 10.52 (s, 1H), 9.58 (s, 1H), 9.08 (s, 1H), 8.57 (d, J = 5.2 Hz, 1H), 8.23-8.15 (m, 2H), 7.86-7.78 (m, 2H), 7.20 (d, J = 5.2 Hz, 1H), 3.85-3.72 (m, 1H), 3.32-3.24 (m, 1H), 2.14-2.01 (m, 1H), 2.00-1.90 (m, 1H), 1.14-1.03 (m, 2H), 1.02-0.85 (m, 5H). |
| P104 | 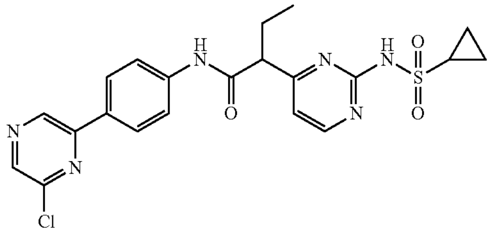 N-(4-(6-chloropyrazin-2-yl)phenyl)-2-(2-(cyclopropanesulfonamido)pyrimidin-4-yl)butanamide | Method 3 using INTC37 and INTD22, [UPLC Acidic], 473, (1.4) | 11.25 (s, 1H), 10.49 (s, 1H), 9.24 (s, 1H), 8.69 (s, 1H), 8.57 (d, J = 5.2 Hz, 1H), 8.15-8.09 (m, 2H), 7.83-7.75 (m, 2H), 7.20 (d, J = 5.2 Hz, 1H), 3.78 (dd, J = 8.6, 6.3 Hz, 1H), 3.30-3.26 (m, 1H), 2.12-2.03 (m, 1H), 1.96-1.92 (m, 1H), 1.13-1.05 (m, 2H), 1.01-0.88 (m, 5H). |
| P105 | 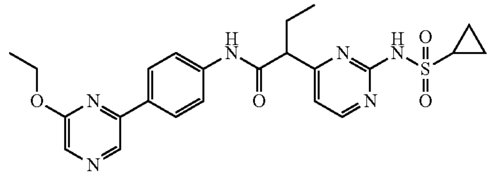 2-(2-(cyclopropanesulfonamido)pyrimidin-4-yl)-N-(4-(6-ethoxypyrazin-2-yl)phenyl) butanamide | Method 1 using INTC37 and INTD18, or Method 5 using INTC46 [UPLC acidic], 483, (1.43) | 11.28 (s, 1H), 10.43 (s, 1H), 8.76 (s, 1H), 8.56 (d, J = 5.2 Hz, 1H), 8.18 (s, 1H), 8.15-8.04 (m, 2H), 7.80-7.71 (m, 2H), 7.19 (d, J = 5.2 Hz, 1H), 4.48 (q, J = 7.0 Hz, 2H), 3.81-3.73 (m, 1H), 3.32-3.26 (m, 1H), 2.13-2.01 (m, 1H), 2.01-1.87 (m, 1H), 1.40 (t, J = 7.0 Hz, 3H), 1.13-1.04 (m, 2H), 1.03-0.85 (m, 5H). |
| P106 | 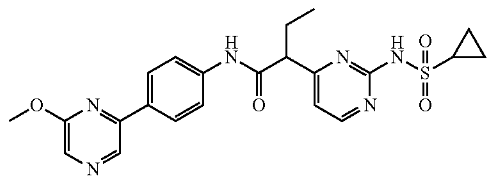 2-(2-(cyclopropanesulfonamido)pyrimidin-4-yl)-N-(4-(6-methoxypyrazin-2-yl)phenyl)butanamide | Method 3 using INTC37 and INTD1, [UPLC Acidic], 469, (1.33) | 11.25 (s, 1H), 10.44 (s, 1H), 8.78 (s, 1H), 8.57 (d, J = 5.2 Hz, 1H), 8.22 (s, 1H), 8.15-8.10 (m, 2H), 7.80-7.73 (m, 2H), 7.21 (d, J = 5.3 Hz, 1H), 4.02 (s, 3H), 3.78 (dd, J = 8.7, 6.3 Hz, 1H), 3.32-3.27 (m, 1H), 2.13-2.03 (m, 1H), 1.99-1.90 (m, 1H), 1.14-1.06 (m, 2H), 1.00-0.89 (m, 5H). |
| P107 | 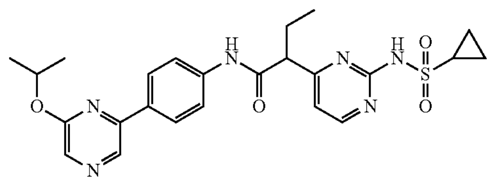 2-(2-(cyclopropanesulfonamido)pyrimidin-4-yl)-N-(4-(6-isopropoxypyrazin-2-yl)phenyl)butanamide | Method 3 using INTC37 and INTD20, [UPLC Acidic], 497, (1.53) | 11.25 (s, 1H), 10.44 (s, 1H), 8.74 (s, 1H), 8.57 (d, J = 5.2 Hz, 1H), 8.13 (s, 1H), 8.11-8.05 (m, 2H), 7.79-7.73 (m, 2H), 7.21 (d, J = 5.2 Hz, 1H), 5.41 (hept, J = 6.1 Hz, 1H), 3.78 (dd, J = 8.7, 6.4 Hz, 1H), 3.32-3.26 (m, 1H), 2.12-2.03 (m, 1H), 1.99-1.90 (m, 1H), 1.38 (d, J = 6.2 Hz, 6H), 1.14-1.06 (m, 2H), 1.00-0.87 (m, 5H). |

TABLE 20-continued

Preparation methods and characterisation data of examples P9-P115, P117-P225

| P | Name/Structure (All examples containing chiral centres are racemates unless stated) | Synthesis Method, [LCMS Method], m/z $(M + H)^+$, (RT/Min) | $^1$H NMR Chemical Shift Data (DMSO-d6 unless stated) |
|---|---|---|---|
| P108 | 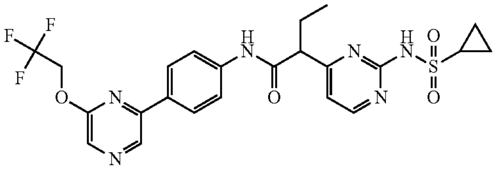 2-(2-(cyclopropanesulfonamido)pyrimidin-4-yl)-N-(4-(6-(2,2,2-trifluoroethoxy)pyrazin-2-yl)phenyl)butanamide | Method 3 using INTC37 and INTD29, [UPLC Acidic], 537, (1.49) | 11.25 (s, 1H), 10.46 (s, 1H), 8.93 (s, 1H), 8.57 (d, J = 5.2 Hz, 1H), 8.38 (s, 1H), 8.20-8.14 (m, 2H), 7.81-7.76 (m, 2H), 7.21 (d, J = 5.3 Hz, 1H), 5.19 (q, J = 9.0 Hz, 2H), 3.78 (dd, J = 8.5, 6.4 Hz, 1H), 2.13-2.03 (m, 1H), 2.01-1.90 (m, 1H), 1.14-1.07 (m, 2H), 0.99-0.89 (m, 5H), 1H obscured by $H_2O$. |
| P109 | 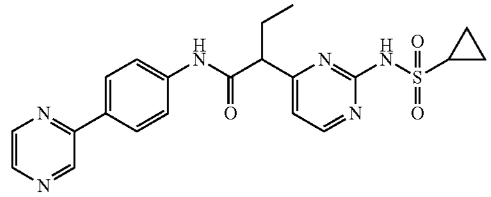 2-(2-(cyclopropanesulfonamido)pyrimidin-4-yl)-N-(4-(pyrazin-2-yl)phenyl)butanamide | Method 3 using INTC37 and INTD43, [UPLC Basic], 439, (0.87) | 11.25 (s, 1H), 10.44 (s, 1H), 9.22 (d, J = 1.6 Hz, 1H), 8.68 (dd, J = 2.5, 1.5 Hz, 1H), 8.60-8.53 (m, 2H), 8.15-8.10 (m, 2H), 7.82-7.75 (m, 2H), 7.20 (d, J = 5.2 Hz, 1H), 3.78 (dd, J = 8.7, 6.3 Hz, 1H), 3.31-3.26 (m, 1H), 2.13-2.02 (m, 1H), 2.00-1.89 (m, 1H), 1.12-1.04 (m, 2H), 1.01-0.88 (m, 5H). |
| P110 | 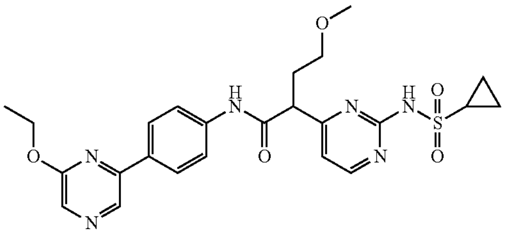 2-(2-(cyclopropanesulfonamido)pyrimidin-4-yl)-N-(4-(6-ethoxypyrazin-2-yl)phenyl)-4-methoxybutanamide | Method 3 using INTC38 and INTD18, [UPLC Acidic], 513, (1.34) | 11.28 (s, 1H), 10.47 (s, 1H), 8.76 (s, 1H), 8.56 (d, J = 5.2 Hz, 1H), 8.18 (s, 1H), 8.11-8.06 (m, 2H), 7.78-7.67 (m, 2H), 7.20 (d, J = 5.2 Hz, 1H), 4.47 (q, J = 7.1 Hz, 2H), 4.06-3.95 (m, 1H), 3.41-3.35 (m, 3H), 3.23 (s, 3H), 2.33-2.25 (m, 1H), 2.20-2.11 (m, 1H), 1.40 (t, J = 7.0 Hz, 3H), 1.18-1.03 (m, 2H), 1.01-0.88 (m, 2H). |
| P111 | 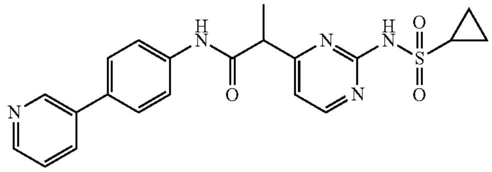 2-(2-(cyclopropanesulfonamido)pyrimidin-4-yl)-N-(4-(pyridin-3-yl)phenyl)propanamide | Method 2, using INTC18 and a commercial aniline, [UPLC acidic], 424, (0.70) | (Methanol-d4) 8.81 (s, 1H), 8.59-8.46 (m, 2H), 8.21-8.02 (m, 2H), 7.81-7.73 (m, 2H), 7.70-7.61 (m, 2H), 7.56-7.48 (m, 1H), 7.17 (d, J = 5.2 Hz, 1H), 4.08-3.92 (m, 1H), 3.32-3.25 (m, 1H), 1.63 (d, J = 6.9 Hz, 3H), 1.29-1.18 (m, 2H), 1.03-0.88 (m, 2H), 1 exchangeable proton not observed. |
| P112 | 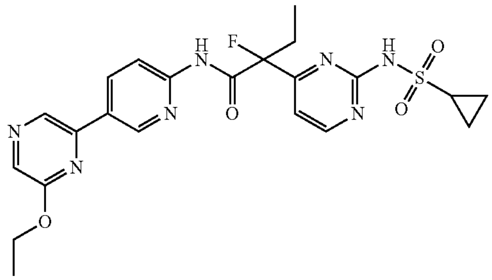 2-(2-(Cyclopropanesulfonamido)pyrimidin-4-yl)-N-(5-(6-ethoxypyrazin-2-yl)pyridin-2-yl)-2-fluorobutanamide | Method 4 using INTC50 and INTD33 then Method 6 using INTC51 [UPLC acidic], 502 (2.28). | 11.50 (s, 1H), 10.60 (d, J = 2.3 Hz, 1H), 9.10 (d, J = 2.4 Hz, 1H), 8.87 (s, 1H), 8.76 (d, J = 5.2 Hz, 1H), 8.53 (dd, J = 8.7, 2.5 Hz, 1H), 8.27 (s, 1H), 8.10 (d, J = 8.8 Hz, 1H), 7.48 (d, J = 5.1 Hz, 1H), 4.49 (q, J = 7.1 Hz, 2H), 3.38-3.27 (m, 1H), 2.44-2.29 (m, 2H), 1.40 (t, J = 7.0 Hz, 3H), 1.20-0.92 (m, 7H). |

TABLE 20-continued

Preparation methods and characterisation data of examples P9-P115, P117-P225

| P | Name/Structure (All examples containing chiral centres are racemates unless stated) | Synthesis Method, [LCMS Method], m/z $(M + H)^+$, (RT/Min) | $^1H$ NMR Chemical Shift Data (DMSO-d6 unless stated) |
|---|---|---|---|
| P113 | 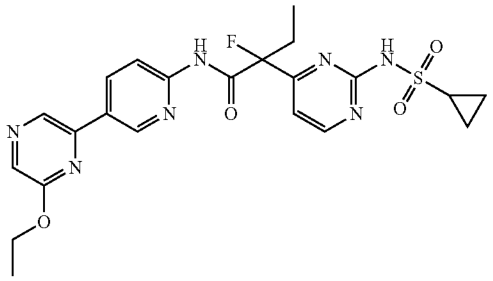 Single enantiomer-stereochemistry not assigned 2-(2-(Cyclopropanesulfonamido)pyrimidin-4-yl)-N-(5-(6-ethoxypyrazin-2-yl)pyridin-2-yl)-2-fluorobutanamide | Method 4 using INTC50 and INTD33 then Method 6 using INTC51 [UPLC acidic], 502, (2.28); [Chiral IC3 HPLC], 10.47 | 11.50 (s, 1H), 10.60 (d, J = 2.2 Hz, 1H), 9.11 (d, J = 2.4 Hz, 1H), 8.87 (s, 1H), 8.76 (d, J = 5.2 Hz, 1H), 8.53 (dd, J = 8.8, 2.5 Hz, 1H), 8.27 (s, 1H), 8.10 (d, J = 8.8 Hz, 1H), 7.48 (d, J = 5.1 Hz, 1H), 4.49 (q, J = 7.0 Hz, 2H), 3.39-3.26 (m, 1H), 2.54-2.43 (m, 1H), 2.41-2.28 (m, 1H), 1.40 (t, J = 7.0 Hz, 3H), 1.22-0.89 (m, 7H). |
| P114 | 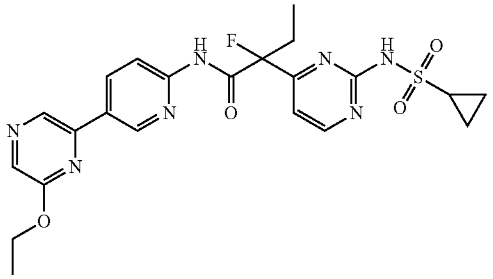 Single enantiomer-stereochemistry not assigned 2-(2-(Cyclopropanesulfonamido)pyrimidin-4-yl)-N-(5-(6-ethoxypyrazin-2-yl)pyridin-2-yl)-2-fluorobutanamide | Method 4 using INTC50 and INTD33 then Method 6 using INTC51 [UPLC acidic], 502, (2.28); [Chiral IC3 HPLC], 14.24 | 11.50 (s, 1H), 10.60 (d, J = 2.3 Hz, 1H), 9.11 (d, J = 2.4 Hz, 1H), 8.87 (s, 1H), 8.76 (d, J = 5.2 Hz, 1H), 8.53 (dd, J = 8.7, 2.5 Hz, 1H), 8.27 (s, 1H), 8.10 (d, J = 8.7 Hz, 1H), 7.48 (d, J = 5.1 Hz, 1H), 4.49 (q, J = 7.0 Hz, 2H), 3.39-3.25 (m, 1H), 2.55-2.42 (m, 1H), 2.42-2.27 (m, 1H), 1.40 (t, J = 7.0 Hz, 3H), 1.25-0.88 (m, 7H). |
| P115 | 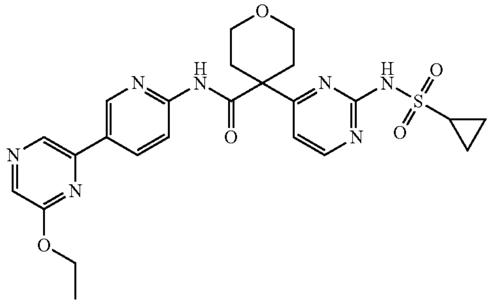 4-(2-(Cyclopropanesulfonamido)pyrimidin-4-yl)-N-(5-(6-ethoxypyrazin-2-yl)pyridin-2-yl)tetrahydro-2H-pyran-4-carboxamide | Method 2 using INTC53 and INTD33, [UPLC, acidic], 528, (1.31) | 11.31 (s, 1H), 10.13 (s, 1H), 9.03 (d, J = 2.5 Hz, 1H), 8.84 (s, 1H), 8.63 (d, J = 5.3 Hz, 1H), 8.50 (dd, J = 8.8, 2.5 Hz, 1H), 8.26 (s, 1H), 8.20 (d, J = 8.8 Hz, 1H), 7.26 (d, J = 5.3 Hz, 1H), 4.48 (q, J = 7.0 Hz, 2H), 3.81-3.69 (m, 2H), 3.67-3.56 (m, 2H), 3.31-3.20 (m, 1H), 2.49-2.41 (m, 2H), 2.25-2.17 (m, 2H), 1.40 (t, J = 7.0 Hz, 3H), 1.09-1.03 (m, 2H), 0.95-0.84 (m, 2H). |
| P117 | 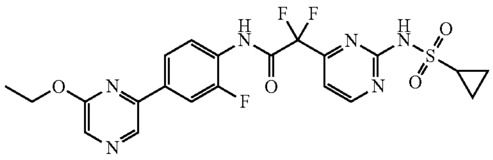 2-(2-(cyclopropanesulfonamido)pyrimidin-4-yl)-N-(4-(6-ethoxypyrazin-2-yl)-2-fluorophenyl)-2,2-difluoroacetamide | Method 1 using INTC101 and INTD24, [UPLC acidic], 509, (1.45) | 11.77 (s, 1H), 10.98 (s, 1H), 8.92-8.82 (m, 2H), 8.28 (s, 1H), 8.11-8.00 (m, 2H), 7.72-7.64 (m, 1H), 7.57-7.46 (m, 1H), 4.50 (q, J = 7.1 Hz, 2H), 3.22-3.14 (m, 1H), 1.41 (t, J = 7.0 Hz, 3H), 1.16-1.05 (m, 2H), 1.02-0.89 (m, 2H). |

TABLE 20-continued

Preparation methods and characterisation data of examples P9-P115, P117-P225

| P | Name/Structure (All examples containing chiral centres are racemates unless stated) | Synthesis Method, [LCMS Method], m/z (M + H)+, (RT/Min) | 1H NMR Chemical Shift Data (DMSO-d6 unless stated) |
|---|---|---|---|
| P118 | 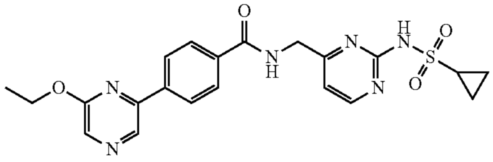 N-((2-(cyclopropanesulfonamido)pyrimidin-4-yl)methyl)-4-(6-ethoxypyrazin-2-yl)benzamide | Method 8 using INTC157 and INTD83, [UPLC acidic], 455, (1.17) Reverse Amide | 11.23 (s, 1H), 9.28 (d, J = 6.1 Hz, 1H), 8.91 (s, 1H), 8.53 (d, J = 5.1 Hz, 1H), 8.32-8.23 (m, 3H), 8.06 (dd, J = 8.4, 1.8 Hz, 2H), 7.07 (d, J = 5.0 Hz, 1H), 4.54-4.47 (m, 4H), 3.29-3.19 (m, 1H), 1.41 (t, J = 7.0 Hz, 3H), 1.10-1.06 (m, 2H), 0.96-0.91 (m, 2H). |
| P122 | 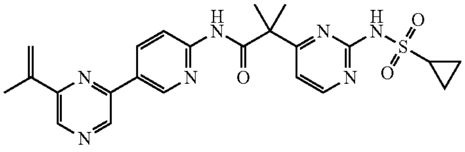 2-(2-(cyclopropanesulfonamido)pyrimidin-4-yl)-2-methyl-N-(5-(6-(prop-1-en-2-yl)pyrazin-2-yl)pyridin-2-yl)propanamide | Method 2b using INTC21 and INTD61, [HPLC acidic], 480, (2.22) | 11.21 (s, 1H), 10.16 (s, 1H), 9.18 (s, 1H), 9.08 (d, J = 2.5 Hz, 1H), 8.90 (s, 1H), 8.59 (d, J = 5.3 Hz, 1H), 8.56 (dd, J = 8.7, 2.5 Hz, 1H), 8.22 (d, J = 8.7 Hz, 1H), 7.20 (d, J = 5.3 Hz, 1H), 6.17-6.14 (m, 1H), 5.53-5.51 (m, 1H), 3.21-3.15 (m, 1H), 2.25 (s, 3H), 1.61 (s, 6H), 1.04-0.99 (m, 2H), 0.80-0.74 (m, 2H). |
| P123 | 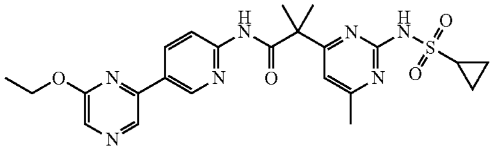 2-(2-(cyclopropanesulfonamido)-6-methylpyrimidin-4-yl)-N-(5-(6-ethoxypyrazin-2-yl)pyridin-2-yl)-2-methylpropanamide | Method 2b using INTC69 and INTD33, [UPLC acidic], 498, (1.45) | 11.08 (s, 1H), 10.04 (s, 1H), 9.00 (d, J = 2.5 Hz, 1H), 8.83 (s, 1H), 8.48 (dd, J = 8.8, 2.5 Hz, 1H), 8.24 (s, 1H), 8.23-8.16 (m, 1H), 7.11 (s, 1H), 4.47 (q, J = 7.0 Hz, 2H), 3.22-3.14 (m, 1H), 2.42 (s, 3H), 1.59 (s, 6H), 1.39 (t, J = 7.0 Hz, 3H), 1.04-0.97 (m, 2H), 0.79-0.70 (m, 2H). |
| P124 | 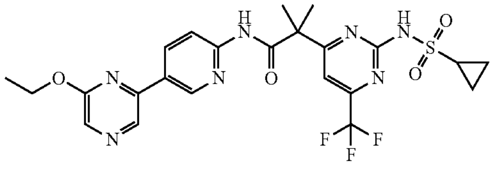 2-(2-(cyclopropanesulfonamido)-6-(trifluoromethyl)pyrimidin-4-yl)-N-(5-(6-ethoxypyrazin-2-yl)pyridin-2-yl)-2-methylpropanamide | Method 2b using INTC70 and INTD33, [UPLC acidic], 552, (1.65) | 11.80 (s, 1H), 10.32 (s, 1H), 9.01 (d, J = 2.5 Hz, 1H), 8.84 (s, 1H), 8.50 (dd, J = 8.8, 2.5 Hz, 1H), 8.24 (s, 1H), 8.22 (d, J = 8.7 Hz, 1H), 7.65 (s, 1H), 4.47 (q, J = 7.0 Hz, 2H), 3.10-3.02 (m, 1H), 1.64 (s, 6H), 1.39 (t, J = 7.0 Hz, 3H), 1.07-0.99 (m, 2H), 0.79-0.71 (m, 2H). |
| P125 | 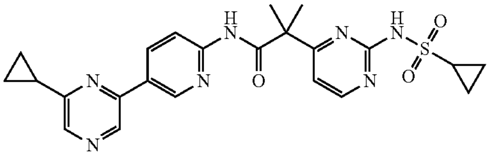 2-(2-(cyclopropanesulfonamido)pyrimidin-4-yl)-N-(5-(6-cyclopropylpyrazin-2-yl)pyridin-2-yl)-2-methylpropanamide | Method 2b using INTC21 and INTD54, [UPLC acidic], 480, (1.37) | 11.21 (s, 1H), 10.13 (s, 1H), 9.00 (s, 1H), 8.97 (d, J = 2.5 Hz, 1H), 8.59 (d, J = 5.3 Hz, 1H), 8.57 (s, 1H), 8.45 (dd, J = 8.8, 2.5 Hz, 1H), 8.19 (d, J = 8.8 Hz, 1H), 7.19 (d, J = 5.3 Hz, 1H), 3.21-3.14 (m, 1H), 2.29-2.22 (m, 1H), 1.60 (s, 6H), 1.13-1.04 (m, 4H), 1.04-0.96 (m, 2H), 0.84-0.70 (m, 2H) |

TABLE 20-continued

| P | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
|---|---|---|---|
| | Preparation methods and characterisation data of examples P9-P115, P117-P225 | | |
| P126 | 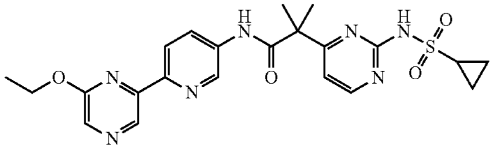 2-(2-(cyclopropanesulfonamido)pyrimidin-4-yl)-N-(6-(6-ethoxypyrazin-2-yl)pyridin-3-yl)-2-methylpropanamide | Method 2 using INTC21 and INTD53, [UPLC acidic], 484, (1.34) | 11.26 (s, 1H), 9.74 (s, 1H), 9.00 (s, 1H), 8.91 (d, J = 2.4 Hz, 1H), 8.61 (d, J = 5.3 Hz, 1H), 8.30-8.18 (m, 3H), 7.22 (d, J = 5.3 Hz, 1H), 4.49 (q, J = 7.0 Hz, 2H), 3.22-3.15 (m, 1H), 1.60 (s, 6H), 1.40 (t, J = 7.0 Hz, 3H), 1.08-1.01 (m, 2H), 0.87-0.81 (m, 2H). |
| P128 | 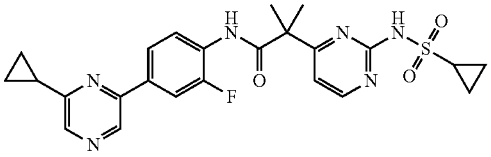 2-(2-(cyclopropanesulfonamido)pyrimidin-4-yl)-N-(4-(6-cyclopropylpyrazin-2-yl)-2-fluorophenyl)-2-methylpropanamide | Method 2b using INTC21 and INTD55, [UPLC acidic], 497, (1.45) | 11.28 (s, 1H), 9.37 (s, 1H), 9.00 (s, 1H), 8.60 (d, J = 5.3 Hz, 1H), 8.58 (s, 1H), 7.97-7.90 (m, 2H), 7.71-7.67 (m, 1H), 7.19 (d, J = 5.3 Hz, 1H), 3.28-3.20 (m, 1H), 2.30-2.23 (m, 1H), 1.60 (s, 6H), 1.12-1.05 (m, 6H), 1.00-0.95 (m, 2H). |
| P129 | 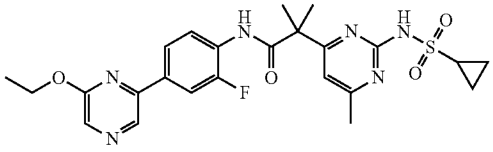 2-(2-(cyclopropanesulfonamido)-6-methylpyrimidin-4-yl)-N-(4-(6-ethoxypyrazin-2-yl)-2-fluorophenyl)-2-methylpropanamide | Method 2b using INTC69 and INTD24, [UPLC acidic], 515, (1.51) | 11.15 (s, 1H), 9.34 (s, 1H), 8.84 (s, 1H), 8.24 (s, 1H), 8.04-7.90 (m, 2H), 7.76-7.64 (m, 1H), 7.11 (s, 1H), 4.48 (q, J = 7.0 Hz, 2H), 3.28-3.22 (m, 1H), 2.43 (s, 3H), 1.59 (s, 6H), 1.40 (t, J = 7.0 Hz, 3H), 1.15-1.04 (m, 2H), 1.01-0.91 (m, 2H). |
| P130 | 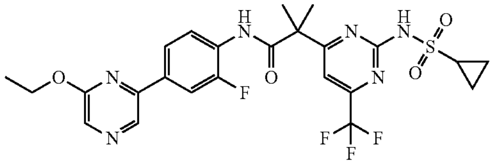 2-(2-(cyclopropanesulfonamido)-6-(trifluoromethyl)pyrimidin-4-yl)-N-(4-(6-ethoxypyrazin-2-yl)-2-fluorophenyl)-2-methylpropanamide | Method 2b using INTC70 and INTD24, [UPLC acidic], 569, (1.7) | 11.87 (s, 1H), 9.39 (s, 1H), 8.84 (s, 1H), 8.25 (s, 1H), 8.04-7.93 (m, 2H), 7.74-7.67 (m, 1H), 7.61 (s, 1H), 4.48 (q, J = 7.0 Hz, 2H), 3.22-3.13 (m, 1H), 1.65 (s, 6H), 1.40 (t, J = 7.0 Hz, 3H), 1.21-1.09 (m, 2H), 1.06-0.96 (m, 2H). |
| P131 | 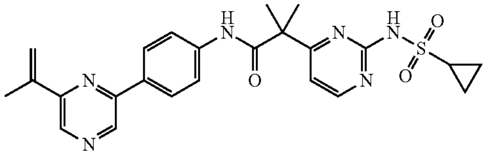 2-(2-(cyclopropanesulfonamido)pyrimidin-4-yl)-2-methyl-N-(4-(6-(prop-1-en-2-yl)pyrazin-2-yl)phenyl)propanamide | Method 2b using INTC21 and INTD52, [HPLC acidic], 479, (2.29) | 11.26 (s, 1H), 9.51 (s, 1H), 9.10 (s, 1H), 8.83 (s, 1H), 8.60 (d, J = 5.3 Hz, 1H), 8.17-8.09 (m, 2H), 7.83-7.74 (m, 2H), 7.19 (d, J = 5.3 Hz, 1H), 6.16-6.12 (m, 1H), 5.51-5.49 (m, 1H), 3.25-3.15 (m, 1H), 2.24 (s, 3H), 1.60 (s, 6H), 1.06-0.97 (m, 2H), 0.84-0.76 (m, 2H). |

TABLE 20-continued

Preparation methods and characterisation data of examples P9-P115, P117-P225

| P | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
|---|---|---|---|
| P132 | 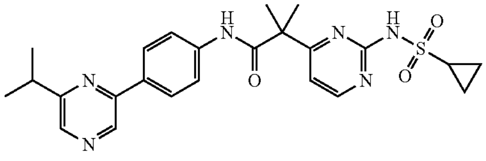 2-(2-(cyclopropanesulfonamido)pyrimidin-4-yl)-N-(4-(6-isopropylpyrazin-2-yl)phenyl)-2-methylpropanamide | Method 2b using INTC21 and INTD62, [HPLC acidic], 481, (2.29) | 11.26 (s, 1H), 9.50 (s, 1H), 9.02 (s, 1H), 8.61 (d, J = 5.3 Hz, 1H), 8.50 (s, 1H), 8.15-8.06 (m, 2H), 7.82-7.74 (m, 2H), 7.20 (d, J = 5.3 Hz, 1H), 3.25-3.11 (m, 2H), 1.60 (s, 6H), 1.33 (d, J = 6.9 Hz, 6H), 1.07-0.99 (m, 2H), 0.86-0.76 (m, 2H). |
| P133 | 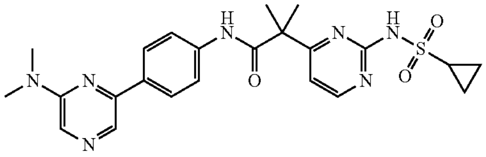 2-(2-(cyclopropanesulfonamido)pyrimidin-4-yl)-N-(4-(6-(dimethylamino)pyrazin-2-yl)phenyl)-2-methylpropanamide | Method 2 using INTC21 and INTD56, [UPLC acidic], 482, (1.28) | 11.25 (s, 1H), 9.45 (s, 1H), 8.60 (d, J = 5.3 Hz, 1H), 8.35 (s, 1H), 8.08-7.99 (m, 3H), 7.77-7.70 (m, 2H), 7.19 (d, J = 5.3 Hz, 1H), 3.25-3.16 (m, 1H), 3.14 (s, 6H), 1.59 (s, 6H), 1.05-0.99 (m, 2H), 0.82-0.76 (m, 2H). |
| P134 | 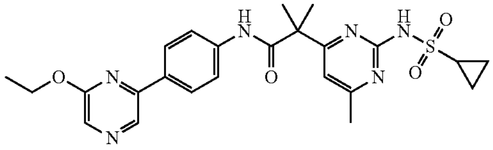 2-(2-(cyclopropanesulfonamido)-6-methylpyrimidin-4-yl)-N-(4-(6-ethoxypyrazin-2-yl)phenyl)-2-methylpropanamide | Method 2b using INTC69 and INTD18, [UPLC acidic], 497, (1.5) | 11.13 (s, 1H), 9.46 (s, 1H), 8.75 (s, 1H), 8.17 (s, 1H), 8.10-8.01 (m, 2H), 7.81-7.72 (m, 2H), 7.10 (s, 1H), 4.47 (q, J = 7.1 Hz, 2H), 3.24-3.16 (m, 1H), 2.42 (s, 3H), 1.58 (s, 6H), 1.39 (t, J = 7.0 Hz, 3H), 1.05-0.96 (m, 2H), 0.82-0.71 (m, 2H). |
| P135 | 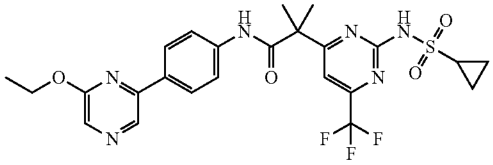 2-(2-(cyclopropanesulfonamido)-6-(trifluoromethyl)pyrimidin-4-yl)-N-(4-(6-ethoxypyrazin-2-yl)phenyl)-2-methylpropanamide | Method 2b using INTC70 and INTD18, [UPLC acidic], 551, (1.7) | 11.85 (s, 1H), 9.49 (s, 1H), 8.75 (s, 1H), 8.17 (s, 1H), 8.11-8.04 (m, 2H), 7.77-7.71 (m, 2H), 7.65 (s, 1H), 4.47 (q, J = 7.0 Hz, 2H), 3.15-3.04 (m, 1H), 1.65 (s, 6H), 1.39 (t, J = 7.0 Hz, 3H), 1.09-1.00 (m, 2H), 0.86-0.74 (m, 2H). |
| P127 | 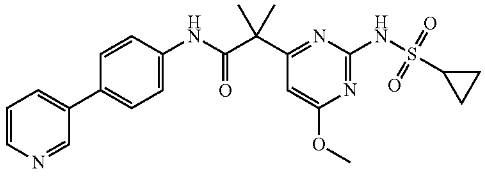 2-(2-(Cyclopropanesulfonamido)-6-methoxypyrimidin-4-yl)-2-methyl-N-(4-(pyridin-3-yl)phenyl)propanamide | Method 2 Using INTC71 and commercial aniline, [UPLC acidic], 468, (0.98) | 11.19 (s, 1H), 9.37 (s, 1H), 8.94-8.82 (m, 1H), 8.58-8.47 (m, 1H), 8.10-7.96 (m, 1H), 7.82-7.61 (m, 4H), 7.52-7.39 (m, 1H), 6.56 (s, 1H), 3.93 (s, 3H), 3.28-3.10 (m, 1H), 1.56 (s, 6H), 1.12-0.94 (m, 2H), 0.90-0.71 (m, 2H). |

TABLE 20-continued

Preparation methods and characterisation data of examples P9-P115, P117-P225

| P | Name/Structure (All examples containing chiral centres are racemates unless stated) | Synthesis Method, [LCMS Method], m/z (M + H)$^+$, (RT/Min) | $^1$H NMR Chemical Shift Data (DMSO-d6 unless stated) |
|---|---|---|---|
| P136 | 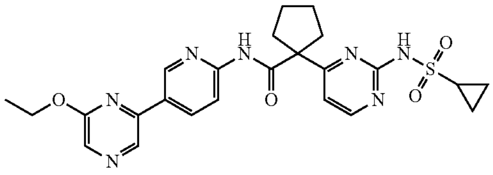 1-(2-(cyclopropanesulfonamido)pyrimidin-4-yl)-N-(5-(6-ethoxypyrazin-2-yl)pyridin-2-yl)cyclopentane-1-carboxamide | Method 2 using INTC29 and INTD33, [HPLC acidic], 510, (2.36) | 11.24 (s, 1H), 10.15 (s, 1H), 9.01 (d, J = 2.5 Hz, 1H), 8.84 (s, 1H), 8.60-8.46 (m, 2H), 8.32-8.15 (m, 2H), 7.15 (s, 1H), 4.48 (q, J = 7.0 Hz, 2H), 2.62-2.42 (m, 3H, oscured by DMSO), 2.28-2.13 (m, 2H), 1.80-1.61 (m, 4H), 1.40 (t, J = 7.0 Hz, 3H), 1.09-1.00 (m, 2H), 0.90-0.79 (m, 2H). |
| P137 | 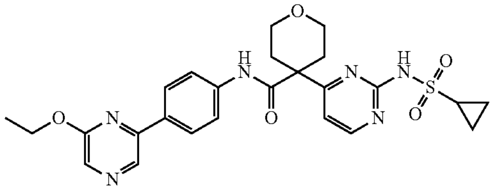 4-(2-(cyclopropanesulfonamido)pyrimidin-4-yl)-N-(4-(6-ethoxypyrazin-2-yl)phenyl) tetrahydro-2H-pyran-4-carboxamide | Method 2 using INTC53 and INTD18, [UPLC acidic], 525, (1.38) | 11.33 (s, 1H), 9.54 (s, 1H), 8.76 (s, 1H), 8.64-8.57 (m, 1H), 8.18 (s, 1H), 8.10-8.05 (m, 2H), 7.76 (d, J = 8.6 Hz, 2H), 7.20 (s, 1H), 4.47 (q, J = 7.0 Hz, 2H), 3.78-3.71 (m, 2H), 3.65-3.57 (m, 2H), 3.28-3.22 (m, 1H), 2.45-2.38 (m, 2H), 2.25-2.16 (m, 2H), 1.39 (t, J = 7.0 Hz, 3H), 1.10-1.04 (m, 2H), 0.95-0.88 (m, 2H). |
| P138 | 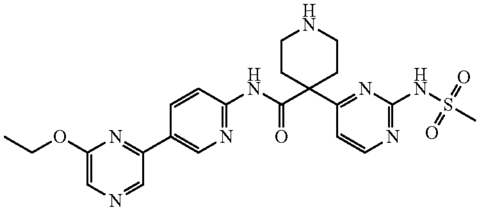 N-(5-(6-ethoxypyrazin-2-yl)pyridin-2-yl)-4-(2-(methylsulfonamido)pyrimidin-4-yl)piperidine-4-carboxamide | Method 2 using INTC76 and INTD33, [UPLC acidic], 499, (0.75) (both Boc-protected and free amine isolated) | 10.35 (s, 1H), 9.04 (d, J = 2.3 Hz, 1H), 8.84 (s, 1H), 8.62 (d, J = 5.3 Hz, 1H), 8.54-8.48 (m, 1H), 8.26 (s, 1H), 8.18 (d, J = 8.8 Hz, 1H), 7.16-7.12 (m, 1H), 4.47 (q, J = 7.1 Hz, 2H), 3.34 (s, 3H), 3.26-3.20 (m, 2H), 3.17-3.09 (m, 2H), 2.61-2.52 (m, 2H), 2.37 (s, 3H), 1.39 (t, J = 7.1 Hz, 3H). 1 × exchangeable NH not observed |
| P139 | 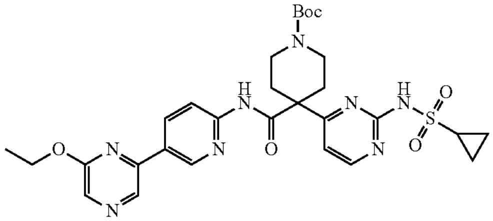 tert-butyl 4-(2-(cyclopropanesulfonamido)pyrimidin-4-yl)-4-((5-(6-ethoxypyrazin-2-yl)pyridin-2-yl)carbamoyl)piperidine-1-carboxylate | Method 2 using INTC77 and INTD33, [UPLC acidic], 625, (1.62) (both Boc-protected and free amine isolated) | 9.00 (d, J = 2.4 Hz, 1H), 8.66 (s, 1H), 8.60 (d, J = 5.3 Hz, 1H), 8.48 (dd, J = 8.7, 2.4 Hz, 1H), 8.39-8.35 (m, 2H), 8.24 (d, J = 8.7 Hz, 1H), 8.14 (s, 1H), 7.24 (d, J = 5.3 Hz, 1H), 4.54 (q, J = 7.0 Hz, 2H), 3.77-3.70 (m, 2H), 3.48-3.44 (m, 2H), 3.32-3.26 (m, 1H), 2.56-2.50 (m, 2H), 2.31-2.23 (m, 2H), 1.51-1.43 (m, 12H), 1.33-1.21 (m, 2H), 1.07-0.99 (m, 2H). |
| P140 | 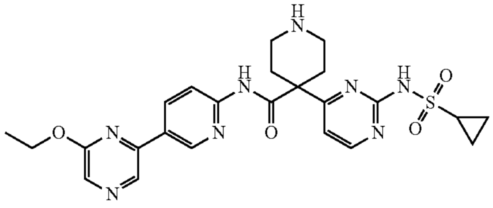 4-(2-(cyclopropanesulfonamido)pyrimidin-4-yl)-N-(5-(6-ethoxypyrazin-2-yl)pyridin-2-yl)piperidine-4-carboxamide | Method 2 using INTC77 and INTD33, followed by Boc deprotection with HCl, [UPLC acidic], 525, (0.86) | 11.38 (s, 1H), 10.37 (s, 1H), 9.03 (dd, J = 2.4, 0.8 Hz, 1H), 8.91-8.76 (m, 2H), 8.65 (d, J = 5.3 Hz, 1H), 8.51 (dd, J = 8.8, 2.4 Hz, 1H), 8.25 (s, 1H), 8.18 (dd, J = 8.8, 0.8 Hz, 1H), 7.21 (d, J = 5.3 Hz, 1H), 4.47 (q, J = 7.0 Hz, 2H), 3.32-3.23 (m, 3H), 3.14-3.08 (m, 2H), 2.67-2.60 (m, 2H), 2.43-2.32 (m, 2H), 1.39 (t, J = 7.0 Hz, 3H), 1.10-1.03 (m, 2H), 0.96-0.87 (m, 2H). |

TABLE 20-continued

| P | Name/Structure (All examples containing chiral centres are racemates unless stated) | Synthesis Method, [LCMS Method], m/z $(M + H)^+$, (RT/Min) | $^1H$ NMR Chemical Shift Data (DMSO-d6 unless stated) |
|---|---|---|---|
| | Preparation methods and characterisation data of examples P9-P115, P117-P225 | | |
| P141 | 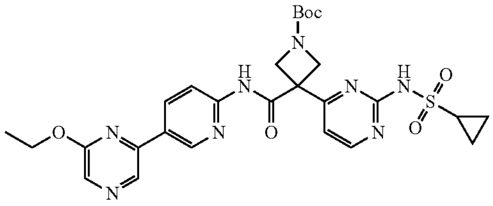 tert-butyl 3-(2-(cyclopropanesulfonamido)pyrimidin-4-yl)-3-((5-(6-ethoxypyrazin-2-yl)pyridin-2-yl)carbamoyl)azetidine-1-carboxylate | Method 2 using INTC72 and INTD33, [UPLC acidic], 597, (1.55) | 11.37 (s, 1H), 10.99 (s, 1H), 9.05 (s, 1H), 8.85 (s, 1H), 8.64 (d, J = 5.2 Hz, 1H), 8.57-8.51 (m, 1H), 8.26 (s, 4H), 7.27 (d, J = 5.2 Hz, 1H), 4.53-4.40 (m, 3H), 4.27 (s, 1H), 3.32-3.15 (m, 1H), 1.42-1.37 (m, 12H), 1.10-1.06 (m, 2H), 0.93-0.88 (m, 2H). |
| P142 | 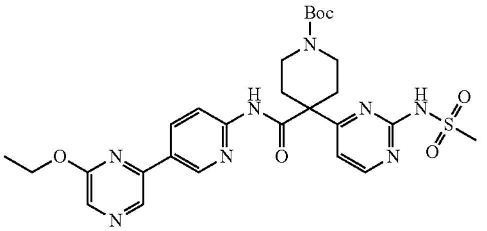 tert-butyl 4-((5-(6-ethoxypyrazin-2-yl)pyridin-2-yl)carbamoyl)-4-(2-(methylsulfonamido)pyrimidin-4-yl)piperidine-1-carboxylate | Method 2 using INTC76 and INTD33, [UPLC acidic], 599, (1.54) (both Boc-protected and free amine isolated) | 11.37 (s, 1H), 10.17 (s, 1H), 9.04 (d, J = 2.3 Hz, 1H), 8.88-8.83 (m, 1H), 8.61 (d, J = 5.2 Hz, 1H), 8.52-8.47 (m, 1H), 8.28-8.24 (m, 1H), 8.19 (d, J = 8.8 Hz, 1H), 7.24-7.20 (m, 1H), 4.48 (q, J = 7.0 Hz, 2H), 3.65-3.58 (m, 2H), 3.35 (s, 3H), 3.30-3.18 (m, 2H), 2.47-2.40 (m, 2H), 2.17-2.09 (m, 2H), 1.45-1.37 (m, 12H). |
| P143 | 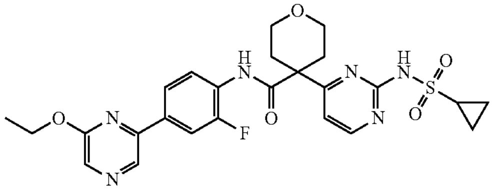 4-(2-(cyclopropanesulfonamido)pyrimidin-4-yl)-N-(4-(6-ethoxypyrazin-2-yl)-2-fluorophenyl)tetrahydro-2H-pyran-4-carboxamide | Method 2 using INTC53 and INTD24, [UPLC acidic], 543, (1.37) | 11.33 (s, 1H), 9.47 (s, 1H), 8.84 (s, 1H), 8.63 (d, J = 5.3 Hz, 1H), 8.25 (s, 1H), 8.03-7.93 (m, 2H), 7.64-7.57 (m, 1H), 7.22 (d, J = 5.3 Hz, 1H), 4.48 (q, J = 7.0 Hz, 2H), 3.79-3.71 (m, 2H), 3.67-3.59 (m, 2H), 3.31-3.27 (m, 1H), 2.44-2.37 (m, 2H), 2.24-2.15 (m, 2H), 1.39 (t, J = 7.0 Hz, 3H), 1.15-1.08 (m, 2H), 1.05-0.98 (m, 2H). |
| P144 | 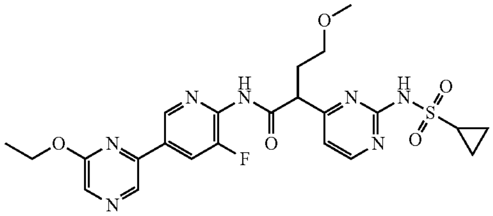 2-(2-(cyclopropanesulfonamido)pyrimidin-4-yl)-N-(5-(6-ethoxypyrazin-2-yl)-3-fluoropyridin-2-yl)-4-methoxybutanamide | Method 7 using INTC88, [UPLC acidic], 532, (1.22) | 11.30 (s, 1H), 10.82 (s, 1H), 9.00 (d, J = 1.9 Hz, 1H), 8.92 (s, 1H), 8.56 (s, 1H), 8.43 (dd, J = 11.0, 1.9 Hz, 1H), 8.32 (s, 1H), 7.17 (s, 1H), 4.50 (q, J = 7.0 Hz, 2H), 4.11 (s, 1H), 3.42-3.36 (m, 2H), 3.35-3.29 (m, 1H), 3.24 (s, 3H), 2.32-2.23 (m, 1H), 2.21-2.11 (m, 1H), 1.40 (t, J = 7.0 Hz, 3H), 1.13-1.09 (m, 2H), 1.03-0.99 (m, 2H). |

TABLE 20-continued

| Preparation methods and characterisation data of examples P9-P115, P117-P225 | | | |
|---|---|---|---|
| P | Name/Structure (All examples containing chiral centres are racemates unless stated) | Synthesis Method, [LCMS Method], m/z $(M + H)^+$, (RT/Min) | $^1H$ NMR Chemical Shift Data (DMSO-d6 unless stated) |
| P145 | 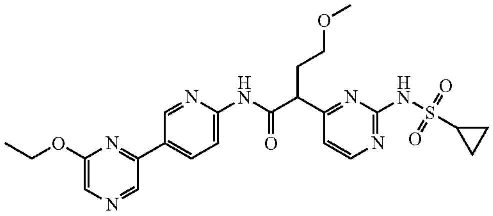 2-(2-(cyclopropanesulfonamido)pyrimidin-4-yl)-N-(5-(6-ethoxypyrazin-2-yl)pyridin-2-yl)-4-methoxybutanamide | Method 7 using INTC89, [UPLC acidic], 514, (1.3) | 11.24 (s, 1H), 11.03 (s, 1H), 9.06 (d, J = 2.4 Hz, 1H), 6.84 (s, 1H), 8.56 (d, J = 5.2 Hz, 1H), 8.49 (dd, J = 8.7, 2.4 Hz, 1H), 8.25 (s, 1H), 8.19 (d, J = 8.7 Hz, 1H), 7.21 (d, J = 5.2 Hz, 1H), 4.48 (q, J = 7.0 Hz, 2H), 4.22 (dd, J = 8.4, 6.1 Hz, 1H), 3.41-3.32 (m, 3H), 3.21 (s, 3H), 2.36-2.25 (m, 1H), 2.20-2.06 (m, 1H), 1.40 (t, J = 7.0 Hz, 3H), 1.16-1.03 (m, 2H), 1.02-0.89 (m, 2H). |
| P146 | 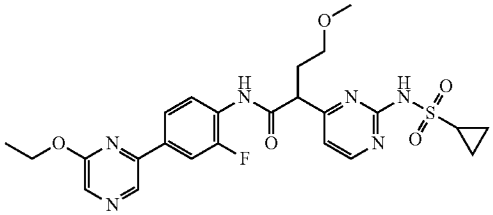 2-(2-(cyclopropanesulfonamido)pyrimidin-4-yl)-N-(4-(6-ethoxypyrazin-2-yl)-2-fluorophenyl)-4-methoxybutanamide | Method 7 using INTC90, [UPLC acidic], 531, (1.38) | 11.25 (s, 1H), 10.24 (s, 1H), 8.83 (s, 1H), 8.56 (d, J = 5.1 Hz, 1H), 8.23 (s, 1H), 8.07-7.98 (m, 2H), 7.99-7.93 (m, 1H), 7.19 (d, J = 5.1 Hz, 1H), 4.48 (q, J = 7.0 Hz, 2H), 4.25-4.18 (m, 1H), 3.43-3.34 (m, 2H), 3.35-3.32 (m, 1H), 3.23 (s, 3H), 2.32-2.23 (m, 1H), 2.21-2.10 (m, 1H), 1.39 (t, J = 7.0 Hz, 3H), 1.13-1.08 (m, 2H), 1.02-0.94 (m, 2H). |
| P147 | 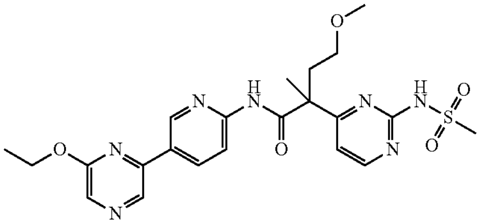 N-(5-(6-ethoxypyrazin-2-yl)pyridin-2-yl)-4-methoxy-2-methyl-2-(2-(methylsulfonamido)pyrimidin-4-yl)butanamide | Method 6 using INTC91, [HPLC acidic], 502, (2.03) | 11.32 (s, 1H), 10.18 (s, 1H), 9.02 (dd, J = 2.5, 0.8 Hz, 1H), 8.84 (s, 1H), 8.59 (d, J = 5.3 Hz, 1H), 8.49 (dd, J = 8.8, 2.5 Hz, 1H), 8.25 (s, 1H), 8.20 (dd, J = 8.8, 0.8 Hz, 1H), 7.16 (d, J = 5.3 Hz, 1H), 4.48 (q, J = 7.1 Hz, 2H), 3.40-3.32 (m, 5H), 3.15 (s, 3H), 2.47-2.39 (m, 1H), 2.33-2.26 (m, 1H), 1.61 (s, 3H), 1.40 (t, J = 7.1 Hz, 3H). |
| P148 | 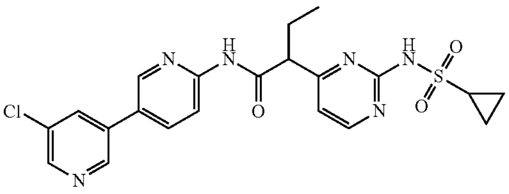 N-(5′-chloro-[3,3′-bipyridin]-6-yl)-2-(2-(cyclopropanesulfonamido)pyrimidin-4-yl)butanamide | Method 3 using INTC37 and INTD57, [HPLC acidic], 473 $^{35}Cl$ isotope, (2.02) | 11.23 (s, 1H), 11.01 (s, 1H), 8.93 (d, J = 2.0 Hz, 1H), 8.81-8.79 (m, 1H), 8.36-8.34 (m, 1H), 8.56 (d, J = 5.2 Hz, 1H), 8.35 (t, J = 2.2 Hz, 1H), 8.27-8.23 (m, 1H), 8.19 (d, J = 8.7 Hz, 1H), 7.21 (d, J = 5.2 Hz, 1H), 4.07-3.97 (m, 1H), 3.32-3.28 (m, 1H), 2.13-2.02 (m, 1H), 1.99-1.89 (m, 1H), 1.15-1.05 (m, 2H), 1.01-0.90 (m, 5H). |

TABLE 20-continued

Preparation methods and characterisation data of examples P9-P115, P117-P225

| P | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
|---|---|---|---|
| P149 | 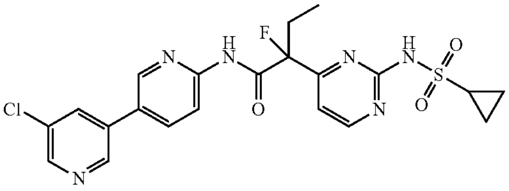 N-(5'-chloro-[3,3'-bipyridin]-6-yl)-2-(2-(cyclopropanesulfonamido)pyrimidin-4-yl)-2-fluorobutanamide | Method 6 using INTC92 [HPLC acidic], 491 $^{35}$Cl isotope, (2.14) | 11.50 (s, 1H), 10.58 (d, J = 2.0 Hz, 1H), 8.94 (d, J = 2.0 Hz, 1H), 8.85-8.82 (m, 1H), 8.76 (d, J = 5.2 Hz, 1H), 8.66 (d, J = 2.3 Hz, 1H), 8.38-8.36 (m, 1H), 8.29 (dd, J = 8.7, 2.6 Hz, 1H), 8.07 (d, J = 8.7 Hz, 1H), 7.49-7.45 (m, 1H), 3.50-3.25 (m, 1H), 2.48-2.43 (m, 1H), 2.39-2.38 (m, 1H), 1.20-1.14 (m, 1H), 1.12-1.02 (m, 2H), 1.00-0.90 (m, 4H). |
| P150 | 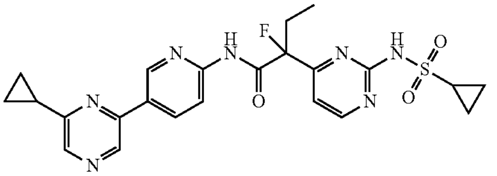 2-(2-(cyclopropanesulfonamido)pyrimidin-4-yl)-N-(5-(6-cyclopropylpyrazin-2-yl)pyridin-2-yl)-2-fluorobutanamide | Method 6 using INTC176, [HPLC acidic], 498, (2.27) | 11.50 (s, 1H), 10.59 (d, J = 2.3 Hz, 1H), 9.06 (d, J = 2.4 Hz, 1H), 9.03 (s, 1H), 8.76 (d, J = 5.2 Hz, 1H), 8.60 (s, 1H), 8.50 (dd, J = 8.7, 2.4 Hz, 1H), 8.09 (d, J = 8.7 Hz, 1H), 7.48 (dd, J = 5.2, 1.2 Hz, 1H), 3.26-3.32 (m, 1H), 2.49-2.44 (m, 1H), 2.40-2.24 (m, 2H), 1.19-1.13 (m, 1H), 1.13-1.01 (m, 6H), 1.00-0.90 (m, 4H). |
| P151 | 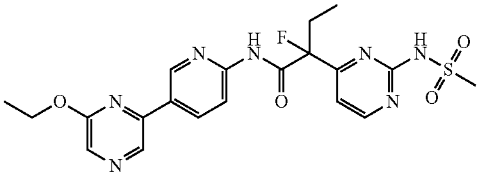 N-(5-(6-ethoxypyrazin-2-yl)pyridin-2-yl)-2-fluoro-2-(2-(methylsulfonamido)pyrimidin-4-yl)butanamide | Method 2 using INTC74 and INTD33, [UPLC acidic], 476, (1.38) | 11.56 (s, 1H), 10.61 (s, 1H), 9.10 (d, J = 2.5 Hz, 1H), 8.86 (s, 1H), 8.77-8.72 (m, 1H), 8.52 (dd, J = 8.7, 2.5 Hz, 1H), 8.26 (s, 1H), 8.10 (d, J = 8.7 Hz, 1H), 7.47-7.43 (m, 1H), 4.48 (q, J = 7.0 Hz, 2H), 3.31 (s, 3H), 2.51-2.42 (m, 1H), 2.36-2.26 (m, 1H), 1.39 (t, J = 7.0 Hz, 3H), 0.92 (t, J = 7.3 Hz, 3H). |
| P155 | 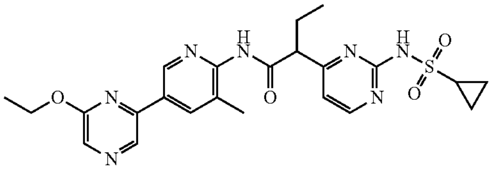 2-(2-(cyclopropanesulfonamido)pyrimidin-4-yl)-N-(5-(6-ethoxypyrazin-2-yl)-3-methylpyridin-2-yl)butanamide | Method 3 using INTC37 and INTD58, [UPLC acidic], 498, (1.22) | 11.25 (s, 1H), 10.51 (s, 1H), 8.96 (d, J = 2.2 Hz, 1H), 8.86 (s, 1H), 8.58 (d, J = 5.2 Hz, 1H), 8.35 (d, J = 2.2 Hz, 1H), 8.28 (s, 1H), 7.21 (d, J = 5.2 Hz, 1H), 4.49 (q, J = 7.0 Hz, 2H), 3.90-3.85 (m, 1H), 3.41-3.34 (m, 1H), 2.18 (s, 3H), 2.14-2.05 (m, 1H), 2.00-1.90 (m, 1H), 1.41 (t, J = 7.0 Hz, 3H), 1.18-1.10 (m, 2H), 1.07-1.01 (m, 2H), 0.98 (t, J = 7.3 Hz, 3H). |
| P156 | 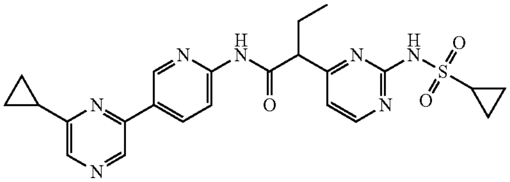 2-(2-(cyclopropanesulfonamido)pyrimidin-4-yl)-N-(5-(6-cyclopropylpyrazin-2-yl)pyridin-2-yl)butanamide | Method 3 using INTC37 and INTD54, [UPLC acidic], 480, (1.36) | 11.22 (s, 1H), 11.03 (s, 1H), 9.02 (d, J = 2.4 Hz, 1H), 9.00 (s, 1H), 8.58 (s, 1H), 8.55 (d, J = 5.2 Hz, 1H), 8.45 (dd, J = 8.7, 2.4 Hz, 1H), 8.19 (d, J = 8.7 Hz, 1H), 7.20 (d, J = 5.2 Hz, 1H), 4.00 (dd, J = 8.6, 6.4 Hz, 1H), 3.31-3.26 (m, 1H), 2.30-2.22 (m, 1H), 2.13-2.00 (m, 1H), 1.94 (dq, J = 13.7, 6.9 Hz, 1H), 1.13-1.04 (m, 6H), 1.00-0.88 (m, 5H) |

TABLE 20-continued

Preparation methods and characterisation data of examples P9-P115, P117-P225

| P | Name/Structure (All examples containing chiral centres are racemates unless stated) | Synthesis Method, [LCMS Method], m/z $(M + H)^+$, (RT/Min) | $^1H$ NMR Chemical Shift Data (DMSO-d6 unless stated) |
|---|---|---|---|
| P157 | 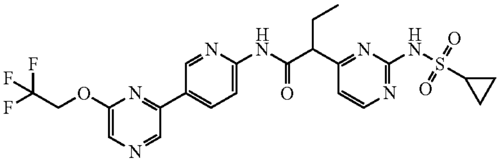 2-(2-(cyclopropanesulfonamido)pyrimidin-4-yl)-N-(5-(6-(2,2,2-trifluoroethoxy) pyrazin-2-yl)pyridin-2-yl)butanamide | Method 3 using INTC37 and INTD59, [UPLC acidic], 538, (1.44) | 11.23 (s, 1H), 11.07 (s, 1H), 9.15 (d, J = 2.4 Hz, 1H), 9.01 (s, 1H), 8.62-8.54 (m, 2H), 8.45 (s, 1H), 8.23 (d, J = 8.8 Hz, 1H), 7.22 (d, J = 5.2 Hz, 1H), 5.23 (d, J = 9.0 Hz, 1H), 5.20 (d, J = 9.1 Hz, 1H), 4.02 (dd, J = 8.5, 6.4 Hz, 1H), 2.12-2.02 (m, 1H), 1.99-1.90 (m, 1H), 1.14-1.06 (m, 2H), 1.01-0.90 (m, 5H). 1H obscured by $H_2O$ |
| P158 | 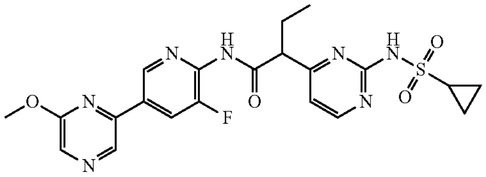 2-(2-(cyclopropanesulfonamido)pyrimidin-4-yl)-N-(3-fluoro-5-(6-methoxypyrazin-2-yl)pyridin-2-yl)butanamide | Method 9 using INTC94 and INTD63, [UPLC acidic], 488, (1.17) | 11.26 (s, 1H), 10.80 (s, 1H), 9.03 (d, J = 1.9 Hz, 1H), 8.95 (s, 1H), 8.59 (d, J = 5.2 Hz, 1H), 8.46 (dd, J = 11.0, 1.9 Hz, 1H), 8.36 (s, 1H), 7.22-7.18 (m, 1H), 4.04 (s, 3H), 3.93-3.86 (m, 1H), 2.13-2.01 (m, 1H), 2.00-1.90 (m, 1H), 1.15-1.11 (m, 2H), 1.07-1.01 (m, 2H), 0.97 (t, 3H). 1H obscured by $H_2O$ |
| P159 | 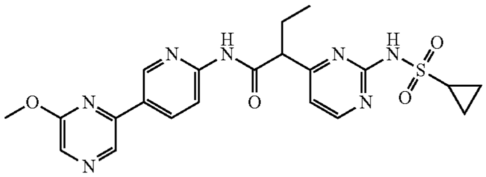 2-(2-(cyclopropanesulfonamido)pyrimidin-4-yl)-N-(5-(6-methoxypyrazin-2-yl)pyridin-2-yl)butanamide | Method 9 using INTC95 and INTD63, [UPLC acidic], 470, (1.25) | 11.23 (s, 1H), 11.06 (s, 1H), 9.10 (d, J = 2.6 Hz, 1H), 8.87 (s, 1H), 8.60-8.50 (m, 2H), 8.29 (s, 1H), 8.22 (d, J = 8.8 Hz, 1H), 7.21 (d, J = 5.2 Hz, 1H), 4.03 (s, 3H), 4.03-3.99 (m, 1H), 3.32-3.28 (m, 1H), 2.13-2.03 (m, 1H), 2.00-1.91 (m, 1H), 1.14-1.07 (m, 2H), 0.93 (t, J = 7.3 Hz, 5H). |
| P160 | 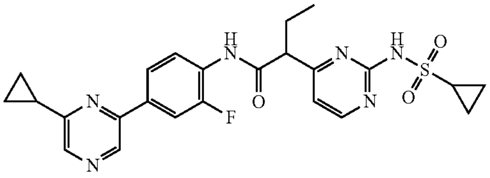 2-(2-(cyclopropanesulfonamido)pyrimidin-4-yl)-N-(4-(6-cyclopropylpyrazin-2-yl)-2-fluorophenyl)butanamide | Method 3 using INTC37 and INTD55, [UPLC acidic], 497, (1.43) | 11.23 (s, 1H), 10.21 (s, 1H), 8.99 (s, 1H), 8.59-8.53 (m, 2H), 8.07-7.99 (m, 1H), 7.97 (dd, J = 12.2, 2.0 Hz, 1H), 7.92 (dd, J = 8.5, 2.0 Hz, 1H), 7.19 (d, J = 5.2 Hz, 1H), 3.98 (dd, J = 8.6, 6.3 Hz, 1H), 3.32-3.26 (m, 1H), 2.29-2.20 (m, 1H), 2.10-2.00 (m, 1H), 2.00-1.88 (m, 1H), 1.13-1.05 (m, 6H), 1.03-0.91 (m, 5H). |
| P161 | 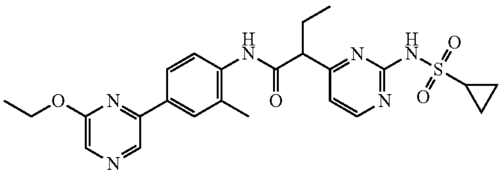 2-(2-(cyclopropanesulfonamido)pyrimidin-4-yl)-N-(4-(6-ethoxypyrazin-2-yl)-2-methylphenyl)butanamide | Method 3 using INTC37 and INTD27, [UPLC acidic], 497, (1.4) | 11.26 (s, 1H), 9.73 (s, 1H), 8.78 (s, 1H), 8.58 (d, J = 5.2 Hz, 1H), 8.21 (s, 1H), 7.99 (d, J = 2.2 Hz, 1H), 7.92 (dd, J = 8.3, 2.2 Hz, 1H), 7.56 (d, J = 8.3 Hz, 1H), 7.23 (d, J = 5.2 Hz, 1H), 4.48 (q, J = 7.0 Hz, 2H), 3.87 (dd, J = 8.7, 6.4 Hz, 1H), 2.27 (s, 3H), 2.13-2.04 (m, 1H), 2.00-1.92 (m, 1H), 1.40 (t, J = 7.1 Hz, 3H), 1.17-1.09 (m, 2H), 1.06-0.94 (m, 5H). 1H obscured by $H_2O$ |

TABLE 20-continued

Preparation methods and characterisation data of examples P9-P115, P117-P225

| P | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
|---|---|---|---|
| P162 | 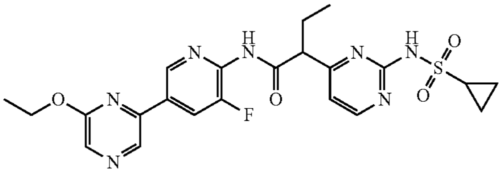 2-(2-(cyclopropanesulfonamido)pyrimidin-4-yl)-N-(5-(6-ethoxypyrazin-2-yl)-3-fluoropyridin-2-yl)butanamide | Method 3 using INTC37 and INTD31, [UPLC acidic], 502, (1.27) | 11.27 (s, 1H), 10.80 (s, 1H), 9.04-8.98 (m, 1H), 8.92 (s, 1H), 8.59 (d, J = 5.2 Hz, 1H), 8.43 (dd, J = 11.1, 1.9 Hz, 1H), 8.32 (s, 1H), 7.20 (d, J = 5.2 Hz, 1H), 4.50 (q, J = 7.0 Hz, 2H), 3.90 (dd, J = 8.7, 6.4 Hz, 1H), 3.38-3.34 (m, 1H), 2.13-2.03 (m, 1H), 2.01-1.89 (m, 1H), 1.41 (t, J = 7.0 Hz, 3H), 1.19-1.09 (m, 2H), 1.08-1.00 (m, 2H), 0.97 (t, J = 7.3 Hz, 3H). |
| P163 | 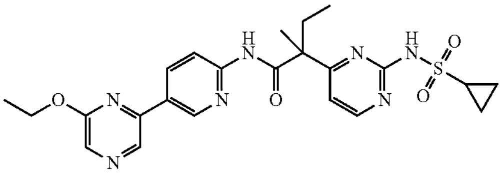 2-(2-(cyclopropanesulfonamido)pyrimidin-4-yl)-N-(5-(6-ethoxypyrazin-2-yl)pyridin-2-yl)-2-methylbutanamide | Method 6 using INTC93, [HPLC acidic], 498, (2.30) | 11.22 (s, 1H), 10.11 (s, 1H), 9.01 (dd, J = 2.5, 0.8 Hz, 1H), 8.84 (s, 1H), 8.59 (d, J = 5.3 Hz, 1H), 8.49 (dd, J = 8.8, 2.5 Hz, 1H), 8.25 (s, 1H), 8.21 (dd, J = 8.8, 0.8 Hz, 1H), 7.17 (d, J = 5.3 Hz, 1H), 4.48 (q, J = 7.0 Hz, 2H), 3.23-3.15 (m, 1H), 2.27-2.17 (m, 1H), 2.07-2.00 (m, 1H), 1.55 (s, 3H), 1.40 (t, J = 7.1 Hz, 3H), 1.06-0.96 (m, 2H), 0.83 (t, J = 7.4 Hz, 3H), 0.80-0.74 (m, 2H). |
| P152 | 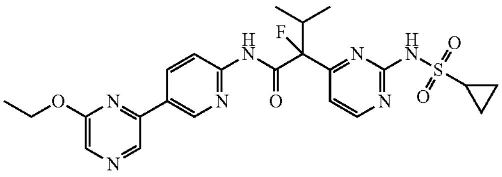 2-(2-(cyclopropanesulfonamido)pyrimidin-4-yl)-N-(5-(6-ethoxypyrazin-2-yl)pyridin-2-yl)-2-fluoro-3-methylbutanamide | Method 6 using INTC96, [UPLC acidic], 516, (1.53) | 11.53 (s, 1H), 10.50 (d, J = 2.5 Hz, 1H), 9.10 (d, J = 2.4 Hz, 1H), 8.86 (s, 1H), 8.75 (d, J = 5.2 Hz, 1H), 8.52 (dd, J = 8.7, 2.4 Hz, 1H), 8.27 (s, 1H), 8.08 (d, J = 8.7 Hz, 1H), 7.52-7.39 (m, 1H), 4.48 (q, J = 7.1 Hz, 2H), 3.44-3.36 (m, 1H), 3.15-2.96 (m, 1H), 1.40 (t, J = 7.1 Hz, 3H), 1.27-0.96 (m, 7H), 0.79 (d, J = 6.9 Hz, 3H). |
| P153 | 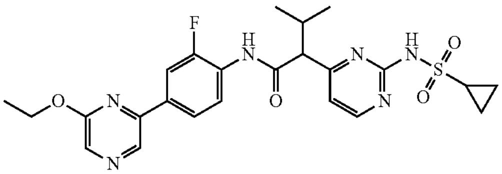 2-(2-(cyclopropanesulfonamido)pyrimidin-4-yl)-N-(4-(6-ethoxypyrazin-2-yl)-2-fluorophenyl)-3-methylbutanamide | Method 6 using INTC97, [HPLC acidic], 515, (2.38) | 11.25 (s, 1H), 10.21 (s, 1H), 8.83 (d, J = 0.6 Hz, 1H), 8.58 (d, J = 5.2 Hz, 1H), 8.24 (s, 1H), 8.04-7.93 (m, 3H), 7.28 (d, J = 5.2 Hz, 1H), 4.48 (q, J = 7.0 Hz, 2H), 3.74 (d, J = 10.2 Hz, 1H), 3.39-3.30 (m, 1H), 2.54-2.47 (m, 1H), 1.40 (t, J = 7.0 Hz, 3H), 1.21-0.92 (m, 7H), 0.81 (d, J = 6.6 Hz, 3H). |
| P154 | 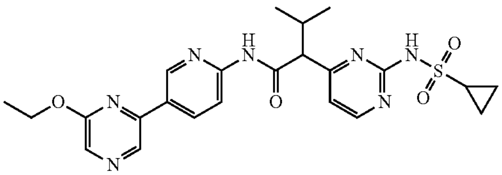 2-(2-(cyclopropanesulfonamido)pyrimidin-4-yl)-N-(5-(6-ethoxypyrazin-2-yl)pyridin-2-yl)-3-methylbutanamide | Method 6 using INTC98, [HPLC acidic], 498, (2.30) | 11.24 (s, 1H), 11.04 (s, 1H), 9.07 (dd, J = 2.4, 0.8 Hz, 1H), 8.84 (s, 1H), 8.57 (d, J = 5.2 Hz, 1H), 8.49 (dd, J = 8.8, 2.4 Hz, 1H), 8.25 (s, 1H), 8.19 (d, J = 8.8 Hz, 1H), 7.28 (d, J = 5.2 Hz, 1H), 4.48 (q, J = 7.0 Hz, 2H), 3.78 (d, J = 10.2 Hz, 1H), 3.42-3.25 (m, 1H), 2.57-2.44 (m, 1H), 1.40 (t, J = 7.0 Hz, 3H), 1.22-0.94 (m, 7H), 0.79 (d, J = 6.6 Hz, 3H). |

TABLE 20-continued

| P | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
|---|---|---|---|
| | Preparation methods and characterisation data of examples P9-P115, P117-P225 | | |
| P164 | 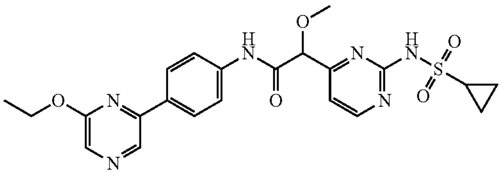 2-(2-(cyclopropanesulfonamido)pyrimidin-4-yl)-N-(4-(6-ethoxypyrazin-2-yl)phenyl)-2-methoxyacetamide | Method 4 using INTC99 and INTD18, [HPLC acidic], 485, (2.05) | 11.38 (s, 1H), 10.45 (s, 1H), 8.78 (s, 1H), 8.66 (d, J = 5.1 Hz, 1H), 8.19 (s, 1H), 8.13-8.09 (m, 2H), 7.85-7.81 (m, 2H), 7.27 (d, J = 5.1 Hz, 1H), 4.98 (s, 1H), 4.54-4.43 (m, 2H), 3.48 (s, 3H), 3.28-3.19 (m, 1H), 1.40 (t, J = 7.0 Hz, 3H), 1.13-0.95 (m, 2H), 0.89-0.78 (m, 2H). |
| P165 | 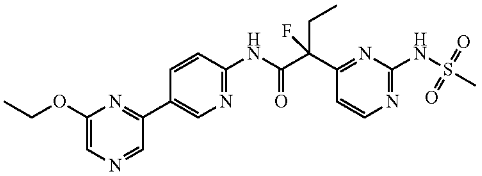 Single enantiomer-stereochemistry unassigned N-(5-(6-ethoxypyrazin-2-yl)pyridin-2-yl)-2-fluoro-2-(2-(methylsulfonamido) pyrimidin-4-yl)butanamide | Method 2 using INTC74 and INTD33, Chiral IC6 (14.67), [UPLC acidic], 476, (1.36) | 11.55 (s, 1H), 10.60 (s, 1H), 9.10 (d, J = 2.4 Hz, 1H), 8.85 (s, 1H), 8.76-8.71 (m, 1H), 8.52 (dd, J = 8.7, 2.4 Hz, 1H), 8.26 (s, 1H), 8.10 (d, J = 8.7 Hz, 1H), 7.47-7.43 (m, 1H), 4.47 (q, J = 7.0 Hz, 2H), 3.39 (s, 3H), 2.48-2.29 (m, 2H), 1.39 (t, J = 7.0 Hz, 3H), 0.92 (t, J = 7.3 Hz, 3H). |
| P166 | 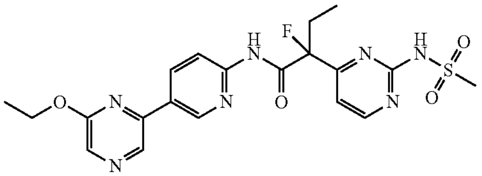 Single enantiomer-stereochemistry unassigned N-(5-(6-ethoxypyrazin-2-yl)pyridin-2-yl)-2-fluoro-2-(2-(methylsulfonamido) pyrimidin-4-yl)butanamide | Method 2 using INTC74 and INTD33, Chiral IC6 (17.03), [UPLC acidic], 476, (1.36) | 11.56 (s, 1H), 10.62 (s, 1H), 9.11 (d, J = 2.4 Hz, 1H), 8.87 (s, 1H), 8.77-8.72 (m, 1H), 8.53 (dd, J = 8.7, 2.4 Hz, 1H), 8.27 (s, 1H), 8.11 (d, J = 8.7 Hz, 1H), 7.46-7.42 (m, 1H), 4.49 (q, J = 7.0 Hz, 2H), 3.38 (s, 3H), 2.44-2.27 (m, 2H), 1.40 (t, J = 7.0 Hz, 3H), 0.93 (t, J = 7.3 Hz, 3H). |
| P167 | 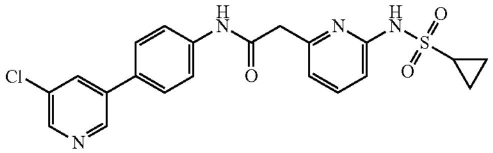 N-(4-(5-chloropyridin-3-yl)phenyl)-2-(6-(cyclopropanesulfonamido)pyridin-2-yl)acetamide | Method 1 using INTC110 and INTD8, [UPLC acidic], 443 35Cl isotope, (1.26) | 10.62 (s, 1H), 10.38 (s, 1H), 8.87 (d, J = 2.0 Hz, 1H), 8.58 (d, J = 2.3 Hz, 1H), 8.26-8.20 (m, 1H), 7.82-7.66 (m, 5H), 7.03 (d, J = 7.4 Hz, 1H), 6.91 (d, J = 8.3 Hz, 1H), 3.82 (s, 2H), 3.13-3.08 (m, 1H), 1.08-0.99 (m, 2H), 0.92-0.80 (m, 2H). |
| P168 | 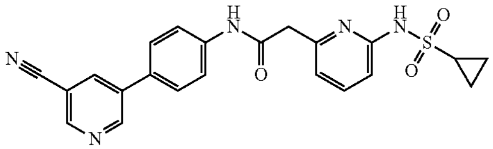 N-(4-(5-cyanopyridin-3-yl)phenyl)-2-(6-(cyclopropanesulfonamido)pyridin-2-yl)acetamide | Method 1 using INTC110 and INTD5, [UPLC acidic], 434, (1.14) | 10.75 (s, 1H), 10.38 (s, 1H), 9.19 (d, J = 2.3 Hz, 1H), 8.97 (d, J = 1.9 Hz, 1H), 8.69-8.57 (m, 1H), 7.88-7.62 (m, 5H), 7.02 (d, J = 7.5 Hz, 1H), 6.91 (d, J = 8.3 Hz, 1H), 3.82 (s, 2H), 3.18-3.00 (m, 1H), 1.11-0.94 (m, 2H), 0.93-0.75 (m, 2H). |

TABLE 20-continued

Preparation methods and characterisation data of examples P9-P115, P117-P225

| P | Name/Structure (All examples containing chiral centres are racemates unless stated) | Synthesis Method, [LCMS Method], m/z $(M + H)^+$, (RT/Min) | $^1$H NMR Chemical Shift Data (DMSO-d6 unless stated) |
|---|---|---|---|
| P169 | 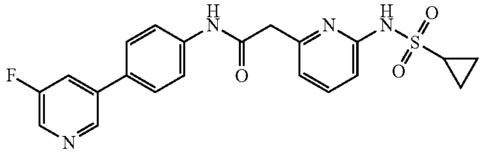 2-(6-(cyclopropanesulfonamido)pyridin-2-yl)-N-(4-(5-fluoropyridin-3-yl)phenyl)acetamide | Method 1 using INTC110 and INTD6, [UPLC acidic], 427, (1.16) | 10.75 (s, 1H), 10.37 (s, 1H), 8.87-8.66 (m, 1H), 8.54 (d, J = 2.8 Hz, 1H), 8.14-7.95 (m, 1H), 7.85-7.58 (m, 5H), 7.01 (d, J = 7.4 Hz, 1H), 6.91 (d, J = 8.3 Hz, 1H), 3.82 (s, 2H), 3.14-3.01 (m, 1H), 1.07-0.95 (m, 2H), 0.93-0.79 (m, 2H). |
| P170 | 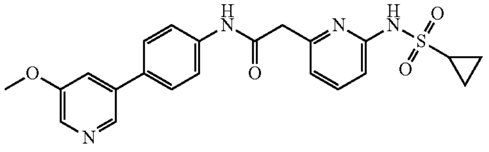 2-(6-(cyclopropanesulfonamido)pyridin-2-yl)-N-(4-(5-methoxypyridin-3-yl)phenyl)acetamide | Method 1 using INTC110 and INTD45, [UPLC acidic], 439, (0.88) | 10.35 (s, 1H), 8.48 (d, J = 1.8 Hz, 1H), 8.25 (d, J = 2.7 Hz, 1H), 7.79-7.65 (m, 6H), 7.60 (dd, J = 2.7, 1.8 Hz, 1H), 7.01 (d, J = 7.4 Hz, 1H), 6.91 (d, J = 8.1 Hz, 1H), 3.91 (s, 3H), 3.81 (s, 2H), 3.20-3.00 (m, 1H), 1.08-0.96 (m, 2H), 0.92-0.80 (m, 2H). |
| P171 | 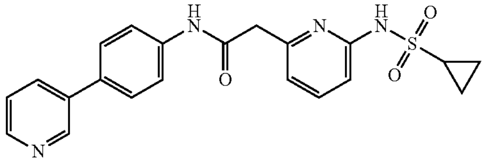 2-(6-(cyclopropanesulfonamido)pyridin-2-yl)-N-(4-(pyridin-3-yl)phenyl)acetamide | Method 1 using INTC110 and commercial aniline, [UPLC acidic], 409, (0.7) | 10.72 (s, 1H), 10.33 (s, 1H), 8.96-8.79 (m, 1H), 8.54 (dd, J = 4.8, 1.6 Hz, 1H), 8.12-7.97 (m, 1H), 7.83-7.60 (m, 5H), 7.51-7.38 (m, 1H), 7.01 (d, J = 7.4 Hz, 1H), 6.91 (d, J = 8.2 Hz, 1H), 3.82 (s, 2H), 3.09 (s, 1H), 1.09-0.97 (m, 2H), 0.92-0.79 (m, 2H). |
| P172 | 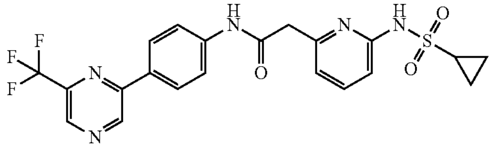 2-(6-(cyclopropanesulfonamido)pyridin-2-yl)-N-(4-(6-(trifluoromethyl)pyrazin-2-yl)phenyl)acetamide | Method 10 using INTC110 and INTD19, [UPLC acidic], 478, (1.4) | 10.51 (d, J = 20.2 Hz, 2H), 9.58 (s, 1H), 9.08 (s, 1H), 8.26-8.13 (m, 2H), 7.88-7.78 (m, 2H), 7.71 (dd, J = 8.3, 7.5 Hz, 1H), 7.07 (d, J = 7.3 Hz, 1H), 6.90 (d, J = 8.3 Hz, 1H), 3.84 (s, 2H), 3.20 3.08 (m, 1H), 1.08-1.01 (m, 2H), 0.94-0.82 (m, 2H). |
| P173 | 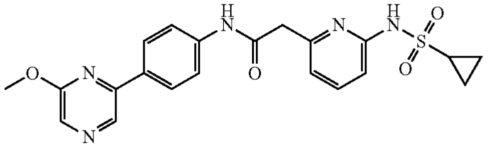 2-(6-(cyclopropanesulfonamido)pyridin-2-yl)-N-(4-(6-methoxypyrazin-2-yl)phenyl)acetamide | Method 10 using INTC110 and INTD1, [UPLC acidic], 440, (1.25) | 10.54 (s, 1H), 10.40 (s, 1H), 8.79 (s, 1H), 8.22 (s, 1H), 8.20-8.09 (m, 2H), 7.85-7.68 (m, 3H), 7.07 (d, J = 7.6 Hz, 1H), 6.89 (d, J = 8.3 Hz, 1H), 4.02 (s, 3H), 3.83 (s, 2H), 3.22-3.07 (m, 1H), 1.04 (s, 2H), 0.96-0.75 (m, 2H). |
| P174 | 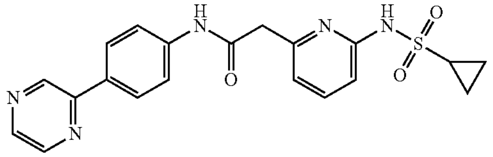 2-(6-(cyclopropanesulfonamido)pyridin-2-yl)-N-(4-(pyrazin-2-yl)phenyl) acetamide | Method 10 using INTC110 and commercial aniline, [HPLC acidic], 410, (1.64) | 10.54 (s, 1H), 10.40 (s, 1H), 9.22 (d, J = 1.6 Hz, 1H), 8.68 (dd, J = 2.5, 1.6 Hz, 1H), 8.56 (d, J = 2.5 Hz, 1H), 8.18-8.07 (m, 2H), 7.84-7.64 (m, 3H), 7.07 (d, J = 7.4 Hz, 1H), 6.90 (d, J = 8.1 Hz, 1H), 3.83 (s, 2H), 3.15 (s, 1H), 1.03 (s, 2H), 0.93-0.79 (m, 2H). |

TABLE 20-continued

Preparation methods and characterisation data of examples P9-P115, P117-P225

| P | Name/Structure (All examples containing chiral centres are racemates unless stated) | Synthesis Method, [LCMS Method], m/z $(M + H)^+$, (RT/Min) | $^1$H NMR Chemical Shift Data (DMSO-d6 unless stated) |
|---|---|---|---|
| P175 | 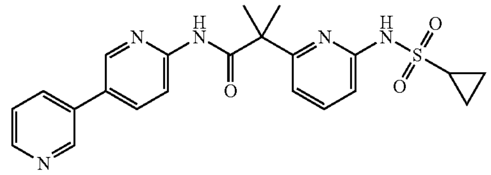 N-([3,3′-bipyridin]-6-yl)-2-(6-(cyclopropanesulfonamido)pyridin-2-yl)-2-methylpropanamide | Method 2 using INTC106 and commercial aniline, [UPLC acidic], 438, (1.52) | 10.63 (s, 1H), 9.68 (s, 1H), 8.96-8.90 (m, 1H), 8.68-8.62 (m, 1H), 8.61-8.55 (m, 1H), 8.19-8.09 (m, 3H), 7.79-7.69 (m, 1H), 7.54-7.46 (m, 1H), 7.17-7.10 (m, 1H), 6.87-6.79 (m, 1H), 3.17-3.08 (m, 1H), 1.62 (s, 6H), 1.02-0.93 (m, 2H), 0.76-0.67 (m, 2H). |
| P176 | 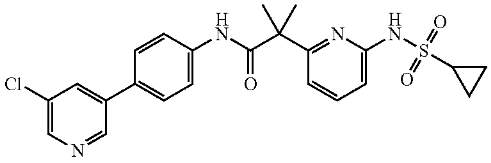 N-(4-(5-chloropyridin-3-yl)phenyl)-2-(6-(cyclopropanesulfonamido)pyridin-2-yl)-2-methylpropanamide | Method 8 using INTC109 and INTD8, [HPLC basic], 471 35Cl isotope, (2.2) | 10.61 (s, 1H), 9.40 (s, 1H), 8.87 (d, J = 2.0 Hz, 1H), 8.58 (d, J = 2.3 Hz, 1H), 8.23-8.21 (m, 1H), 7.82-7.71 (m, 5H), 7.13 (d, J = 7.6 Hz, 1H), 6.82 (d, J = 8.1 Hz, 1H), 3.23-3.11 (m, 1H), 1.62 (s, 6H), 1.06-0.96 (m, 2H), 0.83-0.73 (m, 2H). |
| P177 | 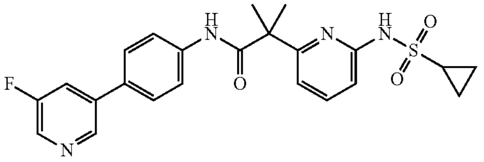 2-(6-(cyclopropanesulfonamido)pyridin-2-yl)-N-(4-(5-fluoropyridin-3-yl)phenyl)-2-methylpropanamide | Method 2 using INTC106 and INTD6, [HPLC acidic], 455, (2.15) | 10.61 (s, 1H), 9.39 (s, 1H), 8.84-8.74 (m, 1H), 8.59-8.45 (m, 1H), 8.09-7.97 (m, 1H), 7.83-7.68 (m, 5H), 7.18-7.06 (m, 1H), 6.87-6.74 (m, 1H), 3.21-3.04 (m, 1H), 1.61 (s, 6H), 1.07-0.92 (m, 2H), 0.84-0.68 (m, 2H). |
| P178 | 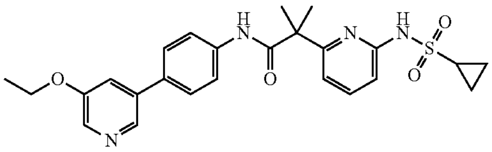 2-(6-(cyclopropanesulfonamido)pyridin-2-yl)-N-(4-(5-ethoxypyridin-3-yl)phenyl)-2-methylpropanamide | Method 2 using INTC106 and INTD4, [HPLC acidic], 481, (1.83) | 10.61 (s, 1H), 9.37 (s, 1H), 8.52-8.37 (m, 1H), 8.30-8.16 (m, 1H), 7.78-7.65 (m, 5H), 7.59-7.55 (m, 1H), 7.15-7.07 (m, 1H), 6.84-6.78 (m, 1H), 4.24-4.14 (m, 2H), 3.22-3.08 (m, 1H), 1.61 (s, 6H), 1.43-1.32 (m, 3H), 1.05-0.95 (m, 2H), 0.84-0.71 (m, 2H). |
| P179 | 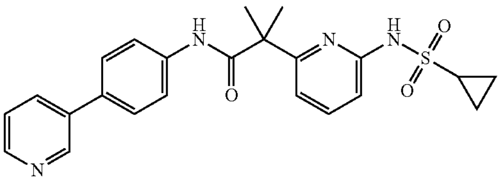 2-(6-(cyclopropanesulfonamido)pyridin-2-yl)-2-methyl-N-(4-(pyridin-3-yl)phenyl)propanamide | Method 2 using INTC106 and commercial aniline, [UPLC acidic], 437, (0.92) | 10.62 (s, 1H), 9.36 (s, 1H), 8.92-8.81 (m, 1H), 8.53 (dd, J = 4.7, 1.6 Hz, 1H), 8.09-8.00 (m, 1H), 7.81-7.61 (m, 5H), 7.51-7.39 (m, 1H), 7.12 (d, J = 7.6 Hz, 1H), 6.82 (d, J = 8.0 Hz, 1H), 3.22-3.10 (m, 1H), 1.61 (s, 6H), 1.06-0.93 (m, 2H), 0.84-0.70 (m, 2H). |

TABLE 20-continued

| Preparation methods and characterisation data of examples P9-P115, P117-P225 | | | |
|---|---|---|---|
| P | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
| P180 | 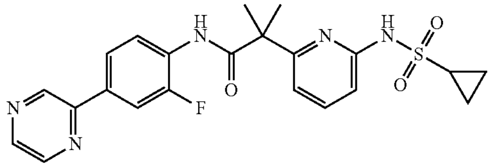 2-(6-(cyclopropanesulfonamido)pyridin-2-yl)-N-(2-fluoro-4-(pyrazin-2-yl)phenyl)-2-methylpropanamide | Method 8 using INTC109 and INTD23, [HPLC basic], 456, (1.90) | 10.61 (s, 1H), 9.31-9.25 (m, 2H), 8.73-8.67 (m, 1H), 8.61 (d, J = 2.5 Hz, 1H), 8.03-7.93 (m, 2H), 7.79-7.69 (m, 2H), 7.13 (d, J = 7.6 Hz, 1H), 6.86 (d, J = 8.1 Hz, 1H), 3.20-3.08 (m, 1H), 1.61 (s, 6H), 1.10-0.96 (m, 2H), 0.99-0.87 (m, 2H). |
| P181 | 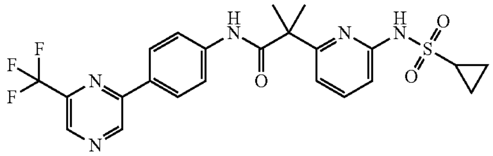 2-(6-(cyclopropanesulfonamido)pyridin-2-yl)-2-methyl-N-(4-(6-(trifluoromethyl)pyrazin-2-yl)phenyl)propanamide | Method 8 using INTC109 and INTD19, [UPLC basic], 506, (1.60) | 10.58 (s, 1H), 9.56 (s, 1H), 9.49 (s, 1H), 9.05 (s, 1H), 8.19-8.10 (m, 2H), 7.88-7.80 (m, 2H), 7.74 (t, J = 7.9 Hz, 1H), 7.12 (d, J = 7.7 Hz, 1H), 6.80 (d, J = 8.1 Hz, 1H), 3.21-3.10 (m, 1H), 1.60 (s, 6H), 1.09-0.91 (m, 2H), 0.79-0.69 (m, 2H). |
| P182 | 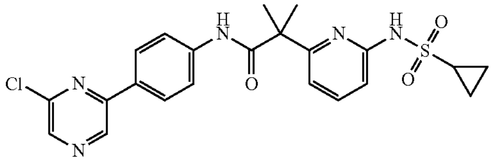 N-(4-(6-chloropyrazin-2-yl)phenyl)-2-(6-(cyclopropanesulfonamido)pyridin-2-yl)-2-methylpropanamide | Method 8 using INTC109 and INTD22, [UPLC basic], 472 35Cl isotope, (1.46) | 10.59 (s, 1H), 9.47 (s, 1H), 9.23 (s, 1H), 8.68 (s, 1H), 8.12-8.04 (m, 2H), 7.86-7.78 (m, 2H), 7.78-7.73 (m, 1H), 7.13 (d, J = 7.7 Hz, 1H), 6.81 (d, J = 8.1 Hz, 1H), 3.22-3.10 (m, 1H), 1.61 (s, 6H), 1.08-0.95 (m, 2H), 0.79-0.69 (m, 2H). |
| P183 | 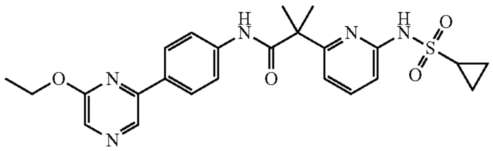 2-(6-(cyclopropanesulfonamido)pyridin-2-yl)-N-(4-(6-ethoxypyrazin-2-yl)phenyl)-2-methylpropanamide | Method 2 using INTC106 and INTD18, [HPLC acidic], 482, (2.36) | 10.60 (s, 1H), 9.43 (s, 1H), 8.76 (s, 1H), 8.17 (s, 1H), 8.12-8.00 (m, 2H), 7.84-7.66 (m, 3H), 7.13 (d, J = 7.7 Hz, 1H), 6.81 (d, J = 8.1 Hz, 1H), 4.54-4.39 (m, 2H), 3.20-3.12 (m, 1H), 1.61 (s, 6H), 1.47-1.32 (m, 3H), 1.04-0.95 (m, 2H), 0.81-0.71 (m, 2H). |
| P184 | 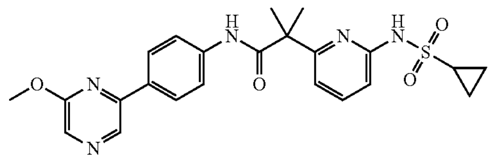 2-(6-(cyclopropanesulfonamido)pyridin-2-yl)-N-(4-(6-methoxypyrazin-2-yl)phenyl)-2-methylpropanamide | Method 2 using INTC106 and INTD1, [HPLC acidic], 468, (2.24) | 10.60 (s, 1H), 9.43 (s, 1H), 8.78 (s, 1H), 8.20 (s, 1H), 8.11-8.04 (m, 2H), 7.83-7.70 (m, 3H), 7.13 (d, J = 7.7 Hz, 1H), 6.81 (d, J = 8.1 Hz, 1H), 4.01 (s, 3H), 3.23-3.11 (m, 1H), 1.61 (s, 6H), 1.05-0.95 (m, 2H), 0.83-0.72 (m, 2H). |

TABLE 20-continued

| Preparation methods and characterisation data of examples P9-P115, P117-P225 | | | |
|---|---|---|---|
| P | Name/Structure (All examples containing chiral centres are racemates unless stated) | Synthesis Method, [LCMS Method], m/z $(M + H)^+$, (RT/Min) | $^1H$ NMR Chemical Shift Data (DMSO-d6 unless stated) |
| P185 | 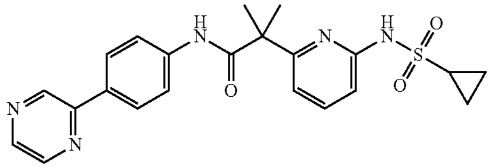 2-(6-(cyclopropanesulfonamido)pyridin-2-yl)-2-methyl-N-(4-(pyrazin-2-yl)phenyl)propanamide | Method 8 using INTC109 and commercial aniline, [UPLC acidic], 438, (1.97) | 10.59 (s, 1H), 9.45 (s, 1H), 9.21 (d, J = 1.6 Hz, 1H), 8.68-8.66 (m, 1H), 8.55 (d, J = 2.5 Hz, 1H), 8.10-8.06 (m, 2H), 7.83-7.78 (m, 2H), 7.78-7.66 (m, 1H), 7.18-7.05 (m, 1H), 6.87-6.69 (m, 1H), 3.20-3.12 (m, 1H), 1.61 (s, 6H), 1.04-0.92 (m, 2H), 0.78-0.62 (m, 2H). |
| P186 | 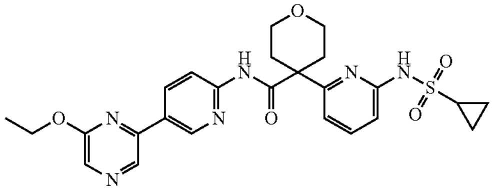 4-(6-(cyclopropanesulfonamido)pyridin-2-yl)-N-(5-(6-ethoxypyrazin-2-yl)pyridin-2-yl)tetrahydro-2H-pyran-4-carboxamide | Method 2 using INTC108 and INTD33, [HPLC acidic], 525, (2.23) | 10.62 (s, 1H), 9.75 (s, 1H), 9.00 (d, J = 2.4 Hz, 1H), 8.83 (s, 1H), 8.49 (dd, J = 8.8, 2.4 Hz, 1H), 8.25 (s, 1H), 8.17 (d, J = 8.8 Hz, 1H), 7.79-7.76 (m, 1H), 7.19 (d, J = 7.7 Hz, 1H), 6.85 (d, J = 8.1 Hz, 1H), 4.47 (q, J = 7.1 Hz, 2H), 3.74-3.60 (m, 4H), 3.24-3.16 (m, 1H), 2.53-2.46 (m, 2H, obscured by DMSO), 2.27-2.19 (m, 2H), 1.40 (t, J = 7.1 Hz, 3H), 1.06-1.01 (m, 2H), 0.94-0.84 (m, 2H). |
| P187 | 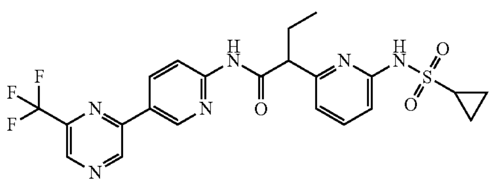 2-(6-(cyclopropanesulfonamido)pyridin-2-yl)-N-(5-(6-(trifluoromethyl)pyrazin-2-yl)pyridin-2-yl)butanamide | Method 10 using INTC111 and INTD2, [HPLC acidic], 507, (2.37) | 10.98 (s, 1H), 10.58 (s, 1H), 9.65 (s, 1H), 9.17-9.10 (m, 2H), 8.56 (dd, J = 8.8, 2.5 Hz, 1H), 8.27 (d, J = 8.8 Hz, 1H), 7.70-7.67 (m, 1H), 7.09 (d, J = 7.6 Hz, 1H), 6.84 (d, J = 8.1 Hz, 1H), 3.98 (dd, J = 8.5, 8.5 Hz, 1H), 3.29-3.24 (m, 1H), 2.14-2.00 (m, 1H), 1.99-1.85 (m, 1H), 1.11-0.98 (m, 2H), 0.97-0.78 (m, 5H). |
| P188 | 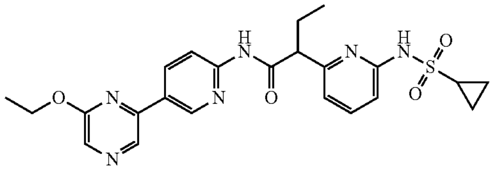 2-(6-(cyclopropanesulfonamido)pyridin-2-yl)-N-(5-(6-ethoxypyrazin-2-yl)pyridin-2-yl)butanamide | Method 10 using INTC111 and INTD33, [HPLC acidic], 483, (2.32) | 10.86 (s, 1H), 10.48 (s, 1H), 9.05 (d, J = 2.5 Hz, 1H), 8.84 (s, 1H), 8.48 (dd, J = 8.8, 2.5 Hz, 1H), 8.25 (s, 1H), 8.21 (d, J = 8.8 Hz, 1H), 7.72-7.68 (m, 1H), 7.12 (d, J = 7.5 Hz, 1H), 6.83 (d, J = 8.1 Hz, 1H), 4.48 (q, J = 7.0 Hz, 2H), 4.00-3.96 (m, 1H), 3.31-3.26 (m, 1H), 2.12-2.02 (m, 1H), 1.97-1.86 (m, 1H), 1.40 (t, J = 7.0 Hz, 3H), 1.12-1.00 (m, 2H), 0.98-0.82 (m, 5H). |
| P189 | 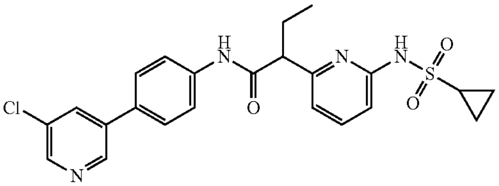 N-(4-(5-chloropyridin-3-yl)phenyl)-2-(6-(cyclopropanesulfonamido)pyridin-2-yl)butanamide | Method 10 using INTC111 and INTD8, [HPLC acidic], 471 35Cl isotope, (2.26) | 10.55 (s, 1H), 10.23 (s, 1H), 8.86 (d, J = 2.0 Hz, 1H), 8.58 (d, J = 2.3 Hz, 1H), 8.22-8.21 (m, 1H), 7.80-7.65 (m, 5H), 7.10 (d, J = 7.5 Hz, 1H), 6.84 (d, J = 8.1 Hz, 1H), 3.73 (dd, J = 8.7, 6.4 Hz, 1H), 3.29-3.20 (m, 1H), 2.13-2.00 (m, 1H), 1.97-1.85 (m, 1H), 1.12-1.01 (m, 2H), 0.98-0.80 (m, 5H). |

TABLE 20-continued

| Preparation methods and characterisation data of examples P9-P115, P117-P225 | | | |
|---|---|---|---|
| P | Name/Structure (All examples containing chiral centres are racemates unless stated) | Synthesis Method, [LCMS Method], m/z $(M + H)^+$, (RT/Min) | $^1$H NMR Chemical Shift Data (DMSO-d6 unless stated) |
| P190 | 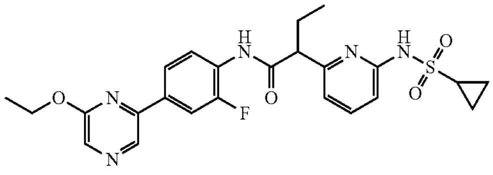<br>2-(6-(cyclopropanesulfonamido)pyridin-2-yl)-N-(4-(6-ethoxypyrazin-2-yl)-2-fluorophenyl)butanamide | Method 10 using INTC111 and INTD24, [HPLC acidic], 500, (2.39) | 10.53 (s, 1H), 10.08 (s, 1H), 8.83 (s, 1H), 8.24 (s, 1H), 8.07-7.98 (m, 2H), 7.95 (dd, J = 8.6, 2.0 Hz, 1H), 7.73-7.70 (m, 1H), 7.11 (d, J = 7.6 Hz, 1H), 6.85 (d, J = 8.1 Hz, 1H), 4.48 (q, J = 7.0 Hz, 2H), 3.96-3.93 (m, 1H), 3.30-3.22 (m, 1H), 2.11-2.01 (m, 1H), 1.97-1.89 (m, 1H), 1.40 (t, J = 7.0 Hz, 3H), 1.11-1.05 (m, 2H), 1.01-0.87 (m, 5H). |
| P191 | 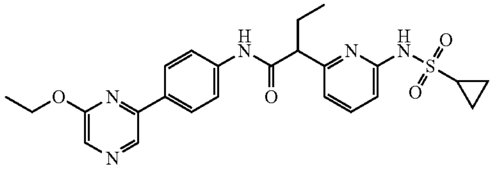<br>2-(6-(cyclopropanesulfonamido)pyridin-2-yl)-N-(4-(6-ethoxypyrazin-2-yl)phenyl)butanamide | Method 10 using INTC111 and INTD18, [HPLC acidic], 482, (2.36) | 10.54 (s, 1H), 10.27 (s, 1H), 8.76 (s, 1H), 8.18 (s, 1H), 8.12-8.05 (m, 2H), 7.79-7.74 (m, 2H), 7.74-7.68 (m, 1H), 7.10 (d, J = 7.6 Hz, 1H), 6.84 (d, J = 8.2 Hz, 1H), 4.47 (q, J = 7.0 Hz, 2H), 3.75 (dd, J = 8.6, 6.5 Hz, 1H), 3.29-3.22 (m, 1H), 2.11-2.03 (m, 1H), 1.96-1.87 (m, 1H), 1.40 (t, J = 7.0 Hz, 3H), 1.10-1.02 (m, 2H), 0.96-0.85 (m, 5H). |
| P192 | 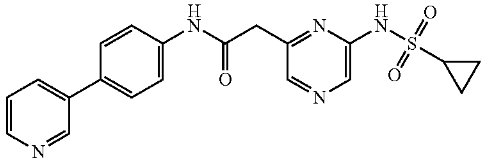<br>2-(6-(cyclopropanesulfonamido)pyrazin-2-yl)-N-(4-(pyridin-3-yl)phenyl)acetamide | Method 7 using INTC135, [UPLC acidic], 410, (0.64) | 11.01 (s, 1H), 10.40 (s, 1H), 8.88 (dd, J = 2.5, 0.9 Hz, 1H), 8.53 (dd, J = 4.8, 1.6 Hz, 1H), 8.27 (s, 1H), 8.20 (s, 1H), 8.05 (ddd, J = 8.0, 2.5, 1.6 Hz, 1H), 7.76-7.67 (m, 4H), 7.46 (ddd, J = 8.0, 4.8, 0.9 Hz, 1H), 3.88 (s, 2H), 3.12-2.99 (m, 1H), 1.11-1.03 (m, 2H), 0.96-0.74 (m, 2H). |
| P193 | 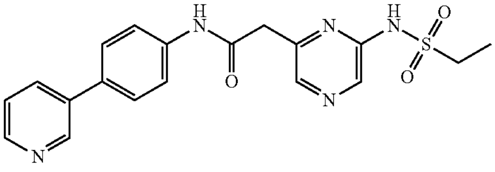<br>2-(6-(ethylsulfonamido)pyrazin-2-yl)-N-(4-(pyridin-3-yl)phenyl)acetamide | Method 7 using INTC135, [UPLC acidic], 398, (0.55) | 10.92 (v. br. s, 1H), 10.38 (s, 1H), 8.88 (dd, J = 2.5, 0.9 Hz, 1H), 8.53 (dd, J = 4.7, 1.6 Hz, 1H), 8.20 (s, 1H), 8.13 (s, 1H), 8.05 (ddd, J = 8.0, 2.5, 1.6 Hz, 1H), 7.79-7.63 (m, 4H), 7.46 (ddd, J = 8.0, 4.8, 0.9 Hz, 1H), 3.84 (s, 2H), 3.42 (q, J = 7.3 Hz, 2H), 1.14 (t, J = 7.3 Hz, 3H). |
| P194 | 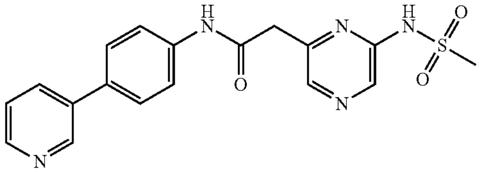<br>2-(6-(methylsulfonamido)pyrazin-2-yl)-N-(4-(pyridin-3-yl)phenyl)acetamide | Method 7 using INTC135, [UPLC acidic], 384, (0.55) | 11.05 (s, 1H), 10.40 (s, 1H), 8.89 (d, J = 2.4 Hz, 1H), 8.54 (dd, J = 4.7, 1.6 Hz, 1H), 8.29 (s, 1H), 8.19 (s, 1H), 8.05 (ddd, J = 8.0, 2.4, 1.6 Hz, 1H), 7.78-7.64 (m, 4H), 7.47 (ddd, J = 8.0, 4.7, 0.9 Hz, 1H), 3.90 (s, 2H), 3.33 (s, 3H). |
| P195 | 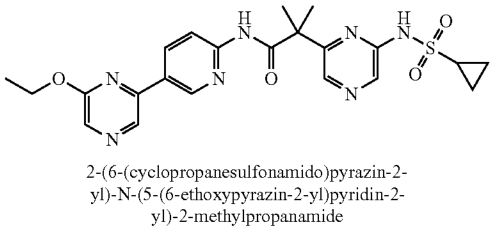 [SMILES: CCOc1cncc(-c2ccc(NC(=O)C(C)(C)c3cncc(NS(=O)(=O)C4CC4)n3)nc2)n1]<br>2-(6-(cyclopropanesulfonamido)pyrazin-2-yl)-N-(5-(6-ethoxypyrazin-2-yl)pyridin-2-yl)-2-methylpropanamide | Method 2 using INTC125 and INTD33, [HPLC acidic], 484, (2.15) | 10.97 (s, 1H), 10.13 (s, 1H), 9.00 (d, J = 2.5 Hz, 1H), 8.84 (s, 1H), 8.49 (dd, J = 8.8, 2.5 Hz, 1H), 8.41 (s, 1H), 8.25 (s, 1H), 8.23-8.17 (m, 2H), 4.48 (q, J = 7.0 Hz, 2H), 3.02-2.95 (m, 1H), 1.66 (s, 6H), 1.40 (t, J = 7.0 Hz, 3H), 1.04-0.95 (m, 2H), 0.75-0.66 (m, 2H). |

TABLE 20-continued

Preparation methods and characterisation data of examples P9-P115, P117-P225

| P | Name/Structure (All examples containing chiral centres are racemates unless stated) | Synthesis Method, [LCMS Method], m/z $(M + H)^+$, (RT/Min) | $^1H$ NMR Chemical Shift Data (DMSO-d6 unless stated) |
|---|---|---|---|
| P196 | 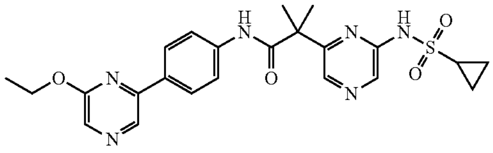 2-(6-(cyclopropanesulfonamido)pyrazin-2-yl)-N-(4-(6-ethoxypyrazin-2-yl)phenyl)-2-methylpropanamide | Method 2 using INTC125 and INTD18, [HPLC acidic], 483, (2.2) | 11.03 (s, 1H), 9.43 (s, 1H), 8.76 (s, 1H), 8.42 (s, 1H), 8.18 (d, J = 7.7 Hz, 2H), 8.11-8.02 (m, 2H), 7.81-7.71 (m, 2H), 4.47 (q, J = 7.0 Hz, 2H), 3.00-3.00 (m, 1H), 1.65 (s, 6H), 1.40 (t, J = 7.0 Hz, 3H), 1.06-0.97 (m, 2H), 0.81-0.66 (m, 2H). |
| P197 | 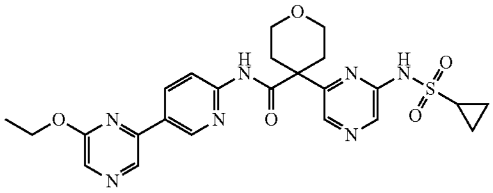 4-(6-(cyclopropanesulfonamido)pyrazin-2-yl)-N-(5-(6-ethoxypyrazin-2-yl)pyridin-2-yl)tetrahydro-2H-pyran-4-carboxamide | Method 2 using INTC127 and INTD33, [UPLC acidic], 526, (1.31) | 11.06 (s, 1H), 10.14 (s, 1H), 9.01 (d, J = 2.5 Hz, 1H), 8.84 (s, 1H), 8.49 (dd, J = 8.7, 2.5 Hz, 1H), 8.45 (s, 1H), 8.25 (s, 1H), 8.22-8.16 (m, 2H), 4.47 (q, J = 7.0 Hz, 2H), 3.79-3.72 (m, 2H), 3.68-3.60 (m, 2H), 3.15-3.05 (m, 1H), 2.56-2.52 (m, 2H), 2.27-2.17 (m, 2H), 1.39 (t, J = 7.0 Hz, 3H), 1.08-1.02 (m, 2H), 0.88-0.80 (m, 2H). |
| P198 | 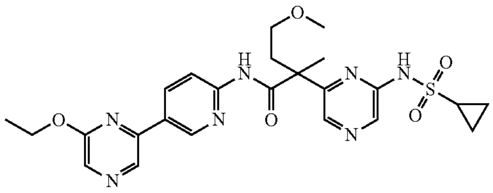 2-(6-(cyclopropanesulfonamido)pyrazin-2-yl)-N-(5-(6-ethoxypyrazin-2-yl)pyridin-2-yl)-4-methoxy-2-methylbutanamide | Method 7 using INTC136, [UPLC acidic], 528, (1.36) | 10.98 (s, 1H), 10.18 (s, 1H), 9.00 (d, J = 2.4 Hz, 1H), 8.84 (s, 1H), 8.49 (dd, J = 8.8, 2.4 Hz, 1H), 8.38 (s, 1H), 8.25 (s, 1H), 8.23-8.16 (m, 2H), 4.48 (q, J = 7.0 Hz, 2H), 3.43-3.27 (m, 2H), 3.14 (s, 3H), 3.03-2.94 (m, 1H), 2.48-2.38 (m, 1H), 2.39-2.29 (m, 1H), 1.67 (s, 3H), 1.40 (t, J = 7.0 Hz, 3H), 1.04-0.94 (m, 2H), 0.73-0.64 (m, 2H). |
| P199 | 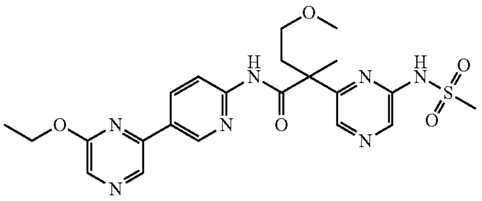 N-(5-(6-ethoxypyrazin-2-yl)pyridin-2-yl)-4-methoxy-2-methyl-2-(6-(methylsulfonamido)pyrazin-2-yl)butanamide | Method 7 using INTC136, [HPLC acidic], 502, (1.98) | 11.03 (s, 1H), 10.16 (s, 1H), 9.06-8.99 (m, 1H), 8.86-8.82 (m, 1H), 8.52-8.45 (m, 1H), 8.35 (s, 1H), 8.27-8.23 (m, 1H), 8.22-8.14 (m, 2H), 4.48 (q, J = 7.0 Hz, 2H), 3.42-3.27 (m, 5H), 3.17-3.12 (m, 3H), 2.49-2.40 (m, 1H), 2.37-2.29 (m, 1H), 1.68-1.62 (m, 3H), 1.40 (t, J = 7.0 Hz, 3H). |
| P200 | 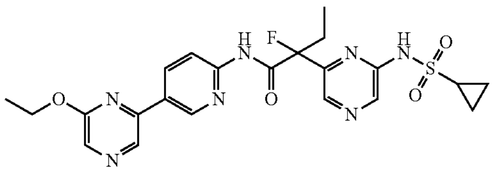 2-(6-(cyclopropanesulfonamido)pyrazin-2-yl)-N-(5-(6-ethoxypyrazin-2-yl)pyridin-2-yl)-2-fluorobutanamide | Method 10 using INTC133 and INTD33, [UPLC acidic], 502, (1.47) | 11.25 (s, 1H), 10.62 (d, J = 2.4 Hz, 1H), 9.10 (d, J = 2.4 Hz, 1H), 8.87 (s, 1H), 8.65 (s, 1H), 8.53 (dd, J = 8.7, 2.4 Hz, 1H), 8.34 (s, 1H), 8.27 (s, 1H), 8.12 (d, J = 8.7 Hz, 1H), 4.49 (q, J = 7.0 Hz, 2H), 3.20-3.12 (m, 1H), 2.48-2.36 (m, 2H), 1.40 (t, J = 7.0 Hz, 3H), 1.23-0.89 (m, 7H). |

TABLE 20-continued

Preparation methods and characterisation data of examples P9-P115, P117-P225

| P | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
|---|---|---|---|
| P201 | 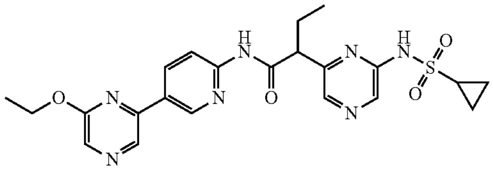 2-(6-(cyclopropanesulfonamido)pyrazin-2-yl)-N-(5-(6-ethoxypyrazin-2-yl)pyridin-2-yl)butanamide | Method 10 using INTC132 and INTD33, [HPLC acidic], 484, (2.15) | 11.00 (s, 2H), 9.06 (d, J = 2.4 Hz, 1H), 8.84 (s, 1H), 8.49 (dd, J = 8.8, 2.4 Hz, 1H), 8.38 (s, 1H), 8.25 (s, 1H), 8.22-8.19 (m, 2H), 4.48 (q, J = 7.0 Hz, 2H), 4.07 (t, J = 7.5 Hz, 1H), 3.23-3.13 (m, 1H), 2.19-2.08 (m, 1H), 2.01-1.95 (m, 1H), 1.40 (t, J = 7.0 Hz, 3H), 1.18-1.05 (m, 2H), 1.02-0.87 (m, 5H). |
| P202 | 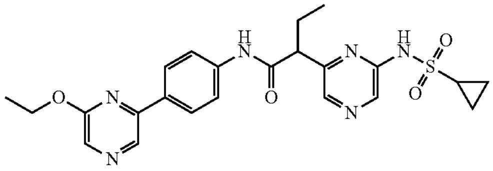 2-(6-(cyclopropanesulfonamido)pyrazin-2-yl)-N-(4-(6-ethoxypyrazin-2-yl)phenyl)butanamide | Method 10 using INTC132 and INTD18, [HPLC acidic], 483, (2.22) | 11.02 (s, 1H), 10.37 (s, 1H), 8.76 (s, 1H), 8.37 (s, 1H), 8.19 (d, J = 11.0 Hz, 2H), 8.15-8.04 (m, 2H), 7.81-7.72 (m, 2H), 4.47 (q, J = 7.0 Hz, 2H), 3.85 (dd, J = 8.4, 8.6 Hz, 1H), 3.21-3.12 (m, 1H), 2.20-2.07 (m, 1H), 2.03-1.90 (m, 1H), 1.40 (t, J = 7.0 Hz, 3H), 1.15-1.04 (m, 2H), 1.02-0.84 (m, 5H). |
| P203 | 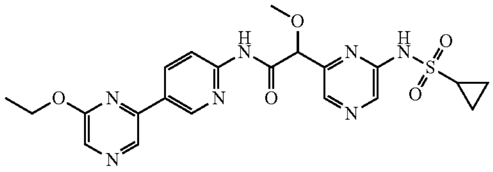 2-(6-(cyclopropanesulfonamido)pyrazin-2-yl)-N-(5-(6-ethoxypyrazin-2-yl)pyridin-2-yl)-2-methoxyacetamide | Method 7 using INTC137 [HPLC acidic], 486, (1.98) | 11.12 (s, 1H), 10.71 (s, 1H), 9.10 (dd, J = 2.4, 0.8 Hz, 1H), 8.86 (s, 1H), 8.53 (dd, J = 8.7, 2.4 Hz, 1H), 8.45 (s, 1H), 8.30 (s, 1H), 8.27 (s, 1H), 8.18 (d, J = 8.7 Hz, 1H), 5.27 (s, 1H), 4.49 (q, J = 7.0 Hz, 2H), 3.48 (s, 3H), 3.12-3.02 (m, 1H), 1.40 (t, J = 7.0 Hz, 3H), 1.12-0.96 (m, 2H), 0.93-0.73 (m, 2H). |
| P204 | 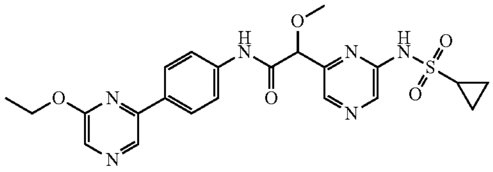 2-(6-(cyclopropanesulfonamido)pyrazin-2-yl)-N-(4-(6-ethoxypyrazin-2-yl)phenyl)-2-methoxyacetamide | Method 10 using INTC134 and INTD18, [HPLC acidic], 485, (2.05) | 11.13 (s, 1H), 10.38 (s, 1H), 8.78 (s, 1H), 8.46 (s, 1H), 8.29 (s, 1H), 8.19 (s, 1H), 8.14-8.07 (m, 2H), 7.89-7.81 (m, 2H), 5.08 (s, 1H), 4.48 (q, J = 7.0 Hz, 2H), 3.48 (s, 3H), 3.13-3.03 (m, 1H), 1.40 (t, J = 7.0 Hz, 3H), 1.11-1.00 (m, 2H), 0.87-0.73 (m, 2H). |
| P205 | 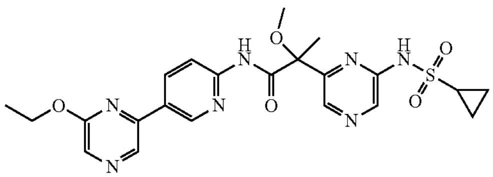 2-(6-(cyclopropanesulfonamido)pyrazin-2-yl)-N-(5-(6-ethoxypyrazin-2-yl)pyridin-2-yl)-2-methoxypropanamide | Method 2 using INTC129 and INTD33, [HPLC acidic], 500, (2.16) | 11.13 (s, 1H), 9.90 (s, 1H), 9.08 (dd, J = 2.4, 0.8 Hz, 1H), 8.86 (s, 1H), 8.58 (s, 1H), 8.53 (dd, J = 8.8, 2.4 Hz, 1H), 8.27 (s, 1H), 8.26 (s, 1H), 8.13 (dd, J = 8.8, 0.8 Hz, 1H), 4.49 (q, J = 7.1 Hz, 2H), 3.31 (s, 3H), 3.12-3.05 (m, 1H), 1.85 (s, 3H), 1.40 (t, J = 7.0 Hz, 3H), 1.15-1.04 (m, 2H), 0.98-0.83 (m, 2H). |

TABLE 20-continued

Preparation methods and characterisation data of examples P9-P115, P117-P225

| P | Name/Structure (All examples containing chiral centres are racemates unless stated) | Synthesis Method, [LCMS Method], m/z (M + H)+, (RT/Min) | $^1H$ NMR Chemical Shift Data (DMSO-d6 unless stated) |
|---|---|---|---|
| P205a | 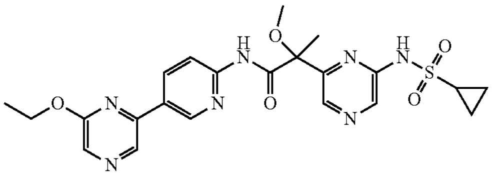 Single enantiomer-stereochemistry unassigned 2-(6-(cyclopropanesulfonamido)pyrazin-2-yl)-N-(5-(6-ethoxypyrazin-2-yl)pyridin-2-yl)-2-methoxypropanamide | Method 2 using INTC129 and INTD33, Chiral IC4 (4.40), [HPLC acidic], 500, (2.16) | 11.13 (s, 1H), 9.90 (s, 1H), 9.08 (dd, J = 2.4, 0.8 Hz, 1H), 8.86 (s, 1H), 8.58 (s, 1H), 8.53 (dd, J = 8.8, 2.4 Hz, 1H), 8.27 (s, 1H), 8.26 (s, 1H), 8.13 (dd, J = 8.8, 0.8 Hz, 1H), 4.49 (q, J = 7.1 Hz, 2H), 3.31 (s, 3H), 3.12-3.05 (m, 1H), 1.85 (s, 3H), 1.40 (t, J = 7.0 Hz, 3H), 1.15-1.04 (m, 2H), 0.98-0.83 (m, 2H). |
| P205b | 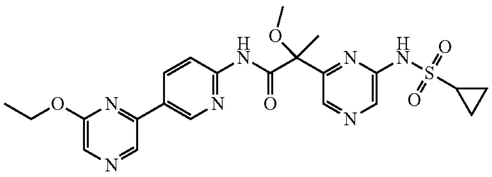 Single enantiomer-stereochemistry unassigned 2-(6-(cyclopropanesulfonamido)pyrazin-2-yl)-N-(5-(6-ethoxypyrazin-2-yl)pyridin-2-yl)-2-methoxypropanamide | Method 2 using INTC129 and INTD33, Chiral IC4 (5.04), [HPLC acidic], 500, (2.16) | 11.13 (s, 1H), 9.90 (s, 1H), 9.08 (dd, J = 2.4, 0.8 Hz, 1H), 8.86 (s, 1H), 8.58 (s, 1H), 8.53 (dd, J = 8.8, 2.4 Hz, 1H), 8.27 (s, 1H), 8.26 (s, 1H), 8.13 (dd, J = 8.8, 0.8 Hz, 1H), 4.49 (q, J = 7.1 Hz, 2H), 3.31 (s, 3H), 3.12-3.05 (m, 1H), 1.85 (s, 3H), 1.40 (t, J = 7.0 Hz, 3H), 1.15-1.04 (m, 2H), 0.98-0.83 (m, 2H). |
| P206 | 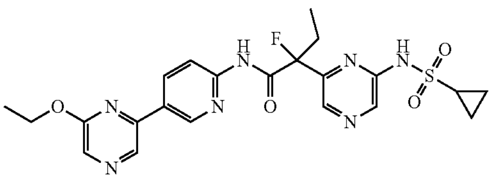 Single enantiomer-stereochemistry unassigned 2-(6-(cyclopropanesulfonamido)pyrazin-2-yl)-N-(5-(6-ethoxypyrazin-2-yl)pyridin-2-yl)-2-fluorobutanamide | Method 10 using INTC133 and INTD33, Chiral IC5 (12.55), [HPLC acidic], 502, (2.27) | 11.25 (s, 1H), 10.61 (d, J = 2.4 Hz, 1H), 9.10 (d, J = 2.4 Hz, 1H), 8.87 (s, 1H), 8.64 (s, 1H), 8.53 (dd, J = 8.7, 2.4 Hz, 1H), 8.34 (s, 1H), 8.27 (s, 1H), 8.12 (d, J = 8.7 Hz, 1H), 4.49 (q, J = 7.0 Hz, 2H), 3.19-3.10 (m, 1H), 2.58-2.34 (m, 2H), 1.40 (t, J = 7.1 Hz, 3H), 1.23-0.91 (m, 7H). |
| P207 | 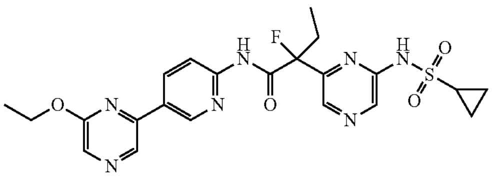 Single enantiomer-stereochemistry unassigned 2-(6-(cyclopropanesulfonamido)pyrazin-2-yl)-N-(5-(6-ethoxypyrazin-2-yl)pyridin-2-yl)-2-fluorobutanamide | Method 10 using INTC133 and INTD33, Chiral IC5 (19.98), [HPLC acidic], 502, (2.27) | 11.25 (s, 1H), 10.81 (d, J = 2.4 Hz, 1H), 9.10 (d, J = 2.4 Hz, 1H), 8.87 (s, 1H), 8.64 (s, 1H), 8.53 (dd, J = 8.7, 2.4 Hz, 1H), 8.33 (s, 1H), 8.27 (s, 1H), 8.12 (d, J = 8.7 Hz, 1H), 4.49 (q, J = 7.1 Hz, 2H), 3.19-3.10 (m, 1H), 2.58-2.34 (m, 2H), 1.40 (t, J = 7.0 Hz, 3H), 1.20-0.90 (m, 7H). |
| P208 | 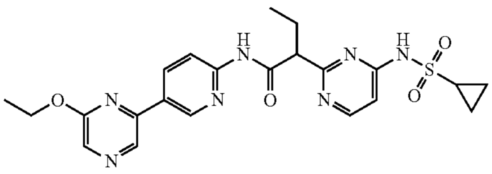 2-(4-(cyclopropanesulfonamido)pyrimidin-2-yl)-N-(5-(6-ethoxypyrazin-2-yl)pyridin-2-yl)butanamide | Method 6 using INTC143, [UPLC acidic], 484, (1.32) | 11.24 (s, 1H), 10.93 (s, 1H), 9.07 (d, J = 2.4 Hz, 1H), 8.85 (s, 1H), 8.49 (dd, J = 8.7, 2.4 Hz, 2H), 8.25 (s, 1H), 8.23 (d, J = 8.7 Hz, 1H), 6.84 (s, 1H), 4.49 (q, J = 7.0 Hz, 2H), 4.15-4.06 (m, 1H), 3.26-3.13 (m, 1H), 2.17-2.00 (m, 2H), 1.41 (t, J = 7.0 Hz, 3H), 1.10-1.04 (m, 2H), 0.96 (t, J = 7.4 Hz, 3H), 0.94-0.88 (m, 2H). |

TABLE 20-continued

Preparation methods and characterisation data of examples P9-P115, P117-P225

| P | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
|---|---|---|---|
| P209 | 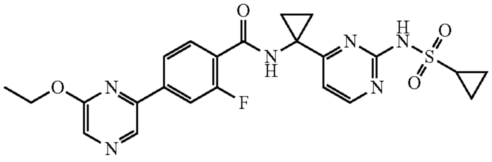 N-(1-(2-(cyclopropanesulfonamido)pyrimidin-4-yl)cyclopropyl)-4-(6-ethoxypyrazin-2-yl)-2-fluorobenzamide | Method 1 using INTC156 and INTD74, [UPLC acidic], 499, (1.32) | 11.16 (s, 1H), 9.29 (s, 1H), 8.94 (s, 1H), 8.47 (d, J = 4.7 Hz, 1H), 8.33 (s, 1H), 8.09 (s, 1H), 8.07 (dd, J = 4.7, 1.5 Hz, 1H), 7.85-7.81 (m, 1H), 7.16-7.09 (m, 1H), 4.51 (q, J = 7.0 Hz, 2H), 3.16-3.08 (m, 1H), 1.66 (q, J = 4.3 Hz, 2H), 1.41 (t, J = 7.0 Hz, 3H), 1.40-1.36 (m, 2H), 1.12-1.00 (m, 4H), |
| P210 | 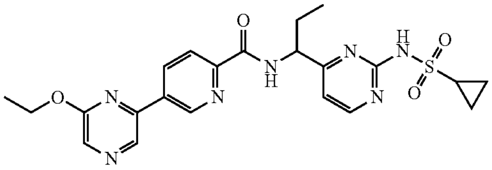 N-(1-(2-(cyclopropanesulfonamido)pyrimidin-4-yl)propyl)-5-(6-ethoxypyrazin-2-yl)picolinamide | Method 7 using INTC163, [UPLC acidic], 484, (1.36) | 11.31 (s, 1H), 9.38 (d, J = 2.2 Hz, 1H), 9.19 (d, J = 8.4 Hz, 1H), 9.00 (s, 1H), 8.74-8.65 (m, 1H), 8.56 (d, J = 5.1 Hz, 1H), 8.38 (s, 1H), 8.17 (d, J = 8.4 Hz, 1H), 7.20 (d, J = 5.1 Hz, 1H), 5.03-4.94 (m, 1H), 4.52 (q, J = 7.0 Hz, 2H), 3.32-3.24 (m, 1H), 2.07-1.87 (m, 2H), 1.43 (t, J = 7.0 Hz, 3H), 1.18-0.89 (m, 7H). |
| P211 | 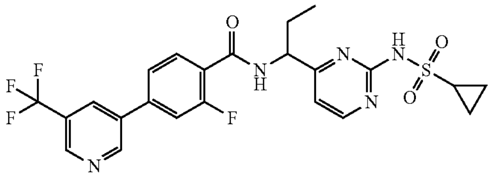 N-(1-(2-(cyclopropanesulfonamido)pyrimidin-4-yl)propyl)-2-fluoro-4-(5-(trifluoromethyl) pyridin-3-yl)benzamide | Method 1 using INTC162 and INTD78, [HPLC Basic], 524, (1.8) | Methanol-d4, 9.22-9.14 (m, 1H), 8.99-8.92 (m, 1H), 8.51-8.46 (m, 2H), 7.92-7.89 (m, 1H), 7.76-7.69 (m, 2H), 7.07 (d, J = 5.2 Hz, 1H), 5.11-4.99 (m, 1H), 3.32-3.23 (m, 1H), 2.14-2.01 (m, 1H), 2.00-1.84 (m, 1H), 1.31-1.20 (m, 2H), 1.08 (t, J = 7.4 Hz, 3H), 1.05-0.93 (m, 2H), 2 × N—H not observed. |
| P212 | 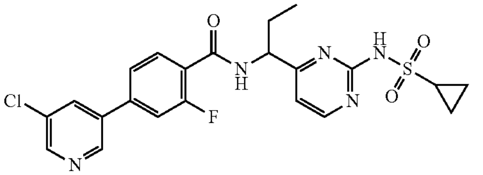 4-(5-chloropyridin-3-yl)-N-(1-(2-(cyclopropanesulfonamido)pyrimidin-4-yl)propyl)-2-fluorobenzamide | Method 1 using INTC162 and INTD76 [HPLC Basic], 490 $^{35}$Cl isotope, (1.68) | Methanol-d4, 8.90-8.78 (m, 1H), 8.70-8.60 (m, 1H), 8.55-8.45 (m, 2H), 8.27-8.23 (m, 1H), 7.91-7.83 (m, 1H), 7.70-7.63 (m, 2H), 7.14-7.03 (m, 1H), 5.09-5.01 (m, 1H), 3.30-3.23 (m, 1H), 2.16-2.02 (m, 1H), 2.02-1.85 (m, 1H), 1.33-1.22 (m, 2H), 1.07 (t, J = 7.3 Hz, 3H), 1.04-0.95 (m, 2H), 2 × N—H not observed. |
| P213 | 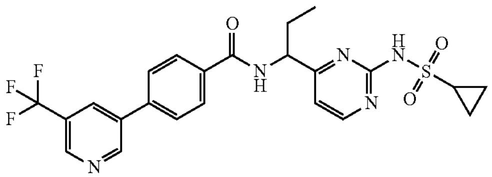 N-(1-(2-(cyclopropanesulfonamido)pyrimidin-4-yl)propyl)-4-(5-(trifluoromethyl)pyridin-3-yl)benzamide | Method 1 using INTC162 and INTD77, [HPLC Basic], 506, (1.76) | Methanol-d4, 9.17 (d, J = 2.1 Hz, 1H), 8.96-8.92 (m, 1H), 8.50 (d, J = 5.2 Hz, 1H), 8.47-8.44 (m, 1H), 8.11-8.07 (m, 2H), 7.93-7.88 (m, 2H), 7.11 (d, J = 5.2 Hz, 1H), 5.10-4.98 (m, 1H), 3.31-3.22 (m, 1H), 2.17-2.06 (m, 1H), 2.03-1.91 (m, 1H), 1.34-1.18 (m, 2H), 1.08 (t, J = 7.4 Hz, 3H), 1.03-0.88 (m, 2H), 2 × N—H not observed. |

TABLE 20-continued

| P | Name/Structure (All examples containing chiral centres are racemates unless stated) | Synthesis Method, [LCMS Method], m/z (M + H)+, (RT/Min) | $^1$H NMR Chemical Shift Data (DMSO-d6 unless stated) |
|---|---|---|---|
| | Preparation methods and characterisation data of examples P9-P115, P117-P225 | | |
| P214 | 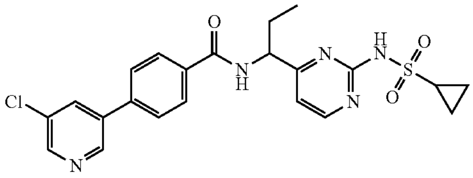 4-(5-chloropyridin-3-yl)-N-(1-(2-(cyclopropanesulfonamido)pyrimidin-4-yl)propyl)benzamide | Method 1 using INTC162 and INTD79 [HPLC Basic], 472 $^{35}$Cl isotope, (1.64) | 11.25 (s, 1H), 8.98-8.95 (m, 1H), 8.92-8.86 (m, 1H), 8.68 (d, J = 2.3 Hz, 1H), 8.59-8.48 (m, 1H), 8.36 (t, J = 2.2 Hz, 1H), 8.10-8.02 (m, 2H), 7.98-7.90 (m, 2H), 7.11 (s, 1H), 4.96-4.82 (m, 1H), 3.30-3.23 (m, 1H), 2.06-1.78 (m, 2H), 1.19-0.68 (m, 7H). |
| P215 | 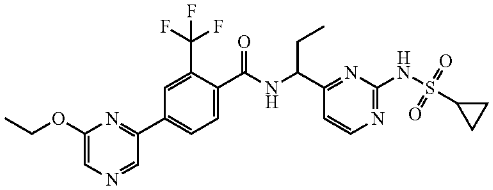 N-(1-(2-(cyclopropanesulfonamido)pyrimidin-4-yl)propyl)-4-(6-ethoxypyrazin-2-yl)-2-(trifluoromethyl)benzamide | Method 7 using INTC164, [UPLC acidic], 551, (1.44) | 11.28 (s, 1H), 9.12 (d, J = 7.9 Hz, 1H), 9.00 (s, 1H), 8.61 (d, J = 5.2 Hz, 1H), 8.53-8.44 (m, 2H), 8.36 (s, 1H), 7.84 (d, J = 7.9 Hz, 1H), 7.17 (d, J = 5.2 Hz, 1H), 4.88-4.80 (m, 1H), 4.51 (q, J = 7.1 Hz, 2H), 3.37-3.33 (m, 1H), 1.99-1.87 (m, 1H), 1.83-1.70 (m, 1H), 1.43 (t, J = 7.0 Hz, 3H), 1.21-1.03 (m, 4H), 1.00 (t, J = 7.3 Hz, 3H). |
| P216 | 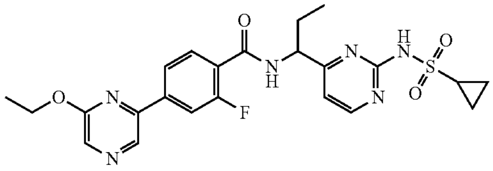 N-(1-(2-(cyclopropanesulfonamido)pyrimidin-4-yl)propyl)-4-(6-ethoxypyrazin-2-yl)-2-fluorobenzamide | Method 7 using INTC165, [HPLC acidic], 501, (2.18) | 11.25 (s, 1H), 8.93 (s, 1H), 8.89 (d, J = 7.8 Hz, 1H), 8.58 (d, J = 5.1 Hz, 1H), 8.32 (s, 1H), 8.09-8.06 (m, 2H), 7.80-7.77 (m, 1H), 7.16 (d, J = 5.2 Hz, 1H), 4.89-4.81 (m, 1H), 4.50 (q, J = 7.0 Hz, 2H), 3.30-3.25 (m, 1H), 1.99-1.90 (m, 1H), 1.84-1.74 (m, 1H), 1.41 (t, J = 7.0 Hz, 3H), 1.15-1.09 (m, 2H), 1.06-1.01 (m, 2H), 0.99 (t, J = 7.3 Hz, 3H). |
| P217 | 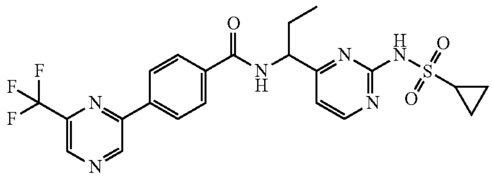 N-(1-(2-(cyclopropanesulfonamido)pyrimidin-4-yl)propyl)-4-(6-(trifluoromethyl)pyrazin-2-yl)benzamide | Method 7 using INTC166, [HPLC acidic], 507, (1.37) | 11.25 (s, 1H), 9.72 (s, 1H), 9.21 (s, 1H), 8.98 (d, J = 7.6 Hz, 1H), 8.56 (d, J = 5.2 Hz, 1H), 8.35-8.31 (m, 2H), 8.16-8.11 (m, 2H), 7.16 (d, J = 5.2 Hz, 1H), 4.95-4.84 (m, 1H), 3.32-3.24 (m, 1H), 2.05-1.94 (m, 1H), 1.93-1.83 (m, 1H), 1.16-1.06 (m, 2H), 1.05-0.92 (m, 5H). |
| P218 | 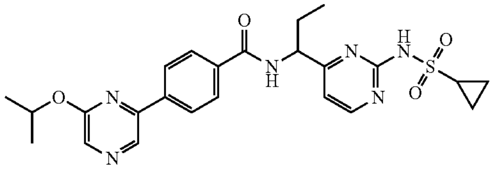 N-(1-(2-(cyclopropanesulfonamido)pyrimidin-4-yl)propyl)-4-(6-isopropoxypyrazin-2-yl)benzamide | Method 7 using INTC167, [UPLC acidic], 497, (1.43) | 11.25 (s, 1H), 3.98-8.82 (m, 2H), 8.55 (d, J = 5.2 Hz, 1H), 8.29-8.16 (m, 3H), 8.07 (d, J = 8.1 Hz, 2H), 7.15 (d, J = 5.2 Hz, 1H), 5.48-5.36 (m, 1H), 4.93-4.82 (m, 1H), 3.30-3.22 (m, 1H), 2.04-1.93 (m, 1H), 1.93-1.81 (m, 1H), 1.40 (d, J = 6.1 Hz, 6H), 1.15-1.05 (m, 2H), 1.05-0.93 (m, 5H). |

TABLE 20-continued

Preparation methods and characterisation data of examples P9-P115, P117-P225

| P | Name/Structure (All examples containing chiral centres are racemates unless stated) | Synthesis Method, [LCMS Method], m/z $(M + H)^+$, (RT/Min) | $^1H$ NMR Chemical Shift Data (DMSO-d6 unless stated) |
|---|---|---|---|
| P219 | 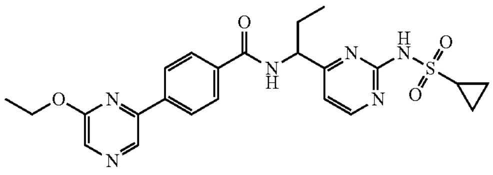 N-(1-(2-(cyclopropanesulfonamido)pyrimidin-4-yl)propyl)-4-(6-ethoxypyrazin-2-yl)benzamide | Method 7 using INTC168, [UPLC acidic], 483, (1.34) | 11.24 (s, 1H), 8.98-8.86 (m, 2H), 8.56 (d, J = 5.2 Hz, 1H), 8.30 (s, 1H), 8.25 (d, J = 8.3 Hz, 2H), 8.09-8.04 (m, 2H), 7.16 (d, J = 5.2 Hz, 1H), 4.92-4.82 (m, 1H), 4.51 (q, J = 7.0 Hz, 2H), 3.32-3.22 (m, 1H), 2.05-1.93 (m, 1H), 1.93-1.81 (m, 1H), 1.42 (t, J = 7.0 Hz, 3H), 1.16-1.06 (m, 2H), 1.05-0.93 (m, 5H). |
| P220 | 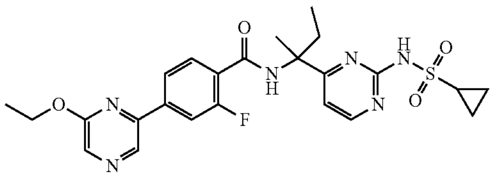 N-(2-(2-(cyclopropanesulfonamido)pyrimidin-4-yl)butan-2-yl)-4-(6-ethoxypyrazin-2-yl)-2-fluorobenzamide | Method 1 using INTC159 and INTD74, [UPLC acidic], 515, (1.46) | 11.21 (s, 1H), 8.93 (s, 1H), 8.67 (s, 1H), 8.54 (d, J = 5.3 Hz, 1H), 8.33 (s, 1H), 8.12-7.98 (m, 2H), 7.77-7.73 (m, 1H), 7.18 (d, J = 5.3 Hz, 1H), 4.51 (q, J = 7.0 Hz, 2H), 3.29-3.22 (m, 1H), 2.17-2.00 (m, 2H), 1.63 (s, 3H), 1.42 (t, J = 7.0 Hz, 3H), 1.18-0.96 (m, 4H), 0.81 (t, J = 7.4 Hz, 3H). |
| P221 | 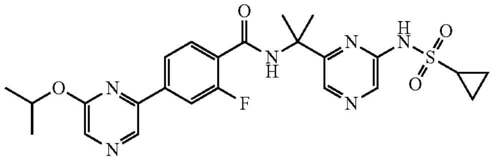 N-(2-(6-(cyclopropanesulfonamido)pyrazin-2-yl)propan-2-yl)-2-fluoro-4-(6-isopropoxypyrazin-2-yl)benzamide | Method 1 using INTC175 and INTD81, [HPLC acidic], 515, (2.3) | 10.96 (s, 1H), 8.90 (s, 1H), 8.83 (s, 1H), 8.40 (s, 1H), 8.27 (s, 1H), 8.15 (s, 1H), 8.06-8.00 (m, 2H), 7.80-7.63 (m, 1H), 5.50-5.31 (m, 1H), 3.18-3.09 (m, 1H), 1.69 (s, 6H), 1.40 (d, J = 6.2 Hz, 6H), 1.15-1.09 (m, 2H), 1.05-0.99 (m, 2H). |
| P222 | 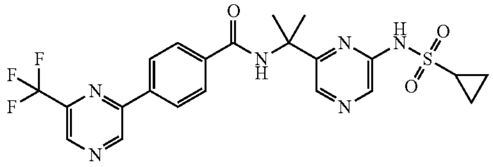 N-(2-(6-(cyclopropanesulfonamido)pyrazin-2-yl)propan-2-yl)-4-(6-(trifluoromethyl) pyrazin-2-yl)benzamide | Method 1 using INTC175 and INTD75, [HPLC acidic], 507, (2.13) | 10.94 (s, 1H), 9.71 (s, 1H), 9.20 (s, 1H), 8.85 (s, 1H), 8.37 (s, 1H), 8.33-8.27 (m, 2H), 8.12 (s, 1H), 8.09-8.04 (m, 2H), 3.13-3.03 (m, 1H), 1.73 (s, 6H), 1.10-1.00 (m, 2H), 0.89-0.77 (m, 2H). |
| P223 | 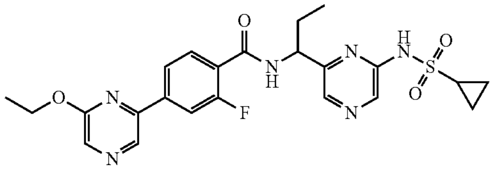 N-(1-(6-(cyclopropanesulfonamido)pyrazin-2-yl)propyl)-4-(6-ethoxypyrazin-2-yl)-2-fluorobenzamide | Method 1 using INTC174 and INTD74, [HPLC acidic], 501, (2.19) | 11.04 (s, 1H), 8.93 (s, 1H), 8.90-8.85 (m, 1H), 8.36-8.30 (m, 2H), 8.22 (s, 1H), 8.09-8.04 (m, 2H), 7.79-7.74 (m, 1H), 5.06-4.93 (m, 1H), 4.51 (q, J = 7.0 Hz, 2H), 3.25-3.09 (m, 1H), 2.03-1.77 (m, 2H), 1.42 (t, J = 7.0 Hz, 3H), 1.16-1.10 (m, 2H), 1.08-1.00 (m, 2H), 0.98 (t, J = 7.3 Hz, 3H). |

TABLE 20-continued

| P | Name/Structure (All examples containing chiral centres are racemates unless stated) | Synthesis Method, [LCMS Method], m/z $(M + H)^+$, (RT/Min) | $^1H$ NMR Chemical Shift Data (DMSO-d6 unless stated) |
|---|---|---|---|
| Preparation methods and characterisation data of examples P9-P115, P117-P225 | | | |
| P224 | 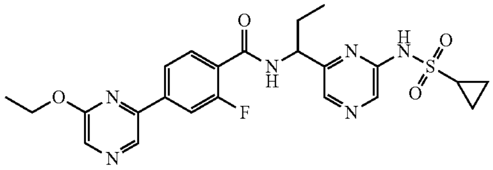 Single enantiomer-stereochemistry unassigned N-(1-(6-(cyclopropanesulfonamido)pyrazin-2-yl)propyl)-4-(6-ethoxypyrazin-2-yl)-2-fluorobenzamide | Method 1 using INTC174 and INTD74, Chiral IC4 (9.28), [HPLC acidic], 501, (2.19) | 11.04 (s, 1H), 8.93 (s, 1H), 8.87 (d, J = 7.8 Hz, 1H), 8.41-8.24 (m, 2H), 8.22 (s, 1H), 8.11-8.03 (m, 2H), 7.82-7.72 (m, 1H), 5.03-4.93 (m, 1H), 4.51 (q, J = 7.0 Hz, 2H), 3.24-3.15 (m, 1H), 2.03-1.79 (m, 2H), 1.41 (t, J = 7.0 Hz, 3H), 1.18-1.09 (m, 2H), 1.09-1.02 (m, 2H), 0.98 (t, J = 7.3 Hz, 3H). |
| P225 | 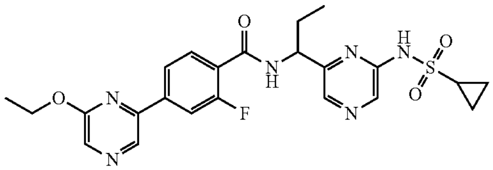 Single enantiomer-stereochemistry unassigned N-(1-(6-(cyclopropanesulfonamido)pyrazin-2-yl)propyl)-4-(6-ethoxypyrazin-2-yl)-2-fluorobenzamide | Method 1 using INTC174 and INTD74, Chiral IC4 (19.90), [HPLC acidic], 501, (2.19) | 11.04 (s, 1H), 8.93 (s, 1H), 8.88 (d, J = 7.8 Hz, 1H), 8.36 (s, 1H), 8.33 (s, 1H), 8.22 (s, 1H), 8.09-8.03 (m, 2H), 7.79-7.74 (m, 1H), 5.02-4.94 (m, 1H), 4.51 (q, J = 7.0 Hz, 2H), 3.25-3.16 (m, 1H), 2.03-1.75 (m, 2H), 1.41 (t, J = 7.0 Hz, 3H), 1.18-1.11 (m, 2H), 1.11-1.02 (m, 2H), 0.98 (t, J = 7.3 Hz, 3H). |

2-(2-(Cyclopropanesulfonamido)pyrimidin 4-yl)-N-(5-(6-isopropylpyrazin-2-yl)pyridin-2-yl)-2-methylpropanamide P116

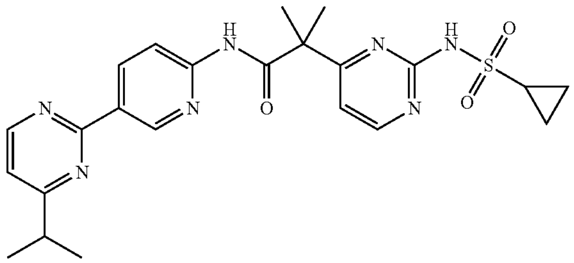 [SMILES: CC(C)c1ccnc(-c2ccc(NC(=O)C(C)(C)c3ccnc(NS(=O)(=O)C4CC4)n3)nc2)n1]

A solution of 2-(2-(cyclopropanesulfonamido)pyrimidin-4-yl)-2-methyl-N-(5-(6-(prop-1-en-2-yl)pyrazin-2-yl)pyridin-2-yl)propanamide P122 (77 mg, 0.161 mmol) in MeOH/DCM (4:1, 10 mL) was hydrogenated using the H-Cube flow hydrogenation apparatus (10% Pd/C, 30×4 mm, Full hydrogen, 25° C., 1 mL/min). The crude product was purified by chromatography on silica gel (12 g column, 50-100% EtOAc/iso-hexane) to afford 2-(2-(cyclopropanesulfonamido)pyrimidin-4-yl)-N-(5-(6-isopropylpyrazin-2-yl)pyridin-2-yl)-2-methylpropanamide (21 mg, 0.043 mmol, 27% yield) as a white solid. Rt 2.22 mins (HPLC acidic); m/z 482 $(M+H)^+$ $(ES^+)$; $^1H$ NMR (500 MHz, DMSO-d6) δ 11.23 (s, 1H), 10.15 (s, 1H), 9.10 (s, 1H), 9.03 (dd, J=2.4, 0.8 Hz, 1H), 8.59 (d, J=5.3 Hz, 1H), 8.56 (s, 1H), 8.52 (dd, J=8.8, 2.5 Hz, 1H), 8.21 (dd, J=8.8, 0.8 Hz, 1H), 7.19 (d, J=5.3 Hz, 1H), 3.23-3.10 (m, 2H), 1.61 (s, 6H), 1.32 (d, J=6.9 Hz, 6H), 1.04-0.97 (m, 2H), 0.80-0.72 (m, 2H).

1-(2-(Cyclopropanesulfonamido)pyrimidin-4-yl)-N-(5-(6-ethoxypyrazin-2-yl)pyridin-2-yl)-4-oxocyclohexanecarboxamide P226

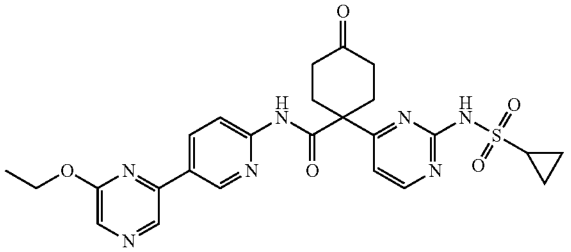 [SMILES: CCOc1cncc(-c2ccc(NC(=O)C3(c4ccnc(NS(=O)(=O)C5CC5)n4)CCC(=O)CC3)nc2)n1]

A solution of HCl (1N in water) (17.19 mL, 17.19 mmol) was added into a stirring solution of 8-(2-(cyclopropanesulfonamido)pyrimidin-4-yl)-N-(5-(6-ethoxypyrazin-2-yl)pyridin-2-yl)-1,4-dioxaspiro[4.5]decane-8-carboxamide P244 (1.0 g, 1.72 mmol) in THF (30 mL). The resulting reaction mixture was stirred at 30° C. for 14 days. The reaction mixture was diluted with EtOAc (200 mL) and washed with water (100 mL) and brine (100 mL). The organic extract was dried ($MgSO_4$), filtered and concentrated in vacuo. The crude product was purified by chromatography on silica gel (40 g cartridge, 0-100% EtOAc/iso-hexanes) to afford 1-(2-(cyclopropanesulfonamido)pyrimidin-4-yl)-N-(5-(6-ethoxypyrazin-2-yl)pyridin-2-yl)-4-oxocyclohexanecarboxamide (414 mg, 0.762 mmol, 44% yield) as a white solid. Rt 2.03 min (HPLC acidic); m/z 538 $(M+H)^+$ $(ES^+)$. $^1H$ NMR (500 MHz, DMSO-d6) δ 11.32 (s, 1H), 10.33 (s, 1H), 9.03 (d, J=2.5 Hz, 1H), 8.85 (s, 1H), 8.64

(d, J=5.3 Hz, 1H), 8.51 (dd, J=8.8, 2.5 Hz, 1H), 8.31-8.20 (m, 2H), 7.30 (d, J=5.3 Hz, 1H), 4.48 (q, J=7.0 Hz, 2H), 3.28-3.21 (m, 1H), 2.78-2.68 (m, 2H), 2.60-2.41 (m, 4H (obscured by DMSO)), 2.39-2.32 (m, 2H), 1.40 (t, J=7.0 Hz, 3H), 110-1.02 (m, 2H), 0.92-0.82 (m, 2H).

1-(2-(Cyclopropanesulfonamido)pyrimidin-4-yl)-N-(5-(6-ethoxypyrazin-2-yl)pyridin-2-yl)-4-hydroxycyclohexane-1-carboxamide

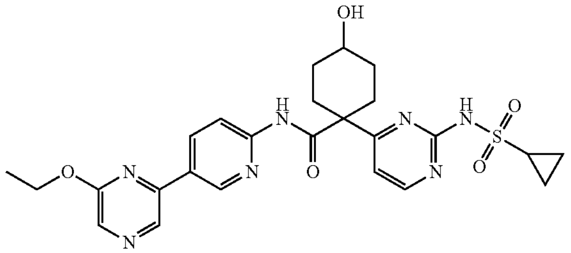 [SMILES: CCOc1cncc(-c2ccc(NC(=O)C3(c4ccnc(NS(=O)(=O)C5CC5)n4)CCC(O)CC3)nc2)n1]

$NaBH_4$ (10.6 mg, 0.28 mmol) was added into a stirring suspension of 1-(2-(cyclopropanesulfonamido)pyrimidin-4-yl)-N-(5-(6-ethoxypyrazin-2-yl)pyridin-2-yl)-4-oxocyclohexanecarboxamide P226 (100 mg, 0.186 mmol) in EtOH (20 mL) and stirred at RT for 3 hrs. The reaction mixture was concentrated in vacuo and the crude product was purified by chromatography on RP Flash C18 (24 g column, 0-100% MeCN/Water 0.1% formic acid) to afford two diastereoisomers of the title compound.

P227—First Eluting Peak from Column 1-(2-(cyclopropanesulfonamido)pyrimidin-4-yl)-N-(5-(6-ethoxypyrazin-2-yl)pyridin-2-yl)-4-hydroxycyclohexanecarboxamide (26 mg, 0.048 mmol, 26% yield) as a white solid. Rt 1.85 min (HPLC, acidic); m/z 540 $(M+H)^+$ $(ES^+)$; $^1H$ NMR (500 MHz, DMSO-d6) δ 11.24 (s, 1H), 10.05 (s, 1H), 9.06-8.98 (m, 1H), 8.85 (s, 1H), 8.57 (d, J=5.3 Hz, 1H), 8.51 (dd, J=8.8, 2.5 Hz, 1H), 8.26 (s, 1H), 8.23-8.20 (m, 1H), 7.19 (d, J=5.3 Hz, 1H), 4.58 (d, J=4.7 Hz, 1H), 4.48 (q, J=7.0 Hz, 2H), 3.56-3.45 (m, 1H), 3.29-3.22 (m, 1H), 2.60 (d, J=13.6 Hz, 2H), 1.91-1.77 (m, 4H), 1.52-1.37 (m, 5H), 1.07-0.99 (m, 2H), 0.88-0.78 (m, 2H).

P228—Second Eluting Peak from Column 1-(2-(cyclopropanesulfonamido)pyrimidin-4-yl)-N-(5-(6-ethoxypyrazin-2-yl)pyridin-2-yl)-4-hydroxycyclohexanecarboxamide (23 mg, 0.042 mmol, 22% yield) as a white solid. Rt 1.95 min (HPLC, acidic); m/z 540 $(M+H)^+$ $(ES^+)$; $^1H$ NMR (500 MHz, DMSO-d6) δ 11.31 (s, 1H), 9.75 (s, 1H), 9.02 (d, J=2.4 Hz, 1H), 8.83 (s, 1H), 8.62 (s, 1H), 8.48 (dd, J=8.8, 2.5 Hz, 1H), 8.25 (s, 1H), 8.13 (d, J=8.8 Hz, 1H), 7.29 (s, 1H), 4.51-4.44 (m, 3H), 3.70-3.62 (m, 1H), 3.29-3.20 (m, 1H), 2.22-2.11 (m, 2H), 1.80-1.68 (m, 2H), 1.41-1.29 (m, 7H), 1.11-1.05 (m, 2H), 0.96-0.88 (m, 2H).

1-(2-(Cyclopropanesulfonamido)pyrimidin-4-yl)-4-(dimethylamino)-N-(5-(6-ethoxypyrazin-2-yl)pyridin-2-yl)cyclohexane-1-carboxamide

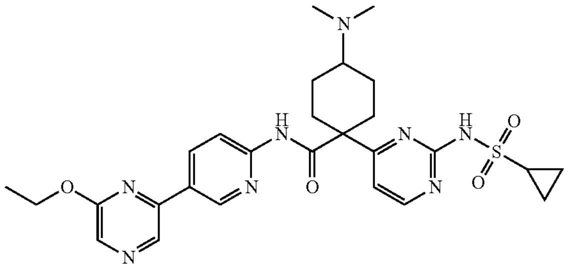 [SMILES: CCOc1cncc(-c2ccc(NC(=O)C3(c4ccnc(NS(=O)(=O)C5CC5)n4)CCC(N(C)C)CC3)nc2)n1]

$NaH(BOAc)_3$ (118 mg, 0.558 mmol) was added into a suspension of 1-(2-(cyclopropanesulfonamido)pyrimidin-4-yl)-N-(5-(6-ethoxypyrazin-2-yl)pyridin-2-yl)-4-oxocyclohexanecarboxamide (100 mg, 0.186 mmol) P226 and dimethylamine (2M in THF) (0.93 mL, 1.86 mmol) in DCM (10 mL) and the resulting reaction mixture was stirred at RT for 18 hrs. The reaction mixture was concentrated in vacuo and the crude product was purified by preparative HPLC (Acidic prep method (5-95% MeCN in water) to afford two diastereoisomers of the title compound.

P229—First Eluting Peak from Prep HPLC 1-(2-(cyclopropanesulfonamido)pyrimidin-4-yl)-4-(dimethylamino)-N-(5-(6-ethoxypyrazin-2-yl)pyridin-2-yl)cyclohexane-1-carboxamide (22 mg, 0.037 mmol, 20% yield) as a white solid. Rt 1.40 min (HPLC, acidic); m/z 567 $(M+H)^+$ $(ES^+)$; $^1H$ NMR (500 MHz, DMSO-d6) δ 10.17 (s, 1H), 9.02 (d, J=2.4 Hz, 1H), 8.84 (s, 1H), 8.60-8.44 (m, 2H), 8.25 (s, 1H), 8.22-8.20 (m, 2H), 7.09 (d, J=5.3 Hz, 1H), 4.48 (q, J=7.0 Hz, 2H), 3.28-3.20 (m, 1H), 2.72 (d, J=13.4 Hz, 2H), 2.32 (s, 6H), 2.25 (s, 1H), 1.91 (d, J=12.3 Hz, 2H), 1.79 (t, J=12.6 Hz, 2H), 1.51 (q, J=12.2 Hz, 2H), 1.40 (t, J=7.0 Hz, 3H), 1.03-0.98 (m, 2H), 0.87-0.73 (m, 2H).

P230—Second Eluting Peak from Prep HPLC 1-(2-(cyclopropanesulfonamido)pyrimidin-4-yl)-4-(dimethylamino)-N-(5-(6-ethoxypyrazin-2-yl)pyridin-2-yl)cyclohexane-1-carboxamide (26 mg, 0.045 mmol, 24% yield) as a white solid. Rt 1.48 min (HPLC, acidic); m/z 567 $(M+H)^+$ $(ES^+)$; $^1H$ NMR (500 MHz, DMSO-d6) δ 9.65 (s, 1H), 9.02 (d, J=2.4 Hz, 1H), 8.83 (s, 1H), 8.55 (d, J=5.2 Hz, 1H), 8.48 (dd, J=8.8, 2.4 Hz, 1H), 8.25 (s, 1H), 8.20 (s, 1H), 8.10 (d, J=8.8 Hz, 1H), 7.19 (d, J=5.3 Hz, 1H), 4.47 (q, J=7.0 Hz, 2H), 3.25-3.18 (m, 1H), 2.78-2.67 (m, 2H), 2.48-2.39 (m, 1H), 2.26 (s, 6H), 2.02 (t, J=12.4 Hz, 2H), 1.87-1.77 (m, 2H), 1.42-1.29 (m, 5H), 1.07-1.00 (m, 2H), 0.97-0.85 (m, 2H).

Method 11: i-PrMgCl Mediated Amide Coupling from Ester

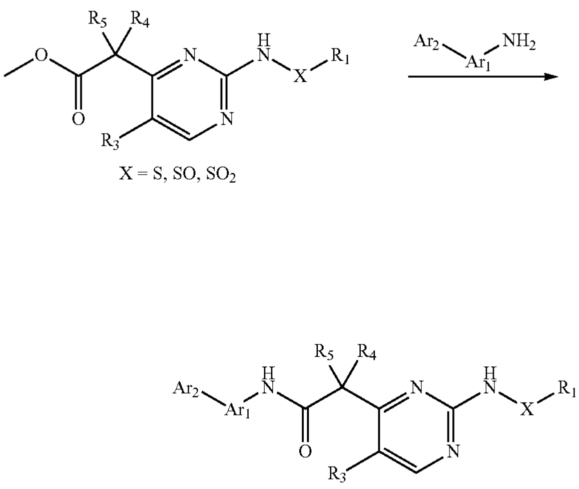

To an ice cooled solution of aniline (1.1 eq) in THF (10-50 volumes) was added i-PrMgCl (2.0 M in THF, 2.0 eq) dropwise over 5-15 mins to maintain an internal temperature of less than 10° C. The reaction mixture was warmed to RT over 45 mins, then a solution of ester (1.0 eq) in THF (5-volumes) was added dropwise over 5-15 min. The reaction mixture was stirred at ambient temperature for 5-15 mins then further i-PrMgCl (2.0 M in THF, 2.0 eq) was added dropwise over 5-20 min. The reaction mixture was stirred at RT for 30 mins and then the solution was slowly poured into 1M HCl (aq) and extracted with EtOAc. The organics were combined, dried (phase separator) and concentrated in vacuo. The crude product was purified by reverse or normal phase chromatography or a combination of both.

Reductive Amination General Method:

Method 12: Reductive Amination

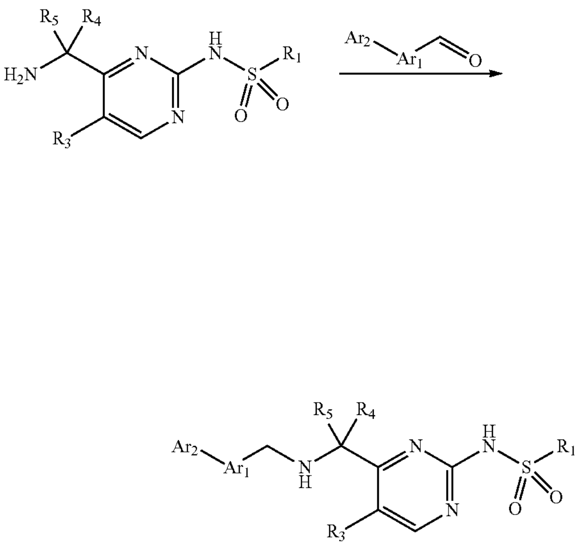

To a suspension of aldehyde (1.5 eq) and amine (HCl salt can be used, 1.0 eq) in an organic solvent such as DCM (2-10 volumes) was added AcOH (1.0 eq) at RT and stirred for up to 1 hr. $NaBH(OAc)_3$ (1-2 eq) was then added and stirring continued for up to 24 hrs and monitored by LCMS. On completion 1% $NH_3$ in MeOH (10 volumes) was added and the volatiles removed in vacuo. The crude product was purified by reverse or normal phase chromatography or a combination of both.

N-(4-(1-((4-(6-Ethoxypyrazin-2-yl)-2-fluorobenzyl)amino)propyl)pyrimidin-2-yl)cyclopropanesulfonamide P235

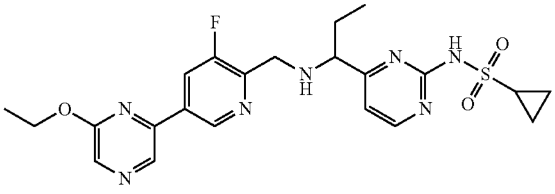 [SMILES: CCOc1cncc(-c2cnc(CNC(CC)c3ccnc(NS(=O)(=O)C4CC4)n3)c(F)c2)n1]

A suspension of 4-(6-ethoxypyrazin-2-yl)-2-fluorobenzaldehyde INTD88 (259 mg, 1.05 mmol) and N-(4-(1-aminopropyl)pyrimidin-2-yl)cyclopropanesulfonamide INTC162 (300 mg, 1.05 mmol) in DCM (2 mL) was treated with AcOH (0.065 mL, 1.14 mmol) and stirred for 15 mins then $NaBH(OAc)_3$ (223 mg, 1.06 mmol) was added and the reaction mixture was stirred at RT for 3 hrs. To the reaction mixture was added 1% $NH_3$ in MeOH (2 mL) and the volatiles were removed in vacuo. The crude product was purified by chromatography on RP Flash C18 (12 g cartridge, 15-70% MeCN/10 mM ammonium bicarbonate). The crude material was purified by capture and release on SCX (1 g) eluting with MeOH (20 mL) then removing product with 1% $NH_3$ in MeOH (30 mL). The crude material was finally purified a second time by chromatography on RP Flash C18 (12 g cartridge, 10-50% MeCN/10 mM Ammonium Bicarbonate) to afford N-(4-(1-((4-(6-ethoxypyrazin-2-yl)-2-fluorobenzyl)amino)propyl)pyrimidin-2-yl)cyclopropanesulfonamide (20 mg, 0.031 mmol, 3% yield) as a yellow gum. Rt 2.02 min (HPLC, basic); m/z 487 $(M+H)^+$ $(ES^+)$; $^1H$ NMR (500 MHz, DMSO-d6) δ 8.85 (s, 1H), 8.27-8.26 (m, 2H), 7.96 (d, J=7.8 Hz, 1H), 7.87 (d, J=11.4 Hz, 1H), 7.67-7.58 (m, 1H), 7.23 (d, J=5.1 Hz, 1H), 5.38 (t, J=5.7 Hz, 1H), 4.62 (d, J=5.8 Hz, 2H), 4.49 (q, J=7.1 Hz, 2H), 3.52-3.50 (m, 1H), 1.71-1.67 (m, 2H), 1.41 (t, J=7.0 Hz, 3H), 1.13-1.09 (m, 2H), 1.04-1.01 (m, 2H), 0.84 (t, J=7.4 Hz, 3H). Two exchangeable protons not observed.

TABLE 21

| P# | Name/Structure (All examples containing chiral centres are racemates unless stated) | Synthesis Method, [LCMS Method], m/z (M + H)+, (Rt/Min) | 1H NMR Chemical Shift Data (DMSO-d6 unless stated) |
|---|---|---|---|
| Preparation methods and characterisation data of examples P242 onwards | | | |
| P242 | 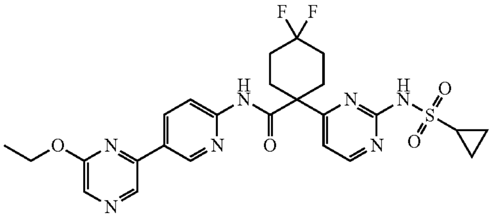 1-(2-(cyclopropanesulfonamido)pyrimidin-4-yl)-N-(5-(6-ethoxypyrazin-2-yl)pyridin-2-yl)-4,4-difluorocyclohexane-1-carboxamide | Method 11: using INTC212 and INTD33, [HPLC Acidic], 560, (2.42) | 11.33 (s, 1H), 10.23 (s, 1H), 9.03 (dd, J = 2.5, 0.8 Hz, 1H), 8.85 (s, 1H), 8.63 (d, J = 5.3 Hz, 1H), 8.51 (dd, J = 8.8, 2.5 Hz, 1H), 8.26 (s, 1H), 8.19 (dd, J = 8.8, 0.8 Hz, 1H), 7.26 (d, J = 5.4 Hz, 1H), 4.48 (q, J = 7.1 Hz, 2H), 3.27-3.18 (m, 1H), 2.65-2.53 (m, 2H), 2.29-2.18 (m, 2H), 2.13-2.01 (m, 4H), 1.40 (t, J = 7.0 Hz, 3H), 1.11-1.02 (m, 2H), 0.92-0.83 (m, 2H). |
| P244 | 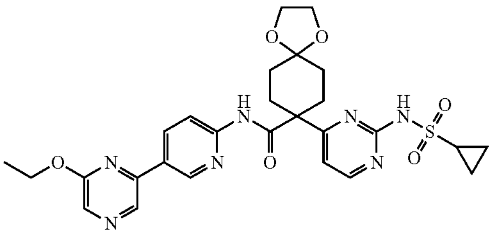 8-(2-(cyclopropanesulfonamido)pyrimidin-4-yl)-N-(5-(6-ethoxypyrazin-2-yl)pyridin-2-yl)-1,4-dioxaspiro[4.5]decane-8-carboxamide | Method 11: using INTC214 and INTD33, [HPLC Acidic], 582, (2.20) | 11.29 (s, 1H), 10.05 (s, 1H), 9.02 (dd, J = 2.5, 0.8 Hz, 1H), 8.84 (s, 1H), 8.60 (d, J = 5.3 Hz, 1H), 8.50 (dd, J = 8.8, 2.5 Hz, 1H), 8.26 (s, 1H), 8.22-8.11 (m, 1H), 7.23 (s, 1H), 4.48 (q, J = 7.0 Hz, 2H), 3.88 (s, 4H), 3.28-3.18 (m, 1H), 2.55-2.47 (m, 2H obscured by water peak), 2.27-2.13 (m, 2H), 1.79-1.62 (m, 4H), 1.40 (t, J = 7.0 Hz, 3H), 1.09-1.00 (m, 2H), 0.94-0.80 (m, 2H). |
| P248 | 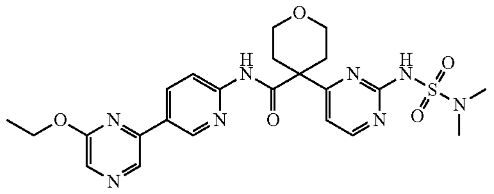 4-(2-((N,N-dimethylsulfamoyl)amino)pyrimidin-4-yl)-N-(5-(6-ethoxypyrazin-2-yl)pyridin-2-yl)tetrahydro-2H-pyran-4-carboxamide | Method R: using INTC204, [HPLC Acidic], 529, (2.10) | 11.04 (s, 1H), 10.02 (s, 1H), 9.04 (d, J = 2.5 Hz, 1H), 8.85 (s, 1H), 8.60 (d, J = 5.3 Hz, 1H), 8.51 (dd, J = 8.8, 2.5 Hz, 1H), 8.26 (s, 1H), 8.19 (d, J = 8.8 Hz, 1H), 7.22 (d, J = 5.3 Hz, 1H), 4.48 (q, J = 7.0 Hz, 2H), 3.73-3.57 (m, 4H), 2.84 (s, 6H), 2.47-2.37 (m, 2H), 2.28-2.17 (m, 2H), 1.40 (t, J = 7.0 Hz, 3H). |
| P251 | 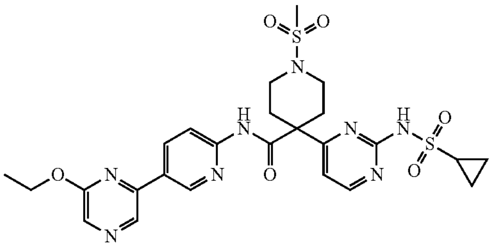 4-(2-(cyclopropanesulfonamido)pyrimidin-4-yl)-N-(5-(6-ethoxypyrazin-2-yl)pyridin-2-yl)-1-(methylsulfonyl)piperidine-4-carboxamide | Method 11: using INTC215 and INTD33, [HPLC Acidic], 603, (2.05) | 11.33 (s, 1H), 10.27 (s, 1H), 9.03 (d, J = 2.4 Hz, 1H), 8.85 (s, 1H), 8.63 (d, J = 5.3 Hz, 1H), 8.54-8.48 (m, 1H), 8.26 (s, 1H), 8.21 (d, J = 8.8 Hz, 1H), 7.26 (d, J = 5.3 Hz, 1H), 4.48 (q, J = 7.0 Hz, 2H), 3.47-3.40 (m, 2H), 3.29-3.21 (m, 1H), 3.10 (t, J = 10.7 Hz, 2H), 2.87 (s, 2H), 2.64-2.57 (m, 2H), 2.33-2.21 (m, 2H), 1.43-1.37 (m, 3H), 1.32-1.09 (m, 1H), 1.09-1.04 (m, 2H), 0.92-0.80 (m, 2H). |

TABLE 21-continued

Preparation methods and characterisation data of examples P242 onwards

| P# | Name/Structure (All examples containing chiral centres are racemates unless stated) | Synthesis Method, [LCMS Method], m/z (M + H)+, (Rt/Min) | $^1H$ NMR Chemical Shift Data (DMSO-d6 unless stated) |
|---|---|---|---|
| P254 | 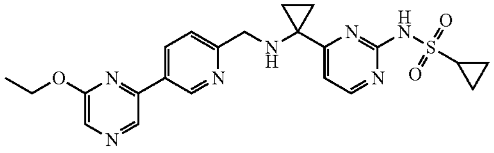 N-(4-(1-(((5-(6-ethoxypyrazin-2-yl)pyridin-2-yl)methyl)amino)cyclopropyl)pyrimidin-2-yl)cyclopropanesulfonamide | Method 12 using INTC156 and INTD85, [UPLC Basic], 468, (1.07) | 11.08 (s, 1H), 9.22 (d, J = 2.3 Hz, 1H), 8.88 (s, 1H), 8.50-8.42 (m, 2H), 8.29 (s, 1H), 7.64 (d, J = 8.2 Hz, 1H), 7.43 (d, J = 5.2 Hz, 1H), 4.50 (q, J = 7.0 Hz, 2H), 3.94 (s, 2H), 3.16-3.13 (m, 1H), 1.41 (t, J = 7.0 Hz, 3H), 1.38-1.33 (m, 2H), 1.26-1.21 (m, 2H), 1.09-0.99 (m, 4H). One exchangeable proton not observed |
| P255 | 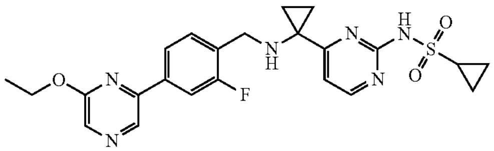 N-(4-(1-((4-(6-ethoxypyrazin-2-yl)-2-fluorobenzyl)amino)cyclopropyl)pyrimidin-2-yl)cyclopropanesulfonamide | Method 12 using INTC156 and INTD88, [UPLC Basic], 485, (1.36) | 11.06 (s, 1H), 8.86 (d, J = 2.4 Hz, 1H), 8.48 (s, 1H), 8.27 (d, J = 2.5 Hz, 1H), 7.97 (d, J = 8.3 Hz, 1H), 7.90 (d, J = 11.5 Hz, 1H), 7.70-7.63 (m, 1H), 7.43 (s, 1H), 4.53-4.45 (m, 2H), 3.84 (s, 2H), 3.16-3.12 (m, 1H), 1.44-1.39 (m, 3H), 1.38-1.32 (m, 2H), 1.27-1.21 (m, 2H), 1.09-1.01 (m, 4H). One exchangeable proton not observed |
| P256 | 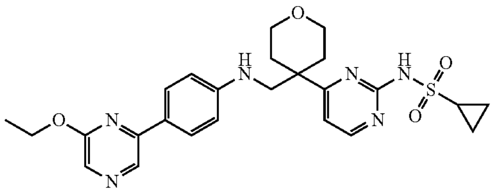 N-(4-(4-(((4-(6-ethoxypyrazin-2-yl)phenyl)amino)methyl)tetrahydro-2H-pyran-4-yl)pyrimidin-2-yl)cyclopropanesulfonamide | Method R using INTC207, [HPLC Acidic], 511, (2.19) | 11.23 (s, 1H), 8.57 (s, 1H), 8.51 (d, J = 5.3 Hz, 1H), 8.00 (s, 1H), 7.83-7.74 (m, 2H), 7.22 (d, J = 5.1 Hz, 1H), 6.67-6.59 (m, 2H), 6.02 (d, J = 6.5 Hz, 1H), 4.42 (q, J = 7.0 Hz, 2H), 3.80-3.69 (m, 2H), 3.42-3.27 (m, 4H), 3.25-3.17 (m, 1H), 2.34-2.25 (m, 2H), 1.89-1.80 (m, 2H), 1.38 (t, J = 7.0 Hz, 3H), 1.14-1.06 (m, 2H), 1.07-0.98 (m, 2H |
| P258 | 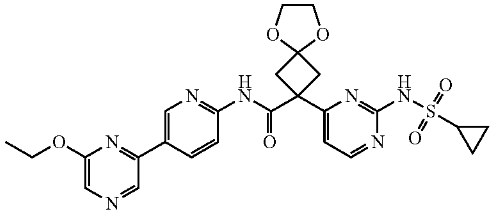 2-(2-(cyclopropanesulfonamido)pyrimidin-4-yl)-N-(5-(6-ethoxypyrazin-2-yl)pyridin-2-yl)-5,8-dioxaspiro[3.4]octane-2-carboxamide | Method 11: using INTC216 and INTD33, [UPLC acidic], 554, (1.32) | 11.31 (s, 1H), 10.56 (s, 1H), 9.03 (d, J = 2.4 Hz, 1H), 8.84 (s, 1H), 8.60 (d, J = 5.3 Hz, 1H), 8.51 (dd, J = 8.8, 2.5 Hz, 1H), 8.26-8.20 (m, 2H), 7.30 (d, J = 5.3 Hz, 1H), 4.48 (q, J = 7.0 Hz, 2H), 3.89-3.78 (m, 4H), 3.32-3.25 (m, 1H), 3.18-3.11 (m, 2H), 2.99-2.92 (m, 2H), 1.39 (t, J = 7.0 Hz, 3H), 1.10-1.01 (m, 2H), 0.94-0.87 (m, 2H). |
| P260 | 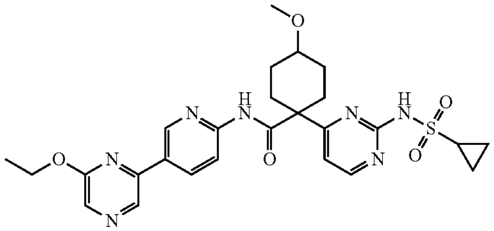 Mix of diastereoisomers: 1-(2-(cyclopropanesulfonamido)pyrimidin-4-yl)-N-(5-(6-ethoxypyrazin-2-yl)pyridin-2-yl)-4-methoxycyclohexane-1-carboxamide | Method 11: using INTC218 and INTD33, [HPLC Acidic], 554, (2.17 and 2.27) | 11.26 (s, 1H), 10.04 (s, 1H), 9.02 (d, J = 2.4 Hz, 1H), 8.84 (d, J = 1.9 Hz, 1H), 8.60 (d, J = 5.6 Hz, 1H), 8.55-8.46 (m, 1H), 8.25 (s, 1H), 8.22-8.14 (m, 1H), 7.22 (d, J = 5.4 Hz, 1H), 4.48 (qd, J = 7.0, 2.3 Hz, 2H), 3.30-3.18 (m, 4H), 2.59 (d, J = 13.3 Hz, 2H), 2.40-2.19 (m, 1H), 1.97-1.84 (m, 2H), 1.83-1.50 (m, 2H), 1.48-1.36 (m, 4H), 1.11-0.98 (m, 2H), 0.94-0.71 (m, 3H). |

TABLE 21-continued

| Preparation methods and characterisation data of examples P242 onwards | | | |
|---|---|---|---|
| P# | Name/Structure (All examples containing chiral centres are racemates unless stated) | Synthesis Method, [LCMS Method], m/z (M + H)+, (Rt/Min) | $^1$H NMR Chemical Shift Data (DMSO-d6 unless stated) |
| P261 | 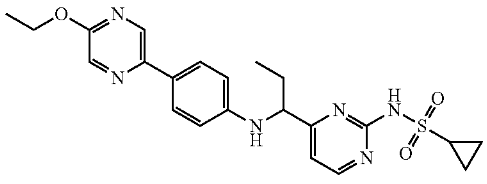 N-(4-(1-((4-(6-ethoxypyrazin-2-yl)phenyl)amino)propyl)pyrimidin-2-yl)cyclopropanesulfonamidearboxamide | Method 12 using INTC155 and INTD18, [UPLC Acidic], 455, (1.48) | Methanol-d4, 8.45-8.39 (m, 2H), 7.90 (s, 1H), 7.86-7.81 (m, 2H), 7.70-7.62 (m, 1H), 7.61-7.54 (m, 1H), 7.12 (d, J = 5.2 Hz, 1H), 6.69-6.64 (m, 2H), 4.49 (q, J = 7.1 Hz, 2H), 4.45-4.39 (m, 1H), 3.24-3.15 (m, 1H), 2.06-1.85 (m, 2H), 1.44 (t, J = 7.1 Hz, 3H), 1.34-1.25 (m, 1H), 1.24-1.15 (m, 1H), 1.09 (t, J = 7.4 Hz, 3H), 1.07-1.00 (m, 1H), 0.96-0.86 (m, 1H). |

Examples of compounds of formula (I) wherein B is

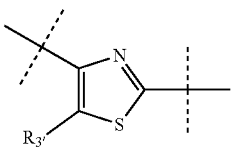

are disclosed in WO2019/106156 and WO2019/106146. INTE9 and INTB35 are also disclosed therein.

N-((2-(cyclopropanesulfonamido)thiazol-4-yl)methyl)-4-(pyridin-3-yl)benzamide R1

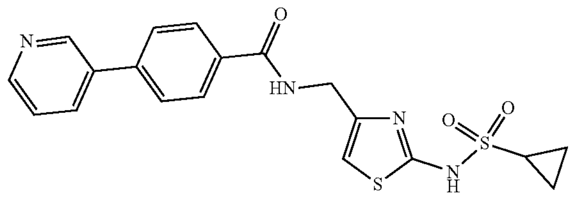 [SMILES: O=C(NCc1csc(NS(=O)(=O)C2CC2)n1)c1ccc(-c2cccnc2)cc1]

A solution of N-(4-(aminomethyl)thiazol-2-yl)cyclopropanesulfonamide INTE9 (64 mg, 0.274 mmol), 4-(pyridin-3-yl)benzoic acid (54.6 mg, 0.274 mmol) and DIPEA (0.14 mL, 0.82 mmol) in DMF (0.5 mL) was treated with HATU (110 mg, 0.288 mmol) and stirred at RT for 18 hrs. EtOAc (20 mL) was added and the organic phase was washed with water (10 mL) and brine (10 mL), dried ($Na_2SO_4$), filtered and concentrated onto silica (300 mg). The crude product was purified by chromatography on silica (12 g column, 0-7% (0.7 M ammonia/MeOH)/DCM). The crude product was further purified by reverse phase chromatography on C18 silica (12 g column, 10-40% MeCN/water 0.1% formic acid) to afford N-((2-(cyclopropanesulfonamido)thiazol-4-yl)methyl)-4-(pyridin-3-yl)benzamide (18 mg, 0.041 mmol, 15% yield) as a colourless solid. Rt 1.08 min (HPLC, HPLC Acidic); m/z 415 $(M+H)^+$ $(ES^+)$; $^1$H NMR (400 MHz, DMSO-$d_6$) δ 12.57 (s, 1H), 9.04-8.94 (m, 2H), 8.62 (dd, J=4.8, 1.6 Hz, 1H), 8.17-8.14 (m, 1H), 8.06-7.98 (m, 2H), 7.92-7.84 (m, 2H), 7.50-7.48 (m, 1H), 6.53 (s, 1H), 4.35-4.33 (m, 2H), 2.64-2.52 (m, 1H), 0.09-0.87 (m, 4H).

N-([1,1'-biphenyl]-4-yl)-2-(2-(methylsulfonamido)thiazol-4-yl)acetamide T1

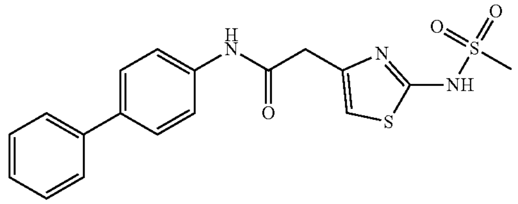 [SMILES: CS(=O)(=O)Nc1nc(CC(=O)Nc2ccc(-c3ccccc3)cc2)cs1]

HATU (133 mg, 0.35 mmol) was added to a solution of 2-(2-(cyclopropanesulfonamido)thiazol-4-yl)acetic acid INTB35 (75 mg, 0.32 mmol), [1,1'-biphenyl]-4-amine (53 mg, 0.32 mmol) and DIPEA (166 uL, 0.95 mmol) in DMF (1 mL) at RT. The reaction was stirred at RT for 18 hrs. The reaction mixture was acidified with addition of formic acid (100 uL), shaken for 5 min then filtered. The crude product was purified by preparative HPLC (Waters, Acidic (0.1% Formic acid), Acidic, Waters X-Select Prep-C18, 5 um, 19×50 mm column, 25-55% MeCN in Water) to afford N-([1,1'-biphenyl]-4-yl)-2-(2-(methylsulfonamido)thiazol-4-yl)acetamide; Rt 1.26 min (UPLC acidic); m/z 388 $(M+H)^+$ (ES+); $^1$H NMR (400 MHz, DMSO-d6) δ 12.51 (s, 1H), 10.27 (s, 1H), 7.77-7.58 (m, 5H), 7.53-7.39 (m, 2H), 7.39-7.26 (m, 2H), 6.59 (s, 1H), 3.67 (s, 2H), 2.90 (s, 3H).

TABLE 22

| P# | Name/Structure (All examples containing chiral centres are racemates unless stated) | Synthesis Method, [LCMS Method], m/z (M + H)*, (Rt/Min) | $^1$H NMR Chemical Shift Data (DMSO-d6 unless stated) |
|---|---|---|---|
| Preparation methods and characterisation data of examples P271 and P284 | | | |
| P271 | 4-(2-((2,2-difluoroethyl)sulfonamido)pyrimidin-4-yl)-N-(5-(6-ethoxypyrazin-2-yl)pyridin-2-yl)tetrahydro-2H-pyran-4-carboxamide 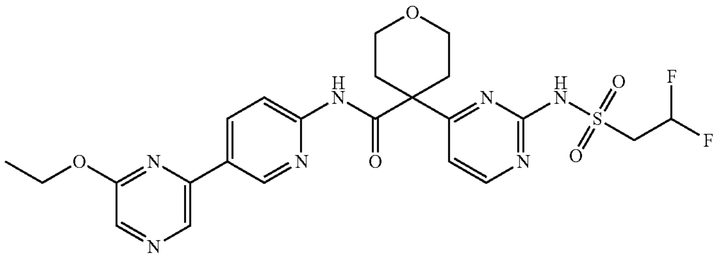 | Method R using INTC204, [HPLC Acidic], 550, (2.05) | 11.97 (s, 1H), 10.19 (s, 1H), 9.03 (dd, J = 2.5, 0.8 Hz, 1H), 8.84 (s, 1H), 8.64 (d, J = 5.4 Hz. 1H), 8.49 (dd, J = 8.8, 2.5 Hz, 1H), 8.25 (s, 1H), 8.21 (dd, J = 8.8, 0.8 Hz, 1H), 7.28 (d, J = 5.4 Hz, 1H), 6.36 (tt, J = 54.6, 4.4 Hz, 1H), 4.48 (q, J = 7.0 Hz, 2H), 4.36-4.26 (m. 2H), 3.75 (dt, J = 11.8, 4.3 Hz, 2H), 3.65-3.57 (m, 2H), 2.47 (d, J = 13.3 Hz, 2H), 2.18 (ddd, J = 13.1, 9.4, 4.4 Hz, 2H), 1.40 (t, J = 7.0 Hz, 3H). |
| P284 | 2-(2-((2,2-difluoroethyl)sulfonamido)pyrimidin-4-yl)-N-(5-(6-ethoxypyrazin-2-yl)pyridin-2-yl)-2-fluorobutanamide 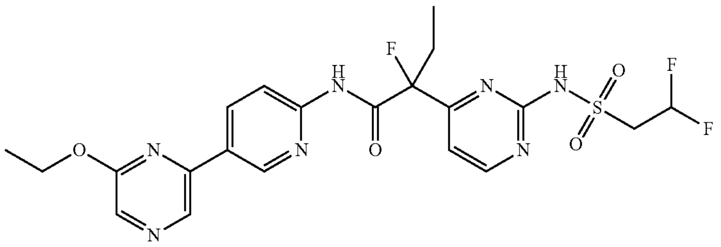 | Method R using INTC230, [HPLC Acidic], 526, (2.29) | No $^1$H NMR data available |

BIOLOGICAL EXAMPLES

Biological Example 1—Human CTPS1 Enzyme Inhibition

The enzyme inhibitory activities of compounds invented against the target of interest were determined using the ADP-Glo™ Max assay (Promega, UK). Assays for human CTPS1 were performed in 1× assay buffer containing 50 mM Tris, 10 mM $MgCl_2$, 0.01% Tween-20, pH to 8.0 accordingly. Finally, immediately before use, L-cysteine was added to the 1× assay buffer to a final concentration of 2 mM. All reagents are from Sigma-Aldrich unless specified otherwise. Human full length active C-terminal FLAG-Hiss-tag CTPS1 (UniProtKB—P17812, CTPS[1-591]-GGDYKDDDDKGGHHHHHHHH) was obtained from Proteros biostructures GmbH.

Assay Procedure

3× human CTPS1 protein was prepared in 1× assay buffer to the final working protein concentration required for the reaction. A 2 uL volume per well of 3× human CTPS1 protein was mixed with 2 uL per well of 3× test compound (compound prepared in 1× assay buffer to an appropriate final 3× compound concentration respective to the concentration response curve designed for the compounds under test) for 10 minutes at 25° C. The enzymatic reaction was then initiated by addition of a 2 uL per well volume of a pre-mixed substrate mix (UltraPure ATP from ADP-Glo™ Max kit (0.31 mM), GTP (0.034 mM), UTP (0.48 mM) and L-glutamine (0.186 mM)) and the mixture was incubated for an appropriate amount of time within the determined linear phase of the reaction at 25° C. under sealed plate conditions with constant agitation at 500 revolutions per minute (rpm). ADP-Glo™ Max reagent was added for 60 minutes (6 μL per well) and subsequently ADP-Glo™ Max development reagent was added for 60 minutes (12 uL per well) prior to signal detection in a microplate reader (EnVision® Multilabel Reader, Perkin Elmer). Following each reagent addition over the course of the assay, assay plates were pulse centrifuged for 30 seconds at 500 rpm.

In all cases, the enzyme converts ATP to ADP and the ADP-Glo™ Max reagent subsequently depletes any remaining endogenous ATP in the reaction system. The ADP-Glo™ Max detection reagent converts the ADP that has been enzymatically produced back into ATP and using ATP as a substrate together with luciferin for the enzyme luciferase, light is generated which produces a detectable luminescence. The luminescent signal measured is directly proportional to the amount of ADP produced by the enzyme reaction and a reduction in this signal upon compound treatment demonstrates enzyme inhibition. The percentage inhibition produced by each concentration of compound was calculated using the equation shown below:

$$\% \text{ Inhibition} = 1 - \frac{(\text{Mean}_{Min} - \text{Mean}_{Inh})}{(\text{Mean}_{Min} - \text{Mean}_{Max})} \times 100$$

Percentage inhibition was then plotted against compound concentration, and the 50% inhibitory concentration ($IC_{50}$) was determined from the resultant concentration-response curve.

The data for a range of compounds tested are presented below.

TABLE 23

Human CTPS1 Enzyme Inhibition data grouped by potency range (± indicates $IC_{50}$ in the range of >10 to 20 micromolar, + indicates $IC_{50}$ in the range >1 to 10 micromolar, ++ indicates $IC_{50}$ in the range >0.1 to 1 micromolar, +++ indicates $IC_{50}$ of ≤0.1 micromolar)

| P | CTPS1 |
|---|---|
| P1 | ++ |
| P2 | +++ |
| P3 | +++ |
| P4 | ++ |
| P5 | + |
| P6 | ++ |
| P7 | ++ |
| P8 | +++ |
| P9 | +++ |
| P10 | +++ |
| P11 | +++ |
| P12 | +++ |
| P13 | ++ |
| P14 | ++ |
| P15 | + |
| P16 | ++ |
| P17 | + |
| P18 | +++ |
| P19 | +++ |
| P20 | +++ |
| P21 | +++ |
| P22 | ++ |
| P23 | ++ |
| P24 | ++ |
| P25 | ++ |
| P26 | ++ |
| P27 | +++ |
| P28 | ++ |
| P29 | + |
| P30 | +++ |
| P31 | +++ |
| P32 | +++ |
| P33 | +++ |
| P34 | +++ |
| P35 | ++ |
| P36 | + |
| P37 | +++ |
| P38 | +++ |
| P39 | +++ |
| P40 | ++ |
| P41 | +++ |
| P42 | + |
| P43 | ++ |
| P44 | ++ |
| P45 | ++ |
| P46 | ++ |
| P47 | +++ |
| P48 | ++ |
| P49 | +++ |
| P50 | + |
| P51 | ++ |
| P52 | ++ |
| P53 | ++ |
| P54 | ++ |
| P55 | +++ |
| P56 | ++ |
| P57 | ++ |
| P58 | ++ |

TABLE 23-continued

Human CTPS1 Enzyme Inhibition data grouped by potency range (± indicates $IC_{50}$ in the range of >10 to 20 micromolar, + indicates $IC_{50}$ in the range >1 to 10 micromolar, ++ indicates $IC_{50}$ in the range >0.1 to 1 micromolar, +++ indicates $IC_{50}$ of ≤0.1 micromolar)

| P | CTPS1 |
|---|---|
| P59 | + |
| P60 | + |
| P61 | + |
| P62 | + |
| P63 | ± |
| P64 | +++ |
| P65 | +++ |
| P66 | ++ |
| P67 | +++ |
| P68 | ++ |
| P69 | ++ |
| P70 | + |
| P71 | + |
| P72 | ++ |
| P73 | ++ |
| P74 | ++ |
| P75 | ++ |
| P76 | ++ |
| P77 | + |
| P78 | ++ |
| P79 | ++ |
| P80 | ++ |
| P81 | +++ |
| P82 | + |
| P83 | +++ |
| P84 | ++ |
| P85 | ++ |
| P86 | + |
| P87 | +++ |
| P88 | +++ |
| P89 | +++ |
| P90 | ++ |
| P91 | ++ |
| P92 | ++ |
| P93 | + |
| P94 | +++ |
| P95 | +++ |
| P96 | +++ |
| P97 | +++ |
| P98 | +++ |
| P99 | ++ |
| P100 | ++ |
| P101 | ++ |
| P102 | ++ |
| P103 | ++ |
| P104 | ++ |
| P105 | +++ |
| P106 | +++ |
| P107 | +++ |
| P108 | +++ |
| P109 | ++ |
| P110 | +++ |
| P111 | ++ |
| P112 | +++ |
| P113 | +++ |
| P114 | +++ |
| P115 | +++ |
| P116 | ++ |
| P117 | +++ |
| P118 | +++ |
| P122 | ++ |
| P123 | ++ |
| P124 | ++ |
| P125 | ++ |
| P126 | +++ |
| P128 | ++ |
| P129 | ++ |
| P130 | ++ |
| P131 | ++ |
| P132 | ++ |
| P133 | + |
| P134 | ++ |

TABLE 23-continued

Human CTPS1 Enzyme Inhibition data grouped by potency range (± indicates $IC_{50}$ in the range of >10 to 20 micromolar, + indicates $IC_{50}$ in the range >1 to 10 micromolar, ++ indicates $IC_{50}$ in the range >0.1 to 1 micromolar, +++ indicates $IC_{50}$ of ≤0.1 micromolar)

| P | CTPS1 |
|---|---|
| P135 | ++ |
| P136 | +++ |
| P137 | +++ |
| P138 | ++ |
| P139 | ++ |
| P140 | ++ |
| P141 | ++ |
| P142 | ++ |
| P143 | +++ |
| P144 | +++ |
| P145 | +++ |
| P146 | +++ |
| P147 | ++ |
| P148 | +++ |
| P149 | +++ |
| P150 | +++ |
| P151 | +++ |
| P152 | +++ |
| P153 | +++ |
| P154 | +++ |
| P155 | +++ |
| P156 | +++ |
| P157 | +++ |
| P158 | ++ |
| P159 | +++ |
| P160 | +++ |
| P161 | +++ |
| P162 | +++ |
| P163 | +++ |
| P164 | +++ |
| P165 | +++ |
| P166 | +++ |
| P167 | ++ |
| P168 | ++ |
| P169 | ++ |
| P170 | ++ |
| P171 | + |
| P172 | ++ |
| P173 | +++ |
| P174 | + |
| P175 | + |
| P176 | + |
| P177 | + |
| P178 | + |
| P179 | + |
| P180 | + |
| P181 | + |
| P182 | ++ |
| P183 | ++ |
| P184 | ++ |
| P185 | + |
| P186 | +++ |
| P187 | ++ |
| P188 | +++ |
| P189 | + |
| P190 | ++ |
| P191 | ++ |
| P192 | + |
| P193 | + |
| P194 | 58.6 uM |
| P195 | +++ |
| P196 | +++ |
| P197 | +++ |
| P198 | +++ |
| P199 | ++ |
| P200 | +++ |
| P201 | +++ |
| P202 | +++ |
| P203 | +++ |
| P204 | +++ |
| P205 | +++ |
| P206 | +++ |
| P207 | +++ |
| P208 | +++ |
| P209 | ++ |
| P210 | ++ |
| P211 | ++ |
| P212 | ++ |
| P213 | ++ |
| P214 | ++ |
| P215 | ++ |
| P216 | +++ |
| P217 | ++ |
| P218 | +++ |
| P219 | ++ |
| P220 | ++ |
| P221 | ++ |
| P222 | ++ |
| P223 | ++ |
| P224 | ++ |
| P225 | +++ |
| R1 | ++ |
| T1 | + |

TABLE 24

Human CTPS1 Enzyme Inhibition data grouped by potency range (± indicates $IC_{50}$ in the range of >10 to 20 micromolar, + indicates $IC_{50}$ in the range >1 to 10 micromolar, ++ indicates $IC_{50}$ in the range >0.1 to 1 micromolar, +++ indicates $IC_{50}$ of ≤0.1 micromolar)

| P | CTPS1 | P | CTPS1 |
|---|---|---|---|
| P226 | +++ | P248 | ++ |
| P227 | +++ | P251 | +++ |
| P228 | + | P254 | ++ |
| P229 | +++ | P255 | ++ |
| P230 | +++ | P256 | ++ |
| P235 | ++ | P258 | +++ |
| P242 | +++ | P260 | +++ |
| P244 | +++ | P261 | ++ |

The data for all compounds of formula (I) tested wherein $R_1$ is $C_{1-5}$fluoroalkyl, with the proviso that $R_1$ is not $CF_3$ are presented below.

TABLE 25

Human CTPS1 Enzyme Inhibition data grouped by potency range (± indicates $IC_{50}$ in the range of >10 to 20 micromolar, + indicates $IC_{50}$ in the range >1 to 10 micromolar, ++ indicates $IC_{50}$ in the range >0.1 to 1 micromolar, +++ indicates $IC_{50}$ of ≤0.1 micromolar)

| P | CTPS1 |
|---|---|
| P271 | +++ |
| P284 | +++ |

All compounds of the invention which have been tested were found to demonstrate inhibition of CTPS1 enzyme in this assay. Consequently, these compounds may be expected to have utility in the inhibition of CTPS1. The compounds of the invention are also expected to have utility as research tools, for example, for use in CTPS assays.

Biological Example 2—RapidFire/MS-Based Enzyme Selectivity Assays

Human CTPS1 versus CTPS2 Selectivity Assessment by RapidFire/MS Analysis.

The enzyme inhibitory activities against each target isoform of interest may be determined for the compounds of the invention using an optimised RapidFire high-throughput mass spectrometry (RF/MS) assay format. RF/MS assays for both human CTPS1 and CTPS2 may be performed in assay buffer consisting of 50 mM HEPES (Merck), 20 mM $MgCl_2$, 5 mM KCl, 1 mM DTT, 0.01% Tween-20, pH to 8.0 accordingly. Human full-length active C-terminal FLAG-His-tag CTPS1 (UniProtKB—P17812, CTPS[1-591]-GGDYKDDDDKGGHHHHHHHH) may be obtained from Proteros biostructures GmbH. Human full length active C-terminal FLAG-His-Avi tagged CTPS2 (UniProtKB-Q9NRF8, CTPS2 [1-586]-DYKDDDDKHHHHHHGLN-DIFEAQKIEWHE) may be obtained from Harker Bio.

Assay Procedure

Human CTPS (1 or 2) protein may be prepared in 1× assay buffer to the final working protein concentration required for the reaction. A 2 uL volume per well of 2×CTPS (1 or 2) protein may be mixed with 40 nL of compound using acoustic (ECHO) delivery and incubated for 10 minutes at 25° C. Each isoform enzymatic reaction may be subsequently initiated by addition of 2 uL per well of a 2× substrate mix in assay buffer. For hCTPS1: ATP (0.3 mM), UTP (0.2 mM), GTP (0.07 mM) and L-glutamine (0.1 mM). For hCTPS2: ATP (0.1 mM), UTP (0.04 mM), GTP (0.03 mM) and L-glutamine (0.1 mM). Each mixture may be incubated for an appropriate amount of time per isoform within the determined linear phase of the reaction at 25'C. A 60 uL volume of stop solution (1% formic acid with 0.5 uM $^{13}C_9$-$^{15}N_3$-CTP in $H_2O$) may be added and the plate immediately heat-sealed and centrifuged for 10 minutes at 4,000 rpm. Following centrifugation, plates may be loaded onto the Agilent RapidFire microfluidic solid phase extraction system coupled to an API4000 triple quadrupole mass spectrometer (RF/MS) for analysis.

In all cases, the enzyme converts UTP to CTP. Highly specific and sensitive multiple reaction monitoring (MRM) MS methods may be optimised for the detection of the enzymatic reaction product, CTP, and the stable isotope labelled product standard $^{13}C_9$-$^{15}N_3$-CTP. Readout for data analysis may be calculated as the ratio between the peak area of the product CTP and the internal standard $^{13}C_9$-$^{15}N_3$-CTP. For data reporting, the following equation may be used:

$$R = \frac{P}{IS}$$

(R=ratio/readout, P=product signal area, IS=internal standard signal area)

For each screening plate, the means of the negative (DMSO) and positive control values were used for the calculation of the respective assay window (S/B) and Z' values. The median of the respective control values was used for calculation of percent inhibition according to the following equation:

$$I = \frac{R_{neg} - R_{sample}}{[R_{neg} - R_{pos}]}\%$$

(I=Inhibition, $R_{neg}$=median of negative control readout values, $R_{pos}$=median of positive control readout values, $R_{sample}$=sample readout value)

Percentage inhibition was then plotted against compound concentration, and the 50% inhibitory concentration ($IC_{50}$) was determined from the resultant concentration-response curve.

Fold selectivity between CTPS1 and CTPS2 was subsequently calculated according to the following equation:

$$\text{Fold selectivity} = \frac{CTPS2IC_{50}}{CTPS1IC_{50}}$$

The data for certain compounds tested are presented below.

TABLE 26

Selectivity data split into grouping of 2-30 fold (+), >30-60 fold (++) or >60 fold (+++)

| P | Selectivity | P | Selectivity |
|---|---|---|---|
| P1 | + | P118 | +++ |
| P2 | +++ | P125 | ++ |
| P9 | +++ | P128 | + |
| P12 | ++ | P132 | ++ |
| P16 | ++ | P136 | +++ |
| P18 | ++ | P143 | +++ |
| P21 | ++ | P145 | +++ |
| P31 | +++ | P146 | +++ |
| P34 | + | P151 | +++ |
| P38 | + | P155 | + |
| P39 | + | P158 | + |
| P59 | + | P159 | +++ |
| P65 | ++ (n = 6)<br>+ (n = 8) | P161 | + |
| P68 | ++ | P162 | ++ |
| P70 | + | P163 | +++ |
| P74 | ++ | P164 | + |
| P76 | ++ | P188 | ++ |
| P83 | +++ | P191 | ++ |
| P87 | ++ | P195 | +++ |
| P88 | +++ | P196 | +++ |
| P89 | +++ | P197 | +++ |
| P95 | + | P198 | +++ |
| P96 | + | P200 | ++ |
| P98 | +++ | P201 | +++ |
| P103 | + | P202 | +++ |
| P105 | ++ | P205a | +++ |
| P108 | +++ | P205b | ++ |
| P110 | ++ | P206 | +++ |
| P112 | ++ | P207 | + |
| P113 | + | P216 | +++ |
| P114 | +++ | P221 | + |
| P115 | +++ | P222 | + |

The data for all compounds of formula (I) tested wherein $R_1$ is $R_{1a}$; and/or $R_4$ and $R_5$ are $R_{4a}$ and $R_{5a}$; and/or A is $A_a$ are presented below.

TABLE 27

Selectivity data split into grouping of 2-30 fold (+), >30-60 fold (++) or >60 fold (+++)

| P | Selectivity |
|---|---|
| P226 | +++ |
| P227 | +++ |
| P228 | + |
| P229 | +++ |
| P230 | +++ |
| P242 | +++ |

TABLE 27-continued

| Selectivity data split into grouping of 2-30 fold (+), >30-60 fold (++) or >60 fold (+++) | |
|---|---|
| P | Selectivity |
| P244 | +++ |
| P248 | +++ |
| P251 | +++ |

Compounds having a selectivity for CTPS1 may be expected to have utility in the treatment of diseases whereby a selective CTPS1 compound is beneficial.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the claims which follow.

All publications, including but not limited to patents and patent applications, cited in this specification are herein incorporated by reference as if each individual publication were specifically and individually indicated to be incorporated by reference herein as though fully set forth.

Clauses of the Invention:

Clause 1. A compound of formula (I):

(I)

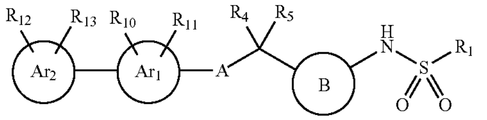

wherein

A is $A_a$ or $A_b$;

wherein $A_a$ is an amine linker having the following structure: —NH—, —$CH_2$NH— or —$NHCH_2$—;

$A_b$ is an amide linker having the following structure: —C(═O)NH— or —NHC(═O)—;

B is

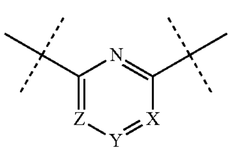

or

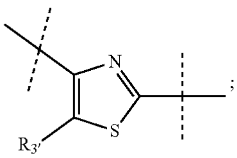

;

X is N or CH;

Y is N or $CR_2$;

Z is N or $CR_3$;

with the proviso that when at least one of X or Z is N, Y cannot be N;

$R_1$ is $C_{1-5}$fluoroalkyl, with the proviso that $R_1$ is not $CF_3$;

$R_2$ is H, halo, $C_{1-2}$alkyl, $OC_{1-2}$alkyl, $C_{1-2}$haloalkyl or $OC_{1-2}$haloalkyl;

$R_3$ is H, halo, $CH_3$, $OCH_3$, $CF_3$ or $OCF_3$;

wherein at least one of $R_2$ and $R_3$ is H;

$R_{3'}$ is H, halo, $CH_3$, $OC_{1-2}$alkyl or $CF_3$; and when A is —NHC(═O)—, additionally $R_{3'}$ together with $R_5$ forms a 5- or 6-membered cycloalkyl or 5 or 6 membered oxygen-containing heterocycloalkyl;

$R_4$ and $R_5$ are $R_{4a}$ and $R_{5a}$, or $R_{4b}$and $R_{5b}$;

wherein $R_{4a}$ and $R_{5a}$ together with the carbon atom to which they are attached form a $C_{3-6}$cycloalkyl which is:

substituted by one or two substituents, each substituent being independently selected from the group consisting of $C_{1-3}$alkyl, oxo, OH, $C_{1-3}$alkylOH, $C_{1-3}$haloalkyl, $C_{0-2}$alkylene$C_{3-6}$cycloalkyl, $C_{0-2}$alkylene$C_{3-6}$heterocycloalkyl, $C_{1-3}$alkylene$OC_{1-3}$alkyl, halo, $OC_{1-3}$haloalkyl, $OC_{0-2}$alkylene$C_{3-6}$cycloalkyl, $OC_{0-2}$alkylene$C_{3-6}$heterocycloalkyl, $OC_{1-3}$alkyl and $NR_{21}R_{22}$; or one of the carbons of the $C_{3-6}$cycloalkyl is a spiro centre such that a spirocyclic ring system is formed by the $C_{3-6}$cycloalkyl ring and a further $C_{3-6}$cycloalkyl ring or a $C_{3-6}$heterocycloalkyl ring, and wherein the $C_{3-6}$cycloalkyl formed by $R_{4a}$ and $R_{5a}$ together with the carbon atom to which they are attached may be substituted by one or two substituents, each substituent being independently selected from the group consisting of $C_{1-3}$ alkyl or $OC_{1-3}$alkyl; or $R_{4a}$ and $R_{5a}$ together with the carbon atom to which they are attached form a $C_{3-6}$heterocycloalkyl wherein one of the carbons of the $C_{3-6}$heterocycloalkyl is a spiro centre such that a spirocyclic ring system is formed by the $C_{3-6}$heterocycloalkyl ring and a further $C_{3-6}$cycloalkyl ring or a $C_{3-6}$heterocycloalkyl ring, and wherein the $C_{3-6}$heterocycloalkyl formed by $R_{4a}$ and $R_{5a}$ together with the carbon atom to which they are attached may be substituted by one or two substituents, each substituent being independently selected from the group consisting of $C_{1-3}$alkyl or $OC_{1-3}$alkyl; or $R_{4a}$ and $R_{5a}$ together with the carbon atom to which they are attached form a $C_{3-6}$heterocycloalkyl comprising one nitrogen atom, wherein said nitrogen atom is substituted by —$S(O)_2R_{29}$; or $R_{4b}$ and $R_{5b}$ are each independently H, $C_{1-6}$alkyl, $C_{1-6}$alkylOH, $C_{1-6}$haloalkyl, $C_{0-2}$alkylene$C_{3-6}$cycloalkyl, $C_{0-2}$alkylene$C_{3-6}$heterocycloalkyl, $C_{1-3}$alkylene $OC_{1-3}$alkyl, or $R_4$ and $R_5$ together with the carbon atom to which they are attached form a $C_{3-6}$cycloalkyl or $C_{3-6}$heterocycloalkyl; and when A is —NHC(═O)— or —$NHCH_2$—:

$R_{4b}$ and $R_{5b}$ may additionally be selected from halo, $OC_{1-6}$haloalkyl, $OC_{0-2}$alkylene$C_{3-6}$cycloalkyl, $OC_{0-2}$alkylene$C_{3-6}$heterocycloalkyl, $OC_{1-6}$alkyl and $NR_{21}R_{22}$;

Ar1 is a 6-membered aryl or heteroaryl;

Ar2 is a 6-membered aryl or heteroaryl and is attached to Ar1 in the para position relative to group A;

$R_{10}$ is H, halo, $C_{1-3}$alkyl, $C_{1-2}$haloalkyl, $OC_{1-2}$alkyl, $OC_{1-2}$haloalkyl or CN;

$R_{11}$ is H, F, Cl, $C_{1-2}$alkyl, $CF_3$, $OCH_3$ or CN;

$R_{12}$ is attached to Ar2 in the ortho or meta position relative to Ar1 and $R_{12}$ is H, halo, $C_{1-4}$ alkyl, $C_{2-4}$alkenyl, $C_{0-2}$alkylene$C_{3-5}$cycloalkyl, $OC_{1-4}$alkyl, $OC_{0-2}$alkylene$C_{3-5}$cycloalkyl, $C_{1-4}$ haloalkyl, $OC_{1-4}$haloalkyl, hydroxy, $C_{1-4}$alkylOH, $SO_2C_{1-2}$alkyl, $C(O)N(C_{1-2}$alkyl$)_2$, $NHC(O)C_{1-3}$alkyl or $NR_{23}R_{24}$; and when A is —NHC(═O)—, —NH— or —$NHCH_2$—: $R_{12}$ may additionally be selected from CN, $OCH_2CH_2N(CH_3)_2$ and a $C_{3-6}$heterocycloalkyl comprising one nitrogen located at the point of attachment to Ar2, or $R_{12}$ together with a nitrogen atom to which it is attached forms an N-oxide ($N^+$—$O^-$);

$R_{13}$ is H or halo;

$R_{21}$ is H, $C_{1-5}$alkyl, $C(O)C_{1-5}$alkyl, $C(O)OC_{1-5}$alkyl;

$R_{22}$ is H or $CH_3$;

$R_{23}$ is H or $C_{1-2}$alkyl; and $R_{24}$ is H or $C_{1-2}$alkyl;

$R_{29}$ is $C_{1-5}$alkyl, $C_{0-2}$alkylene$C_{3-5}$cycloalkyl which cycloalkyl is optionally substituted by $CH_3$, or $CF_3$;

$R_{32}$ is $C_{1-3}$alkyl and $R_{33}$ is $C_{1-3}$alkyl; or $R_{32}$ and $R_{33}$ together with the nitrogen atom to which they are attached form a $C_{3-6}$heterocycloalkyl;

or a salt and/or solvate thereof and/or derivative thereof.

Clause 2. The compound according to clause 1 wherein A is —C(═O)NH—.

Clause 3. The compound according to clause 1 wherein A is —NHC(═O)—.

Clause 4. The compound according to clause 1 wherein A is —NH—.

Clause 5. The compound according to clause 1 wherein A is —$CH_2NH$—.

Clause 6. The compound according to clause 1 wherein A is —$NHCH_2$—.

Clause 7. The compound according to any one of clauses 1 to 6 wherein X is N.

Clause 8. The compound according to any one of clauses 1 to 6 wherein X is CH.

Clause 9. The compound according to any one of clauses 1 to 6 or 8 wherein Y is N.

Clause 10. The compound according to any one of clauses 1 to 8 wherein Y is $CR_2$.

Clause 11. The compound according to any one of clauses 1 to 8 or 10 wherein Z is N.

Clause 12. The compound according to any one of clauses 1 to 10 wherein Z is $CR_3$.

Clause 13. The compound according to any one of clauses 1 to 6 wherein X is N, Y is $CR_2$ and Z is N.

Clause 14. The compound according to any one of clauses 1 to 6 wherein X is N, Y is $CR_2$ and Z is $CR_3$.

Clause 15. The compound according to any one of clauses 1 to 6 wherein X is CH, Y is N and Z is $CR_3$.

Clause 16. The compound according to any one of clauses 1 to 6 wherein X is CH, Y is $CR_2$ and Z is $CR_3$.

Clause 17. The compound according to any one of clauses 1 to 6 wherein X is CH, Y is $CR_2$ and Z is N.

Clause 18. The compound according to any one of clauses 1 to 17 wherein $R_1$ is $C_1$fluoroalkyl.

Clause 19. The compound according to clause 18 wherein $R_1$ is $CH_2F$.

Clause 20. The compound according to clause 18 wherein $R_1$ is $CHF_2$.

Clause 21. The compound according to any one of clauses 1 to 17 wherein $R_1$ is $C_2$fluoroalkyl.

Clause 22. The compound according to clause 21 wherein $R_1$ is $CH_2CF_3$.

Clause 23. The compound according to clause 21 wherein $R_1$ is $CH_2CHF_2$.

Clause 24. The compound according to clause 21 wherein $R_1$ is $CF_2CF_3$.

Clause 25. The compound according to any one of clauses 1 to 17 wherein $R_1$ is $C_3$fluoroalkyl.

Clause 26. The compound according to any one of clauses 1 to 17 wherein $R_1$ is $C_4$fluoroalkyl.

Clause 27. The compound according to any one of clauses 1 to 17 wherein $R_1$ is $C_5$fluoroalkyl.

Clause 28. The compound according to clause 25 wherein $R_1$ is a fluorinated n-propyl.

Clause 29. The compound according to clause 25 wherein $R_1$ is a fluorinated isopropyl.

Clause 30. The compound according to clause 26 wherein $R_1$ is a fluorinated n-butyl.

Clause 31. The compound according to clause 26 wherein $R_1$ is a fluorinated isobutyl.

Clause 32. The compound according to clause 26 wherein $R_1$ is a fluorinated sec-butyl.

Clause 33. The compound according to clause 26 wherein $R_1$ is a fluorinated tert-butyl.

Clause 34. The compound according to any one of clauses 1 to 17, 18, 21, 25, 26 or 27 to 33 wherein $R_1$ is $C_{1-5}$monofluoroalkyl.

Clause 35. The compound according to any one of clauses 1 to 17, 18, 21, 25, 26 or 27 to 33 wherein $R_1$ is $C_{1-5}$difluoroalkyl.

Clause 36. The compound according to any one of clauses 1 to 17, 21, 25, 26 or 27 to 33 wherein $R_1$ is $C_{2-5}$trifluoroalkyl.

Clause 37. The compound according to any one of clauses 1 to 36 wherein $R_2$ is H.

Clause 38. The compound according to any one of clauses 1 to 36 wherein $R_2$ is halo, such as F, Cl or Br e.g. Cl or Br.

Clause 39. The compound according to any one of clauses 1 to 36 wherein $R_2$ is $C_{1-2}$alkyl such as $CH_3$.

Clause 40. The compound according to any one of clauses 1 to 36 wherein $R_2$ is $OC_{1-2}$alkyl such as $OCH_3$.

Clause 41. The compound according to any one of clauses 1 to 36 wherein $R_2$ is $C_{1-2}$haloalkyl such as $CF_3$.

Clause 42. The compound according to any one of clauses 1 to 36 wherein $R_2$ is $OC_{1-2}$ haloalkyl such as $OCF_3$.

Clause 43. The compound according to any one of clauses 1 to 42 wherein $R_3$ is H.

Clause 44. The compound according to any one of clauses 1 to 42 wherein $R_3$ is halo.

Clause 45. The compound according to clause 44 wherein $R_3$ is fluoro.

Clause 48. The compound according to any one of clauses 1 to 42 wherein $R_3$ is $CH_3$.

Clause 47. The compound according to any one of clauses 1 to 42 wherein $R_3$ is $OCH_3$.

Clause 48. The compound according to any one of clauses 1 to 42 wherein $R_3$ is $CF_3$.

Clause 49. The compound according to any one of clauses 1 to 42 wherein $R_3$ is $OCF_3$.

Clause 50. The compound according to any one of clauses 1 to 49 wherein at least one of $R_2$ and $R_3$ is H.

Clause 51. The compound according to any one of clauses 1 to 50 wherein $R_4$ and $R_5$ are $R_{4a}$ and $R_{5a}$.

Clause 52. The compound according to clause 51 wherein $R_{4a}$ and $R_{5a}$ together with the carbon atom to which they are attached form a $C_{3-6}$cycloalkyl which is substituted by one or two substituents, each substituent being independently selected from the group consisting of $C_{1-3}$alkyl, oxo, OH, $C_{1-5}$alkylOH, $C_{1-3}$haloalkyl, $C_{0-2}$alkylene$C_{3-6}$cycloalkyl, $C_{0-2}$alkylene$C_{3-6}$heterocycloalkyl, $C_{1-3}$alkylene$OC_{1-3}$alkyl, halo, $OC_{1-3}$haloalkyl, $OC_{0-2}$alkylene$C_{3-6}$cycloalkyl, $OC_{0-2}$alkylene$C_{3-6}$heterocycloalkyl, $OC_{1-3}$alkyl and $NR_{21}R_{22}$.

Clause 53. The compound according to clause 52 wherein $R_{4a}$ and $R_{5a}$ together with the carbon atom to which they are attached form a $C_{3-6}$cycloalkyl which is substituted by one substituent.

Clause 54. The compound according to either clause 52 or 53 wherein each substituent is independently selected from the group consisting of $C_{1-3}$alkyl, oxo, OH, $C_{1-3}$alkylOH, $C_{1-3}$haloalkyl, halo, $OC_{1-3}$haloalkyl, $OC_{1-3}$alkyl and $NR_{21}R_{22}$.

Clause 55. The compound according to clause 54 wherein each substituent is independently selected from the group consisting of oxo, OH, halo, $OC_{1-3}$alkyl and $NR_{21}R_{22}$.

Clause 56. The compound according to clause 55 wherein each substituent is independently selected from the group consisting of oxo, OH, fluoro and $NR_{21}R_{22}$.

Clause 57. The compound according to clause 51 wherein $R_{4a}$ and $R_{5a}$ together with the carbon atom to which they are attached form a $C_{3-6}$cycloalkyl wherein one of the carbons of the $C_{3-6}$cycloalkyl is a spiro centre such that a spirocyclic ring system is formed by the $C_{3-6}$cycloalkyl ring and a further $C_{3-6}$cycloalkyl ring or a $C_{3-6}$heterocycloalkyl ring, and wherein the $C_{3-6}$cycloalkyl formed by $R_{4a}$ and $R_{5a}$ together with the carbon atom to which they are attached may be substituted by one or two substituents, each substituent being independently selected from the group consisting of $C_{1-5}$alkyl or $OC_{1-5}$alkyl.

Clause 58. The compound according to clause 51 wherein $R_{4a}$ and $R_{5a}$ together with the carbon atom to which they are attached form a $C_{3-6}$heterocycloalkyl wherein one of the carbons of the $C_{3-6}$heterocycloalkyl is a spiro centre such that a spirocyclic ring system is formed by the $C_{3-6}$heterocycloalkyl ring and a further $C_{3-6}$cycloalkyl ring or a $C_{3-6}$heterocycloalkyl ring, and wherein the $C_{3-6}$heterocycloalkyl formed by $R_{4a}$ and $R_{5a}$ together with the carbon atom to which they are attached may be substituted by one or two substituents, each substituent being independently selected from the group consisting of $C_{1-3}$alkyl or $OC_{1-3}$alkyl.

Clause 59. The compound according to either clause 57 or 58 wherein $R_{4a}$ and $R_{5a}$ together with the carbon atom to which they are attached form a $C_{3-6}$cycloalkyl or $C_{3-6}$heterocycloalkyl which is substituted by one substituent.

Clause 60. The compound according to either clause 57 or 58 wherein $R_{4a}$ and $R_{5a}$ together with the carbon atom to which they are attached form a $C_{3-6}$cycloalkyl or $C_{3-6}$heterocycloalkyl which is unsubstituted.

Clause 61. The compound according to any one of clauses 57, 58 or 59 wherein each substituent is independently selected from the group consisting of $C_{1-2}$alkyl or $OCH_3$.

Clause 62. The compound according to any one of clauses 57 to 61 wherein a spirocyclic ring system is formed by the $C_{3-6}$cycloalkyl or $C_{3-6}$heterocycloalkyl ring and a further $C_{3-6}$cycloalkyl ring.

Clause 63. The compound according to any one of clauses 57 to 61 wherein a spirocyclic ring system is formed by the $C_{3-6}$cycloalkyl or $C_{3-6}$heterocycloalkyl ring and a further $C_{3-6}$heterocycloalkyl ring.

Clause 64. The compound according to any one of clauses 57 or 59 to 63 wherein the $C_{3-6}$cycloalkyl formed by $R_{4a}$ and $R_{5a}$ together with the carbon atom to which they are attached is cyclopropyl.

Clause 65. The compound according to any one of clauses 57 or 59 to 63 wherein the $C_{3-6}$cycloalkyl formed by $R_{4a}$ and $R_{5a}$ together with the carbon atom to which they are attached is cyclobutyl.

Clause 66. The compound according to any one of clauses 57 or 59 to 63 wherein the $C_{3-6}$cycloalkyl formed by $R_{4a}$ and $R_{5a}$ together with the carbon atom to which they are attached is cyclopentyl.

Clause 67. The compound according to any one of clauses 57 or 59 to 63 wherein the $C_{3-6}$cycloalkyl formed by $R_{4a}$ and $R_{5a}$ together with the carbon atom to which they are attached is cyclohexyl.

Clause 68. The compound according to any one of clauses 58 to 63 wherein the $C_{3-6}$heterocycloalkyl formed by $R_{4a}$ and $R_{5a}$ together with the carbon atom to which they are attached is heterocyclopropyl.

Clause 69. The compound according to any one of clauses 58 to 63 wherein the $C_{3-6}$heterocycloalkyl formed by $R_{4a}$ and $R_{5a}$ together with the carbon atom to which they are attached is heterocyclobutyl.

Clause 70. The compound according to any one of clauses 58 to 63 wherein the $C_{3-6}$heterocycloalkyl formed by $R_{4a}$ and $R_{5a}$ together with the carbon atom to which they are attached is heterocyclopentyl.

Clause 71. The compound according to any one of clauses 58 to 63 wherein the $C_{3-6}$heterocycloalkyl formed by $R_{4a}$ and $R_{5a}$ together with the carbon atom to which they are attached is heterocyclohexyl.

Clause 72. The compound according to any one of clauses 57 or 59 to 67 wherein one of the carbons is quaternary and is attached to a 5-membered dioxolane ring to form the following structure:

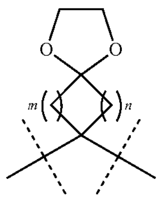

wherein m is 1 or 2 and n is 0, 1 or 2.

Clause 73. The compound according to any one of clauses 52 to 56 wherein $R_{21}$ is H.

Clause 74. The compound according to any one of clauses 52 to 56 wherein $R_{21}$ is $C_{1-6}$ alkyl, such as methyl, ethyl or propyl.

Clause 75. The compound according to any one of clauses 52 to 56 wherein $R_{21}$ is $C(O)C_{1-5}$alkyl, such as $C(O)CH_3$.

Clause 76. The compound according to any one of clauses 52 to 56 wherein $R_{21}$ is $C(O)OC_{1-5}$alkyl, such as $C(O)OCH_3$ or C(O)Otert-butyl.

Clause 77. The compound according to any one of clauses 52 to 56 or 73 to 76 wherein $R_{22}$ is H.

Clause 78. The compound according to any one of clauses 52 to 56 or 73 to 76 wherein $R_{22}$ is $CH_3$.

Clause 79. The compound according to clause 51 wherein $R_{4a}$ and $R_{5a}$ together with the carbon atom to which they are attached form a $C_{3-6}$heterocycloalkyl comprising one nitrogen atom, wherein said nitrogen atom is substituted by $—S(O)_2R_{29}$.

Clause 80. The compound according to clause 79 wherein the $C_{3-6}$heterocycloalkyl is piperidinyl and the nitrogen atom is in the 4-position relative to the quaternary carbon:

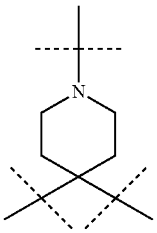

.

Clause 81. The compound according to either clause 79 or 80 wherein $R_{29}$ is $C_{1-3}$alkyl.

Clause 82. The compound according to clause 81 wherein $R_{29}$ is methyl.

Clause 83. The compound according to any one of clauses 1 to 50 wherein $R_4$ and $R_5$ are $R_{4b}$ and $R_{5b}$.

Clause 84. The compound according to any one of clauses 1 to 50 wherein $R_4$ is H.

Clause 85. The compound according to any one of clauses 1 to 50 wherein $R_4$ is $C_{1-6}$alkyl.

Clause 86. The compound according to clause 85 wherein $R_4$ is methyl or ethyl.

Clause 87. The compound according to any one of clauses 1 to 50 wherein $R_4$ is $C_{1-6}$alkylOH.

Clause 88. The compound according to any one of clauses 1 to 50 wherein $R_4$ is $C_{1-6}$haloalkyl such as $CF_3$.

Clause 89. The compound according to any one of clauses 1 to 50 wherein $R_4$ is $C_{0-2}$alkylene$C_{3-6}$cycloalkyl.

Clause 90. The compound according to any one of clauses 1 to 50 wherein $R_4$ is $C_{0-2}$alkylene$C_{3-6}$heterocycloalkyl.

Clause 91. The compound according to any one of clauses 1 to 50 wherein $R_4$ is $C_{1-3}$alkyleneO$C_{1-3}$alkyl.

Clause 92. The compound according to clause 91 wherein $R_4$ is $C_2$alkyleneO$C_{1-3}$alkyl.

Clause 93. The compound according to clause 92 wherein $R_4$ is $CH_2CH_2OCHS$.

Clause 94. The compound according to any one of clauses 1 to 50 wherein $R_4$ is halo.

Clause 95. The compound according to clause 94 wherein $R_4$ is fluoro.

Clause 96. The compound according to any one of clauses 1 to 50 wherein $R_4$ is O$C_{1-6}$haloalkyl, such as O$C_{1-4}$haloalkyl.

Clause 97. The compound according to any one of clauses 1 to 50 wherein $R_4$ is O$C_{0-2}$alkylene$C_{3-6}$cycloalkyl.

Clause 98. The compound according to any one of clauses 1 to 50 wherein $R_4$ is O$C_{0-2}$alkylene$C_{3-6}$heterocycloalkyl.

Clause 99. The compound according to any one of clauses 1 to 50 wherein $R_4$ is O$C_{1-6}$alkyl, in particular O$C_{1-4}$alkyl.

Clause 100. The compound according to any one of clauses 1 to 50 wherein $R_4$ is $NR_{21}R_{22}$.

Clause 101. The compound according to clause 100 wherein $R_{21}$ is H, $CH_3$, $C(O)CH_3$, $C(O)OCH_3$ or C(O)Otert-butyl.

Clause 102. The compound according to either clause 100 or 101 wherein $R_{22}$ is H or $CH_3$ such as H.

Clause 103. The compound according to any one of clauses 100 to 102 wherein $R_{21}$ is $C(O)OCH_3$ and $R_2$ is H, $R_{21}$ is $C(O)CH_3$ and $R_2$ is H, $R_{21}$ and $R_{22}$ are both $CH_3$, or $R_{21}$ and $R_{22}$ are both H.

Clause 104. The compound according to any one of clauses 1 to 50 wherein $R_4$ is H, $C_{1-6}$alkyl, $C_{1-6}$alkylOH. $C_{1-6}$haloalkyl, $C_{0-2}$alkylene$C_{3-6}$cycloalkyl, $C_{0-2}$ alkylene$C_{3-6}$heterocycloalkyl, $C_{1-3}$alkyleneO$C_{1-3}$alkyl, or $R_4$ and $R_5$ together with the carbon atom to which they are attached form a $C_{3-6}$cycloalkyl or $C_{3-6}$heterocycloalkyl.

Clause 105. The compound according to any one of clauses 1 to 50 wherein $R_4$ is halo, O$C_{1-6}$haloalkyl, O$C_{0-2}$alkylene$C_{3-6}$cycloalkyl, O$C_{0-2}$alkylene$C_{3-6}$heterocycloalkyl, O$C_{1-6}$alkyl or $NR_{21}R_{22}$.

Clause 106. The compound according to any one of clauses 1 to 50 or 84 to 105 wherein $R_5$ is H.

Clause 107. The compound according to any one of clauses 1 to 50 or 84 to 105 wherein $R_6$ is $C_{1-6}$alkyl.

Clause 108. The compound according to clause 107 wherein $R_5$ is methyl or ethyl.

Clause 109. The compound according to any one of clauses 1 to 50 or 84 to 105 wherein $R_5$ is $C_{1-6}$alkylOH.

Clause 110. The compound according to any one of clauses 1 to 50 or 84 to 105 wherein $R_5$ is $C_{1-6}$haloalkyl such as CFs.

Clause 111. The compound according to any one of clauses 1 to 50 or 84 to 105 wherein $R_6$ is $C_{0-2}$alkylene $C_{3-6}$cycloalkyl.

Clause 112. The compound according to any one of clauses 1 to 50 or 84 to 105 wherein $R_6$ is $C_{0-2}$alkylene $C_{3-6}$heterocycloalkyl.

Clause 113. The compound according to any one of clauses 1 to 50 or 84 to 105 wherein $R_5$ is $C_{1-6}$alkylene O$C_{1-3}$alkyl, such as $C_2$alkyleneO$C_{1-3}$alkyl e.g. $CH_2CH_2OCH_3$.

Clause 114. The compound according to any one of clauses 1 to 50 or 84 to 105 wherein $R_5$ is halo.

Clause 115. The compound according to clause 114 wherein $R_6$ is fluoro.

Clause 116. The compound according to any one of clauses 1 to 50 or 84 to 105 wherein $R_5$ is O$C_{1-6}$haloalkyl, such as O$C_{1-4}$haloalkyl.

Clause 117. The compound according to any one of clauses 1 to 50 or 84 to 105 wherein $R_5$ is O$C_{0-2}$alkylene $C_{3-6}$cycloalkyl.

Clause 118. The compound according to any one of clauses 1 to 50 or 84 to 105 wherein $R_5$ is O$C_{0-2}$alkylene $C_{3-6}$heterocycloalkyl.

Clause 119. The compound according to any one of clauses 1 to 50 or 84 to 105 wherein $R_5$ is O$C_{1-6}$alkyl, in particular O$C_{1-4}$alkyl.

Clause 120. The compound according to any one of clauses 1 to 50 or 84 to 105 wherein $R_5$ is $NR_{21}R_{22}$.

Clause 121. The compound according to clause 120 wherein $R_{21}$ is H, $CH_3$, $C(O)CH_3$, $C(O)OCH_3$ or C(O)Otert-butyl.

Clause 122. The compound according to either clause 120 or 121 wherein $R_2$ is H or $CH_3$ such as H.

Clause 123. The compound according to any one of clauses 120 to 122 wherein $R_{21}$ is $C(O)OCH_3$ and $R_{22}$ is H, $R_{21}$ is $C(O)CH_3$ and $R_{22}$ is H, $R_{21}$ and $R_{22}$ are both $CH_3$, or $R_{21}$ and $R_{22}$ are both H.

Clause 124. The compound according to any one of clauses 1 to 50 or 84 to 105 wherein $R_5$ is H, $C_{1-6}$alkyl, $C_{1-6}$alkylOH, $C_{1-5}$haloalkyl, $C_{0-2}$alkylene$C_{3-6}$cycloalkyl, $C_{0-2}$alkylene$C_{3-6}$heterocycloalkyl, $C_{1-5}$alkyleneO$C_{1-5}$alkyl, or $R_4$ and $R_5$ together with the carbon atom to which they are attached form a $C_{3-6}$cycloalkyl or $C_{3-6}$heterocycloalkyl.

Clause 125. The compound according to any one of clauses 1 to 50 or 84 to 105 wherein $R_5$ is halo, O$C_{1-6}$-haloalkyl, O$C_{0-2}$alkylene$C_{3-6}$cycloalkyl, O$C_{0-2}$alkylene $C_{3-6}$heterocycloalkyl, O$C_{1-6}$alkyl or $NR_{21}R_{22}$.

Clause 126. The compound according to any one of clauses 1 to 50 or 84 or 106 wherein $R_4$ and $R_5$ are both H.

Clause 127. The compound according to any one of clauses 1 to 50 or 86 or 108 wherein $R_4$ and $R_5$ are both methyl.

Clause 128. The compound according to any one of clauses 1 to 50 or 86 or 108 wherein $R_4$ and $R_5$ are both ethyl.

Clause 129. The compound according to any one of clauses 1 to 50 or 84 to 125 wherein $R_4$ and $R_5$ are both fluoro.

Clause 130. The compound according to any one of clauses 1 to 50 or 95 or 115 wherein $R_4$ is ethyl and $R_5$ is H.

Clause 131. The compound according to any one of clauses 1 to 50 or 84 to 125 wherein $R_4$ is fluoro and $R_5$ is ethyl.

Clause 132. The compound according to any one of clauses 1 to 50 or 84 to 125 wherein $R_4$ is $CH_2CH_2OCH_3$ and $R_5$ is H.

Clause 133. The compound according to any one of clauses 130 to 132 wherein $R_4$ and $R_5$ are arranged in an S configuration.

Clause 134. The compound according to any one of clauses 1 to 50 wherein $R_4$ and $R_5$ together with the carbon atom to which they are attached form a $C_{3-6}$cycloalkyl.

Clause 135. The compound according to clause 134 wherein $R_4$ and $R_5$ together with the carbon atom to which they are attached form a cyclopropyl ring or a cyclopentyl ring, such as a cyclopentyl ring.

Clause 136. The compound according to any one of clauses 1 to 50 wherein $R_4$ and $R_5$ together with the carbon atom to which they are attached form a $C_3$-heterocycloalkyl, such as heterocyclohexyl, such as tetrahydropyranal.

Clause 137. The compound according to any one of clauses 1 to 136 wherein Ar1 is phenyl.

Clause 138. The compound according to any one of clauses 1 to 136 wherein Ar1 is 2-pyridyl.

Clause 139. The compound according to any one of clauses 1 to 136 wherein Ar1 is 3-pyridyl.

Clause 140. The compound according to any one of clauses 1 to 139 wherein Ar2 is 3-pyridyl.

Clause 141. The compound according to any one of clauses 1 to 139 wherein Ar2 is 2,5-pyrazinyl.

Clause 142. The compound according to any one of clauses 1 to 141 wherein $R_{10}$ is H.

Clause 143. The compound according to any one of clauses 1 to 141 wherein $R_{10}$ is halo such as fluoro or chloro.

Clause 144. The compound according to any one of clauses 1 to 141 wherein $R_{10}$ is $C_{1-3}$ alkyl.

Clause 145. The compound according to clause 144 wherein $R_{10}$ is $C_{1-2}$alkyl such as $CH_3$.

Clause 146. The compound according to any one of clauses 1 to 141 wherein $R_{10}$ is $C_{1-2}$haloalkyl such as $CF_3$.

Clause 147. The compound according to any one of clauses 1 to 141 wherein $R_{10}$ is $OC_{1-2}$alkyl such as $OCH_3$.

Clause 148. The compound according to any one of clauses 1 to 141 wherein $R_{10}$ is $OC_{1-2}$ haloalkyl such as $OCF_3$.

Clause 149. The compound according to any one of clauses 1 to 141 wherein $R_{10}$ is CN.

Clause 150. The compound according to any one of clauses 1 to 149 wherein $R_{11}$ is H.

Clause 151. The compound according to any one of clauses 1 to 149 wherein $R_{11}$ is F.

Clause 152. The compound according to any one of clauses 1 to 149 wherein $R_{11}$ is Cl.

Clause 153. The compound according to any one of clauses 1 to 149 wherein $R_{11}$ is $C_{1-2}$alkyl.

Clause 154. The compound according to clause 153 wherein $R_{11}$ is $CH_3$.

Clause 155. The compound according to any one of clauses 1 to 149 wherein $R_{11}$ is $CF_3$.

Clause 156. The compound according to any one of clauses 1 to 149 wherein $R_{11}$ is $OCH_3$.

Clause 157. The compound according to any one of clauses 1 to 149 wherein $R_{11}$ is CN.

Clause 158. The compound according to any one of clauses 1 to 157 wherein $R_{12}$ is H.

Clause 159. The compound according to any one of clauses 1 to 157 wherein $R_{12}$ is halo such as fluoro or chloro.

Clause 160. The compound according to any one of clauses 1 to 157 wherein $R_{12}$ is $C_{1-4}$alkyl such as $CH_3$.

Clause 161. The compound according to any one of clauses 1 to 157 wherein $R_{12}$ is $C_{2-4}$alkenyl.

Clause 162. The compound according to any one of clauses 1 to 157 wherein $R_{12}$ is $C_{0-2}$alkylene$C_{3-5}$cycloalkyl such as $C_0$alkylene$C_3$cycloalkyl.

Clause 163. The compound according to any one of clauses 1 to 157 wherein $R_{12}$ is $OC_{1-4}$alkyl such as methoxy, ethoxy or isopropoxy.

Clause 164. The compound according to any one of clauses 1 to 157 wherein $R_{12}$ is $OC_{0-2}$alkylene$C_{3-5}$cycloalkyl such as $OC_0$alkylene$C_3$cycloalkyl.

Clause 165. The compound according to any one of clauses 1 to 157 wherein $R_{12}$ is $C_{1-4}$haloalkyl such as $CF_3$.

Clause 166. The compound according to any one of clauses 1 to 157 wherein $R_{12}$ is $OC_{1-4}$ haloalkyl such as $OCH_2CF_3$ or $OCHF_2$.

Clause 167. The compound according to any one of clauses 1 to 157 wherein $R_{12}$ is OH.

Clause 168. The compound according to any one of clauses 1 to 157 wherein $R_{12}$ is $C_{1-4}$ alkylOH.

Clause 169. The compound according to any one of clauses 1 to 157 wherein $R_{12}$ is $SO_2C_{1-2}$alkyl.

Clause 170. The compound according to any one of clauses 1 to 157 wherein $R_{12}$ is $NHC(O)C_{1-3}$alkyl.

Clause 171. The compound according to any one of clauses 1 to 157 wherein $R_{12}$ is $NR_{23}R_{24}$.

Clause 172. The compound according to clause 171 wherein $R_{23}$ is H or $C_{1-2}$alkyl such as H or $CH_3$.

Clause 173. The compound according to clause 171 or 172 wherein $R_{24}$ is H or $C_{1-2}$alkyl such as $CH_3$ or ethyl.

Clause 174. The compound according to any one of clauses 171 to 173 wherein $R_{23}$ is H and $R_{24}$ is ethyl; or $R_{23}$ is $CH_3$ and $R_{24}$ is $CH_3$.

Clause 175. The compound according to any one of clauses 1 to 157 wherein $R_{12}$ is CN.

Clause 176. The compound according to any one of clauses 1 to 157 wherein $R_{12}$ is $OCH_2CH_2N(CH_3)_2$.

Clause 177. The compound according to any one of clauses 1 to 157 wherein $R_{12}$ is a $C_{3-6}$heterocycloalkyl comprising one nitrogen located at the point of attachment to Ar2.

Clause 178. The compound according to any one of clauses 1 to 157 wherein $R_{12}$ together with a nitrogen atom to which it is attached forms an N-oxide ($N^+$—$O^-$).

Clause 179. The compound according to any one of clauses 1 to 157 wherein $R_{12}$ is $C(O)N(C_{1-2}alkyl)_2$.

Clause 180. The compound according to any one of clauses 1 to 179 wherein $R_{13}$ is H.

Clause 181. The compound according to any one of clauses 1 to 179 wherein $R_{13}$ is halo such as fluoro or chloro e.g. fluoro.

Clause 182. The compound according to any one of clauses 1 to 181 when $R_1$ is methyl, at least one of $R_4$, $R_5$, $R_{10}$, $R_{11}$, $R_{12}$ and $R_{13}$ is other than H.

Clause 183. The compound according to any one of clauses 1 to 182 wherein at least one, such as only one, nitrogen atom in any of the $C_{3-6}$heterocycloalkyl rings, such as only one of the $C_{3-6}$heterocycloalkyl rings is substituted, for example by $C_{1-4}$alkyl, C(O)H, C(O)$C_{1-4}$alkyl, C(O)O$C_{1-4}$alkyl, C(O)O$C_{1-4}$alkylaryl such as C(O)OBz, C(O)NH$C_{1-4}$alkyl, C(O)NH$C_{1-4}$alkylaryl such as C(O)NHBz, an Fmoc group, C(O)$C_{1-4}$haloalkyl, C(O)O$C_{1-4}$haloalkyl or C(O)NH$C_{1-4}$ haloalkyl, such as C(O)OtBu.

Clause 184. The compound according to any one of clauses 1 to 182 wherein all nitrogen atoms in all $C_{3-6}$heterocycloalkyl rings are not substituted.

Clause 185. The compound according to any one of clauses 1 to 184 wherein at least one, such as only one, sulphur atom in any of the $C_{3-6}$heterocycloalkyl rings, such as only one of the $C_{3-6}$heterocycloalkyl rings is substituted, for example by one oxygen atom to form S═O or by two oxygen atoms to form $S(O)_2$.

Clause 186. The compound according to any one of clauses 1 to 184 wherein all sulphur atoms in all $C_{3-6}$heterocycloalkyl rings are not substituted.

Clause 187. The compound according to any one of clauses 1 to 186 which is a compound of formula (I):

(I)

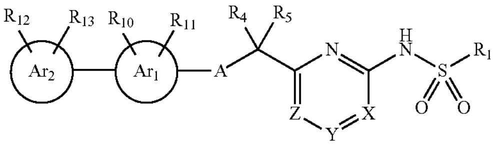

wherein

A is $A_a$ or $A_b$;

wherein $A_a$ is an amine linker having the following structure: —NH—, —$CH_2$NH— or —NH$CH_2$—;

$A_b$ is an amide linker having the following structure: —C(═O)NH— or —NHC(═O)—;

X is N or CH;

Y is N or $CR_2$;

Z is N or $CR_3$;

with the proviso that when at least one of X or Z is N, Y cannot be N;

$R_1$ is $C_{1-5}$fluoroalkyl, with the proviso that $R_1$ is not $CF_3$;

$R_2$ is H, halo, $C_{1-2}$alkyl, O$C_{1-2}$alkyl, $C_{1-2}$haloalkyl or O$C_{1-2}$haloalkyl;

$R_3$ is H, halo, $CH_3$, $OCH_3$, $CF_3$ or $OCF_3$;

wherein at least one of $R_2$ and $R_3$ is H;

$R_4$ and $R_5$ are $R_{4a}$ and $R_{5a}$, or $R_{4b}$ and $R_{5b}$;

wherein $R_{4a}$ and $R_{5a}$ together with the carbon atom to which they are attached form a $C_{3-6}$cycloalkyl which is:

substituted by one or two substituents, each substituent being independently selected from the group consisting of $C_{1-3}$alkyl, oxo, OH, $C_{1-3}$alkylOH, $C_{1-3}$haloalkyl, $C_{0-2}$alkylene$C_{3-6}$cycloalkyl, $C_{0-2}$alkylene$C_{3-6}$heterocycloalkyl, $C_{1-5}$alkyleneO$C_{1-5}$alkyl, halo, O$C_{1-3}$haloalkyl, O$C_{0-2}$alkylene$C_{3-6}$cycloalkyl, O$C_{0-2}$alkylene$C_{3-6}$heterocycloalkyl, O$C_{1-5}$alkyl and $NR_{21}R_{22}$; or one of the carbons of the $C_{3-6}$cycloalkyl is a spiro centre such that a spirocyclic ring system is formed by the $C_{3-6}$cycloalkyl ring and a further $C_{3-6}$cycloalkyl ring or a $C_{3-6}$heterocycloalkyl ring, and wherein the $C_{3-6}$cycloalkyl formed by $R_{4a}$ and $R_{5a}$ together with the carbon atom to which they are attached may be substituted by one or two substituents, each substituent being independently selected from the group consisting of $C_{1-3}$ alkyl or O$C_{1-3}$alkyl; or $R_{4a}$ and $R_{5a}$ together with the carbon atom to which they are attached form a $C_{3-6}$heterocycloalkyl wherein one of the carbons of the $C_{3-6}$heterocycloalkyl is a spiro centre such that a spirocyclic ring system is formed by the $C_{3-6}$heterocycloalkyl ring and a further $C_{3-6}$cycloalkyl ring or a $C_{3-6}$heterocycloalkyl ring, and wherein the $C_{3-6}$heterocycloalkyl formed by $R_{4a}$ and $R_{5a}$ together with the carbon atom to which they are attached may be substituted by one or two substituents, each substituent being independently selected from the group consisting of $C_{1-3}$alkyl or O$C_{1-3}$alkyl; or $R_{4a}$ and $R_{5a}$ together with the carbon atom to which they are attached form a $C_{3-6}$ heterocycloalkyl comprising one nitrogen atom, wherein said nitrogen atom is substituted by —$S(O)_2R_{29}$; or $R_{4b}$ and $R_{5b}$ are each independently H, $C_{1-6}$alkyl, $C_{1-6}$alkylOH, $C_{1-6}$haloalkyl, $C_{0-2}$alkylene$C_{3-6}$cycloalkyl, $C_{0-2}$alkylene$C_{3-6}$heterocycloalkyl, $C_{1-3}$alkyleneO$C_{1-3}$alkyl, or $R_4$ and R together with the carbon atom to which they are attached form a $C_{3-6}$cycloalkyl or $C_{3-5}$heterocycloalkyl; and when A is —NHC(═O)— or —NH$CH_2$—:

$R_{4b}$ and $R_{5b}$ may additionally be selected from halo, O$C_{1-6}$haloalkyl, O$C_{0-2}$alkylene$C_{3-6}$cycloalkyl, O$C_{0-2}$alkylene$C_{3-6}$heterocycloalkyl, O$C_{1-6}$alkyl and $NR_{21}R_{22}$;

Ar1 is a 6-membered aryl or heteroaryl;

Ar2 is a 6-membered aryl or heteroaryl and is attached to Ar1 in the para position relative to group A;

$R_{10}$ is H, halo, $C_{1-3}$alkyl, $C_{1-2}$haloalkyl, O$C_{1-2}$alkyl, O$C_{1-2}$haloalkyl or CN;

$R_{11}$ is H, F, Cl, $C_{1-2}$alkyl, $CF_3$, $OCH_3$ or CN;

$R_{12}$ is attached to Ar2 in the ortho or meta position relative to Ar1 and $R_{12}$ is H, halo, $C_{1-4}$alkyl, $C_{2-4}$alkenyl, $C_{0-2}$alkylene$C_{3-5}$cycloalkyl, O$C_{1-4}$alkyl, O$C_{0-2}$alkylene$C_{3-5}$cycloalkyl, $C_{1-4}$ haloalkyl, O$C_{1-4}$haloalkyl, hydroxy, $C_{1-4}$alkylOH, $SO_2C_{1-2}$alkyl, C(O)N($C_{1-2}$alkyl$)_2$, NHC(O)$C_{1-3}$alkyl or $NR_{23}R_{24}$; and when A is —NHC(═O)—, —NH— or —NH$CH_2$—:

$R_{12}$ may additionally be selected from CN, $OCH_2CH_2N(CH_3)_2$ and a $C_{3-6}$heterocycloalkyl comprising one nitrogen located at the point of attachment to Ar2, or $R_{12}$ together with a nitrogen atom to which it is attached forms an N-oxide ($N^+$—$O^-$);

$R_{13}$ is H or halo;

$R_{21}$ is H, $C_{1-5}$alkyl, C(O)$C_{1-5}$alkyl, C(O)O$C_{1-5}$alkyl;

$R_{22}$ is H or $CH_3$;

$R_{23}$ is H or $C_{1-2}$alkyl; and $R_{24}$ is H or $C_{1-2}$alkyl;

$R_{29}$ is $C_{1-3}$alkyl, $C_{0-2}$alkylene$C_{3-5}$cycloalkyl which cycloalkyl is optionally substituted by $CH_3$, or $CF_3$;

$R_{32}$ is $C_{1-3}$alkyl and $R_{33}$ is $C_{1-5}$alkyl; or $R_{32}$ and $R_{33}$ together with the nitrogen atom to which they are attached form a $C_{3-6}$heterocycloalkyl;

or a salt and/or solvate thereof and/or derivative thereof.

Clause 188. The compound according to any one of clauses 1 to 186 wherein B is

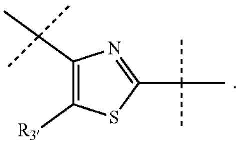

Clause 189. The compound according to any one of clauses 1 to 188 wherein $R_{3'}$ is H, halo, $CH_3$, $OC_{1-2}$alkyl or $CF_3$ e.g. H.

Clause 190. The compound according to any one of clauses 1 to 188 wherein A is —NHC(═O)— and $R_{3'}$ together with $R_5$ forms a 5- or 6-membered cycloalkyl or 5 or 6 membered oxygen-containing heterocycloalkyl.

Clause 191. A compound of the examples P271 or P284.

Clause 192. A compound of formula (II):

(II)

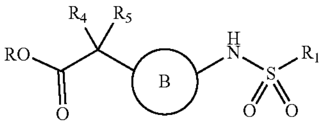

wherein B, $R_1$, $R_4$ and $R_5$ are as defined in any preceding clause and R is H, $C_{1-6}$alkyl (e.g. methyl or ethyl) or benzyl, or salts such as pharmaceutically acceptable salts, thereof.

Clause 193. A compound of formula (XX):

(XX)

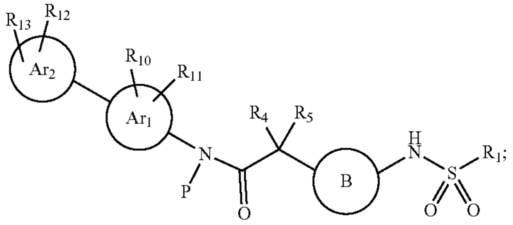

wherein B, Ar1, Ar2, $R_1$, $R_4$, $R_5$, $R_{10}$, $R_{11}$, $R_{12}$ and $R_{13}$ are as defined in any preceding clause and P is a nitrogen protecting group such as para-methoxybenzyl, or salts such as pharmaceutically acceptable salts, thereof.

Clause 194. A compound of formula (XXIV):

(XXIV)

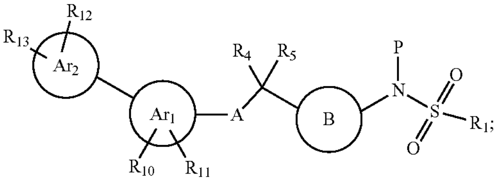

wherein B, Ar1, Ar2, A, $R_1$, $R_4$, $R_5$, $R_{10}$, $R_{11}$, $R_{12}$ and $R_{13}$ are as defined in any preceding clause and P is a nitrogen protecting group such as para-methoxybenzyl, or salts such as pharmaceutically acceptable salts, thereof.

Clause 195. A compound of formula (XXXXII):

(XXXXII)

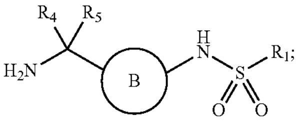

wherein B, $R_1$, $R_4$ and $R_5$ are as defined in any preceding clause, or salts such as pharmaceutically acceptable salts, thereof.

Clause 196. A compound of formula (LVIII):

(LVIII)

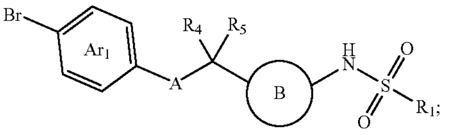

wherein B, $R_1$, Ar1, A, $R_4$ and $R_5$ are as defined in any preceding clause, or salts such as pharmaceutically acceptable salts, thereof.

Clause 197. A compound of INTC224 to INTC230, or salt such as pharmaceutically acceptable salt thereof.

Clause 198. A compound according to any one of clauses 1 to 191, for use as a medicament Clause 199. The compound according to clause 198, for use in the inhibition of CTPS1 in a subject.

Clause 200. The compound according to clause 198, for use in the reduction of T-cell and/or B-cell proliferation in a subject.

Clause 201. The compound according to clause 198, for use in the treatment or prophylaxis of: inflammatory skin diseases such as psoriasis or lichen planus; acute and/or chronic GVHD such as steroid resistant acute GVHD; acute lymphoproliferative syndrome (ALPS); systemic lupus erythematosus, lupus nephritis or cutaneous lupus; or transplantation.

Clause 202. The compound according to clause 198, for use in the treatment or prophylaxis of myasthenia gravis, multiple sclerosis, and scleroderma/systemic sclerosis.

Clause 203. A method for the inhibition of CTPS1 in a subject, which comprises administering to the subject an effective amount of a compound according to any one of clauses 1 to 191.

Clause 204. Use of a compound according to any one of clauses 1 to 191, in the manufacture of a medicament for the inhibition of CTPS1 in a subject.

Clause 205. A compound according to clause 198, for use in the treatment of cancer.

Clause 206. A method for treating cancer in a subject, by administering to a subject in need thereof a compound according to any one of clauses 1 to 191.

Clause 207. Use of a compound according to any one of clauses 1 to 191, in the manufacture of a medicament for the treatment of cancer in a subject.

Clause 208. The compound according to clause 205, the method according to clause 206 or the use according to clause 207 wherein the cancer is a haematological cancer.

Clause 209. The compound, method or use according to clause 208 wherein the haematological cancer is selected from the group consisting of Acute myeloid leukemia, Angioimmunoblastic T-cell lymphoma, B-cell acute lymphoblastic leukemia, Sweet Syndrome, T-cell Non-Hodgkins lymphoma (including natural killer/T-cell lymphoma, adult T-cell leukaemia/lymphoma, enteropathy type T-cell lymphoma, hepatosplenic T-cell lymphoma and cutaneous T-cell lymphoma), T-cell acute lymphoblastic leukemia, B-cell Non-Hodgkins lymphoma (including Burkitt lymphoma, diffuse large B-cell lymphoma, Follicular lymphoma, Mantle cell lymphoma, Marginal Zone lymphoma), Hairy Cell Leukemia, Hodgkin lymphoma, Lymphoblastic lymphoma, Lymphoplasmacytic lymphoma, Mucose-associated lymphoid tissue lymphoma, Multiple myeloma, Myelodysplastic syndrome, Plasma cell myeloma, Primary mediastinal large B-cell lymphoma, chronic myeloproliferative disorders (such as chronic myeloid leukemia, primary myelofibrosis, essential thrombocytemia, polycytemia vera) and chronic lymphocytic leukemia.

Clause 210. The compound, method or use according to clause 208 wherein the haematological cancer is Peripheral T-cell Lymphoma.

Clause 211. The compound according to clause 205, the method according to clause 206 or the use according to clause 207 wherein the cancer is a non-haematological cancer such as bladder cancer, breast cancer, melanoma, neuroblastoma, malignant pleural mesothelioma, and sarcoma, such as breast cancer and melanoma.

Clause 212. The compound according to clause 198, for use in enhancing recovery from vascular injury or surgery and reducing morbidity and mortality associated with neointima and restenosis in a subject.

Clause 213. A method for enhancing recovery from vascular injury or surgery and reducing morbidity and mortality associated with neointima and restenosis in a subject, by administering to a subject in need thereof a compound according to any one of clauses 1 to 191.

Clause 214. Use of a compound according to any one of clauses 1 to 191, in the manufacture of a medicament for enhancing recovery from vascular injury or surgery and reducing morbidity and mortality associated with neointima and restenosis in a subject.

Clause 215. A pharmaceutical composition comprising a compound according to any one of clauses 1 to 191.

Clause 216. The compound, method or use according to any one of clauses 198 to 215, for administration to a human subject.

Clause 217. The compound, method, use or composition according to any one of clauses 198 to 216, for administration in conjunction with a further pharmaceutically acceptable active ingredient or ingredients.

Clause 218. The compound, method, use or composition according to any one of clauses 198 to 217, for topical administration to the skin, eye or gut.

Clause 219. A compound of formula (XX-a):

(XX-a)

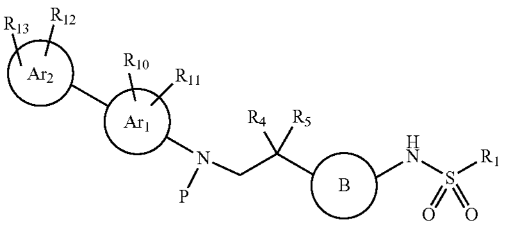

wherein $R_1$, B, $R_4$, $R_5$, $R_{10}$, $R_{11}$, $R_{12}$, $R_{13}$, $Ar_1$ and $Ar_2$ are as defined in any preceding clause and P is a nitrogen protecting group such as para-methoxybenzyl, or salts such as pharmaceutically acceptable salts, thereof.

Clause 220. A compound of formula (XX-b):

(XX-b)

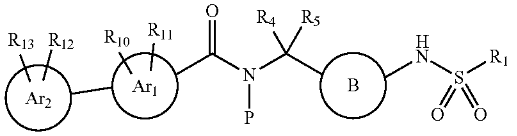

wherein $R_1$, B, $R_4$, $R_5$, $R_{10}$, $R_{11}$, $R_{12}$, $R_{13}$, $Ar_1$ and Ar2 are as defined in any preceding clause and P is a nitrogen protecting group such as para-methoxybenzyl, or salts such as pharmaceutically acceptable salts, thereof.

Clause 221. A compound of formula (XX-c):

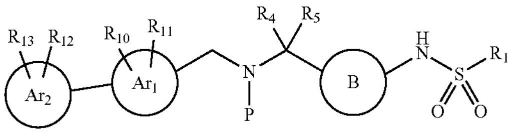

wherein $R_1$, B, $R_4$, $R_5$, $R_{10}$, $R_{11}$, $R_{12}$, $R_{13}$, $Ar_1$ and $Ar_2$ are as defined in any preceding clause and P is a nitrogen protecting group such as para-methoxybenzyl, or salts such as pharmaceutically acceptable salts, thereof.

Clause 222. A compound of formula (XX-d):

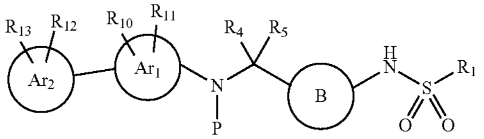

wherein $R_1$, B, $R_4$, $R_5$, $R_{10}$, $R_{11}$, $R_{12}$, $R_{13}$, $Ar_1$ and $Ar_2$ are as defined in any preceding clause and P is a nitrogen protecting group such as para-methoxybenzyl, or salts such as pharmaceutically acceptable salts, thereof.

Clause 223. A compound of formula (IV'):

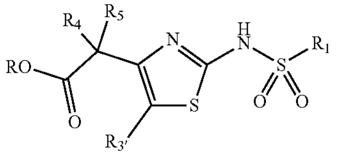

wherein $R_1$, $R_{3'}$, $R_4$ and $R_5$ are as defined in any preceding clause and R is H, $C_{1-6}$alkyl (e.g. methyl or ethyl) or benzyl, or salts such as pharmaceutically acceptable salts, thereof.

Clause 224. The compound, method, composition or use according to any one of clauses 192 to 222 wherein B is

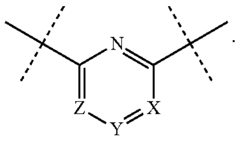

Clause 225. The compound, method, composition or use according to any one of clauses 192 to 222 wherein B is

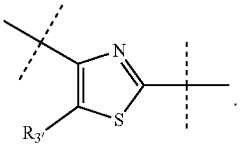

Clause 228. The compound according to any one of clauses 1 to 197 and 219 to 225, which is in natural isotopic form.

REFERENCES

Evans, D. R. & Guy, H. I. Mammalian pyrimidine biosynthesis: fresh insights into an ancient pathway. J. Biol. Chem. 279, 33035-33038 (2004).

Fairbanks, L. D. et al. Importance of ribonucleotide availability to proliferating T-lymphocytes from healthy humans. Disproportionate expansion of pyrimidine pools and contrasting effects of de novo synthesis inhibitors. J. Biol. Chem. 270, 29682-29689 (1995).

Higgins, M. J. et al. Regulation of human cytidine triphosphate synthetase 1 by glycogen synthase kinase 3. J. Biol. Chem. 282, 29493-29503 (2007).

Kursula, P. et al. Structure of the synthetase domain of human CTP synthetase, a target for anticancer therapy. Acta Crystallogr Sect F Struct Biol Cryst Commun. 62 (Pt7): 613-617 (2006).

Lieberman I. Enzymatic amination of uridine triphosphate to cytidine triphosphate. The J. Biol. Chem. 222 (2): 765-75 (1956).

Martin E. et al. CTP synthase 1 deficiency in humans reveals its central role in lymphocytes proliferation. Nature. June 12; 510(7504):288-92 (2014). Erratum in: Nature. July 17; 511(7509):370 (2014).

McCluskey G D et al., Exploring the Potent Inhibition of CTP Synthase by Gemcitabine-5-Triphosphate. Chembiochem. 17, 2240-2249 (2016).

Ostrander, D. B. et al. Effect of CTP synthetase regulation by CTP on phospholipid synthesis in *Saccharomyces cerevisiae*. J. Biol. Chem. 273, 18992-19001 (1998).

Sakamoto K et al. Identification of cytidine-5-triphosphate synthase1-selective inhibitory peptide from random peptide library displayed on T7 phage. Peptides. 2017; 94:56-63 (2017).

Salu et al. Drug-eluting stents: a new treatment in the prevention of restenosis Part I: experimental studies. Acta Cardiol, 59, 51-61 (2004).

Sousa J. E. et al. Drug-Eluting Stents. Circulation, 107 (2003) 2274 (Part 1), 2283 (Part II).

Tang R. et al. CTP synthase 1, a smooth muscle-sensitive therapeutic target for effective vascular repair. Arterioscler Thromb Vasc Biol. 33(10), 1-19, (2013).

van den Berg, A. A. et al. Cytidine triphosphate (CTP) synthetase activity during cell cycle progression in normal and malignant T-lymphocytic cells. Eur. J. Cancer 31, 108-112 (1995).

van Kuilenburg, A. B. P. et al. Identification of a cDNA encoding an isoform of human CTP synthetase. Biochimica et Biophysica Acta 1492548-552 (2000).

What is claimed is:

1. A compound of formula (II):

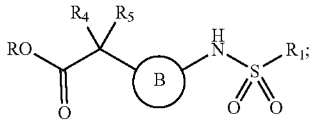

(II)

wherein:

B is

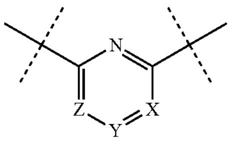

X is N or CH;

Y is N or $CR_2$;

Z is N or $CR_3$;

with the proviso that when at least one of X or Z is N, Y cannot be N;

$R_1$ is $CH_2CHF_2$;

$R_2$ is H, halo, $C_{1-2}$alkyl, $OC_{1-2}$alkyl, $C_{1-2}$haloalkyl or $OC_{1-2}$haloalkyl;

$R_3$ is H, halo, $CH_3$, $OCH_3$, $CF_3$ or $OCF_3$;

wherein at least one of $R_2$ and $R_3$ is H;

$R_4$ is fluoro and $R_5$ is ethyl;

R is H, $C_{1-6}$alkyl or benzyl;

or salts thereof.

2. The compound or salt according to claim 1, wherein X is N, Y is $CR_2$ and Z is $CR_3$, wherein $R_2$ is H and $R_3$ is H.

3. The compound or salt according to claim 1, wherein R is methyl or ethyl.

4. The compound or salt according to claim 1, wherein X is N, Y is CH and Z is CH; $R_4$ is fluoro, $R_5$ is ethyl and R is methyl.

* * * * *

SEQUENCE LISTING

```
<160> NUMBER OF SEQ ID NOS: 2

<210> SEQ ID NO 1
<211> LENGTH: 20
<212> TYPE: PRT
<213> ORGANISM: Artificial Sequence
<220> FEATURE:
<223> OTHER INFORMATION: synthetic

<400> SEQUENCE: 1

Gly Gly Asp Tyr Lys Asp Asp Asp Asp Lys Gly Gly His His His His
1               5                   10                  15

His His His His
            20


<210> SEQ ID NO 2
<211> LENGTH: 29
<212> TYPE: PRT
<213> ORGANISM: Artificial Sequence
```

-continued

```
<220> FEATURE:
<223> OTHER INFORMATION: synthetic

<400> SEQUENCE: 2

Asp Tyr Lys Asp Asp Asp Asp Lys His His His His His His Gly Leu
1               5                   10                  15

Asn Asp Ile Phe Glu Ala Gln Lys Ile Glu Trp His Glu
            20                  25
```